United States Patent
Fujimoto et al.

[11] Patent Number: 5,843,983
[45] Date of Patent: Dec. 1, 1998

[54] DIPHENYLETHANE COMPOUNDS CONTAINING A SATURATED HETEROCYCLIC GROUP, THEIR PREPARATION, AND THEIR THERAPEUTIC USE

[75] Inventors: Koichi Fujimoto, Yokohama; Naoki Tanaka, Matsudo; Fumitoshi Asai, Tanashi; Taketoshi Ogawa, Tokyo; Teiichiro Koga, Yokohama; Tatsuo Tanimoto, Toda; Yoshio Tsujita, Ichikawa; Hiroyuki Koike, Tokyo, all of Japan

[73] Assignee: Sankyo Company, Limited, Tokyo, Japan

[21] Appl. No.: 798,489

[22] Filed: Feb. 10, 1997

[30] Foreign Application Priority Data

Feb. 15, 1996 [JP] Japan .................................. 8-028041

[51] Int. Cl.$^6$ .......................... C07C 37/055; C07C 39/17; A61K 31/135; A61K 31/205
[52] U.S. Cl. .......................... 514/425; 514/415; 514/427; 514/428; 548/544; 548/556; 548/570; 548/578
[58] Field of Search ...................... 548/544, 556, 548/570, 578; 514/425, 415, 427, 428

[56] References Cited

U.S. PATENT DOCUMENTS

| | | | |
|---|---|---|---|
| 3,360,526 | 12/1967 | Minor | 546/343 X |
| 5,252,586 | 10/1993 | Cain et al. | 514/317 |
| 5,556,864 | 9/1996 | Fujimoto et al. | 514/315 |

FOREIGN PATENT DOCUMENTS

| | | |
|---|---|---|
| 0 001 759 | 5/1979 | European Pat. Off. |
| 0 398 326 | 11/1990 | European Pat. Off. |
| WO 92/02501 | 2/1992 | WIPO |
| WO 92/02502 | 2/1992 | WIPO |
| WO 92/22527 | 12/1992 | WIPO |
| WO 93/15052 | 8/1993 | WIPO |
| 0 600 717 | 6/1994 | WIPO |
| WO 94/13291 | 6/1994 | WIPO |
| WO 95/33723 | 12/1995 | WIPO |
| WO 96/06822 | 3/1996 | WIPO |
| WO 96/11902 | 4/1996 | WIPO |

OTHER PUBLICATIONS

Kikumoto et al, "Syntheses and Platelet Aggregation Inhibitory and Antithrombotic Properties of [2-[(ω-Aminoalkoxy)phenyl]ethyl]benzenes" Journal of Medicinal Chemistry, vol. 33, No. 6, 1990, pp. 1818–1823.

*Primary Examiner*—Floyd D. Higel
*Attorney, Agent, or Firm*—Frishauf, Holtz, Goodman, Langer & Chick, P.C.

[57] ABSTRACT

Compounds of formula (I):

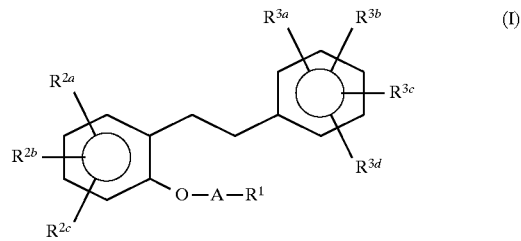

wherein: $R^1$ represents a saturated heterocyclic group attached to the bond or group represented by A through a ring carbon atom; $R^{2a}$, $R^{2b}$, $R^{2c}$, $R^{3a}$, $R^{3b}$, $R^{3c}$ and $R^{3d}$ are hydrogen or various other groups or atoms; and A represents a single bond or an alkylene group having from 1 to 6 carbon atoms are serotonin 2 receptor antagonists and have the ability to inhibit the activity of squalene synthase. They can not only prevent and inhibit the development and progression of arteriosclerosis but can also inhibit thrombosis in arteriosclerotic lesions and can improve hemodynamics.

71 Claims, No Drawings

DIPHENYLETHANE COMPOUNDS CONTAINING A SATURATED HETEROCYCLIC GROUP, THEIR PREPARATION, AND THEIR THERAPEUTIC USE

BACKGROUND TO THE INVENTION

The present invention relates to a series of new diaryl alkane derivatives containing an alicyclic group. These compounds are serotonin 2 receptor antagonists and have the ability to inhibit the activity of squalene synthase. The invention also provides methods and compositions using these compounds as well as processes for their preparation.

Serotonin, a classic autacoid, is also known to be a neurotransmitter and plays a variety of physiological roles in the body through various types of receptors. It is known that serotonin has several receptor subtypes. Among the subtypes are the serotonin 2 receptors which are distributed throughout the vascular endothelial cells and platelets, and which are closely involved in vascular contractions and platelet aggregation [S. J. Peroutka et. al., Fed. Proc., 42, 213 (1983)]. Serotonin antagonists which act at the serotonin 2 receptors are thus useful for the prevention of vascular contractions and the inhibition of platelet aggregation. Ketanserin is known to have a serotonin 2 receptor antagonistic effect [J. I. S. Robertson, Curr. Opinion Cardiol., 3, 702 (1988)], but its usefulness is limited by its potent hypotensive effect because this drug originally was developed as an adrenaline α1 antagonist. A diaryl alkane derivative has recently been introduced as a platelet aggregation inhibitor with serotonin 2 receptor antagonistic action [J. Med. Chem., 35, 189 (1992); ibid., 33, 1818 (1990); EP 600 717]. It has not, however, been demonstrated that these two compounds have the ability to inhibit squalene synthase.

Hyperlipidemia is one of the three major risk factors for ischemic heart diseases such as arteriosclerosis. It is recognised that such cardiac diseases can be prevented by lowering excessively increased blood cholesterol levels. Since squalene synthase acts at several sites below the site of action of HMG-CoA reductase in the cholesterol synthesis system, this enzyme does not affect the synthetic pathway of isoprene-derived compounds. Therefore, the biosynthesis of cholesterol can be inhibited by blocking squalene synthase without any inhibitory effect on the biosynthesis of ubiquinone, dolichol and other important metabolic compounds [Nature, 343, 425 (1990)]. This indicates that squalene synthase inhibitors are very useful as therapeutic and prophylactic drugs for hyperlipidemia. Currently available squalene synthase inhibitors are isoprenoid (phosphinylmethyl) phosphate, zaragozic acids containing dioxabicyclooctane ring as a basic structure, and others (U.S. Pat. No. 4,871,721; U.S. Pat. No. 5,102,907).

A compound having both serotonin 2 receptor antagonistic action and squalene synthase inhibitory action can not only prevent and inhibit the development and progression of arteriosclerosis because of its antihyperlipidemic effect (resulting from the squalene synthase inhibitory action), but can also inhibit thrombosis in arteriosclerotic lesions because of its serotonin 2 receptor antagonistic action, and can improve hemodynamics by inhibiting vascular contractions. This type of compound will, therefore, be of value for the prophylaxis and therapy of these diseases.

BRIEF SUMMARY OF INVENTION

We have now discovered a series of new alicyclic derivatives, which are preferably alicyclic amines, and pharmacologically acceptable salts thereof which are useful for the prophylaxis and therapy of cardiovascular diseases (including thrombotic diseases, arteriosclerotic diseases or hyperlipidemic diseases, especially thrombotic diseases) which have potent serotonin 2 receptor antagonistic action and additionally squalene synthase inhibitory action, and which have prolonged serotonin 2 receptor antagonistic action in vivo.

The compounds of the present invention are those compounds of formula (I):

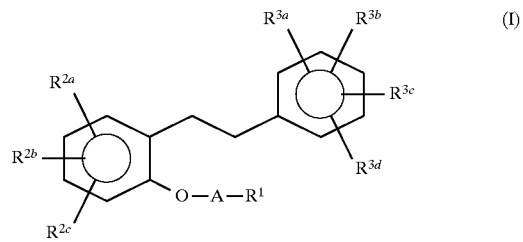

wherein:
  $R^1$ represents a saturated heterocyclic group attached to the bond or group represented by A through a ring carbon atom, said saturated heterocyclic group having from 3 to 6 ring atoms, of which one or two are hetero-atoms selected from the group consisting of nitrogen, oxygen and sulfur hetero-atoms, and being substituted on at least one carbon atom by at least one substituent selected from the group consisting of substituents α defined below or being unsubstituted on a nitrogen atom or being substituted on a nitrogen atom by at least one substituent selected from the group consisting of substituents β defined below;
  $R^{2a}$, $R^{2b}$ and $R^{2c}$ are the same as or different from each other and each represents a hydrogen atom, a methyl group, an ethyl group, a methoxy group, an ethoxy group, a fluorine atom, a chlorine atom, a bromine atom, an iodine atom, a cyano group or a nitro group, at least one of $R^{2a}$, $R^{2b}$ and $R^{2c}$ being a group or atom other than hydrogen;
  $R^{3a}$, $R^{3b}$, $R^{3c}$ and $R^{3d}$ are the same as or different from each other and each represents a hydrogen atom, an alkyl group having from 1 to 6 carbon atoms, a haloalkyl group having from 1 to 6 carbon atoms, an alkenyl group having from 2 to 6 carbon atoms, an alkynyl group having from 2 to 6 carbon atoms, a hydroxy group, an alkoxy group having from 1 to 6 carbon atoms, a haloalkoxy group having from 1 to 6 carbon atoms, an alkoxycarbonyloxy group having from 2 to 6 carbon atoms, an alkanoyloxy group having from 1 to 6 carbon atoms, a carbamoyloxy group, an alkylcarbamoyloxy group in which the alkyl part has from 1 to 6 carbon atoms, a dialkylcarbamoyloxy group in which each alkyl part has from 1 to 6 carbon atoms, a halogen atom, a cyano group, a nitro group or an aryl group as defined below;
  A represents a single bond or an alkylene group having from 1 to 6 carbon atoms;
  said substituents α are selected from the group consisting of hydroxy groups, alkoxycarbonyloxy groups in which the alkoxy part has from 1 to 20 carbon atoms, alkanoyloxy groups having from 1 to 20 carbon atoms, alkanoyloxy groups having from 2 to 7 carbon atoms and substituted by a carboxy group, carbamoyloxy groups, alkylcarbamoyloxy groups having from 1 to 6 carbon atoms, and dialkylcarbamoyloxy groups in which each alkyl part has from 1 to 10 carbon atoms;

said substituents β are selected from the group consisting of alkyl groups having from 1 to 6 carbon atoms, alkyl groups having from 1 to 6 carbon atoms and substituted by at least one aryl group as defined below, aryl groups as defined below, and alkoxycarbonyl groups having from 2 to 10 carbon atoms;

said aryl groups are carbocyclic aromatic groups which have from 6 to 10 ring carbon atoms and which are unsubstituted or are substituted by at least one substituent selected from the group consisting of substituents γ, defined below;

said substituents γ are selected from the group consisting of alkyl groups having from 1 to 6 carbon atoms, alkoxy groups having from 1 to 6 carbon atoms, and halogen atoms;

and pharmaceutically acceptable salts and esters thereof.

The invention also provides a composition for the prevention and treatment of cardiovascular diseases comprising a serotonin 2 receptor antagonist, wherein said serotonin 2 receptor antagonist also has squalene synthase inhibitory activity and is an active compound selected from the group consisting of compounds of formula (I) and pharmaceutically acceptable salts thereof, as defined above.

The invention still further provides a method for the prevention or treatment of cardiovascular diseases in a mammal susceptible thereto, comprising administering to said mammal, which may be human, an effective amount of an active compound having serotonin 2 receptor antagonist and squalene synthase inhibitory activities, said active compound being selected from the group consisting of compounds of formula (I) and pharmaceutically acceptable salts thereof, as defined above.

The invention also provides processes for the preparation of compounds of formula (I) and salts thereof, as shown in more detail below.

DETAILED DESCRIPTION OF INVENTION

In the compounds of the present invention, $R^1$ represents a saturated heterocyclic group attached to the bond or group represented by A through a ring carbon atom. The saturated heterocyclic group has from 3 to 6 ring atoms, of which one or two are hetero-atoms selected from the group consisting of nitrogen, oxygen and sulfur hetero-atoms. The group represented by $R^1$ preferably contains one nitrogen hetero-atom in the ring, and no or one further hetero-atom selected from the group consisting of nitrogen, oxygen and sulfur hetero-atoms, the remaining ring atoms being carbon atoms. The group is substituted on at least one of its carbon atoms by at least one substituent selected from the group consisting of substituents α defined above and exemplified below. Where the group includes, as is preferred, a nitrogen atom, this nitrogen atom is unsubstituted or may be substituted by at least one substituent selected from the group consisting of substituents β defined above and exemplified below. Examples of the heterocyclic parts of such groups include the aziridinyl, azetidinyl, pyrrolidinyl, piperidyl, piperazinyl, morpholinyl, thiomorpholinyl, imidazolidinyl, pyrazolidinyl, triazinyl and tetrazolidinyl groups, of which the azetidinyl, pyrrolidinyl, piperidyl, piperazinyl, morpholinyl and thiomorpholinyl groups are preferred, and the 2-pyrrolidinyl, 3-pyrrolidinyl, 2-piperidyl, 3-piperidyl, 4-piperidyl, 1-piperazinyl, 2-morpholinyl and 3-morpholinyl groups are more preferred. Still more preferred groups are the 2-pyrrolidinyl, 3-pyrrolidinyl, 2-piperidyl, 3-piperidyl and 4-piperidyl groups, and specific preferred groups are the 2-pyrrolidinyl and 3-piperidyl groups. The most preferred group is the 2-pyrrolidinyl group.

These groups are substituted. There is no particular restriction on the number of substituents, except such as may be imposed by the number of substitutable positions and possibly by steric constraints. In general, we prefer 2 or 3 substituents, 2 substituents being more preferred.

Where $R^{3a}$, $R^{3b}$, $R^{3c}$ or $R^{3d}$ represents an alkyl group, this may be a straight or branched chain group having from 1 to 6, preferably from 1 to 4, carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl and ethyl groups, and most preferably the methyl group.

Where $R^{3a}$, $R^{3b}$, $R^{3c}$ or $R^{3d}$ represents a haloalkyl group, this may be a straight or branched chain group having from 1 to 6, preferably from 1 to 4, carbon atoms, and examples include the fluoromethyl, difluoromethyl, trifluoromethyl, chloromethyl, bromomethyl, iodomethyl, 2-fluoroethyl, 2-chloroethyl, 2-bromoethyl, 2-iodoethyl, 3-fluoropropyl, 4-fluorobutyl, 5-fluoropentyl and 6-fluorohexyl groups. Of these, we prefer the fluoromethyl, difluoromethyl, trifluoromethyl, chloromethyl, 2-fluoroethyl and 2-chloroethyl groups, more preferably the fluoromethyl, difluoromethyl, trifluoromethyl, 2-fluoroethyl and 2-chloroethyl groups, and most preferably the trifluoromethyl group.

Where $R^{3a}$, $R^{3b}$, $R^{3c}$ or $R^{3d}$ represents an alkenyl group, this may be a straight or branched chain group having from 2 to 6, preferably 3 or 4, carbon atoms, and examples include the vinyl, allyl, methallyl, 1-propenyl, isopropenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl and 5-hexenyl groups, of which the vinyl, allyl, methallyl, 2-butenyl, 2-pentenyl and 2-hexenyl groups are preferred, the allyl and methallyl groups being more preferred, and the allyl group being most preferred.

Where $R^{3a}$, $R^{3b}$, $R^{3c}$ or $R^{3d}$ represents an alkynyl group, this may be a straight or branched chain group having from 2 to 6, preferably 3 or 4, carbon atoms, and examples include the ethynyl, propargyl (2-propynyl), 1-propynyl, 1-butynyl, 2-butynyl, 3-butynyl, 1-pentynyl, 2-pentynyl, 3-pentynyl, 4-pentynyl and 2-hexynyl groups, of which the ethynyl, propargyl, 2-butynyl, 2-pentynyl and 2-hexynyl groups are preferred, the propargyl and 2-butynyl groups being more preferred, and the propargyl group being most preferred.

Where $R^{3a}$, $R^{3b}$, $R^{3c}$ or $R^{3d}$ represents an alkoxy group, this may be a straight or branched chain group having from 1 to 6, preferably from 1 to 4, carbon atoms, and examples include the methoxy, ethoxy, propoxy, isopropoxy, butoxy, isobutoxy, sec-butoxy, t-butoxy, pentyloxy, isopentyloxy, neopentyloxy, 2-methylbutoxy, 1-ethylpropoxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy, 2-ethylbutoxy, hexyloxy and isohexyloxy groups. Of these, we prefer those alkoxy groups having from 1 to 4 carbon atoms, preferably the methoxy and ethoxy groups, and most preferably the methoxy group.

Where $R^{3a}$, $R^{3b}$, $R^{3c}$ or $R^{3d}$ represents a haloalkoxy group, this may be a straight or branched chain group having from 1 to 6, preferably from 1 to 4, carbon atoms, and examples include the fluoromethoxy, difluoromethoxy, trifluoromethoxy, chloromethoxy, bromomethoxy, iodomethoxy, 2-fluoroethoxy, 2-chloroethoxy, 2-bromoethoxy, 2-iodoethoxy, 3-fluoropropoxy, 4-fluorobutoxy, 5-fluoropentyloxy and 6-fluorohexyloxy groups. Of these, we prefer the fluoromethoxy, difluoromethoxy, trifluoromethoxy, chloromethoxy, 2-fluoroethoxy and 2-chloroethoxy groups, more preferably the fluoromethoxy, difluoromethoxy, trifluoromethoxy, 2-fluoroethoxy and 2-chloroethoxy groups, and most preferably the trifluoromethoxy and difluoromethoxy groups.

Where $R^{3a}$, $R^{3b}$, $R^{3c}$ or $R^{3d}$ represents an alkoxycarbonyloxy group having from 2 to 7 carbon atoms, the alkoxy part of this may be a straight or branched chain group having from 1 to 6, preferably from 1 to 4, carbon atoms, and examples include the methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy, t-butoxycarbonyloxy, pentyloxycarbonyloxy, isopentyloxycarbonyloxy, neopentyloxycarbonyloxy, 2-methylbutoxycarbonyloxy, 1-ethylpropoxycarbonyloxy, 4-methylpentyloxycarbonyloxy, 3-methylpentyloxycarbonyloxy, 2-methylpentyloxycarbonyloxy, 1-methylpentyloxycarbonyloxy, 3,3-dimethylbutoxycarbonyloxy, 2,2-dimethylbutoxycarbonyloxy, 1,1-dimethylbutoxycarbonyloxy, 1,2-dimethylbutoxycarbonyloxy, 1,3-dimethylbutoxycarbonyloxy, 2,3-dimethylbutoxycarbonyloxy, 2-ethylbutoxycarbonyloxy, hexyloxycarbonyloxy and isohexyloxycarbonyloxy groups. Of these, we prefer those alkoxycarbonyloxy groups having from 1 to 4 carbon atoms, preferably the methoxycarbonyloxy and ethoxycarbonyloxy groups, and most preferably the methoxycarbonyloxy group.

Where $R^{3a}$, $R^{3b}$, $R^{3c}$ or $R^{3d}$ represents an alkanoyloxy group, the alkanoyl part may be a straight or branched chain group having from 1 to 6, preferably from 2 to 5, carbon atoms, and examples include the formyloxy, acetoxy, propionyloxy, butyryloxy, isobutyryloxy, valeryloxy, pivaloyloxy and hexanoyloxy groups, of which we prefer the acetoxy, propionyloxy, butyryloxy, isobutyryloxy, valeryloxy and pivaloyloxy groups. The acetoxy and propionyloxy groups are more preferred, and the acetoxy group is most preferred.

Where $R^{3a}$, $R^{3b}$, $R^{3c}$ or $R^{3d}$ represents an alkylcarbamoyloxy group, the alkyl part of this group may be a straight or branched chain group having from 1 to 6, preferably from 1 to 4, carbon atoms, and examples include the methylcarbamoyloxy, ethylcarbamoyloxy, propylcarbamoyloxy, isopropylcarbamoyloxy, butylcarbamoyloxy, isobutylcarbamoyloxy, sec-butylcarbamoyloxy, t-butylcarbamoyloxy, pentylcarbamoyloxy, isopentylcarbamoyloxy, neopentylcarbamoyloxy, 2-methylbutylcarbamoyloxy, 1-ethylpropylcarbamoyloxy, 4-methylpentylcarbamoyloxy, 3-methylpentylcarbamoyloxy, 2-methylpentylcarbamoyloxy, 1-methylpentylcarbamoyloxy, 3,3-dimethylbutylcarbamoyloxy, 2,2-dimethylbutylcarbamoyloxy, 1,1-dimethylbutylcarbamoyloxy, 1,2-dimethylbutylcarbamoyloxy, 1,3-dimethylbutylcarbamoyloxy, 2,3-dimethylbutylcarbamoyloxy, 2-ethylbutylcarbamoyloxy, hexylcarbamoyloxy and isohexylcarbamoyloxy groups. Of these, we prefer those alkylcarbamoyloxy groups having from 1 to 4 carbon atoms in the alkyl part, preferably the methylcarbamoyloxy and ethylcarbamoyloxy groups, and most preferably the methylcarbamoyloxy group.

Where $R^{3a}$, $R^{3b}$, $R^{3c}$ or $R^{3d}$ represents a dialkylcarbamoyloxy group, each alkyl part of this group (which may be the same as or different from each other) may be a straight or branched chain group having from 1 to 6, preferably from 1 to 4, carbon atoms, and examples include the N,N-dimethylcarbamoyloxy, N-ethyl-N-methylcarbamoyloxy, N-isopropyl-N-methylcarbamoyloxy, N,N-diethylcarbamoyloxy, N,N-dipropylcarbamoyloxy, N,N-diisopropylcarbamoyloxy, N,N-dibutylcarbamoyloxy, N,N-diisobutylcarbamoyloxy, N,N-di-sec-butylcarbamoyloxy, N,N-di-t-butylcarbamoyloxy, N,N-dipentylcarbamoyloxy, N,N-diisopentylcarbamoyloxy, N,N-dineopentylcarbamoyloxy, N,N-dihexylcarbamoyloxy and N,N-diisohexylcarbamoyloxy groups. Of these, we prefer those dialkylcarbamoyloxy groups having from 1 to 4 carbon atoms in each alkyl part, preferably the N,N-dimethylcarbamoyloxy, N-ethyl-N-methylcarbamoyloxy and N,N-diethylcarbamoyloxy groups, and most preferably the N,N-dimethylcarbamoyloxy group.

Where $R^{3a}$, $R^{3b}$, $R^{3c}$ or $R^{3d}$ represents a halogen atom, this may be a fluorine atom, a chlorine atom, a bromine atom or an iodine atom, preferably a fluorine atom or a chlorine atom.

Where $R^{3a}$, $R^{3b}$, $R^{3c}$ or $R^{3d}$ represents an aryl group, this is a carbocyclic aromatic group which has from 6 to 10 ring carbon atoms and which is unsubstituted or is substituted by at least one substituent selected from the group consisting of substituents γ, defined above and exemplified below. Where the group is substituted, there is no particular restriction on the number of substituents, except such as may be imposed by the number of substitutable positions, and possibly by steric constraints. Examples of such groups include the phenyl, 2-methylphenyl, 3-methylphenyl, 4-methylphenyl, 2-methoxyphenyl, 3-methoxyphenyl, 4-methoxyphenyl, 2-ethoxyphenyl, 3-ethoxyphenyl, 4-ethoxyphenyl, 2-propoxyphenyl, 3-propoxyphenyl, 4-propoxyphenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-bromophenyl, 3-bromophenyl, 4-bromophenyl, 2,4-dimethylphenyl, 2,4-dichlorophenyl, 2,4-difluorophenyl, 1-naphthyl, 2-naphthyl, 2-methyl-1-naphthyl, 3-methyl-1-naphthyl, 4-methyl-1-naphthyl, 5-methyl-1-naphthyl, 6-methyl-1-naphthyl, 7-methyl-1-naphthyl, 8-methyl-1-naphthyl, 2-methoxy-1-naphthyl, 3-methoxy-1-naphthyl, 4-methoxy-1-naphthyl, 2-ethoxy-1-naphthyl, 3-ethoxy-1-naphthyl, 4-ethoxy-1-naphthyl, 2-propoxy-1-naphthyl, 3-propoxy-1-naphthyl, 4-propoxy-1-naphthyl, 2-fluoro-1-naphthyl, 3-fluoro-1-naphthyl, 4-fluoro-1-naphthyl, 2-chloro-1-naphthyl, 3-chloro-1-naphthyl, 4-chloro-1-naphthyl, 2-bromo-1-naphthyl, 3-bromo-1-naphthyl, 4-bromo-1-naphthyl, 2-bromo-1-naphthyl, 3-bromo-1-naphthyl, 4-bromo-1-naphthyl, 2-methyl-2-naphthyl, 3-methyl-2-naphthyl, 4-methyl-2-naphthyl, 5-methyl-2-naphthyl, 6-methyl-2-naphthyl, 7-methyl-2-naphthyl, 8-methyl-2-naphthyl, 2-methoxy-2-naphthyl, 3-methoxy-2-naphthyl, 4-methoxy-2-naphthyl, 2-ethoxy-2-naphthyl, 3-ethoxy-2-naphthyl, 4-ethoxy-2-naphthyl, 2-propoxy-2-naphthyl, 3-propoxy-2-naphthyl, 4-propoxy-2-naphthyl, 2-fluoro-2-naphthyl, 3-fluoro-2-naphthyl, 4-fluoro-2-naphthyl, 2-chloro-2-naphthyl, 3-chloro-2-naphthyl, 4-chloro-2-naphthyl, 2-bromo-2-naphthyl, 3-bromo-2-naphthyl, 4-bromo-2-naphthyl, 2-bromo-2-naphthyl, 3-bromo-2-naphthyl and 4-bromo-2-naphthyl groups. Of these, we prefer the phenyl, methylphenyl, methoxyphenyl, fluorophenyl, chlorophenyl and naphthyl groups; and most prefer the phenyl group.

Where A represents an alkylene group, this has from 1 to 6, preferably from 1 to 4, carbon atoms and may be a straight or branched chain group. Examples of such groups include the methylene, ethylene, propylene, trimethylene, tetramethylene, pentamethylene and hexamethylene groups. Of these, we prefer the methylene, ethylene and trimethylene groups, more preferably the methylene and ethylene groups, and most preferably the ethylene group.

Where substituent β represents an alkyl group, this may be a straight or branched chain group having from 1 to 6, preferably from 1 to 4, carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl and ethyl groups, and most preferably the methyl group.

Where substituent α represents an alkoxycarbonyloxy group, the alkoxy part of this may be a straight or branched chain group having from 1 to 20 carbon atoms (i.e. the alkoxycarbonyloxy group as a whole has from 2 to 21 carbon atoms), and examples include the methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy, t-butoxycarbonyloxy, pentyloxycarbonyloxy, hexyloxycarbonyloxy, heptyloxycarbonyloxy, octyloxycarbonyloxy, nonyloxycarbonyloxy, decyloxycarbonyloxy, undecyloxycarbonyloxy, dodecyloxycarbonyloxy, tridecyloxycarbonyloxy, tetradecyloxycarbonyloxy, pentadecyloxycarbonyloxy, hexadecyloxycarbonyloxy, heptadecyloxycarbonyloxy, octadecyloxycarbonyloxy, nonadecyloxycarbonyloxy and icosyloxycarbonyloxy groups. Of these, we prefer those alkoxycarbonyloxy groups in which the alkoxy part has from 1 to 6 or from 8 to 18 carbon atoms, more preferably from 1 to 4 or from 8 to 18 carbon atoms. Specific preferred groups include the ethoxycarbonyloxy, isopropoxycarbonyloxy, t-butoxycarbonyloxy, octyloxycarbonyloxy, hexadecyloxycarbonyloxy, and octadecyloxycarbonyloxy groups, more preferably the ethoxycarbonyloxy, isopropoxycarbonyloxy, t-butoxycarbonyloxy, octyloxycarbonyloxy, and hexadecyloxycarbonyloxy group, and most preferably the octyloxycarbonyloxy group.

Where substituent a represents an alkanoyloxy group, this may be a straight or branched chain group having from 1 to 20 carbon atoms, and examples include the formyloxy, acetoxy, propionyloxy, butyryloxy, isobutyryloxy, valeryloxy, pivaloyloxy, hexanoyloxy, heptanoyloxy, octanoyloxy, nonanoyloxy, decanoyloxy, lauryloxy, myristoyloxy, palmitoyloxy, stearoyloxy and icosanoyloxy groups. Of these, we prefer those groups having from 2 to 5 or from 10 to 18 carbon atoms, more preferably from 10 to 16 carbon atoms. Specific preferred groups include the decanoyloxy, lauroyloxy, myristoyloxy and palmitoyloxy groups, and most preferably the decanoyloxy and lauroyloxy groups.

Where substituent a represents an alkanoyloxy group substituted by a carboxy group, this is a residue of a dicarboxylic acid. The group may be a straight or branched chain group and has from 2 to 7 carbon atoms in the alkanoyl part (i.e. from 3 to 8 carbon atoms in the whole carboxy-substituted alkanoyloxy group). Examples of such carboxy-substituted alkanoyloxy groups include the malonyloxy, succinyloxy, glutaryloxy, adipoyloxy, pimeloyloxy and suberoyloxy groups. Of these, we prefer those alkanoyloxy groups having from 3 to 6 carbon atoms, most preferably the succinyloxy and glutaryloxy groups. If desired, the carboxy substituent may be esterified, for example as described below.

Where substituent α represents an alkylcarbamoyloxy group, the alkyl part of this group may be a straight or branched chain group having from 1 to 6, preferably from 1 to 4, carbon atoms, and examples include the methylcarbamoyloxy, ethylcarbamoyloxy, propylcarbamoyloxy, isopropylcarbamoyloxy, butylcarbamoloxy, isobutylcarbamoyloxy, sec-butylcarbamoyloxy, t-butylcarbamoyloxy, pentylcarbamoyloxy, isopentylcarbamoyloxy, neopentylcarbamoyloxy, 2-methylbutylcarbamoyloxy, 1-ethylpropylcarbamoyloxy, 4-methylpentylcarbamoyloxy, 3-methylpentylcarbamoyloxy, 2-methylpentylcarbamoyloxy, 1-methylpentylcarbamoyloxy, 3,3-dimethylbutylcarbamoyloxy, 2,2-dimethylbutylcarbamoyloxy, 1,1-dimethylbutylcarbamoyloxy, 1,2-dimethylbutylcarbamoyloxy, 1,3-dimethylbutylcarbamoyloxy, 2,3-dimethylbutylcarbamoyloxy, 2-ethylbutylcarbamoyloxy, hexylcarbamoyloxy and isohexylcarbarnoyloxy groups. Of these, we prefer those alkylcarbamnoyloxy groups having from 1 to 4 carbon atoms in the alkyl part, preferably the methylcarbamoyloxy and ethylcarbamoyloxy groups, and most preferably the methylcarbamoyloxy group.

Where substituent α represents a dialkylcarbamoyloxy group, each alkyl part of this group (which may be the same as or different from each other) may be a straight or branched chain group having from 1 to 6, preferably from 1 to 4, carbon atoms, and examples include the N,N-dimethylcarbamoyloxy, N-ethyl-N-methylcarbamoyloxy, N-isopropyl-N-methylcarbamoyloxy, N,N-diethylcarbamoyloxy, N,N-dipropylcarbamoyloxy, N,N-diisopropylcarbamoyloxy, N,N-dibutylcarbamoyloxy, N,N-diisobutylcarbamoyloxy, N,N-di-sec-butylcarbamoyloxy, N,N-di-t-butylcarbamoyloxy, N,N-dipentylcarbamoyloxy, N,N-diisopentylcarbamoyloxy, N,N-dineopentylcarbamoyloxy, N,N-dihexylcarbamoyloxy, carbamoyloxy and N,N-diisohexylcarbamoyloxy groups. Of these, we prefer those dialkylcarbamoyloxy groups having from 1 to 4 carbon atoms in each alkyl part, preferably the N,N-dimethylcarbamoyloxy, N-ethyl-N-methylcarbamoyloxy and N,N-diethylcarbamoyloxy groups, and most preferably the N,N-dimethylcarbamoyloxy, group.

Where substituent β represents an alkyl group substituted by at least one aryl group, the alkyl part has from 1 to 6 carbon atoms and may be any of the groups defined and exemplified above in relation to substituents β. The aryl part, which itself may be substituted or unsubstituted, may be any of the groups defined and exemplified above in relation to $R^{3a}$, $R^{3b}$, $R^{3c}$ or $R^{3d}$. The aryl group is preferably a phenyl group, which may be substituted or unsubstituted. There is no particular restriction on the number of aryl groups which are substituents on the alkyl group, except such as may be imposed by the number of substitutable positions and possibly by steric constraints. In general, we prefer from 1 to 3 aryl groups, 1 aryl group being more preferred. Specific examples of such arylsubstituted alkyl groups include the benzyl, o-, m- and p-methylbenzyl, o-, m- and p-methoxybenzyl, o-, m- and p-fluorobenzyl, o-, m- and p-chlorobenzyl, o-, m- and p-bromobenzyl, phenethyl, 3-phenylpropyl, 4-phenylbutyl, 5-phenylpentyl, 6-phenylhexyl, benzhydryl, o-, m- and p-methylbenzhydryl, o-, m- and p-methoxybenzhydryl, o-, m- and p-fluorobenzhydryl, o-, m- and p-chlorobenzhydryl, o,o'-, m,m'- and p,p'-difluorobenzhydryl, o,o'-, m,m'- and p,p'-dichlorobenzhydryl and trityl groups. Of which we prefer the benzyl, o-, m- and p-methylbenzyl, o-, m- and p-methoxybenzyl, o-, m- and p-fluorobenzyl, o-, m- and p-chlorobenzyl, o-, m- and p-bromobenzyl, phenethyl and benzhydryl groups, most preferably the benzyl group.

Where substituent β represents an aryl group, this may be any of the aryl groups defined and exemplified above in relation to $R^{3a}$, $R^{3b}$, $R^{3c}$ or $R^{3d}$, most preferably a phenyl group.

Where substituent β represents an alkoxycarbonyl group having from 2 to 10 carbon atoms, the alkoxy part of this may be a straight or branched chain group having from 1 to 9, preferably from 1 to 4, 7 or 8, carbon atoms, and examples of these alkoxycarbonyl groups include the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl, isopentyloxycarbonyl, neopentyloxycarbonyl, 2-methylbutoxycarbonyl, 1-ethylpropoxycarbonyl, 4-methylpentyloxycarbonyl, 3-methylpentyloxycarbonyl, 2-methylpentyloxycarbonyl, 1-methylpentyloxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, 2,3-dimethylbutoxycarbonyl, 2-ethylbutoxycarbonyl, hexyloxycarbonyl, isohexyloxycarbonyl, heptyloxycarbonyl, octyloxycarbonyl and nonyloxycarbonyl groups. Of these, we prefer those alkoxycarbonyl groups having from 2 to 5, 8 or 9 carbon atoms, preferably the methoxycarbonyl, ethoxycarbonyl and octyloxycarbonyl groups, and most preferably the methoxycarbonyl group.

Substituent γ represents an alkyl group having from 1 to 6 carbon atoms, an alkoxy group having from 1 to 6 carbon atoms, or a halogen atom; these may be as defined and exemplified above in relation to $R^{3a}$, $R^{3b}$, $R^{3c}$ or $R^{3d}$.

Substituent α the substituent on the carbon atom of a heterocyclic group represented by $R^1$, is preferably a hydroxy group, an alkoxycarbonyloxy group having from 1 to 6 or from 8 to 18 carbon atoms in the alkoxy part, an alkanoyloxy group having from 1 to 20 carbon atoms, carboxy-substituted alkanoyloxy group having from 3 to 7 carbon atoms in the alkanoyl part, a carbamoyloxy group, or a mono- or di-alkylcarbamoyloxy group in which the or each alkyl group has 1 or 2 carbon atoms, more preferably a hydroxy group, an alkoxycarbonyloxy group having from 1 to 4 or from 8 to 18 carbon atoms in the alkoxy part, an alkanoyloxy group having from 2 to 5 or 10 to 18 carbon atoms, a carboxy-substituted alkanoyloxy group having from 3 to 6 carbon atoms in the alkanoyl part, a carbamoyloxy group, or a mono- or di-alkylcarbamoyloxy group in which the or each alkyl group has 1 or 2 carbon atoms. More preferred groups included in substituents α are the hydroxy, methoxycarbonyloxy, ethoxycarbonyloxy, isopropoxycarbonyloxy, t-butoxycarbonyloxy, octyloxycarbonyloxy, decyloxycarbonyloxy, hexadecyloxycarbonyloxy, octadecyloxycarbonyloxy, acetoxy, propionyloxy, butyryloxy, valeryloxy, pivaloyloxy, decanoyloxy, undecanoyloxy, lauroyloxy, myristoyloxy, palmitoyloxy, stearoyloxy, succinyloxy, glutaryloxy, carbamoyloxy, N-methylcarbamoyloxy, N-ethylcarbamoyloxy, N,N-dimethylcarbamoyloxy and N,N-diethylcarbamoyloxy groups. Still more preferred groups are the hydroxy, ethoxycarbonyloxy, isopropoxycarbonyloxy, t-butoxycarbonyloxy, octyloxycarbonyloxy, hexadecyloxycarbonyloxy, acetoxy, decanoyloxy, lauroyloxy, palmitoyloxy, stearoyloxy, succinyloxy, carbamoyloxy and N,N-dimethylcarbamoyloxy groups, and most preferably the hydroxy, octyloxycarbonyloxy, decanoyloxy, lauroyloxy and palmitoyloxy groups.

Substituent β, the substituent on the nitrogen atom of a heterocyclic group represented by $R^1$, is preferably an alkyl group having from 1 to 4 carbon atoms, or phenyl group that is unsubstituted or is substituted by at least one methyl group, methoxy group, fluorine atom or chlorine atom. More preferred groups include in substituents β are the methyl, ethyl and phenyl groups, and most preferably the methyl group.

Preferred compounds of the present invention are those compounds of formula (I) in which $R^1$ represents a heterocyclic group having a nitrogen atom in the ring.

Specific examples of five- or six-membered saturated heterocyclic groups which may be represented by $R^1$ include the following groups. In these, "?" means that the subsequently referred to substituent may be at any otherwise free position. Such groups include the hydroxypyrrolidinyl, methoxycarbonyloxypyrrolidinyl, ethoxycarbonyloxypyrrolidinyl, propoxycarbonyloxypyrrolidinyl, isopropoxycarbonyloxypyrrolidinyl, butoxycarbonyloxypyrrolidinyl, t-butoxycarbonyloxypyrrolidinyl, pentyloxycarbonyloxypyrrolidinyl, hexyloxycarbonyloxypyrrolidinyl, octyloxycarbonyloxypyrrolidinyl, nonyloxycarbonyloxypyrrolidinyl, decyloxycarbonyloxypyrrolidinyl, undecyloxycarbonyloxypyrrolidinyl, dodecyloxycarbonyloxypyrrolidinyl, tridecyloxycarbonyloxypyrrolidinyl, pentadecyloxycarbonyloxypyrrolidinyl, hexadecyloxycarbonyloxypyrrolidinyl, heptadecyloxycarbonyloxypyrrolidinyl, octadecyloxycarbonyloxypyrrolidinyl, formyloxypyrrolidinyl, acetoxypyrrolidinyl, propionyloxypyrrolidinyl, butyryloxypyrrolidinyl, valeryloxypyrrolidinyl, pivaloyloxypyrrolidinyl, hexanoyloxypyrrolidinyl, 3,3-dimethylbutyryloxypyrrolidinyl, heptanoyloxypyrrolidinyl, octanoyloxypyrrolidinyl, nonanoyloxypyrrolidinyl, decanoyloxypyrrolidinyl, undecanoyloxypyrrolidinyl, lauroyloxypyrrolidinyl, myristoyloxypyrrolidinyl, palmitoyloxypyrrolidinyl, stearoyloxypyrrolidinyl, icosanoyloxypyrrolidinyl, docosanoyloxypyrrolidinyl, succinyloxypyrrolidinyl, glutaryloxypyrrolidinyl, adipoyloxypyrrolidinyl, pimeloyloxypyrrolidinyl, carbamoyloxypyrrolidinyl, N-methylcarbamoyloxypyrrolidinyl, N-ethylcarbamoyloxypyrrolidinyl, N,N-dimethylcarbamoyloxypyrrolidinyl, N,N-diethylcarbamoyloxypyrrolidinyl, N-methyl-N- ethylcarbamoyloxypyrrolidinyl, 1-methyl-?-hydroxypyrrolidinyl, 1-methyl-?-methoxycarbonyloxypyrrolidinyl, 1-methyl-?-ethoxycarbonyloxypyrrolidinyl, 1-methyl-?-propoxycarbonyloxypyrrolidinyl, 1-methyl-?-isopropoxycarbonyloxypyrrolidinyl, 1-methyl-?-butoxycarbonyloxypyrrolidinyl, 1-methyl-t-butoxycarbonyloxypyrrolidinyl, 1-methyl-?-pentyloxycarbonyloxypyrrolidinyl, 1-methyl-?-hexyloxycarbonyloxypyrrolidinyl, 1-methyl-?-heptyloxycarbonyloxypyrrolidinyl, 1-methyl-?-octyloxycarbonyloxypyrrolidinyl, 1-methyl-?-nonyloxycarbonyloxypyrrolidinyl, 1-methyl-?-decyloxycarbonyloxypyrrolidinyl, 1-methyl-?-undecyloxycarbonyloxypyrrolidinyl, 1-methyl-?-dodecyloxycarbonyloxypyrrolidinyl, 1-methyl-?-tridecyloxycarbonyloxypyrrolidinyl, 1-methyl-?-pentadecyloxycarbonyloxypyrrolidinyl, 1-methyl-?-hexadecyloxycarbonyloxypyrrolidinyl, 1-methyl-?-heptadecyloxycarbonyloxypyrrolidinyl, 1-methyl-?-octadccyloxycarbonyloxypyrrolidinyl, 1-methyl-?-formyloxypyrrolidinyl, 1-methyl-?-acetoxypyrrolidinyl, 1-methyl-?-propionyloxypyrrolidinyl, 1-methyl-?-butyryloxypyrrolidinyl, 1-methyl-?-valeryloxypyrrolidinyl, 1-methyl-?-pivaloyloxypyrrolidinyl, 1-methyl-?-hexanoyloxypyrrolidinyl, 1-methyl-?-(3,3-dimethylbutyryloxy)pyrrolidinyl, 1-methyl-?-heptanoyloxypyrrolidinyl, 1-methyl-?-octanoyloxypyrrolidinyl, 1-methyl-?-nonanoyloxypyrrolidinyl, 1-methyl-?-decanoyloxypyrrolidinyl, 1-methyl-?-undecanoyloxypyrrolidinyl, 1-methyl-?-lauroyloxypyrrolidinyl, 1-methyl-?-myristoyloxypyrrolidinyl, 1-methyl-?-palmitoyloxypyrrolidinyl, 1-methyl-?-stearoyloxypyrrolidinyl, 1-methyl-?-icosanoyloxypyrrolidinyl, 1-methyl-?-docosanoyloxypyrrolidinyl, 1-methyl-?-succinyloxypyrrolidinyl, 1-methyl-?-glutaryloxypyrrolidinyl, 1-methyl-?-adipoyloxypyrrolidinyl, 1-methyl-?-pimeloyloxypyrrolidinyl, 1-methyl-?-carbamoyloxypyrrolidinyl, 1-methyl-?-(N-methylcarbamoyloxy)pyrrolidinyl, 1-methyl-?-(N-ethylcarbamoyloxy)pyrrolidinyl, 1-methyl-?-(N,N-dimethyl-carbamoyloxy)pyrrolidinyl, 1-methyl-?-(N,N-diethylcarbamoyloxy)pyrrolidinyl, 1-methyl-?-(N-methyl-N-ethylcarbamoyloxy)pyrrolidinyl, 1-ethyl-?-hydroxypyrrolidinyl, 1-ethyl-?-methoxycarbonyloxypyrrolidinyl, 1-ethyl-?-ethoxycarbonyloxypyrrolidinyl, 1-ethyl-?-propoxycarbonyloxypyrrolidinyl, 1-ethyl-?-isopropoxycarbonyloxypyrrolidinyl, 1-ethyl-?-butoxycarbonyloxypyrrolidinyl, 1-ethyl-?-t-butoxycarbonyloxypyrrolidinyl, 1-ethyl-?-pentyloxycarbonyloxypyrrolidinyl, 1-ethyl-?-hexyloxycarbonyloxypyrrolidinyl, 1-ethyl-?-heptyloxycarbonyloxypyrrolidinyl, 1-ethyl-?-octyloxycarbonyloxypyrrolidinyl, 1-ethyl-?-nonyloxycarbonyloxypyrrolidinyl, 1-ethyl-?-decyloxycarbonyloxypyrrolidinyl, 1-ethyl-?-hexadecyloxycarbonyloxypyrrolidinyl, 1-ethyl-?-octadecyloxycarbonyloxypyrrolidinyl, 1-ethyl-?-acetoxypyrrolidinyl, 1-ethyl-?-propionyloxypyrrolidinyl, 1-ethyl-?-butyryloxypyrrolidinyl, 1-ethyl-?-valeryloxypyrrolidinyl, 1-ethyl-?-pivaloyloxypyrrolidinyl, 1-ethyl-?-octanoyloxypyrrolidinyl, 1-ethyl-?-nonanoyloxypyrrolidinyl, 1-ethyl-?-decanoyloxypyrrolidinyl, 1-ethyl-?-undecanoyloxypyrrolidinyl, 1-ethyl-?-lauroyloxypyrrolidinyl, 1-ethyl-?-myristoyloxypyrrolidinyl, 1-ethyl-?-palmitoyloxypyrrolidinyl, 1-ethyl-?-stearoyloxypyrrolidinyl, 1-ethyl-?-succinyloxypyrrolidinyl, 1-ethyl-?-glutaryloxypyrrolidinyl, 1-ethyl-?-adipoyloxypyrrolidinyl, 1-ethyl-?-pimeloyloxypyrrolidinyl, 1-ethyl-?-carbamoyloxypyrrolidinyl, 1-ethyl-?-(N-methylcarbamoyloxy)pyrrolidinyl, 1-ethyl-?-(N,N-dimethylcarbamoyloxy)pyrrolidinyl, hydroxypiperidyl, methoxycarbonyloxypiperidyl, ethoxycarbonyloxypiperidyl, isopropoxycarbonyloxypiperidyl, t-butoxycarbonyloxypiperidyl, octyloxycarbonyloxypiperidyl, nonyloxycarbonyloxypiperidyl, decyloxycarbonyloxypiperidyl, hexadecyloxycarbonyloxypiperidyl, octadecyloxycarbonyloxypiperidyl, acetoxypiperidyl, propionyloxypiperidyl, butyryloxypiperidyl, valeryloxypiperidyl, pivaloyloxypiperidyl, decanoyloxypiperidyl, lauroyloxypiperidyl, myristoyloxypiperidyl, palmitoyloxypiperidyl, stearoyloxypiperidyl, succinyloxypiperidyl, glutaryloxypiperidyl, carbamoyloxypiperidyl, N-methylcarbamoyloxypiperidyl, N-ethylcarbamoyloxypiperidyl, N,N-dimethylcarbamoyloxypiperidyl, 1-methyl-?-hydroxypiperidyl, 1-methyl-?-methoxycarbonyloxypiperidyl, 1-methyl-?-ethoxycarbonyloxypiperidyl, 1-methyl-?-isopropoxycarbonyloxypiperidyl, 1-methyl-?-t-butoxycarbonyloxypiperidyl, 1-methyl-?-octyloxycarbonyloxypiperidyl, 1-methyl-?-nonyloxycarbonyloxypiperidyl, 1-methyl-?-decyloxycarbonyloxypiperidyl, 1-methyl-?-hexadecyloxycarbonyloxypiperidyl, 1-methyl-?-octadecyloxycarbonyloxypiperidyl, 1-methyl-?-acetoxypiperidyl, 1-methyl-?-propionyloxypiperidyl, 1-methyl-?-butyryloxypiperidyl, 1-methyl-?-valeryloxypiperidyl, 1-methyl-?-pivaloyloxypiperidyl, 1-methyl-?-decanoyloxypiperidyl, 1-methyl-?-lauroyloxypiperidyl, 1-methyl-?-myristoyloxypiperidyl, 1-methyl-?-palmitoyloxypiperidyl, 1-methyl-?-stearoyloxypiperidyl, 1-methyl-?-succinyloxypiperidyl, 1-methyl-?-glutaryloxypiperidyl, 1-methyl-?-carbamoyloxypiperidyl, 1-methyl-?-(N-methylcarbamoyloxy)piperidyl, 1-methyl-?-(N-ethylcarbamoyloxy)piperidyl, 1-methyl-?-(N,N-dimethylcarbamoyloxy)piperidyl, 1-ethyl-?-hydroxypiperidyl, 1-ethyl-?-ethoxycarbonyloxypiperidyl, 1-ethyl-?-isopropoxycarbonyloxypiperidyl, 1-ethyl-?-t-butoxycarbonyloxypiperidyl, 1-ethyl-?-octyloxycarbonyloxypiperidyl, 1-ethyl-?-nonyloxycarbonyloxypiperidyl, 1-ethyl-?-decyloxycarbonyloxypiperidyl, 1-ethyl-?-hexadecyloxycarbonyloxypiperidyl, 1-ethyl-?-octadecyloxycarbonyloxypiperidyl, 1-ethyl-?-acetoxypiperidyl, 1-ethyl-?-propionyloxypiperidyl, 1-ethyl-?-butyryloxypiperidyl, 1-ethyl-?-valeryloxypiperidyl, 1-ethyl-?-pivaloyloxypiperidyl, 1-ethyl-?-decanoyloxypiperidyl, 1-ethyl-?-lauroyloxypiperidyl, 1-ethyl-?-myristoyloxypiperidyl, 1-ethyl-?-palmitoyloxypiperidyl, 1-ethyl-?-stearoyloxypiperidyl, 1-ethyl-?-acryloyloxypiperidyl, 1-ethyl-?-succinyloxypiperidyl, and 1-ethyl-?-glutaryloxypiperidyl groups.

Of these, preferred groups are the hydroxypyrrolidinyl, methoxycarbonyloxypyrrolidinyl, ethoxycarbonyloxypyrrolidinyl, isopropoxycarbonyloxypyrrolidinyl, t-butoxycarbonyloxypyrrolidinyl, octyloxycarbonyloxypyrrolidinyl, nonyloxycarbonyloxypyrrolidinyl, decyloxycarbonyloxypyrrolidinyl, hexadecyloxycarbonyloxypyrrolidinyl, octadecyloxycarbonyloxypyrrolidinyl, acetoxypyrrolidinyl, propionyloxypyrrolidinyl, valeryloxypyrrolidinyl, pivaloyloxypyrrolidinyl, decanoyloxypyrrolidinyl, undecanoyloxypyrrolidinyl, lauroyloxypyrrolidinyl, myristoyloxypyrrolidinyl, palmitoyloxypyrrolidinyl, stearoyloxypyrrolidinyl, succinyloxypyrrolidinyl, glutaryloxypyrrolidinyl, carbamoyloxypyrrolidinyl, N-methylcarbamoyloxypyrrolidinyl, N,N-dimethylcarbamoyloxypyrrolidinyl, 1-methyl-?-hydroxypyrrolidinyl, 1-methyl-?-methoxycarbonyloxypyrrolidinyl, 1-methyl-?-ethoxycarbonyloxypyrrolidinyl, 1-methyl-?-isopropoxycarbonloxypyrrolidinyl, 1-methyl-?-t-butoxycarbonyloxypyrrolidinyl, 1-methyl-?-octyloxycarbonyloxypyrrolidinyl, 1-methyl-?-nonyloxycarbonyloxypyrrolidinyl, 1-methyl-?-decyloxycarbonyloxypyrrolidinyl, 1-methyl-?-hexadecyloxycarbonyloxypyrrolidinyl, 1-methyl-?-octadecyloxycarbonyloxypyrrolidinyl, 1-methyl-?-acetoxypyrrolidinyl, 1-methyl-?-propionyloxypyrrolidinyl, 1-methyl-?-valeryloxypyrrolidinyl, 1-methyl-?-pivaloyloxypyrrolidinyl, 1-methyl-?-decanoyloxypyrrolidinyl, 1-methyl-?-undecanoyloxypyrrolidinyl, 1-methyl-?-lauroyloxypyrrolidinyl, 1-methyl-?-myristoyloxypyrrolidinyl, 1-methyl-?-palmitoyloxypyrrolidinyl, 1-methyl-?-stearoyloxypyrrolidinyl, 1-methyl-?-succinyloxypyrrolidinyl, 1-methyl-?-glutaryloxypyrrolidinyl, 1-methyl-?-carbamoyloxypyrrolidinyl, 1-methyl-?-(N-methylcarbamoyloxy)pyrrolidinyl, 1-methyl-?-(N,N-dimethylcarbamoyloxy)pyrrolidinyl, 1-ethyl-?-hydroxypyrrolidinyl, 1-ethyl-?-methoxycarbonyloxypyrrolidinyl, 1-ethyl-?-ethoxycarbonyloxypyrrolidinyl, 1-ethyl-?-isopropoxycarbonyloxypyrrolidinyl, 1-ethyl-?-t-butoxycarbonyloxypyrrolidinyl, 1-ethyl-?-octyloxycarbonyloxypyrrolidinyl, 1-ethyl-?-nonyloxycarbonyloxypyrrolidinyl, 1-ethyl-?-decyloxycarbonyloxypyrrolidinyl, 1-ethyl-?-hexadecyloxycarbonyloxypyrrolidinyl, 1-ethyl-?-octadecyloxycarbonyloxypyrtolidinyl, 1-ethyl-?-acetoxypyrrolidinyl, 1-ethyl-?-propionyloxypyrrolidinyl, 1-ethyl-?-valeryloxypyrrolidinyl, 1-ethyl-?-pivaloyloxypyrrolidinyl, 1-ethyl-?-lauroyloxypyrrolidinyl, 1-ethyl-?-myristoyloxypyrrolidinyl, 1-ethyl-?-palmitoyloxypyrrolidinyl, 1-ethyl-?-stearoyloxypyrrolidinyl, 1-ethyl-?-succinyloxypyrrolidinyl, 1-ethyl-?-glutaryloxypyrrolidinyl, 1-ethyl-?-carbamoyloxypyrrolidinyl, hydroxypiperidyl, methoxycarbonyloxypiperidyl, ethoxycarbonyloxypiperidyl, isopropoxycarbonyloxypiperidyl, t-butoxycarbonyloxypiperidyl, octyloxycarbonyloxypiperidyl, decyloxycarbonyloxypiperidyl, hexadecyloxycarbonyloxypiperidyl, octadecyloxycarbonyloxypiperidyl, acetoxypiperidyl, propionyloxypiperidyl, valeryloxypiperidyl, pivaloyloxypiperidyl, decanoyloxypiperidyl, undecanoyloxypiperidyl, lauroyloxypiperidyl, myristoyloxypiperidyl, palmitoyloxypiperidyl, stearoyloxypiperidyl, succinyloxypiperidyl, glutaryloxypiperidyl, carbamoyloxypiperidyl, N-methylcarbamoyloxypiperidyl, N,N-dimethylcarbamoyloxypiperidyl, 1-methyl-?-hydroxypiperidyl, 1-methyl-?-methoxycarbonyloxypiperidyl, 1-methyl-?-ethoxycarbonyloxypiperidyl, 1-methyl-?-isopropoxycarbonyloxypiperidyl, 1-methyl-?-t-butoxycarbonyloxypiperidyl, 1-methyl-?-octyloxycarbonyloxypiperidyl, 1-methyl-?-decyloxycarbonyloxypiperidyl, 1-methyl-?-hexadecyloxycarbonyloxypiperidyl, 1-methyl-?-octadecyloxycarbonyloxypiperidyl, 1-methyl-?-acetoxypiperidyl, 1-methyl-?-propionyloxypiperidyl, 1-methyl-?-valeryloxypiperidyl, 1-methyl-?-pivaloyloxypiperidyl, 1-methyl-?-decanoyloxypiperidyl, 1-methyl-?-undecanoyloxypiperidyl, 1-methyl-?-lauroyloxypiperidyl, 1-methyl-?-myristoyloxypiperidyl, 1-methyl-?-palmitoyloxypiperidyl, 1-methyl-?-stearoyloxypiperidyl, 1-methyl-?-succinyloxypiperidyl, 1-methyl-?-glutaryloxypiperidyl, 1-methyl-?-carbamoyloxypiperidyl, 1-methyl-?-(N,N-dimethylcarbamoyloxy)piperidyl, 1-ethyl-?-hydroxypiperidyl, 1-ethyl-?-methoxycarbonyloxypiperidyl, 1-ethyl-?-ethoxycarbonyloxypiperidyl, 1-ethyl-?-isopropoxycarbonyloxypiperidyl, 1-ethyl-?-t-butoxycarbonyloxypiperidyl, 1-ethyl-?-octyloxycarbonyloxypiperidyl, 1-ethyl-?-decyloxycarbonyloxypiperidyl, 1-ethyl-?-hexadecyloxycarbonyloxypiperidyl, 1-ethyl-?-octadecyloxycarbonyloxypiperidyl, 1-ethyl-?-acetoxypiperidyl, 1-ethyl-?-propionyloxypiperidyl, 1-ethyl-?-valeryloxypiperidyl, 1-ethyl-?-pivaloyloxypiperidyl, 1-ethyl-?-decanoyloxypiperidyl, 1-ethyl-?-lauroyloxypiperidyl, 1-ethyl-?-myristoyloxypiperidyl, 1-ethyl-?-palmitoyloxypiperidyl, 1-ethyl-?-stearoyloxypiperidyl, 1-ethyl-?-succinyloxypiperidyl, 1-ethyl-?-glutaryloxypiperidyl, and 1-ethyl-?-carbamoyloxypiperidyl groups.

More preferred groups are the 4-hydroxy-2-pyrrolidinyl, 4-ethoxycarbonyloxy-2-pyrrolidinyl, 4-isopropoxycarbonyloxy-2-pyrrolidinyl, 4-t-butoxycarbonyloxy-2-pyrrolidinyl, 4-octyloxycarbonyloxy-2-pyrrolidinyl, 4-decyloxycarbonyloxy-2-pyrrolidinyl, 4-hexadecyloxycarbonyloxy-2-pyrrolidinyl, 4-octadecyloxycarbonyloxy-2-pyrrolidinyl, 4-acetoxy-2-pyrrolidinyl, 4-propionyloxy-2-pyrrolidinyl, 4-valeryloxy-2-pyrrolidinyl, 4-pivaloyloxy-2-pyrrolidinyl, 4-decanoyloxy-2-pyrrolidinyl, 4-lauroyloxy-2-pyrrolidinyl, 4-myristoyloxy-2-pyrrolidinyl, 4-palmitoyloxy-2-pyrrolidinyl, 4-stearoyloxy-2-pyrrolidinyl, 4-succinyloxy-2-pyrrolidinyl, 4-glutaryloxy-2-pyrrolidinyl, 4-carbamoyloxy-2-pyrrolidinyl, 4-(N-methylcarbamoyloxy)-2-pyrrolidinyl, 4-(,N-dimethyl-carbamoyloxy)-2-pyrrolidinyl, 1-methyl-4-hydroxy-2-pyrrolidinyl, 1-methyl-4-ethoxycarbonyloxy-2-pyrrolidinyl, 1-methyl-4-isopropoxycarbonyloxy-2-pyrrolidinyl, 1-methyl-4-t-butoxycarbonyloxy-2-pyrrolidinyl, 1-methyl-4-octyloxycarbonyloxy-2-pyrrolidinyl, 1-methyl-4-decyloxycarbonyloxy-2-pyrrolidinyl, 1-methyl-4-hexadecyloxycarbonyloxy-2-pyrrolidinyl, 1-methyl-4-octadecyloxycarbonyloxy-2-pyrrolidinyl, 1-methyl-4-acetoxy-2-pyrrolidinyl, 1-methyl- 4-propionyloxy-2-pyrrolidinyl, 1-methyl-valeryloxy-2-pyrrolidinyl, 1-methyl-4-pivaloyloxy-2-pyrrolidinyl, 1-methyl-4-decanoyloxy-2-pyrrolidinyl, 1-methyl-4-lauroyloxy-2-pyrrolidinyl, 1-methyl-4-myristoyloxy-2-pyrrolidinyl, 1-methyl-4-palmitoyloxy-2-pyrrolidinyl, 1-methyl-4-stearoyloxy-2-pyrrolidinyl, 1-methyl-4-succinyloxy-2-pyrrolidinyl, 1-methyl-4-glutaryloxy-2-pyrrolidinyl, 1-methyl-4-carbamoyloxy-2-pyrrolidinyl, 1-methyl-4-(N-methylcarbamoyloxy)-2-pyrrolidinyl, 1-methyl-4-(N,N-dimethylcarbamoyloxy)-2-pyrrolidinyl, 1-ethyl-4-hydroxy-2-pyrrolidinyl, 1-ethyl-4-ethoxycarbonyloxy-2-pyrrolidinyl, 1-ethyl-4-isopropoxycarbonyloxy-2-pyrrolidinyl, 1-ethyl-4-t-butoxycarbonyloxy-2-pyrrolidinyl, 1-ethyl-4-octyloxycarbonyloxy-2-pyrrolidinyl, 1-ethyl-4-hexadecyloxycarbonyloxy-2-pyrrolidinyl, 1-ethyl-4-octadecyloxycarbonyloxy-2-pyrrolidinyl, 1-ethyl-4-acetoxy-2-pyrrolidinyl, 1-ethyl-4-decanoyloxy-2-pyrrolidinyl, 1-ethyl-4-lauroyloxy-2-pyrrolidinyl, 1-ethyl-4-myristoyloxy-2-pyrrolidinyl, 1-ethyl-4-palmitoyloxy-2-pyrrolidinyl, 1-ethyl-4-stearoyloxy-2-pyrrolidinyl, 1-ethyl-4-succinyloxy-2-pyrrolidinyl, 4-hydroxy-2-piperidyl, and 1-methyl-4-hydroxy-2-piperidyl groups.

Still more preferred groups are the 4-hydroxy-2-pyrrolidinyl, 4-ethoxycarbonyloxy-2-pyrrolidinyl, 4-isopropoxycarbonyloxy-2-pyrrolidinyl, 4-t-butoxycarbonyloxy-2-pyrrolidinyl, 4-octyloxycarbonyloxy-2-pyrrolidinyl, 4-hexadecyloxycarbonyloxy-2-pyrrolidinyl, 4-octadecyloxycarbonyloxy-2-pyrrolidinyl, 4-acetoxy-2-pyrrolidinyl, 4-pivaloyloxy-2-pyrrolidinyl, 4-decanoyloxy-2-pyrrolidinyl, 4-lauroyloxy-2-pyrrolidinyl, 4-myristoyloxy-2-pyrrolidinyl, 4-palmitoyloxy-2-pyrrolidinyl, 4-stearoyloxy-2-pyrrolidinyl, 4-succinyloxy-2-pyrrolidinyl, 4-carbamoyloxy-2-pyrrolidinyl, 4-(N,N-dimethylcarbamoyloxy)-2-pyrrolidinyl, 1-methyl-4-hydroxy-2-pyrrolidinyl, 1-methyl-4-ethoxycarbonyloxy-2-pyrrolidinyl, 1-methyl-4-isopropoxycarbonyloxy-2-pyrrolidinyl, 1-methyl-4-t-butoxycarbonyloxy-2-pyrrolidinyl, 1-methyl-4-octyloxycarbonyloxy-2-pyrrolidinyl, 1-methyl-4-hexadecyloxycarbonyloxy-2-pyrrolidinyl, 1-methyl-4-octadecyloxycarbonyloxy-2-pyrrolidinyl, 1-methyl-4-acetoxy-2-pyrrolidinyl, 1-methyl-4-pivaloyloxy-2-pyrrolidinyl, 1-methyl-4-decanoyloxy-2-pyrrolidinyl, 1-methyl-4-lauroyloxy-2-pyrrolidinyl, 1-methyl-4-myristoyloxy-2-pyrrolidinyl, 1-methyl-4-palmitoyloxy-2-pyrrolidinyl, 1-methyl-4-stearoyloxy-2-pyrrolidinyl, 1-methyl-4-succinyloxy-2-pyrrolidinyl, 1-methyl-4-carbamoyloxy-2-pyrrolidinyl, and 1-methyl-4-(N,N-dimethylcarbamoyloxy)-2-pyrrolidinyl groups.

Much more preferred groups are the 4-hydroxy-2-pyrrolidinyl, 4-ethoxycarbonyloxy-2-pyrrolidinyl, 4-isopropoxycarbonyloxy-2-pyrrolidinyl, 4-t-butoxycarbonyloxy-2-pyrrolidinyl, 4-octyloxycarbonyloxy-2-pyrrolidinyl, 4-hexadecyloxycarbonyloxy-2-pyrrolidinyl, 4-octadecyloxycarbonyloxy-2-pyrrolidinyl, 4-acetoxy-2-pyrrolidinyl, 4-decanoyloxy-2-pyrrolidinyl, 4-lauroyloxy-2-pyrrolidinyl, 4-myristoyloxy-2-pyrrolidinyl, 4-palmitoyloxy-2-pyrrolidinyl, 4-stearoyloxy-2-pyrrolidinyl, 4-succinyloxy-2-pyrrolidinyl, 4-carbamoyloxy-2-pyrrolidinyl, 1-methyl-4-hydroxy-2-pyrrolidinyl, 1-methyl-4-ethoxycarbonyloxy-2-pyrrolidinyl, 1-methyl-4-isopropoxycarbonyloxy-2-pyrrolidinyl, 1-methyl-4-t-utoxycarbonyloxy-2-pyrrolidinyl, 1-methyl-4-octyloxycarbonyloxy-2-pyrrolidinyl, 1-methyl-4-hexadecyloxycarbonyloxy-2-pyrrolidinyl, 1-methyl-4-octadecyloxycarbonyloxy-2-pyrrolidinyl, 1-methyl-4-acetoxy-2-pyrrolidinyl, 1-methyl-4-decanoyloxy-2-pyrrolidinyl, 1-methyl-4-lauroyloxy-2-pyrroidinyl, 1-methyl-4-myristoyloxy-2-pyrrolidinyl, 1-methyl-4-palmitoyloxy-2-pyrrolidinyl, 1-methyl-4-stearoyloxy-2-pyrrolidinyl, and 1-methyl-4-succinyloxy-2-pyrrolidinyl groups.

Even more preferred groups are the 4-hydroxy-2-pyrrolidinyl, 4-ethoxycarbonyloxy-2-pyrrolidinyl, 4-t-butoxycarbonyloxy-2-pyrrolidinyl, 4-octyloxycarbonyloxy-2-pyrrolidinyl, 4-hexadecyloxycarbonyloxy-2-pyrrolidinyl, 4-octadecyloxycarbonyloxy-2-pyrrolidinyl, 4-decanoyloxy-2-pyrrolidinyl, 4-lauroyloxy-2-pyrrolidinyl, 4-myristoyloxy-2-pyrrolidinyl, 4-palmitoyloxy-2-pyrrolidinyl, 4-stearoyloxy-2-pyrrolidinyl, 1-methyl-4-hydroxy-2-pyrrolidinyl, 1-methyl-4-ethoxycarbonyloxy-2-pyrrolidinyl, 1-methyl-4-t-butoxycarbonyloxy-2-pyrrolidinyl, 1-methyl-4-octyloxycarbonyloxy-2-pyrrolidinyl, 1-methyl-4-hexadecyloxycarbonyloxy-2-pyrrolidinyl, 1-methyl-4-octadecyloxycarbonyloxy-2-pyrrolidinyl, 1-methyl-4-decanoyloxy-2-pyrrolidinyl, 1-methyl-4-lauroyloxy-2-pyrrolidinyl, 1-methyl-4-myristoyloxy-2-pyrrolidinyl, 1-methyl-4-palmitoyloxy-2-pyrrolidinyl and 1-methyl-4-stearoyloxy-2-pyrrolidinyl groups.

The most preferred groups are the 4-hydroxy-2-pyrrolidinyl, 4-decanoyloxy-2-pyrrolidinyl, 4-lauroyloxy-2-pyrrolidinyl, 4-myristoyloxy-2-pyrrolidinyl, 4-palmitoyloxy-2-pyrrolidinyl, 4-stearoyloxy-2-pyrrolidinyl, 1-methyl-4-hydroxy-2-pyrrolidinyl, 1-methyl-4-decanoyloxy-2-pyrrolidinyl, 1-methyl-4-lauroyloxy-2-pyrrolidinyl, 1-methyl-4-myristoyloxy-2-pyrrolidinyl, 1-methyl-4-palmitoyloxy-2-pyrrolidinyl and 1-methyl-4-stearoyloxy-2-pyrrolidinyl groups.

Where $R^1$ represents a pyrrolidinyl group, it is preferably a substituted 2-pyrrolidinyl group, more preferably a 4-hydroxy-1-methyl-2-pyrrolidinyl group or a 4-hydroxy-2-pyrrolidinyl group or such a group in which the hydroxy group has been esterified.

Where the compound of the present invention contains a basic group in its molecule, it can form acid addition salts. Examples of such acid addition salts include: salts with mineral acids, especially hydrohalic acids (such as hydrofluoric acid, hydrobromic acid, hydroiodic acid or hydrochloric acid), nitric acid, perchloric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid; and salts with amino acids, such as glutamic acid or aspartic acid.

In addition, where the compound of the present invention contains a free carboxy group, it can form an ester. There is no particular restriction on the nature of the ester, provided that, where it is to be used in therapy, it is pharmaceutically acceptable, that is it is no less active (or not unacceptably less active) than the free acid and it is no more toxic (or not unacceptably more toxic ) than the free acid. Examples of ester groups include:

alkyl groups having from 1 to 20 carbon atoms, more preferably from 1 to 6 carbon atoms, such as those exemplified above and higher alkyl groups as are well known in the art, such as the heptyl, octyl, nonyl, decyl, dodecyl, tridecyl, pentadecyl, octadecyl, nonadecyl and icosyl groups, but more preferably alkyl groups having from 1 to 4 carbon atoms, and most preferably the methyl and ethyl groups;

cycloalkyl groups having from 3 to 7 carbon atoms, for example the cyclopropyl, cyclobutyl, cyclopentyl, cyclohexyl and cycloheptyl groups;

aralkyl groups, in which the alkyl part has from 1 to 3 carbon atoms and the aryl part is a carbocyclic aromatic group having from 6 to 14 carbon atoms, which may be substituted or unsubstituted and, if substituted, has at least one of the substituents defined and exemplified above, although the unsubstituted groups are preferred; examples of such aralkyl groups include the benzyl, phenethyl, 1-phenylethyl, 3-phenylpropyl, 2-phenylpropyl, 1-naphthylmethyl, 2-naphthylmethyl, 2-(1-naphthyl)ethyl, 2-(2-naphthyl)ethyl, benzhydryl (i.e. diphenylmethyl), triphenylmethyl, bis(o-nitrophenyl)methyl, 9-anthrylmethyl, 2,4,6-trimethylbenzyl, 4-bromobenzyl, 2-nitrobenzyl, 4-nitrobenzyl, 3-nitrobenzyl, 4-methoxybenzyl and piperonyl groups;

alkenyl groups having from 2 to 6 carbon atoms, such as the vinyl, allyl, 2-methylallyl, 1-propenyl, isopropenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl and 5-hexenyl groups, of which the vinyl, allyl, 2-methylallyl, 1-propenyl, isopropenyl and butenyl groups are preferred, the allyl and 2-methylallyl groups being most preferred;

halogenated alkyl groups having from 1 to 6, preferably from 1 to 4, carbon atoms, in which the alkyl part is as defined and exemplified in relation to the alkyl groups above, and the halogen atom is chlorine, fluorine, bromine or iodine, such as the 2,2,2-trichloroethyl, 2-haloethyl (e.g. 2-chloroethyl, 2-fluoroethyl, 2-bromoethyl or 2-iodoethyl), 2,2-dibromoethyl and 2,2,2-tribromoethyl groups;

substituted silylalkyl groups, in which the alkyl part is as defined and exemplified above, and the silyl group has up to 3 substituents selected from alkyl groups having from 1 to 6 carbon atoms and phenyl groups which are unsubstituted or have at least one substituent selected from the substituents defined and exemplified above, for example a 2-trimethylsilylethyl group;

phenyl groups, in which the phenyl group is unsubstituted or substituted, preferably with at least one alkyl group having from 1 to 4 carbon atoms or acylamino group, for example the phenyl, tolyl and benzamidophenyl groups;

phenacyl groups, which may be unsubstituted or have at least one of the substituents defined and exemplified above, for example the phenacyl group itself or the p-bromophenacyl group;

cyclic and acyclic terpenyl groups, for example the geranyl, neryl, linalyl, phytyl, menthyl (especially m- and p-menthyl), thujyl, caryl, pinanyl, bornyl, norcaryl, norpinanyl, norbornyl, menthenyl, camphenyl and nor-bornenyl groups;

alkoxymethyl groups, in which the alkoxy part has from 1 to 6, preferably from 1 to 4, carbon atoms and may itself be substituted by a single unsubstituted alkoxy group, such as the methoxymethyl, ethoxymethyl, propoxymethyl, isopropoxymethyl, butoxymethyl and methoxyethoxymethyl groups;

aliphatic acyloxyalkyl groups, in which the acyl group is preferably an alkanoyl group and is more preferably an alkanoyl group having from 2 to 6 carbon atoms, and the alkyl part has from 1 to 6, and preferably from 1 to 4, carbon atoms such as the acetoxymethyl, propionyloxymethyl, buty-ryloxymethyl, isobutyryloxymethyl, pivaloyloxymethyl, 1-pivaloyloxyethyl, 1-acetoxyethyl, 1-isobutyryloxyethyl, 1-pivaloyloxypropyl, 2-methyl-1-pivaloyloxypropyl, 2-pivaloyloxypropyl, 1-isobutyryloxyethyl, 1-isobutyryloxypropyl, 1-acetoxypropyl, 1-acetoxy-2-methylpropyl, 1-propionyloxyethyl, 1-propionyloxypropyl, 2-acetoxypropyl and 1-butyryloxyethyl groups;

cycloalkyl-substituted aliphatic acyloxyalkyl groups, in which the acyl group is preferably an alkanoyl group and is more preferably an alkanoyl group having from 2 to 6 carbon atoms, the cycloalkyl substituent has from 3 to 7 carbon atoms, and the alkyl part has from 1 to 6, preferably from 1 to 4, carbon atoms, such as the (cyclohexylacetoxy)methyl, 1-(cyclohexylacetoxy) ethyl, 1-(cyclohexylacetoxy)-propyl, 2-methyl-1-(cyclohexylacetoxy)propyl, (cyclopentylacetoxy) methyl, 1-(cyclopentylacetoxy)ethyl, 1-(cyclopentylacetoxy)propyl and 2-methyl-1-(cyclopentylacetoxy)propyl, groups;

alkoxycarbonyloxyalkyl groups, especially 1-(alkoxycarbonyloxy)ethyl groups, in which the alkoxy part has from 1 to 10, preferably from 1 to 6, and more preferably from 1 to 4, carbon atoms, and the alkyl part has from 1 to 6, preferably from 1 to 4, carbon atoms, such as the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-sec-butoxycarbonyloxyethyl, 1-t-butoxycarbonyloxyethyl, 1-(1-ethylpropoxycarbonyloxy)-ethyl and 1-(1,1-dipropylbutoxycarbonyloxy)ethyl groups, and other alkoxycarbonylalkyl groups, in which both the alkoxy and alkyl groups have from 1 to 6, preferably from 1 to 4, carbon atoms, such as the 2-methyl-1-(isopropoxycarbonyloxy)propyl, 2-(isopropoxycarbonyloxy)propyl, isopropoxycarbonyloxymethyl, t-butoxycarbonyloxymethyl, methoxycarbonyloxymethyl and ethoxycarbonyloxymethyl groups;

cycloalkylcarbonyloxyalkyl and cycloalkyloxycarbony-loxyalkyl groups, in which the cycloalkyl group has from 3 to 10, preferably from 3 to 7, carbon atoms, is mono- or polycyclic and is optionally substituted by at least one (and preferably only one) alkyl group having from 1 to 4 carbon atoms (e.g. selected from those alkyl groups exemplified above) and the alkyl part has from 1 to 6, more preferably from 1 to 4, carbon atoms (e.g. selected from those alkyl groups exemplified above) and is most preferably methyl, ethyl or propyl, for example the 1-methylcyclohexylcarbonyloxymethyl, 1-methylcyclohexyloxycarbonyloxymethyl, cyclopentyloxycarbonyloxymethyl, cyclopentylcarbonyloxymethyl, 1-cyclohexyloxycarbonyloxyethyl, 1-cyclohexylcarbonyloxyethyl, 1-cyclopentyloxycarbonyloxyethyl, 1-cyclopentylcarbonyloxyethyl, 1-cycloheptyloxycarbonyloxyethyl, 1-cycloheptylcarbonyloxyethyl, 1-methylcyclopentylcarbonyloxymethyl, 1-methylcyclopentyloxycarbonyloxymethyl, 2-methyl-1-(1-methylcyclohexylcarbonyloxy)-propyl, 1-(1-methylcyclohexylcarbonyloxy)propyl, 2-(1-methylcyclohexylcarbonyloxy)propyl, 1-(cyclohexylcarbonyloxy)propyl, 2-(cyclohexylcarbonyloxy)propyl, 2-methyl-1-(1methylcyclopentylcarbonyloxy)propyl, 1-(1-methylcyclopentylcarbonyloxy)propyl, 2-(1-methylcyclopentylcarbonyloxy)propyl, 1-(cyclopentylcarbonyloxy)propyl, 2-(cyclopentylcarbonyloxy)propyl, 1-(1-methylcyclopentylcarbonyloxy)ethyl, 1-(1-methylcyclopentylcarbonyloxy)propyl, adamantyloxycarbonyloxymethyl, adamantylcarbonyloxymethyl, 1-adamantyloxycarbonyloxyethyl and 1-adamantylcarbonyloxyethyl groups;

cycloalkylalkoxycarbonyloxyalkyl groups in which the alkoxy group has a single cycloalkyl substituent, the cycloalkyl substituent having from 3 to 10, preferably from 3 to 7, carbon atoms and mono- or polycyclic, for example the cyclopropylmethoxycarbonyloxymethyl, cyclobutylmethoxycarbonyloxymethyl, cyclopentylmethoxycarbonyloxymethyl, cyclohexylmethoxycarbonyloxymethyl, 1-(cyclopropylmethoxycarbonyloxy)ethyl, 1-(cyclobutylmethoxycarbonyloxy)-ethyl, 1-(cyclopentylmethoxycarbonyloxy)ethyl and 1-(cyclohexylmethoxycarbonyloxy)ethyl groups;

terpenylcarbonyloxyalkyl and terpenyloxycarbonyloxyalkyl groups, in which the terpenyl group is as exemplified above, and is preferably a cyclic terpenyl group, for example the 1-(menthyloxycarbonyloxy)ethyl, 1-(menthylcarbonyloxy)-ethyl, menthyloxycarbonyloxymethyl, menthylcarbonyloxymethyl, 1-(3-pinanyloxycarbonyloxy)ethyl, 1-(3-pinanylcarbonyloxy)ethyl, 3-pinanyloxycarbonyloxymethyl and 3-pinanylcarbonyloxymethyl groups;

5-alkyl or 5-phenyl [which may be substituted by at least one of the substituents, defined and exemplified above] (2-oxo-1,3-dioxolen-4-yl)alkyl groups in which each alkyl group (which may be the same or different) has from 1 to 6, preferably from 1 to 4, carbon atoms, for example the (5-methyl-2-oxo-1,3-dioxolen-4-yl)methyl, (5-phenyl-2-oxo-1,3-dioxolen-4-yl)methyl, (5-isopropyl-2-oxo-1,3-dioxolen-4-yl)methyl, (5-t-butyl-2-oxo-1,3-dioxolen-4-yl)methyl and 1-(5-methyl-2-oxo-1,3-dioxolen-4-yl)ethyl groups; and other groups, especially groups which are easily removed in vivo such as the phthalidyl, indanyl and 2-oxo-4,5,6,7-tetrahydro-1,3-benzodioxolen-4-yl groups.

The compounds of the present invention can exist in the form of various stereoisomers, depending upon the presence of asymmetric carbon atoms. The present invention covers both the individual isomers [preferably the (2R,4R) isomer] and mixtures thereof, including racemic mixtures.

The compounds of the invention may take up water upon exposure to the atmosphere to absorb water or to produce a hydrate. The present invention covers such hydrates, especially hydrates of certain salts of the compounds of formula (I).

Preferred compounds of the present invention are those compounds of formula (I) and salts and esters thereof, in which:

(1) $R^1$ represents a pyrrolidinyl group, a piperidyl group, a morpholinyl group, a thiomorpholinyl group or a piperazinyl group, which is substituted on a carbon atom by at least one of substituents $\alpha^1$ and is unsubstituted or is substituted on a nitrogen atom by at least one of substituents $\beta^1$, said substituents $\alpha^1$ are selected from the group consisting of hydroxy groups, alkoxycarbonyloxy groups having from 1 to 6 or from 8 to 18 carbon atoms in the alkoxy part, alkanoyloxy groups having from 1 to 20 carbon atoms, carboxy-substituted alkanoyloxy groups having from 3 to 6 carbon atoms in the alkanoyl part, carbamoyloxy groups, and mono- or di-alkylcarbamoyloxy groups having 1 or 2 carbon atoms in the or each alkyl part;

said substituents $\beta^1$ are selected from the group consisting of alkyl groups having from 1 to 4 carbon atoms, and phenyl groups which are unsubstituted or are substituted by at least one substituent selected from the group consisting of methyl groups, methoxy groups, fluorine atoms and chlorine atoms.

(2) $R^1$ represents a pyrrolidinyl group, a piperidyl group, a morpholinyl group or a thiomorpholinyl group, which is substituted on a carbon atom by at least one of substituents $\alpha^2$ and is unsubstituted or is substituted on a nitrogen atom by at least one of substituents $\beta^2$, said substituents $\alpha^2$ are selected from the group consisting of hydroxy groups, alkoxycarbonyloxy groups having from 1 to 4 or from 8 to 18 carbon atoms in the alkoxy part, alkanoyloxy groups having from 2 to 5 carbon atoms, alkanoyloxy groups having from 10 to 18 carbon atoms, carboxy-substituted alkanoyloxy groups having from 3 to 6 carbon atoms in the alkanoyl part, carbamoyloxy groups, and mono- or di-alkylcarbamoyloxy groups having 1 or 2 carbon atoms in the or each alkyl part;

said substituents $\beta^2$ are selected from the group consisting of alkyl groups having from 1 to 4 carbon atoms.

(3) $R^1$ represents a pyrrolidinyl group, a piperidyl group, a morpholinyl group or a thiomorpholinyl group, which is substituted on a carbon atom by at least one of substituents $\alpha^3$ and is unsubstituted or is substituted on a nitrogen atom by at least one of substituents $\beta^3$, said substituents $\alpha^3$ are selected from the group consisting of hydroxy, methoxycarbonyloxy, ethoxycarbonyloxy, isopropoxycarbonyloxy, t-butoxycarbonyloxy, octyloxycarbonyloxy, decyloxycarbonyloxy, hexadecyloxycarbonyloxy, octadecyloxycarbonyloxy, acetoxy, propionyloxy, butyryloxy, valeryloxy, pivaloyloxy, decanoyloxy, undecanoyloxy, lauroyloxy, myristoyloxy, palmitoyloxy, stearoyloxy, succinyloxy, glutaryloxy, carbamoyloxy, N-methylcarbamoyloxy, N-ethylcarbamoyloxy and N,N-dimethylcarbamoyloxy groups;

said substituents $\beta^3$ are selected from the group consisting of methyl and ethyl groups.

(4) $R^1$ represents a pyrrolidinyl group, a piperidyl group or a morpholinyl group, which is substituted on a carbon atom by at least one of substituents $\alpha^4$ and is unsubstituted or is substituted on a nitrogen atom by at least one of substituents $\beta^3$, said substituents $\alpha^4$ are selected from the group consisting of hydroxy, ethoxycarbonyloxy, isopropoxycarbonyloxy, t-butoxycarbonyloxy, octyloxycarbonyloxy, hexadecyloxycarbonyloxy, octadecyloxycarbonyloxy, decanoyloxy, lauroyloxy, palmitoyloxy, stearyloxy, succinyloxy, carbamoyloxy and N,N-dimethylcarbamoyloxy groups;
said substituents $\beta^3$ are as defined above.

(5) $R^1$ represents a 4-hydroxy-2-pyrrolidinyl group, a 4-ethoxycarbonyloxy-2-pyrrolidinyl group, a 4-isopropoxycarbonyloxy-2-pyrrolidinyl group, a 4-t-butoxy-carbonyloxy-2-pyrrolidinyl goup, a 4-octyloxycarbonyloxy-2-pyrrolidinyl group, a 4-hexadecyloxycarbonyloxy-2-pyrrolidinyl group, a 4-octadecyloxycarbonyloxy-2-pyrrolidinyl group, a 4-acetoxy-2-pyrrolidinyl group, a 4-decanoyloxy-2-pyrrolidinyl group, a 4-lauroyloxy-2-pyrrolidinyl group, a 4-myristoyloxy-2-pyrrolidinyl group, a 4-palmitoyloxy-2-pyrrolidinyl group, a 4-stearoyloxy-2-pyrrolidinyl group, a 4-succinyloxy-2-pyrrolidinyl group, a 4-carbamoyloxy-2-pyrrolidinyl group, a 1-methyl-4-hydroxy-2-pyrrolidinyl group, a 1-methyl-4-ethoxycarbonyloxy-2-pyrrolidinyl group, a 1-methyl-4-isopropoxycarbonyloxy-2-pyrrolidinyl group, a 1-methyl-4-t-butoxycarbonyloxy-2-pyrrolidinyl group, a 1-methyl-4-octyloxycarbonyloxy-2-pyrrolidinyl group, a 1-methyl-4-hexadecyloxycarbonyloxy-2-pyrrolidinyl group, a 1-methyl-4-octadecyloxy-carbonyloxy-2-pyrrolidinyl group, a 1-methyl-4-acetoxy-2-pyrrolidinyl group, a 1-methyl-4-decanoyloxy-2-pyrrolidinyl group, a 1-methyl-4-lauroyloxy-2-pyrrolidinyl group, a 1-methyl-4-myristoyloxy-2-pyrrolidinyl group, a 1-methyl-4-palmitoyloxy-2-pyrrolidinyl group, a 1-methyl-4-stearoyloxy-2-pyrrolidinyl group, or a 1-methyl-4-succinyloxy-2-pyrrolidinyl group.

(6) $R^1$ represents a 4-hydroxy-2-pyrrolidinyl group, a 4-ethoxycarbonyloxy-2-pyrrolidinyl group, a 4-t-butoxycarbonyloxy-2-pyrrolidinyl group, a 4-octyloxy-carbonyloxy-2-pyrrolidinyl group, a 4-hexadecyloxycarbonyloxy-2-pyrrolidinyl a 4-octadecyloxycarbonyloxy-2-pyrrolidinyl group, a 4-decanoyloxy-2-pyrrolidinyl group, a 4-lauroyloxy-2-pyrrolidinyl group, a 4-myristoyloxy-2-pyrrolidinyl group, a 4-palmitoyloxy-2-pyrrolidinyl group, a 4-stearoyloxy-2-pyrrolidinyl group, a 1-methyl-4-hydroxy-2-pyrrolidinyl group, a 1-methyl-4-ethoxycarbonyloxy-2-pyrrolidinyl group, a 1-methyl-4-t-butoxycarbonyloxy-2-pyrrolidinyl group, a 1-methyl-4-octyloxycarbonyloxy-2-pyrrolidinyl group, a 1-methyl-4-hexadecyloxycarbonyloxy-2-pyrrolidinyl group, a 1-methyl-4-octadecyloxycarbonyloxy-2-pyrrolidinyl group, a 1-methyl-4-decanoyloxy-2-pyrrolidinyl group, a 1-methyl-4-lauroyloxy-2-pyrrolidinyl group, a 1-methyl-4-myristoyloxy-2-pyrrolidinyl group, a 1-methyl-4-palmitoyloxy-2-pyrrolidinyl group or a 1-methyl-4-stearoyloxy-2-pyrrolidinyl group.

(7) $R^1$ represents a 4-hydroxy-2-pyrrolidinyl group, a 4-decanoyloxy-2-pyrrolidinyl group, a 4-lauroyloxy-2-pyrrolidinyl group, a 4-myristoyloxy-2-pyrrolidinyl group, a 4-palmitoyloxy-2-pyrrolidinyl group, a 4-stearoyloxy-2-pyrrolidinyl group, a 1-methyl-4-hydroxy-2-pyrrolidinyl group, a 1-methyl-4-decanoyloxy-2-pyrrolidinyl group, a 1-methyl-4-lauroyloxy-2-pyrrolidinyl group, a 1-methyl-4-myristoyloxy-2-pyrrolidinyl group, a 1-methyl-4-palmitoyloxy-2-pyrrolidinyl group or a 1-methyl-4-stearoyloxy-2-pyrrolidinyl group.

(8) $R^{2a}$ and $R^{2b}$, which are the same as or different from each other, each represents a hydrogen atom, a methyl group, a methoxy group, a fluorine atom, a chlorine atom, a bromine atom, a cyano group or a nitro group, and $R^{2c}$ represents a hydrogen atom.

(9) $R^{2a}$ and $R^{2b}$, which are the same as or different from each other, each represents a hydrogen atom, a methyl group, a methoxy group, a fluorine atom, a chlorine atom or a bromine atom, and $R^{2c}$ represents a hydrogen atom.

(10) $R^{2a}$ and $R^{2b}$, which are the same as or different from each other, each represents a hydrogen atom, a fluorine atom or a chlorine atom, and $R^{2c}$ represents a hydrogen atom.

(11) $R^{2a}$ represents a fluorine atom, and $R^{2b}$ and $R^{2c}$ both represent hydrogen atoms.

(12) $R^{3a}$, $R^{3b}$ and $R^{3c}$, which are the same as or different from each other, each represents a hydrogen atom, an alkyl group having from 1 to 4 carbon atoms, a halogen-substituted alkyl group having 1 or 2 carbon atoms, an alkenyl group having 3 or 4 carbon atoms, an alkynyl group having 3 or 4 carbon atoms, a hydroxy group, an alkoxy group having from 1 to 4 carbon atoms, a halogen-substituted alkoxy group having 1 or 2 carbon atoms, an alkoxycarbonyl group having from 1 to 4 carbon atoms in the alkoxy part, an alkanoyloxy group having from 2 to 5 carbon atoms, a carbamoyl group, a mono- or di-alkylcarbamoyl group having 1 or 2 carbon atoms in the or each alkyl part, a halogen atom, a cyano group, a nitro group, or a phenyl group which is unsubstituted or is substituted by at least one of substituents $\gamma^1$, defined below, and $R^{3d}$ represents a hydrogen atom;
said substituents $\gamma^1$ are selected from the group consisting of methyl, ethyl, methoxy and ethoxy groups and halogen atoms.

(13) $R^{3a}$, $R^{3b}$ and $R^{3c}$, which are the same as or different from each other, each represents a hydrogen atom, a methyl or ethyl group, a fluorine- or chlorine-substituted alkyl group having 1 or 2 carbon atoms, an allyl group, a propargyl group, a hydroxy group, a methoxy group, an ethoxy group, a fluoromethoxy group, a difluoromethoxy group, a chloromethoxy group, a 2-fluoroethoxy group, a 2-chloroethoxy group, a methoxycarbonyl group, an ethoxycarbonyl group, an alkanoyloxy group having 2 or 3 carbon atoms, a carbamoyl group, a methylcarbamoyl group, a dimethylcarbamoyl group, a fluorine atom, a chlorine atom, a bromine atom, a cyano group, a nitro group, or a phenyl group which is unsubstituted or is substituted by at least one of substituents $\gamma^2$, defined below, and $R^{3d}$ represents a hydrogen atom;
said substituents $\gamma^2$ are selected from the group consisting of methyl and methoxy groups and fluorine and chlorine atoms.

(14) $R^{3a}$, $R^{3b}$ and $R^{3c}$, which are the same as or different from each other, each represents a hydrogen atom, a methyl group, an ethyl group, a fluoromethyl group, a trifluoromethyl group, a chloromethyl group, a hydroxy group, a methoxy group, an ethoxy group, a fluoromethoxy group, a difluoromethoxy group, a 2-fluoroethoxy group, a fluorine atom, a chlorine atom, a bromine atom, a cyano group, a carbamoyl group or a phenyl group, and $R^{3d}$ represents a hydrogen atom.

(15) $R^{3a}$ and $R^{3b}$, which are the same as or different from each other, each represents a hydrogen atom, a methyl group, a hydroxy group, a methoxy group, an ethoxy group, a fluoromethoxy group, a difluoromethoxy group, a fluorine atom, a chlorine atom, a bromine atom or a cyano group, and $R^{3c}$ and $R^{3d}$ both represent hydrogen atoms.

(16) $R^{3a}$ and $R^{3b}$, which are the same as or different from each other, each represents a hydrogen atom, a methoxy group or a fluorine atom, and $R^{3c}$ and $R^{3d}$ both represent hydrogen atoms.

(17) A represents a single bond or an alkylene group having from 1 to 4 carbon atoms.

(18) A represents a single bond, a methylene group, an ethylene group or a trimethylene group.

(19) A represents a single bond, a methylene group or an ethylene group.

(20) A represents an ethylene group.

Of the above compounds, we particularly prefer those in which $R^1$ is as defined in any one of (1) to (7), $R^{2a}$, $R^{2b}$ and $R^{2c}$ are as defined in any one of (8) to (11), $R^{3a}$, $R^{3b}$, $R^{3c}$ and $R^{3d}$ are as defined in any one of (12) to (16) and A is as defined in any one of (17) to (20).

More preferred compounds are as follows:

(21) Compounds of formula (I) and salts and esters thereof, in which:

$R^1$ represents a pyrrolidinyl group, a piperidyl group, a morpholinyl group, a thiomorpholinyl group or a piperazinyl group, which is substituted on a carbon atom by at least one of substituents $\alpha^1$ and is unsubstituted or is substituted on a nitrogen atom by at least one of substituents $\beta^1$, defined above;

$R^{2a}$ and $R^{2b}$, which are the same as or different from each other, each represents a hydrogen atom, a methyl group, a methoxy group, a fluorine atom, a chlorine atom, a bromine atom, a cyano group or a nitro group, and $R^{2c}$ represents a hydrogen atom;

$R^{3a}$, $R^{3b}$ and $R^{3c}$, which are the same as or different from each other, each represents a hydrogen atom, an alkyl group having from 1 to 4 carbon atoms, a halogen-substituted alkyl group having 1 or 2 carbon atoms, an alkenyl group having 3 or 4 carbon atoms, an alkynyl group having 3 or 4 carbon atoms, a hydroxy group, an alkoxy group having from 1 to 4 carbon atoms, a halogen-substituted substituted alkoxy group having 1 or 2 carbon atoms, an alkoxycarbonyl group having from 1 to 4 carbon atoms in the alkoxy part, an alkanoyloxy group having from 2 to 5 carbon atoms, a carbamoyl group, a mono- or di-alkylcarbamoyl group having 1 or 2 carbon atoms in the or each alkyl part, a halogen atom, a cyano group, a nitro group, or a phenyl group which is unsubstituted or is substituted by at least one of substituents $\gamma^1$, defined above, and $R^{3d}$ represents a hydrogen atom; and A represents a single bond or an alkylene group having from 1 to 4 carbon atoms.

(22) Compounds of formula (I) and salts and esters thereof, in which:

$R^1$ represents a pyrrolidinyl group, a piperidyl group, a morpholinyl group or a thiomorpholinyl group, which is substituted on a carbon atom by at least one of substituents $\alpha^2$ and is unsubstituted or is substituted on a nitrogen atom by at least one of substituents $\beta^2$, defined above;

$R^{2a}$ and $R^{2b}$, which are the same as or different from each other, each represents a hydrogen atom, a methyl group, a methoxy group, a fluorine atom, a chlorine atom, a bromine atom, a cyano group or a nitro group, and $R^{2c}$ represents a hydrogen atom;

$R^{3a}$, $R^{3b}$ and $R^{3c}$, which are the same as or different from each other, each represents a hydrogen atom, an alkyl group having from 1 to 4 carbon atoms, a halogen-substituted alkyl group having 1 or 2 carbon atoms, an alkenyl group having 3 or 4 carbon atoms, an alkynyl group having 3 or 4 carbon atoms, a hydroxy group, an alkoxy group having from 1 to 4 carbon atoms, a halogen-substituted alkoxy group having 1 or 2 carbon atoms, an alkoxycarbonyl group having from 1 to 4 carbon atoms in the alkoxy part, an alkanoyloxy group having from 2 to 5 carbon atoms, a carbamoyl group, a mono- or di-alkylcarbamoyl group having 1 or 2 carbon atoms in the or each alkyl part, a halogen atom, a cyano group, a nitro group, or a phenyl group which is unsubstituted or is substituted by at least one of substituents $\gamma^1$, defined above, and $R^{3d}$ represents a hydrogen atom; and A represents a single bond or an alkylene group having from 1 to 4 carbon atoms.

(23) Compounds of formula (I) and salts and esters thereof, in which:

$R^1$ represents a pyrrolidinyl group, a piperidyl group, a morpholinyl group or a thiomorpholinyl group, which is substituted on a carbon atom by at least one of substituents $\alpha^3$ and is unsubstituted or is substituted on a nitrogen atom by at least one of substituents $\beta^3$, defined above;

$R^{2a}$ and $R^{2b}$, which are the same as or different from each other, each represents a hydrogen atom, a methyl group, a methoxy group, a fluorine atom, a chlorine atom or a bromine atom, and $R^{2c}$ represents a hydrogen atom;

$R^{3a}$, $R^{3b}$ and $R^{3c}$, which are the same as or different from each other, each represents a hydrogen atom, a methyl group, an ethyl group, a fluorine- or chlorine-substituted alkyl group having 1 or 2 carbon atoms, an allyl group, a propargyl group, a hydroxy group, a methoxy group, an ethoxy group, a fluoromethoxy group, a difluoromethoxy group, a chloromethoxy group, a 2-fluoroethoxy group, a 2-chloroethoxy group, a methoxycarbonyl group, an ethoxycarbonyl group, an alkanoyloxy group having 2 or 3 carbon atoms, a carbamoyl group, a methylcarbamoyl group, a dimethylcarbamoyl group, a fluorine atom, a chlorine atom, a bromine atom, a cyano group, a nitro group, or a phenyl group which is unsubstituted or is substituted by at least one of substituents $\gamma^2$, defined above, and $R^{3d}$ represents a hydrogen atom; and A represents a single bond, a methylene group, an ethylene group or a trimethylene group.

(24) Compounds of formula (I) and salts and esters thereof, in which:

$R^1$ represents a pyrrolidinyl group, a piperidyl group or a morpholinyl group, which is substituted on a carbon atom by at least one of substituents $\alpha^4$ and is unsubstituted or is substituted on a nitrogen atom by at least one of substituents $\beta^3$, defined above;

$R^{2a}$ and $R^{2b}$, which are the same as or different from each other, each represents a hydrogen atom, a fluorine atom or a chlorine atom, and $R^{2c}$ represents a hydrogen atom;

$R^{3a}$, $R^{3b}$ and $R^{3c}$, which are the same as or different from each other, each represents a hydrogen atom, a methyl group, an ethyl group, a fluoromethyl group, a trifluoromethyl group, a chloromethyl group, a hydroxy group, a methoxy group, an ethoxy group, a fluoromethoxy group, a difluoromethoxy group, a 2-fluoroethoxy group, a fluorine atom, a chlorine atom, a bromine atom, a cyano group, a carbamoyl group or a phenyl group, and $R^{3d}$ represents a hydrogen atom; and A represents a single bond, a methylene group, an ethylene group or a trimethylene group.

(25) Compounds of formula (I) and salts and esters thereof, in which:

$R^1$ represents a 4-hydroxy-2-pyrrolidinyl group, a 4-ethoxycarbonyloxy-2-pyrrolidinyl group, a 4-isopropoxycarbonyloxy-2-pyrrolidinyl group, a 4-t-butoxycarbonyloxy-2-pyrrolidinyl group, a 4-octyloxycarbonyloxy-2-pyrrolidinyl group, a 4-hexadecyloxycarbonyloxy-2-pyrrolidinyl group, a 4-octadecyloxy-carbonyloxy-2-pyrrolidinyl group, a 4-acetoxy-2-pyrrolidinyl group, a 4-decanoyloxy-2-pyrrolidinyl group, a 4-lauroyloxy-2-pyrrolidinyl group, a 4-myristoyloxy-2-pyrrolidinyl group, a 4-palmitoyloxy-2-pyrrolidinyl group, a 4-stearoyloxy-2-pyrrolidinyl group, a 4-succinyloxy-2-pyrrolidinyl group, a 4-carbamoyloxy-2-pyrrolidinyl group, a 1-methyl-4-hydroxy-2-pyrrolidinyl group, a 1-methyl-4-ethoxycarbonyloxy-2-pyrrolidinyl group, a 1-methyl-4-isopropoxycarbonyloxy-2-pyrrolidinyl group, a 1-methyl-4-t-butoxycarbonyloxy-2-pyrrolidinyl group, 1-methyl-4-octyloxycarbonyloxy-2-pyrrolidinyl group, a 1-methyl-4-hexadecyl-oxycarbonyloxy-2-pyrrolidinyl group, a 1-methyl-4-octadecyloxycarbonyloxy-2-pyrrolidinyl group, a 1-methyl-4-acetoxy-2-pyrrolidinyl group, a 1-methyl-4-decanoyloxy-2-pyrrolidinyl group, a 1-methyl-4-lauroyloxy-2-pyrrolidinyl group, a 1-methyl-4-myristoyloxy-2-pyrrolidinyl group, a 1-methyl-4-palmitoyloxy-2-pyrrolidinyl group, a 1-methyl-4-stearoyloxy-2-pyrrolidinyl group, or a 1-methyl-4-succinyloxy-2-pyrrolidinyl group;

$R^{2a}$ and $R^{2b}$, which are the same as or different from each other, each represents a hydrogen atom, a fluorine atom or a chlorine atom, and $R^{2c}$ represents a hydrogen atom;

$R^{3a}$ and $R^{3b}$, which are the same as or different from each other, each represents a hydrogen atom, a methyl group, a hydroxy group, a methoxy group, an ethoxy group, a fluoromethoxy group, a difluoromethoxy group, a fluorine atom, a chlorine atom, a bromine atom or a cyano group, and $R^{3c}$ and $R^{3d}$ both represent hydrogen atoms; and A represents a single bond, a methylene group or an ethylene group.

(26) Compounds of formula (I) and salts and esters thereof, in which:

$R^1$ represents a 4-hydroxy-2-pyrrolidinyl group, a 4-ethoxycarbonyloxy-2-pyrrolidinyl group, a 4-t-butoxycarbonyloxy-2-pyrrolidinyl group, a 4-octyloxycarbonyloxy-2-pyrrolidinyl group, a 4-hexadecyloxycarbonyloxy-2-pyrrolidinyl group, a 4-octadecyloxycarbonyloxy-2-pyrrolidinyl group, a 4-decanoyloxy-2-pyrrolidinyl group, a 4-lauroyloxy-2-pyrrolidinyl group, a 4-myristoyloxy-2-pyrrolidinyl group, a 4-palmitoyloxy-2-pyrrolidinyl group, a 4-stearoyloxy-2-pyrrolidinyl group, a 1-methyl-4-hydroxy-2-pyrrolidinyl group, a 1-methyl-4-ethoxycarbonyloxy-2-pyrrolidinyl group, a 1-methyl-4-t-butoxycarbonyloxy-2-pyrrolidinyl group, 1-methyl-4-octyloxycarbonyloxy-2-pyrrolidinyl group, a 1-methyl-4-hexadecyloxycarbonyloxy-2-pyrrolidinyl group, a 1-methyl-4-octadecyloxycarbonyloxy-2-pyrrolidinyl group, a 1-methyl-4-decanoyloxy-2-pyrrolidinyl group, a 1-methyl-4-lauroyloxy-2-pyrrolidinyl group, a 1-methyl-4-myristoyloxy-2-pyrrolidinyl group, a 1-methyl-4-palmitoyloxy-2-pyrrolidinyl group or a 1-methyl-4-stearoyloxy-2-pyrrolidinyl group;

$R^{2a}$ represents a fluorine atom, and $R^{2b}$ and $R^{2c}$ both represent hydrogen atoms;

$R^{3a}$ and $R^{3b}$, which are the same as or different from each other, each represents a hydrogen atom, a methoxy group or a fluorine atom, and $R^{3c}$ and $R^{3d}$ both represent hydrogen atoms; and A represents an ethylene group.

(27) Compounds of formula (I) and salts and esters thereof, in which:

$R^1$ represents a 4-hydroxy-2-pyrrolidinyl group, a 4-decanoyloxy-2-pyrrolidinyl group, a 4-lauroyloxy-2-pyrrolidinyl group, a 4-myristoyloxy-2-pyrrolidinyl group, a 4-palmitoyloxy-2-pyrrolidinyl group, a 4-stearoyloxy-2-pyrrolidinyl group, a 1-methyl-4-hydroxy-2-pyrrolidinyl group, a 1-methyl-4-decanoyloxy-2-pyrrolidinyl group, a 1-methyl-4-lauroyloxy-2-pyrrolidinyl group, a 1-methyl-4-myristoyloxy-2-pyrrolidinyl group, a 1-methyl-4-palmitoyloxy-2-pyrrolidinyl group or a 1-methyl-4-stearoyloxy-2-pyrrolidinyl group;

$R^{2a}$ represents a fluorine atom, and $R^{2b}$ and $R^{2c}$ both represent hydrogen atoms;

$R^{3a}$ and $R^{3b}$, which are the same as or different from each other, each represents a hydrogen atom, a methoxy group or a fluorine atom, and $R^{3c}$ and $R^{3d}$ both represent hydrogen atoms; and A represents an ethylene group.

Specific examples of certain compounds of the present invention are those compounds of formula (I-1):

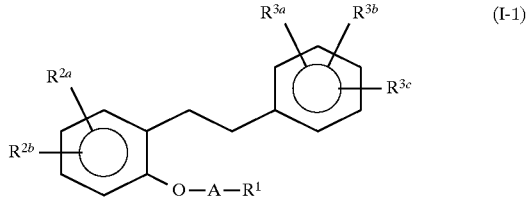

In the above formula, the substituent groups are as defined in the following Table 1. In the Table, the following abbreviations are used:

Ac: Acetyl
Adp: Adipoyl
Boc: t-Butoxycarbonyl
Bu: Butyl
tBu: t-Butyl
Bur: Butyryl
iBur: Isobutyryl
Bz: Benzyl
Dc: Decyl
Dec: Decanoyl
Dod: Dodecyl Et: Ethyl
Glu: Glutaryl
Hep: Heptanoyl
Hex: Hexanoyl
Hpd: Heptadecyl
Hxd: Hexadecyl
Lau: Lauroyl
Mal: Malonyl
Me: Methyl
Mor: Morpholinyl
Myr: Myristoyl
Non: Nonanoyl
Oc: Octyl
Ocd: Octadecyl
Oct: Octanoyl
Pal: Palmitoyl
Pnd: Pentadecyl
Ph: Phenyl
Pip: Piperidyl
Pir: Piperazinyl
Piv: Pivaloyl
Pr: Propyl
iPr: Isopropyl
Prp: Propionyl
Pyr: Pyrrolidinyl
Ste: Stearoyl
Suc: Succinyl
Ttd: Tetradecyl
Trd: Tridecyl
Tmor: Thiomorpholinyl
Und: Undecyl
Val: Valeryl

TABLE 1

| Cpd. No. | $R^1$—A— | $R^{2a}$ & $R^{2b}$ | $R^{3a}$, $R^{3b}$, & $R^{3c}$ |
|---|---|---|---|
| 1 | (1-Me-4-OH-2-Pyr)—CH$_2$CH$_2$— | 4-F | H |
| 2 | (1-Et-4-OH-2-Pyr)—CH$_2$CH$_2$— | 4-F | H |
| 3 | (1-iPr-4-OH-2-Pyr)—CH$_2$CH$_2$— | 4-F | H |
| 4 | (1-Bzr-OH-2-Pyr)—CH$_2$CH$_2$— | 4-F | H |
| 5 | (1-Boc-4-OH-2-Pyr)—CH$_2$CH$_2$— | 4-F | H |
| 6 | (1-EtOCO$_4$—OH-2-Pyr)—CH$_2$CH$_2$— | 4-F | H |
| 7 | (4-OH-2-Pyr)—CH$_2$CH$_2$— | 4-F | H |
| 8 | (1-Me-4-OAc-2-Pyr)—CH$_2$CH$_2$— | 4-F | H |
| 9 | (1-Me-4-OPrp-2-Pyr)—CH$_2$CH$_2$— | 4-F | H |
| 10 | (1-Me-4-OBur-2-Pyr)—CH$_2$CH$_2$— | 4-F | H |
| 11 | (1-Me-4-OVal-2-Pyr)—CH$_2$CH$_2$— | 4-F | H |
| 12 | (1-Me-4-OPiv-2-Pyr)—CH$_2$CH$_2$— | 4-F | H |
| 13 | (1-Me-4-OHex-2-Pyr)—CH$_2$CH$_2$— | 4-F | H |
| 14 | (1-Me-4-OHep-2-Pyr)—CH$_2$CH$_2$— | 4-F | H |
| 15 | (1-Me-4-O(Oct)-2-Pyr)—CH$_2$CH$_2$— | 4-F | H |
| 16 | (1-Me-4-ODec-2-Pyr)—CH$_2$CH$_2$— | 4-F | H |
| 17 | (1-Me-4-OLau-2-Pyr)—CH$_2$CH$_2$— | 4-F | H |
| 18 | (1-Me-4-OMyr-2-Pyr)—CH$_2$CH$_2$— | 4-F | H |
| 19 | (1-Me-4-OPal-2-Pyr)—CH$_2$CH$_2$— | 4-F | H |
| 20 | (1-Me-4-OSte-2-Pyr)—CH$_2$CH$_2$— | 4-F | H |
| 21 | (1-Me-4-OMal-2-Pyr)—CH$_2$CH$_2$— | 4-F | H |
| 22 | (1-Me-4-OSuc-2-Pyr)—CH$_2$CH$_2$— | 4-F | H |
| 23 | (1-Me-4-OGlu-2-Pyr)—CH$_2$CH$_2$— | 4-F | H |
| 24 | (1-Me-4-OAdp-2-Pyr)—CH$_2$CH$_2$— | 4-F | H |
| 25 | (1-Me-4-OCOOEt-2-Pyr)—CH$_2$CH$_2$— | 4-F | H |
| 26 | (1-Me-4-OCOOiPr-2-Pyr)—CH$_2$CH$_2$— | 4-F | H |
| 27 | (1-Me-4-OCOOtBu-2-Pyr)—CH$_2$CH$_2$— | 4-F | H |
| 28 | (1-Me-4-OCOO(Oc)-2-Pyr)—CH$_2$CH$_2$ | 4-F | H |
| 29 | (1-Me-4-OCOODc-2-Pyr)—CH$_2$CH$_2$— | 4-F | H |
| 30 | (1-Me-4-OCOODOd-2-Pyr)—CH$_2$CH$_2$— | 4-F | H |
| 31 | (1-Me-4-OCOOTtd-2-Pyr)—CH$_2$CH$_2$— | 4-F | H |
| 32 | (1-Me-4-OCOOHxd-2-Pyr)—CH$_2$CH$_2$— | 4-F | H |
| 33 | (1-Me-4-OCOO(Ocd)-2-Pyr)—CH$_2$CH$_2$— | 4-F | H |
| 34 | (1-Me-4-OCONH$_2$-2-Pyr)—CH$_2$CH$_2$— | 4-F | H |
| 35 | (1-Me-4-OCONHMe-2-Pyr)—CH$_2$CH$_2$— | 4-F | H |
| 36 | (1-Me-4-OCONHEt-2-Pyr)—CH$_2$CH$_2$— | 4-F | H |
| 37 | (1-Me-4-OCONMe$_2$-2-Pyr)—CH$_2$CH$_2$— | 4-F | H |
| 38 | (1-Me-4-OCONMeEt-2-Pyr)—CH$_2$CH$_2$— | 4-F | H |
| 39 | (1-Me-4-OCOMe-2-Pyr)—CH$_2$CH$_2$— | 4-F | H |
| 40 | (4-OAc-2-Pyr)—CH$_2$CH$_2$— | 4-F | H |
| 41 | (4-OPiv-2-Pyr)—CH$_2$CH$_2$— | 4-F | H |
| 42 | (4-O(Oct)-2-Pyr)—CH$_2$CH$_2$— | 4-F | H |
| 43 | (4-ODec-2-Pyr)—CH$_2$CH$_2$— | 4-F | H |
| 44 | (4-OLau-2-Pyr)—CH$_2$CH$_2$— | 4-F | H |
| 45 | (4-OPal-2-Pyr)—CH$_2$CH$_2$— | 4-F | H |
| 46 | (4-OSuc-2-Pyr)—CH$_2$CH$_2$— | 4-F | H |
| 47 | (4-OAdp-2-Pyr)—CH$_2$CH$_2$— | 4-F | H |
| 48 | (4-OCOOEt-2-Pyr)—CH$_2$CH$_2$— | 4-F | H |
| 49 | (4-OCOOiPr-2-Pyr)—CH$_2$CH | 4-F | H |
| 50 | (4-dCOO(Oc)-2-Pyr)—CH$_2$CH | 4-F | H |
| 51 | (4-OCOODc-2-Pyr)—CH$_2$CH$_2$— | 4-F | |
| 52 | (4-OCOOHxd-2-Pyr)—CH$_2$CH$_2$— | 4-F | H |
| 53 | (4-OCOO(Ocd)-2-Pyr)—CH$_2$CH$_2$— | 4-F | H |
| 54 | (4-OCONH$_2$-2-Pyr)—CH$_2$CH$_2$— | 4-F | H |
| 55 | (4-OCONHMe-2-Pyr)—CH$_2$CH$_2$— | 4-F | H |
| 56 | (4-OCONMe$_2$-2-Pyr)—CH$_2$CH$_2$— | 4-F | H |
| 57 | (1-Et-4-OAc-2-Pyr)—CH$_2$CH$_2$— | 4-F | H |
| 58 | (1-Et-4-O(Oct)-2-Pyr)—CH$_2$CH$_2$— | 4-F | H |
| 59 | (1-Et-4-OLau-2-Pyr)—CH$_2$CH$_2$— | 4-F | H |
| 60 | (1-Et-4-OPal-2-Pyr)—CH$_2$CH$_2$— | 4-F | H |
| 61 | (1-Et-4-OSuc-2-Pyr)—CH$_2$CH$_2$— | 4-F | H |
| 62 | (1-iPr-4-OVal-2-Pyr)—CH$_2$CH$_2$— | 4-F | H |
| 63 | (1-iPr-4-OLau-2-Pyr)—CH$_2$CH$_2$— | 4-F | H |
| 64 | (1-iPr-4-OPal-2-Pyr)—CH$_2$CH$_2$— | 4-F | H |
| 65 | (1-iPr-4-OSuc-2-Pyr)—CH$_2$CH$_2$— | 4-F | H |
| 66 | (1-Boc-4-OLau-2-Pyr)—CH$_2$CH$_2$— | 4-F | 3-OMe |
| 67 | (1-Me-4-OH-2-Pyr)—CH$_2$CH$_2$— | 4-F | 3-OMe |
| 68 | (1-iPr-4-OH-2-Pyr)—CH$_2$CH$_2$— | 4-F | 3-OMe |
| 69 | (1-Bz-4-OH-2-Pyr)—CH$_2$CH$_2$— | 4-F | 3-OMe |
| 70 | (4-OH-2-Pyr)—CH$_2$CH$_2$— | 4-F | 3-OMe |
| 71 | (1-Me-4-OAc-2-Pyr)—CH$_2$CH$_2$— | 4-F | 3-OMe |
| 72 | (1-Me-4-OBur-2-Pyr)—CH$_2$CH$_2$— | 4-F | 3-OMe |
| 73 | (1-Me-4-OPiv-2-Pyr)—CH$_2$CH$_2$— | 4-F | 3-OMe |
| 74 | (1-Me-4-OHex-2-Pyr)—CH$_2$CH$_2$— | 4-F | 3-OMe |
| 75 | (1-Me-4-O(Oct)-2-Pyr)—CH$_2$CH$_2$— | 4-F | 3-OMe |
| 76 | (1-Me-4-Opec-2-Pyr)—CH$_2$CH$_2$— | 4-F | 3-OMe |
| 77 | (1-Me-4-OLau-2-Pyr)—CH$_2$CH$_2$— | 4-F | 3-OMe |
| 78 | (1-Me-4-OMyr-2-Pyr)—CH$_2$CH$_2$— | 4-F | 3-OMe |
| 79 | (1-Me-4-OPal-2-Pyr)—CH$_2$CH$_2$— | 4-F | 3-OMe |
| 80 | (1-Me-4-OSte-2-Pyr)—CH$_2$CH$_2$— | 4-F | 3-OMe |
| 81 | (1-Me-4-OSuc-2-Pyr)—CH$_2$CH$_2$— | 4-F | 3-OMe |
| 82 | (1-Me-4-OGlu-2-Pyr)—CH$_2$CH$_2$— | 4-F | 3-OMe |
| 83 | (1-Me-4-OAdp-2-Pyr)—CH$_2$CH$_2$— | 4-F | 3-OMe |
| 84 | (1-Me-4-OCOOEt-2-Pyr)—CH$_2$CH$_2$— | 4-F | 3-OMe |
| 85 | (1-Me-4-OCOOiPr-2-Pyr)—CH$_2$CH$_2$— | 4-F | 3-OMe |
| 86 | (1-Me-4-OCOO(Oc)-2-Pyr)—CH$_2$CH$_2$— | 4-F | 3-OMe |
| 87 | (1-Me-4-OCOODod-2-Pyr)—CH$_2$CH$_2$ | 4-F | 3-OMe |
| 88 | (1-Me-4-OCOOTtd-2-Pyr)—CH$_2$CH$_2$— | 4-F | 3-OMe |
| 89 | (1-Me-4-OCOOHpd-2-Pyr)—CH$_2$CH$_2$— | 4-F | 3-OMe |
| 90 | (1-Me-4-OCONH$_2$-2-Pyr)—CH$_2$CH$_2$— | 4-F | 3-OMe |
| 91 | (1-Me-4-OCONHMe-2-Pyr)—CH$_2$CH$_2$— | 4-F | 3-OMe |
| 92 | (1-Me-4-OCONMe$_2$-2-Pyr)—CH$_2$CH$_2$— | 4-F | 3-OMe |
| 93 | (4-OAc-2-Pyr)—CH$_2$CH$_2$ | 4-F | 3-OMe |
| 94 | (4-OPiv-2-Pyr)—CH$_2$CH$_2$ | 4-F | 3-OMe |
| 95 | (4-O(Oct)-2-Pyr)—CH$_2$CH$_2$ | 4-F | 3-OMe |
| 96 | (4-OLau-2-Pyr)—CH$_2$CH$_2$— | 4-F | 3-OMe |
| 97 | (4-OPal-2-Pyr)—CH$_2$CH$_2$— | 4-F | 3-OMe |
| 98 | (4-OSuc-2-Pyr)—CH$_2$CH$_2$— | 4-F | 3-OMe |
| 99 | (4-OCOOEt-2-Pyr)—CH$_2$CH$_2$— | 4-F | 3-OMe |
| 100 | (4-OCOOiPr-2-Pyr)—CH$_2$CH$_2$— | 4-F | 3-OMe |
| 101 | (4-OCOO(Oc)-2-Pyr)—CH$_2$CH$_2$— | 4-F | 3-OMe |
| 102 | (4-OCOODc-2-Pyr)—CH$_2$CH$_2$— | 4-F | 3-OMe |

TABLE 1-continued

| Cpd. No. | R¹—A— | R²ᵃ & R²ᵇ | R³ᵃ, R³ᵇ, & R³ᶜ |
|---|---|---|---|
| 103 | (4-OCOO(Ocd)-2-Pyr)—CH₂CH₂— | 4-F | 3-OMe |
| 104 | (4-OCONH₂-2-Pyr)—CH₂CH₂— | 4-F | 3-OMe |
| 105 | (4-OCONHMe-2-Pyr)—CH₂CH₂— | 4-F | 3-OMe |
| 106 | (4-OCONMe₂-2-Pyr)—CH₂CH₂— | 4-F | 3-OMe |
| 107 | (1-Et-4-OAc-2-Pyr)—CH₂CH₂— | 4-F | 3-OMe |
| 108 | (1-Et-4-OLau-2-Pyr)—CH₂CH₂— | 4-F | 3-OMe |
| 109 | (1-Et-4-OPal-2-Pyr)—CH₂CH₂— | 4-F | 3-OMe |
| 110 | (1-Et-4-OSuc-2-Pyr)—CH₂CH₂— | 4-F | 3-OMe |
| 111 | (1-iPr-4-OPrp-2-Pyr)—CH₂CH₂— | 4-F | 3-OMe |
| 112 | (1-iPr-4-OLau-2-Pyr)—CH₂CH₂— | 4-F | 3-OMe |
| 113 | (1-iPr-4-OSuc-2-Pyr)—CH₂CH₂— | 4-F | 3-OMe |
| 114 | (1-Me-4-OH-2-Pyr)—CH₂CH₂— | 4-F | 4-F |
| 115 | (1-Et-4-OH-2-Pyr)—CH₂CH₂— | 4-F | 4-F |
| 116 | (1-iPr-4-OH-2-Pyr)—CH₂CH₂— | 4-F | 4-F |
| 117 | (1-Boc-4-OH-2-Pyr)—CH₂CH₂— | 4-F | 4-F |
| 118 | (4-OH-2-Pyr)—CH₂CH₂— | 4-F | 4-F |
| 119 | (1-Me-4-OAc-2-Pyr)—CH₂CH₂— | 4-F | 4-F |
| 120 | (1-Me-4-OVal-2-Pyr)—CH₂CH₂ | 4-F | 4-F |
| 121 | (1-Me-4-OPiv-2-Pyr)—CH₂CH₂— | 4-F | 4-F |
| 122 | (1-Me-4-O(Oct)-2-Pyr)—CH₂CH₂— | 4-F | 4-F |
| 123 | (1-Me-4-OLau-2-Pyr)—CH₂CH₂— | 4-F | 4-F |
| 124 | (1-Me-4-OMyr-2-Pyr)—CH₂CH₂— | 4-F | 4-F |
| 125 | (1-Me-4-OPal-2-Pyr)—CH₂CH₂— | 4-F | 4-F |
| 126 | (1-Me-4-OSuc-2-Pyr)—CH₂CH₂— | 4-F | 4-F |
| 127 | (1-Me-4-OGlu-2-Pyr)—CH₂CH₂— | 4-F | 4-F |
| 128 | (1-Me-4-OAdp-2-Pyr)—CH₂CH₂— | 4-F | 4-F |
| 129 | (1-Me-4-OCOOEt-2-Pyr)—CH₂CH₂— | 4-F | 4-F |
| 130 | (1-Me-4-OCOOiPr-2-Pyr)—CH₂CH₂— | 4-F | 4-F |
| 131 | (1-Me-4-OCOO(Oc)-2-Pyr)—CH₂CH₂— | 4-F | 4-F |
| 132 | (1-Me-4-OCOODc-2-Pyr)—CH₂CH₂— | 4-F | 4-F |
| 133 | (1-Me-4-OCOODod-2-Pyr)—CH₂CH₂— | 4-F | 4-F |
| 134 | (1-Me-4-OCONH₂-2-Pyr)—CH₂CH₂— | 4-F | 4-F |
| 135 | (1-Me-4-OCONHMe-2-Pyr)—CH₂CH₂— | 4-F | 4-F |
| 136 | (1-Me-4-OCONMe₂-2-Pyr)—CH₂CH₂— | 4-F | 4-F |
| 137 | (4-O(Oct)-2-Pyr)—CH₂CH₂— | 4-F | 4-F |
| 138 | (4-OLau-2-Pyr)—CH₂CH₂— | 4-F | 4-F |
| 139 | (4-OPal-2-Pyr)—CH₂CH₂— | 4-F | 4-F |
| 140 | (4-OSuc-2-Pyr)—CH₂CH₂— | 4-F | 4-F |
| 141 | (4-OCOOiPr-2-Pyr)—CH₂CH₂— | 4-F | 4-F |
| 142 | (4-OCOO(Oc)-2-Pyr)—CH₂CH₂— | 4-F | 4-F |
| 143 | (4-OCOODc-2-Pyr)—CH₂CH₂— | 4-F | 4-F |
| 144 | (4-OCONH₂-2-Pyr)—CH₂CH₂— | 4-F | 4-F |
| 145 | (1-Et-4-OAc-2-Pyr)—CH₂CH₂— | 4-F | 4-F |
| 146 | (1-Et-4-OPrp-2-Pyr)—CH₂CH₂— | 4-F | 4-F |
| 147 | (1-Et-4-OLau-2-Pyr)—CH₂CH₂— | 4-F | 4-F |
| 148 | (1-Et-4-OSuc-2-Pyr)—CH₂CH₂— | 4-F | 4-F |
| 149 | (1-iPr-4-OSur-2-Pyr)—CH₂CH₂— | 4-F | 4-F |
| 150 | (1-iPr-4-OPal-2-Pyr)—CH₂CH₂— | 4-F | 4-F |
| 151 | (1-iPr-4-OSuc-2-Pyr)—CH₂CH₂— | 4-F | 4-F |
| 152 | (1-Me-4-OH-2-Pyr)—CH₂CH₂— | 4-F | 3-OMe, 4-F |
| 153 | (1-Et-4-OH-2-Pyr)—CH₂CH₂— | 4-F | 3-OMe, 4-F |
| 154 | (4-OH-2-Pyr)—CH₂CH₂— | 4-F | 3-OMe, 4-F |
| 155 | (1-Me-4-OAc-2-Pyr)—CH₂CH₂— | 4-F | 3-OMe, 4-F |
| 156 | (1-Me-4-OVal-2-Pyr)—CH₂CH₂— | 4-F | 3-OMe, 4-F |
| 157 | (1-Me-4-OPiv-2-Pyr)—CH₂CH₂— | 4-F | 3-OMe, 4-F |
| 158 | (1-Me-4-ONon-2-Pyr)—CH₂CH₂— | 4-F | 3-OMe, 4-F |
| 159 | (1-Me-4-OLau-2-Pyr)—CH₂CH₂— | 4-F | 3-OMe, 4-F |
| 160 | (1-Me-4-OMyr-2-Pyr)—CH₂CH₂— | 4-F | 3-OMe, 4-F |
| 161 | (1-Me-4-OPal-2-Pyr)—CH₂CH₂— | 4-F | 3-OMe, 4-F |
| 162 | (1-Me-4-OSuc-2-Pyr)—CH₂CH₂— | 4-F | 3-OMe, 4-F |
| 163 | (1-Me-4-OAdp-2-Pyr)—CH₂CH₂— | 4-F | 3-OMe, 4-F |
| 164 | (1-Me-4-OCOOEt-2-Pyr)—CH₂CH₂— | 4-F | 3-OMe, 4-F |
| 165 | (1-Me-4-OCOOiPr-2-Pyr)—CH₂CH₂— | 4-F | 3-OMe, 4-F |
| 166 | (1-Me-4-OCOODc-2-Pyr)—CH₂CH₂— | 4-F | 3-OMe, 4-F |
| 167 | (1-Me-4-OCOODod-2-Pyr)—CH₂CH₂— | 4-F | 3-OMe, 4-F |
| 168 | (1-Me-4-OCOOTd-2-Pyr)—CH₂CH₂ | 4-F | 3-OMe, 4-F |
| 169 | (1-Me-4-OCONH₂-2-Pyr)—CH₂CH₂— | 4-F | 3-OMe, 4-F |
| 170 | (1-Me-4-OCONMe₂-2-Pyr)—CH₂CH₂— | 4-F | 3-OMe, 4-F |
| 171 | (4-OAc-2-Pyr)—CH₂CH₂ | 4-F | 3-OMe, 4-F |
| 172 | (4-OPal-2-Pyr)—CH₂CH₂— | 4-F | 3-OMe, 4-F |
| 173 | (4-OSuc-2-Pyr)—CH₂CH₂— | 4-F | 3-OMe, 4-F |
| 174 | (4-OCOOEt-2-Pyr)—CH₂CH₂— | 4-F | 3-OMe, 4-F |
| 175 | (4-OCOOiPr-2-Pyr)—CH₂CH₂— | 4-F | 3-OMe, 4-F |
| 176 | (4-OCOO(Oc)-2-Pyr)—CH₂CH₂— | 4-F | 3-OMe, 4-F |
| 177 | (4-OCONH₂-2-Pyr)—CH₂CH₂— | 4-F | 3-OMe, 4-F |
| 178 | (1-Et-4-OLau-2-Pyr)—CH₂CH₂— | 4-F | 3-OMe, 4-F |
| 179 | (1-Et-4-OPal-2-Pyr)—CH₂CH₂— | 4-F | 3-OMe, 4-F |
| 180 | (1-iPr-4-OLau-2-Pyr)—CH₂CH₂— | 4-F | 3-OMe, 4-F |
| 181 | (1-iPr-4-OSuc-2-Pyr)—CH₂CH₂— | 4-F | 3-OMe, 4-F |
| 182 | (1-Me-4-OH-2-Pyr)—CH₂CH₂— | 4-F | 2-OMe |
| 183 | (4-OH-2-Pyr)—CH₂CH₂— | 4-F | 2-OMe |
| 184 | (1-Me-4-OAc-2-Pyr)—CH₂CH₂— | | |
| 185 | (1-Me-4-OPiv-2-Pyr)—CH₂CH₂— | 4-F | 2-OMe |
| 186 | (1-Me-4-OLau-2-Pyr)—CH₂CH₂— | 4-F | 2-OMe |
| 187 | (1-Me-4-OSuc-2-Pyr)—CH₂CH₂— | 4-F | 2-OMe |
| 188 | (1-Me-4-OCOOEt-2-Pyr)—CH₂CH₂— | 4-F | 2-OMe |
| 189 | (1-Me-4-OH-2-Pyr)—CH₂CH₂— | 4-F | 4-OMe |
| 190 | (4-OH-2-Pyr)—CH₂CH₂— | 4-F | 4-OMe |
| 191 | (1-Me-4-OVal-2-Pyr)—CH₂CH₂— | 4-F | 4-OMe |
| 192 | (1-Me-4-OLau-2-Pyr)—CH₂CH₂— | 4-F | 4-OMe |
| 193 | (1-Me-4-OSte-2-Pyr)—CH₂CH₂— | 4-F | 4-OMe |
| 194 | (1-Me-4-OSuc-2-Pyr)—CH₂CH₂— | 4-F | 4-OMe |
| 195 | (1-Me-4-OCOOEt-2-Pyr)—CH₂CH₂— | 4-F | 4-OMe |
| 196 | (1-Me-4-OH-2-Pyr)—CH₂CH₂— | 4-F | 3,4-diF |
| 197 | (1-Et-4-OH-2-Pyr)—CH₂CH₂— | 4-F | 3,4-diF |
| 198 | (4-OH-2-Pyr)—CH₂CH₂— | 4-F | 3,4-diF |
| 199 | (1-Me-4-OVal-2-Pyr)—CH₂CH₂— | 4-F | 3,4-diF |
| 200 | (1-Me-4-OPiv-2-Pyr)—CH₂CH₂ | 4-F | 3,4-diF |
| 201 | (1-Me-4-ONon-2-Pyr)—CH₂CH₂— | 4-F | 3,4-diF |
| 202 | (1-Me-4-OLau-2-Pyr)—CH₂CH₂— | 4-F | 3,4-diF |
| 203 | (1-Me-4-OPal-2-Pyr)—CH₂CH₂— | 4-F | 3,4-diF |
| 204 | (1-Me-4-OSuc-2-Pyr)—CH₂CH₂— | 4-F | 3,4-diF |
| 205 | (1-Me-4-OAdp-2-Pyr)—CH₂CH₂— | 4-F | 3,4-diF |
| 206 | (1-Me-4-OCOOEt-2-Pyr)—CH₂CH₂— | 4-F | 3,4-diF |
| 207 | (1-Me-4-OCOOiPr-2-Pyr)—CH₂CH₂— | 4-F | 3,4-diF |
| 208 | (1-Me-4-OCOODc-2-Pyr)—CH₂CH₂— | 4-F | 3,4-diF |
| 209 | (1-Me-4-OCONH₂-2-Pyr)—CH₂CH₂— | 4-F | 3,4-diF |
| 210 | (1-Me-4-OCONMe₂-2-Pyr)—CH₂CH₂— | 4-F | 3,4-diF |
| 211 | (4-OPal-2-Pyr)—CH₂CH₂— | 4-F | 3,4-diF |
| 212 | (4-OSuc-2-Pyr)—CH₂CH₂— | 4-F | 3,4-diF |
| 213 | (4-OCOOEt-2-Pyr)—CH₂CH₂— | 4-F | 3,4-diF |
| 214 | (4-OCONH₂-2-Pyr)—CH₂CH₂— | 4-F | 3,4-diF |
| 215 | (1-Et-4-OPal-2-Pyr)—CH₂CH₂— | 4-F | 3,4-diF |
| 216 | (1-Me-4-OH-2-Pyr)—CH₂CH₂— | 4-F | 2-Me |
| 217 | (4-OH-2-Pyr)—CH₂CH₂— | 4-F | 2-Me |
| 218 | (1-Me-4-OH-2-Pyr)—CH₂CH₂— | 4-F | 3-Me |
| 219 | (4-OH-2-Pyr)—CH₂CH₂— | 4-F | 3-Me |
| 220 | (1-Me-4-OH-2-Pyr)—CH₂CH₂— | 4-F | 4-Me |
| 221 | (4-OH-2-Pyr)—CH₂CH₂— | 4-F | 4-Me |
| 222 | (1-Me-4-OH-2-Pyr)—CH₂CH₂— | 4-F | 2-Cl |
| 223 | (4-OH-2-Pyr)—CH₂CH₂— | 4-F | 2-Cl |
| 224 | (1-Me-4-OH-2-Pyr)—CH₂CH₂— | 4-F | 3-Cl |
| 225 | (4-OH-2-Pyr)—CH₂CH₂— | 4-F | 3-Cl |
| 226 | (1-Me-4-OH-2-Pyr)—CH₂CH₂— | 4-F | 4-Cl |
| 227 | (4-OH-2-Pyr)—CH₂CH₂— | 4-F | 4-Cl |
| 228 | (1-Me-4-OH-2-Pyr)—CH₂CH₂— | 4-F | 2-Br |
| 229 | (4-OH-2-Pyr)—CH₂CH₂— | 4-F | 2-Br |
| 230 | (1-Me-4-OH-2-Pyr)—CH₂CH₂— | 4-F | 3-Br |
| 231 | (4-OH-2-Pyr)—CH₂CH₂— | 4-F | 3-Br |
| 232 | (1-Me-4-OH-2-Pyr)—CH₂CH₂— | 4-F | 4-Br |
| 233 | (4-OH-2-Pyr)—CH₂CH₂— | 4-F | 4-Br |
| 234 | (1-Me-4-OH-2-Pyr)—CH₂CH₂— | 4-Cl | H |
| 235 | (4-OH-2-Pyr)—CH₂CH₂— | 4-Cl | H |
| 236 | (1-Me-4-OH-2-Pyr)—CH₂CH₂— | 4-Cl | 3-OMe |
| 237 | (4-OH-2-Pyr)—CH₂CH₂— | 4-Cl | 3-OMe |
| 238 | (1-Me-4-OH-2-Pyr)—CH₂CH₂— | 4-Cl | 2-Cl, 4-F |
| 239 | (4-OH-2-Pyr)—CH₂CH₂— | 4-Cl | 3-Me, 4-F |
| 240 | (1-Me-4-OH-2-Pyr)—CH₂CH₂— | 4-Br | H |
| 241 | (4-OH-2-Pyr)—CH₂CH₂— | 4-Br | H |
| 242 | (1-Me-4-OH-2-Pyr)—CH₂CH₂— | 4-Br | 3-OMe |
| 243 | (4-OH-2-Pyr)—CH₂CH₂— | 4-Br | 3-OMe |
| 244 | (1-Me-4-OH-2-Pyr)—CH₂CH₂— | 4-Br | 4-F |
| 245 | (4-OH-2-Pyr)—CH₂CH₂— | 4-Br | 4-F |
| 246 | (1-Me-4-OH-2-Pyr)—CH₂CH₂— | 5-Cl | H |
| 247 | (1-Me-4-OH-2-Pyr)—CH₂CH₂— | 6-Cl | H |
| 248 | (4-OH-2-Pyr)—CH₂CH₂— | 5-Cl | H |
| 249 | (4-OH-2-Pyr)—CH₂CH₂— | 3-Cl | H |
| 250 | (1-Me-4-OH-2-Pyr)—CH₂CH₂— | 5-Cl | 3-OMe |
| 251 | (4-OH-2-Pyr)—CH₂CH₂— | 5-Cl | 3-OMe |
| 252 | (1-Me-4-OH-2-Pyr)—CH₂CH₂— | 5-Cl | 4-F |
| 253 | (4-OH-2-Pyr)—CH₂CH₂— | 5-Cl | 4-F |
| 254 | (1-Me-4-OH-2-Pyr)—CH₂CH₂— | 3-Br | H |

TABLE 1-continued

| Cpd. No. | R¹—A— | R²ᵃ & R²ᵇ | R³ᵃ, R³ᵇ, & R³ᶜ |
|---|---|---|---|
| 255 | (1-Me-4-OH-2-Pyr)—CH₂CH₂— | 5-Br | H |
| 256 | (1-Me-4-OH-2-Pyr)—CH₂CH₂— | 6-Br | H |
| 257 | (4-OH-2-Pyr)—CH₂CH₂— | 5-Br | H |
| 258 | (1-Me-4-OH-2-Pyr)—CH₂CH₂— | 5-Br | 3-OMe |
| 259 | (4-OH-2-Pyr)—CH₂CH₂— | 5-Br | 3-OMe |
| 260 | (1-Me-4-OH-2-Pyr)—CH₂CH₂— | 5-Br | 4-F |
| 261 | (1-Me-4-OH-2-Pyr)—CH₂CH₂— | 5-Br | 3,4-diF |
| 262 | (1-Me-4-OH-2-Pyr)—CH₂CH₂— | 5-Br | 3-OMe, 4-F |
| 263 | (4-OH-2-Pyr)—CH₂CH₂— | 5-OMe | 3-OMe |
| 264 | (4-OH-2-Pyr)—CH₂CH₂— | 6-OMe | H |
| 265 | (1-Me-4-OH-2-Pyr)—CH₂CH₂— | 3-OMe | H |
| 266 | (1-Me-4-OH-2-Pyr)—CH₂CH₂— | 4-OMe | H |
| 267 | (1-Me-4-OH-2-Pyr)—CH₂CH₂— | 5-OMe | H |
| 268 | (1-Me-4-OH-2-Pyr)—CH₂CH₂— | 6-OMe | H |
| 269 | (1-Me-4-OH-2-Pyr)—CH₂CH₂— | 5-OMe | 3-OMe, 4-F |
| 270 | (1-Me-4-OH-2-Pyr)—CH₂CH₂— | 4-OMe | 3-OMe |
| 271 | (1-Me-4-OH-2-Pyr)—CH₂CH₂— | 6-OMe | 3-OMe |
| 272 | (1-Me-4-OH-2-Pyr)—CH₂CH₂— | 5-OMe | 3-OMe |
| 273 | (1-Me-4-OH-2-Pyr)—CH₂CH₂— | 4-OMe | 4-F |
| 274 | (1-Me-4-OH-2-Pyr)—CH₂CH₂— | 5-OMe | 4-F |
| 275 | (1-Me-4-OH-2-Pyr)—CH₂CH₂— | 5-OMe | 3,4-diF |
| 276 | (1-Me-4-OH-2-Pyr)—CH₂CH₂— | 5-OMe | 3-OMe, 4-F |
| 277 | (1-Me-4-OSuc-2-Pyr)—CH₂CH₂— | 5-OMe | H |
| 278 | (1-Me-4-OLau-2-Pyr)—CH₂CH₂— | 5-OMe | H |
| 279 | (1-Et-4-OH-2-Pyr)—CH₂CH₂— | 4-OMe | H |
| 280 | (1-iPr-4-OH-2-Pyr)—CH₂CH₂— | 5-OMe | H |
| 281 | (4-OH-2-Pyr)—CH₂CH₂— | 5-Me | H |
| 282 | (4-OH-2-Pyr)—CH₂CH₂— | 5-Me | 3-OMe |
| 283 | (1-Me-4-OH-2-Pyr)—CH₂CH₂— | 3-Me | 4-Br |
| 284 | (1-Me-4-OH-2-Pyr)—CH₂CH₂— | 4-Me | H |
| 285 | (1-Me-4-OH-2-Pyr)—CH₂CH₂— | 5-Me | H |
| 286 | (1-Me-4-OH-2-Pyr)—CH₂CH₂— | 6-Me | H |
| 287 | (1-Me-4-OH-2-Pyr)—CH₂CH₂— | 5-Me | 4-F |
| 288 | (1-Me-4-OH-2-Pyr)—CH₂CH₂— | 4-Me | 3-OMe |
| 289 | (1-Me-4-OH-2-Pyr)—CH₂CH₂— | 5-Me | 3-OMe |
| 290 | (1-Me-4-OH-2-Pyr)—CH₂CH₂— | 5-Me | 4-Cl |
| 291 | (1-Me-4-OH-2-Pyr)—CH₂CH₂— | 5-Me | 3,4-diF |
| 292 | (1-Me-4-OH-2-Pyr)—CH₂CH₂— | 4-Me | 3-OMe, 4-F |
| 293 | (1-Me-4-OH-2-Pyr)—CH₂CH₂— | 5-Me | 3-OMe, 4-F |
| 294 | (1-Et-4-OH-2-Pyr)—CH₂CH₂— | 5-Me | H |
| 295 | (1-iPr-4-OH-2-Pyr)—CH₂CH₂— | 4-Me | H |
| 296 | (4-OCOOEt-2-Pyr)—CH₂CH₂— | 4-F | 4-OH |
| 297 | (1-Me-4-OH-2-Pyr)—CH₂CH₂— | 3-CN | H |
| 298 | (1-Me-4-OH-2-Pyr)—CH₂CH₂— | 4-CN | H |
| 299 | (1-Me-4-OH-2-Pyr)—CH₂CH₂— | 5-CN | H |
| 300 | (1-Me-4-OH-2-Pyr)—CH₂CH₂— | 5-CN | 3-OMe |
| 301 | (1-Me-4-OH-2-Pyr)—CH₂CH₂— | 4-CN | 4-F |
| 302 | (4-OH-2-Pyr)—CH₂CH₂— | 5-NO₂ | 3-OMe |
| 303 | (4-OH-2-Pyr)—CH₂CH₂— | 5-NO₂ | H |
| 304 | (1-Me-4-OH-2-Pyr)—CH₂CH₂— | 3-NO₂ | H |
| 305 | (1-Me-4-OH-2-Pyr)—CH₂CH₂— | 4-NO₂ | H |
| 306 | (1-Me-4-OH-2-Pyr)—CH₂CH₂— | 5-NO₂ | H |
| 307 | (1-Me-4-OH-2-Pyr)—CH₂CH₂— | 5-NO₂ | 4-F |
| 308 | (1-Me-4-OH-2-Pyr)—CH₂CH₂— | 5-NO₂ | 3-OMe |
| 309 | (1-Me-4-OH-2-Pyr)—CH₂CH₂— | 5-NO₂ | 3,4-diF |
| 310 | (1-Me-4-OH-2-Pyr)—CH₂CH₂— | 4-NO₂ | 3-OMe, 4-F |
| 311 | (1-Et-4-OH-2-Pyr)—CH₂CH₂— | 6-NO₂ | H |
| 312 | (I-Et-4-OH-2-Pyr)—CH₂CH₂— | 4-NO₂ | 4-F |
| 313 | (1-Me-4-OH-2-Pyr)—CH₂CH₂— | 3-F | H |
| 314 | (4-OH-2-Pyr)—CH₂CH₂— | 3-F | H |
| 315 | (1-Me-4-OAc-2-Pyr)—CH₂CH₂— | 3-F | H |
| 316 | (1-Me-4-OLau-2-Pyr)—CH₂CH₂— | 3-F | H |
| 317 | (1-Me-4-OSte-2-Pyr)—CH₂CH₂— | 3-F | H |
| 318 | (1-Me-4-OSuc-2-Pyr)—CH₂CH₂— | 3-F | H |
| 319 | (1-Me-4-OCOOEt-2-Pyr)—CH₂CH₂— | 3-F | H |
| 320 | (1-Me-4-OCOOiPr-2-Pyr)—CH₂CH₂— | 3-F | H |
| 321 | (1-Me-4-OCOO(Ocd)-2-Pyr)—CH₂CH₂— | 3-F | H |
| 322 | (1-Me-4-OCONH₂-2-Pyr)—CH₂CH₂— | 3-F | H |
| 323 | (1-Me-4-OCONMe₂-2-Pyr)—CH₂CH₂— | 3-F | H |
| 324 | (4-OPal-2-Pyr)—CH₂CH₂— | 3-F | H |
| 325 | (4-OSuc-2-Pyr)—CH₂CH₂— | 3-F | H |
| 326 | (4-OCOOEt-2-Pyr)—CH₂CH₂— | 3-F | H |
| 327 | (1-Me-4-OH-2-Pyr)—CH₂CH₂— | 5-F | H |
| 328 | (1-Et-4-OH-2-Pyr)—CH₂CH₂— | 5-F | H |
| 329 | (1-iPr-4-OH-2-Pyr)—CH₂CH₂— | 5-F | H |
| 330 | (4-OH-2-Pyr)—CH₂CH₂— | 5-F | H |
| 331 | (1-Me-4-OAc-2-Pyr)—CH₂CH₂— | 5-F | H |
| 332 | (1-Me-4-OPrp-2-Pyr)—CH₂CH₂— | 5-F | H |
| 333 | (1 Me-4-OVal-2-Pyr)—CH₂CH₂— | 5-F | H |
| 334 | (1-Me-4-OPiv-2-Pyr)—CH₂CH₂— | 5-F | H |
| 335 | (1-Me-4-OHep-2-Pyr)—CH₂CH₂— | 5-F | H |
| 336 | (1-Me-4-OOct-2-Pyr)—CH₂CH₂— | 5-F | H |
| 337 | (1-Me-4-ODec-2-Pyr)—CH₂CH₂— | 5-F | H |
| 338 | (1-Me-4-OLau-2-Pyr)—CH₂CH₂— | 5-F | H |
| 339 | (1-Me-4-OPal-2-Pyr)—CH₂CH₂— | 5-F | H |
| 340 | (1-Me-4-OSuc-2-Pyr)—CH₂CH₂— | 5-F | H |
| 341 | (1-Me-4-OCOOEt-2-Pyr)—CH₂CH₂— | 5-F | H |
| 342 | (1-Me-4-OCOOiPr-2-Pyr)—CH₂CH₂— | 5-F | H |
| 343 | (1-Me-4-OCOO(Oc)-2-Pyr)—CH₂CH₂— | 5-F | H |
| 344 | (1-Me-4-OCOOHxd-2-Pyr)—CH₂CH₂— | 5-F | H |
| 345 | (1-Me-4-OCONH₂-2-Pyr)—CH₂CH₂— | 5-F | |
| 346 | (1-Me-4-OCONHEt-2-Pyr)—CH₂CH₂— | 5-F | H |
| 347 | (1-Me-4-OCONMe₂-2-Pyr)—CH₂CH₂— | 5-F | H |
| 348 | (1-Me-4-OCONMePr-2-Pyr)—CH₂CH₂— | 5-F | H |
| 349 | (4-OAc-2-Pyr)—CH₂CH₂— | 5-F | H |
| 350 | (4-OPiv-2-Pyr)—CH₂CH₂— | 5-F | H |
| 351 | (4-OLau-2-Pyr)—CH₂CH₂— | 5-F | H |
| 352 | (4-OPal-2-Pyr)—CH₂CH₂— | 5-F | H |
| 353 | (4-OSuc-2-Pyr)—CH₂CH₂— | 5-F | H |
| 354 | (4-OCOOPr-2-Pyr)—CH₂CH₂— | 5-F | H |
| 355 | (4-OCOO(Oc)-2-Pyr)—CH₂CH₂— | 5-F | H |
| 356 | (4-OCOODc-2-Pyr)—CH₂CH₂— | 5-F | H |
| 357 | (4-OCONH₂-2-Pyr)—CH₂CH₂— | 5-F | H |
| 358 | (4-OCONMe₂-2-Pyr)—CH₂CH₂— | 5-F | H |
| 359 | (1-Me-4-OH-2-Pyr)—CH₂CH₂— | 6-F | H |
| 360 | (4-OH-2-Pyr)—CH₂CH₂— | 6-F | H |
| 361 | (1-Me-4-O(Oct)-2-Pyr)—CH₂CH₂— | 6-F | H |
| 362 | (1-Me-4-OLau-2-Pyr)—CH₂CH₂— | 6-F | H |
| 363 | (1-Me-4-OSte-2-Pyr)—CH₂CH₂— | 6-F | H |
| 364 | (1-Me-4-OSuc-2-Pyr)—CH₂CH₂— | 6-F | H |
| 365 | (1-Me-4-OCOOEt-2-Pyr)—CH₂CH₂— | 6-F | H |
| 366 | (1-Me-4-OCOODc-2-Pyr)—CH₂CH₂— | 6-F | H |
| 367 | (1-Me-4-OCONH₂-2-Pyr)—CH₂CH₂— | 6-F | H |
| 368 | (1-Me-4-OCONHMe-2-Pyr)—CH₂CH₂— | 6-F | H |
| 369 | (4-OPiv-2-Pyr)—CH₂CH₂— | 6-F | H |
| 370 | (4-OPal-2-Pyr)—CH₂CH₂— | 6-F | H |
| 371 | (4-OSuc-2-Pyr)—CH₂CH₂— | 6-F | H |
| 372 | (4-OCOO(Oc)-2-Pyr)—CH₂CH₂— | 6-F | H |
| 373 | (4-OCONH₂-2-Pyr)—CH₂CH₂— | 6-F | H |
| 374 | (1-Me-4-OH-2-Pyr)—CH₂CH₂ | 4,5-diF | H |
| 375 | (1-Et-4-OH-2-Pyr)—CH₂CH₂ | 4,5-diF | H |
| 376 | (1-iPr-4-OH-2-Pyr)—CH₂CH₂— | 4,5-diF | H |
| 377 | (1-Bz-4-OH-2-Pyr)—CH₂CH₂— | 4,5-diF | H |
| 378 | (1-Boc-4-OH-2-Pyr)—CH₂CH₂— | 4,5-diF | H |
| 379 | (1-EtOCO-4-OH-2-Pyr)—CH₂CH₂— | 4,5-diF | H |
| 380 | (4-OH-2-Pyr)—CH₂CH₂— | 4,5-diF | H |
| 381 | (1-Me-4-OAc-2-Pyr)—CH₂CH₂— | 4,5-diF | H |
| 382 | (1-Me-4-OPrp-2-Pyr)—CH₂CH₂— | 4,5-diF | H |
| 383 | (1-Me-4-OBur-2-Pyr)—CH₂CH₂— | 4,5-diF | H |
| 384 | (1-Me-4-OVal-2-Pyr)—CH₂CH₂— | 4,5-diF | H |
| 385 | (1-Me-4-OPiv-2-Pyr)—CH₂CH₂— | 4,5-diF | |
| 386 | (1-Me-4-OHex-2-Pyr)—CH₂CH₂— | 4,5-diF | H |
| 387 | (1-Me-4-OHep-2-Pyr)—CH₂CH₂— | 4,5-diF | H |
| 388 | (1-Me-4-O(Oct)-2-Pyr)—CH₂CH₂— | 4,5-diF | H |
| 389 | (1-Me-4-ODec-2-Pyr)—CH₂CH₂— | 4,5-diF | H |
| 390 | (1-Me-4-OLau-2-Pyr)—CH₂CH₂— | 4,5-diF | H |
| 391 | (1-Me-4-OMyr-2-Pyr)—CH₂CH₂— | 4,5-diF | H |
| 392 | (1-Me-4-OPal-2-Pyr)—CH₂CH₂— | 4,5-diF | H |
| 393 | (1-Me-4-OSte-2-Pyr)—CH₂CH₂— | 4,5-diF | H |
| 394 | (1-Me-4-OMal-2-Pyr)—CH₂CH₂— | 4,5-diF | H |
| 395 | (1-Me-4-OSuc-2-Pyr)—CH₂CH₂— | 4,5-diF | H |
| 396 | (1-Me-4-OGlu-2-Pyr)—CH₂CH₂— | 4,5-diF | H |
| 397 | (1-Me-4-OAdp-2-Pyr)—CH₂CH₂— | 4,5-diF | H |
| 398 | (1-Me-4-OCOOEt-2-Pyr)—CH₂CH₂— | 4,5-diF | H |
| 399 | (1-Me-4-OCOOiPr-2-Pyr)—CH₂CH₂— | 4,5-diF | H |
| 400 | (1-Me-4-OCOOBu-2-Pyr)—CH₂CH₂— | 4,5-diF | H |
| 401 | (1-Me-4-OCOO(Oc)-2-Pyr)—CH₂CH₂— | 4,5-diF | H |
| 402 | (1-Me-4-OCOODc-2-Pyr)—CH₂CH₂— | 4,5-diF | H |
| 403 | (1-Me-4-OCOOUnd-2-Pyr)—CH₂CH₂— | 4,5-diF | H |
| 404 | (1-Me-4-OCOOPnd-2-Pyr)—CH₂CH₂— | 4,5-diF | H |

TABLE 1-continued

| Cpd. No. | R¹—A— | R²ᵃ & R²ᵇ | R³ᵃ, R³ᵇ, & R³ᶜ |
|---|---|---|---|
| 405 | (1-Me-4-OCOOHxd-2-Pyr)—CH₂CH₂— | 4,5-diF | H |
| 406 | (1-Me-4-OCOOHpd-2-Pyr)—CH₂CH₂— | 4,5-diF | H |
| 407 | (1-Me-4-OCONH₂-2-Pyr)—CH₂CH₂— | 4,5-diF | H |
| 408 | (1-Me-4-OCONHMe-2-Pyr)—CH₂CH₂— | 4,5-diF | H |
| 409 | (1-Me-4-OCONHEt-2-Pyr)—CH₂CH₂— | 4,5-diF | H |
| 410 | (1-Me-4-OCONMe₂-2-Pyr)—CH₂CH₂— | 4,5-diF | H |
| 411 | (1-Me-4-OCONMeBt-2-Pyr)—CH₂CH₂— | 4,5-diF | H |
| 412 | (4-OAc-2-Pyr)—CH₂CH₂— | 4,5-diF | H |
| 413 | (4-OiBur-2-Pyr)—CH₂CH₂— | 4,5-diF | H |
| 414 | (4-O(Oct)-2-Pyr)—CH₂CH₂— | 4,5-diF | H |
| 415 | (4-OLau-2-Pyr)—CH₂CH₂— | 4,5-diF | H |
| 416 | (4-OPal-2-Pyr)—CH₂CH₂— | 4,5-diF | H |
| 417 | (4-OSuc-2-Pyr)—CH₂CH₂— | 4,5-diF | H |
| 418 | (4-OAdp-2-Pyr)—CH₂CH₂— | 4,5-diF | H |
| 419 | (4-OCOOEt-2-Pyr)—CH₂CH₂— | 4,5-diF | H |
| 420 | (4-OCOOiPr-2-Pyr)—CH₂CH₂— | 4,5-diF | H |
| 421 | (4-OCOO(Oc)-2-Pyr)—CH₂CH₂— | 4,5-diF | H |
| 422 | (4-OCOODc-2-Pyr)—CH₂CH₂— | 4,5-diF | H |
| 423 | (4-OCOOTrd-2-Pyr)—CH₂CH₂— | 4,5-diF | H |
| 424 | (4-OCOO(Ocd)-2-Pyr)—CH₂CH₂— | 4,5-diF | H |
| 425 | (4-OCONH₂-2-Pyr)—CH₂CH₂— | 4,5-diF | H |
| 426 | (4-OCONMe₂-2-Pyr)—CH₂CH₂— | 4,5-diF | H |
| 427 | (1-Et-4-OLau-2-Pyr)—CH₂CH₂— | 4,5-diF | H |
| 428 | (1-Et-4-OPal-2-Pyr)—CH₂CH₂— | 4,5-diF | H |
| 429 | (1-iPr-4-OLau-2-Pyr)—CH₂CH₂— | 4,5-diF | H |
| 430 | (1-Pr-4-OPal-2-Pyr)CH₂CH₂— | 4,5-diF | H |
| 431 | (1-Et-4-OSuc-2-Pyr)—CH₂CH₂— | 4,5-diF | H |
| 432 | (1-Me-4-OH-2-Pyr)—CH₂CH₂— | 3,5-diF | H |
| 433 | (1-Me-4-OH-2-Pyr)—CH₂CH₂— | 3,6-diF | H |
| 434 | (1-Me-4-OH-2-Pyr)—CH₂CH₂— | 3,4-diF | H |
| 435 | (1-Me-4-OH-2-Pyr)—CH₂CH₂— | 4,6-diF | H |
| 436 | (1-Me-4-OH-2-Pyr)—CH₂CH₂ | 5,6-diF | H |
| 437 | (4-OH-2-Pyr)—CH₂CH₂— | 3,4-diF | H |
| 438 | (4-OH-2-Pyr)—CH₂CH₂— | 4,6-diF | H |
| 439 | (1-Me-4-OVal-2-Pyr)—CH₂CH₂— | 4,6-diF | H |
| 440 | (1-Me-4-OLau-2-Pyr)—CH₂CH₂— | 3,4-diF | H |
| 441 | (1-Me-4-OPal-2-Pyr)—CH₂CH₂— | 3,4-diF | H |
| 442 | (1-Me-4-OSuc-2-Pyr)—CH₂CH₂— | 4,6-diF | H |
| 443 | (1-Me-4-OSuc-2-Pyr)—CH₂CH₂— | 3,4-diF | H |
| 444 | (4-OAc-2-Pyr)—CH₂CH₂— | 3,5-diF | H |
| 445 | (4-OLau-2-Pyr)—CH₂CH₂— | 3,6-diF | H |
| 446 | (4-OPal-2-Pyr)—CH₂CH₂— | 4,6-diF | H |
| 447 | (4-OSuc-2-Pyr)—CH₂CH₂— | 3,4-diF | H |
| 448 | (1-Me-4-OH-2-Pyr)—CH₂CH₂— | 4-F, 5-OMe | 3,4-diF |
| 449 | (1-Me-4-OH-2-Pyr)—CH₂CH₂— | 4-F, 6-OMe | H |
| 450 | (1-Me-4-OH-2-Pyr)—CH₂CH₂— | 4-F, 5-Me | H |
| 451 | (1-Me-4-OH-2-Pyr)—CH₂CH₂— | 3-Cl, 4-F | 3-OMe, 4-F |
| 452 | (4-OH-2-Pyr)—CH₂CH₂— | 4-F, 5-OMe | 4-F |
| 453 | (4-OH-2-Pyr)—CH₂CH₂— | 3-OMe, 4-F | 3-OMe, 4-F |
| 454 | (4-OH-2-Pyr)—CH₂CH₂— | 4-F, 6-Cl | 3-OMe |
| 455 | (1-Me-4-OLau-2-Pyr)—CH₂CH₂— | 4-F, 5-OMe | H |
| 456 | (1-Me-4-OLau-2-Pyr)—CH₂CH₂— | 4-F, 5-Cl | 3-OMe |
| 457 | (1-Me-4-OPal-2-Pyr)—CH₂CH₂— | 4-F, 5-Cl | H |
| 458 | (1-Me-4-OSuc-2-Pyr)—CH₂CH₂— | 4-F, 5-Cl | 3-OMe |
| 459 | (1-Me-4-OSuc-2-Pyr)—CH₂CH₂— | 4-F, 5-OMe | 4-F |
| 460 | (4-OAc-2-Pyr)—CH₂CH₂— | 4-F, 5-Cl | 3,4-diF |
| 461 | (4-OLau-2-Pyr)—CH₂CH₂— | 4-F, 5-OMe | H |
| 462 | (4-OPal-2-Pyr)—CH₂CH₂— | 3-Me, 4-F | 4-F |
| 463 | (4-OSuc-2-Pyr)—CH₂CH₂— | 4-F, 5-Cl | H |
| 464 | (1-Me-4-OH-2-Pyr)—CH₂CH₂— | 4-F | 3,4,5-triCl |
| 465 | (1-Me-4-OH-2-Pyr)—CH₂CH₂— | 4-F | 3,4,5-triF |
| 466 | (1-Me-4-OH-2-Pyr)—CH₂CH₂— | 4-F | 2,4,5-triF |
| 467 | (1-Me-4-OH-2-Pyr)—CH₂CH₂— | 4-F, 5-Cl | 2,3,4-triF |
| 468 | (1-Me-4-OH-2-Pyr)—CH₂CH₂— | 4-F | 2,4-diCl, 5-F |
| 469 | (1-Me-4-OH-2-Pyr)—CH₂CH₂— | 4,6-di-F | 2-Cl, 4,5-diF |
| 470 | (1-Me-4-OH-2-Pyr)—CH₂CH₂— | 4-F | 3-Br, 4,5-diOMe |
| 471 | (1-Me-4-OH-2-Pyr)—CH₂CH₂— | 4-F | 5-Br, 3,4-diOMe |
| 472 | (1-Me-4-OH-2-Pyr)—CH₂CH₂— | 4-F | 2,4-diOMe, 3-Me |
| 473 | (1-Me-4-OH-2-Pyr)—CH₂CH₂— | 4-F | 2,4-diOMe, 5-OH |
| 474 | (1-Me-4-OH-2-Pyr)—CH₂CH₂— | 4-F | 2,6-diOMe, 4-OH |
| 475 | (1-Me-4-OH-2-Pyr)—CH₂CH₂— | 4-F | 4,6-diOMe, 2-OH |
| 476 | (1-Me-4-OH-2-Pyr)—CH₂CH₂— | 4-F | 3,5-diCl, 4-OH |
| 477 | (1-Me-4-OH-2-Pyr)—CH₂CH₂— | 4-F | 3,5-diCl, 2-OH |
| 478 | (1-Me-4-OH-2-Pyr)—CH₂CH₂— | 4-F | 3,5-diBr, 4-OH |
| 479 | (1-Et-4-OH-2-Pyr)—CH₂CH₂— | 4-F | 2,4,6-triF |
| 480 | (4-OH-2-Pyr)—CH₂CH₂— | 4,5-diF | 2,4,6-triMe |
| 481 | (1-Me-4-OAc-2-Pyr)—CH₂CH₂— | 4-F | 2,3,4-triOMe |
| 482 | (1-Me-4-OPiv-2-Pyr)—CH₂CH₂— | 4-F | 3,4,5-triOMe |
| 483 | (1-Me-4-OLau-2-Pyr)—CH₂CH₂— | 4-F | 3,4,5-triF |
| 484 | (1-Me-4-OPal-2-Pyr)—CH₂CH₂— | 4-F | 2,4,6-trioMe |
| 485 | (1-Me-4-OSuc-2-Pyr)—CH₂CH₂— | 4,5-diF | 3,4,5-triF |
| 486 | (4-OAc-2-Pyr)—CH₂CH₂— | 4-F | 3,4,5-triF |
| 487 | (4-OLau-2-Pyr)—CH₂CH₂ | 4-F | 2,4,6-triF |
| 488 | (4-OSuc-2-Pyr)—CH₂CH₂— | 4-F | 2,4,6-triCl |
| 489 | (1-Me-4-OH-2-Pyr)—CH₂CH₂— | 5-F | 3-OCF₃ |
| 490 | (1-Me-4-OH-2-Pyr)—CH₂CH₂— | 4-F | 3-OCHF₂ |
| 491 | (1-Me-4-OH-2-Pyr)—CH₂CH₂— | 4-F | 4-OCHF₂ |
| 492 | (1-Me-4-OH-2-Pyr)—CH₂CH₂— | 5-F | 4-CF₃ |
| 493 | (1-Me-4-OH-2-Pyr)—CH₂CH₂— | 4-F | 4-CN |
| 494 | (1-Me-4-OH-2-Pyr)—CH₂CH₂— | 4-F | 2-OH |
| 495 | (1-Me-4-OH-2-Pyr)—CH₂CH₂— | 4-F | 4-OH |
| 496 | (1-Me-4-OH-2-Pyr)—CH₂CH₂— | 4,5-diF | 3-OCCl₃ |
| 497 | (1-Me-4-OH-2-Pyr)—CH₂CH₂— | 4-F | 3-CCl₃ |
| 498 | (1-Me-4-OH-2-Pyr)—CH₂CH₂— | 4-F | 4-Ph |
| 499 | (1-Me-4-OH-2-Pyr)—CH₂CH₂— | 4-F | 2-NO₂ |
| 500 | (1-Me-4-OH-2-Pyr)—CH₂CH₂— | 6-F | 4-OAc |
| 501 | (1-Me-4-OH-2-Pyr)—CH₂CH₂— | 4-F | 3-OCONH₂ |
| 502 | (4-OH-2-Pyr)—CH₂CH₂— | 4-F | 3-OCHF₂ |
| 503 | (1-Me-4-OAc-2-Pyr)—CH₂CH₂— | 5-F | 3-CCl₃ |
| 504 | (1-Me-4-OLau-2-Pyr)—CH₂CH₂— | 4-F | 4-OH |
| 505 | (1-Me-4-OPal-2-Pyr)—CH₂CH₂— | 4-F | 3-OCHF₂ |
| 506 | (1-Me-4-OSuc-2-Pyr)—CH₂CH₂— | 4,5-diF | 4-CH₂CH=CH₂ |
| 507 | (1-Me-4-OAdp-2-Pyr)—CH₂CH₂— | 5-F | 3-OCHF₂ |
| 508 | (1-Me-4-OCOOEt-2-Pyr)—CH₂CH₂— | 4-F | 4-Ph |
| 509 | (1-Me-4-OCONH₂-2-Pyr)—CH₂CH₂— | 4-F | 4-OH |
| 510 | (1-Me-4-OCONMe₂-2-Pyr)—CH₂CH₂— | 4-F | 4-CCl₃ |
| 511 | (4-OAc-2-Pyr)—CH₂CH₂— | 4-F | 3-OCHF₂ |
| 512 | (4-OLau-2-Pyr)—CH₂CH₂— | 4-F | 3-OCHCl₂ |
| 513 | (4-OPal-2-Pyr)—CH₂CH₂— | 4-F | 4-CH₂C≡CH |
| 514 | (4-OSuc-2-Pyr)—CH₂CH₂— | 4,6-diF | 4-OCONMe₂ |

Of the compounds listed above, preferred compounds are Compounds No. 1, 2, 7, 8, 12, 17, 19, 22, 26, 28, 34, 37, 44, 46, 67, 77, 81, 114, 118, 125, 126, 152, 154, 159, 162, 196, 198, 202, 203, 204, 224, 225, 226, 227, 230, 234, 236, 240, 246, 250, 252, 266, 267, 268, 284, 285, 286 and 359, whilst Compounds No. 1, 7, 17, 19, 22, 28, 67, 77, 81, 114, 118, 125, 126, 152, 154, 159, 162, 196, 198, 202, 204, 224, 226, 230, 234, 236, 240, 250, 252, 266, 267, 268, 284, 285, 286 and 359 are more preferred.

Still more preferred compounds are Compounds No. 1, 7, 17, 19, 22, 67, 77, 81, 114, 118, 125, 126, 152, 154, 159, 162, 196, 198, 202, 204, 226, 236 and 266.

The most preferred compounds are Compounds No.:
1. 2-{2-[4-Fluoro-2-(2-phenylethyl)phenoxy]ethyl}-4-hydroxy-1-methylpyrrolidine;
7. 2-{2-[4-Fluoro-2-(2-phenylethyl)phenoxy]ethyl}-4-hydroxypyrrolidine;
17. 2-{2-[4-Fluoro-2-(2-phenylethyl)phenoxy]ethyl}-4-lauroyloxy-1-methylpyrrolidine;
22. 2-{2-[4-Fluoro-2-(2-phenylethyl)phenoxy]ethyl}-1-methyl-4-succinyloxypyrrolidine;
67. 2-[2-{4-Fluoro-2-[2-(3-methoxyphenyl)ethyl]phenoxy}ethyl]-4-hydroxy-1-methylpyrrolidine;
77. 2-[2-{4-Fluoro-2-[2-(3-methoxyphenyl)ethyl]phenoxy}ethyl]-4-lauroyloxy-1-methylpyrrolidine;
81. 2-[2-{4-Fluoro-2-[2-(3-methoxyphenyl)ethyl]phenoxy}ethyl]-1-methyl-4-succinyloxypyrrolidine;
114. 2-[2-{4-Fluoro-2-[2-(4-fluorophenyl)ethyl]phenoxy}ethyl]-4-hydroxy-1-methylpyrrolidine;
118. 2-[2-{4-Fluoro-2-[2-(4-fluorophenyl)ethyl]phenoxy}ethyl]-4-hydroxypyrrolidine;
125. 2-[2-{4-Fluoro-2-[2-(4-fluorophenyl)ethyl]phenoxy}ethyl]-1-methyl-4-palmitoyloxypyrrolidine;
126. 2-[2-{4-Fluoro-2-[2-(4-fluorophenyl)ethyl]phenoxy}ethyl]-1-methyl-4-succinyloxypyrrolidine;
152. 2-[2-{4-Fluoro-2-[2-(4-fluoro-3-methoxyphenyl)ethyl]phenoxy}ethyl]-4-hydroxy-1-methylpyrrolidine;
154. 2-[2-{4-Fluoro-2-[2-(4-fluoro-3-methoxyphenyl)ethyl]phenoxy}ethyl]-4-hydroxypyrrolidine;
159. 2-[2-{4-Fluoro-2-[2-(4-fluoro-3-methoxyphenyl)ethyl]phenoxy}ethyl]-4-lauroyloxy-1-methylpyrrolidine;
162. 2-[2-{4-Fluoro-2-[2-(4-fluoro-3-methoxyphenyl)ethyl]phenoxy}ethyl]-1-methyl-4-succinyloxypyrrolidine;
196. 2-[2-{2-[2-(3,4-Difluorophenyl)ethyl]-4-fluorophenoxy}ethyl]-4-hydroxy-1-methylpyrrolidine;
198. 2-[2-{2-[2-(3,4-Difluorophenyl)ethyl]-4-fluorophenoxy}ethyl]-4-hydroxypyrrolidine;
202. 2-[2-{2-[2-(3,4-Difluorophenyl)ethyl]-4-fluorophenoxy}ethyl]-4-lauroyloxy-1-methylpyrrolidine; and
204. 2-[2-{2-[2-(3,4-Difluorophenyl)ethyl]-4-fluorophenoxy}ethyl]-1-methyl-4-succinyloxypyrrolidine;
and pharmaceutically acceptable salts thereof.

The compounds of the present invention may be prepared by a variety of methods known for the preparation of this type of compound. For example, they may be prepared by the processes described in EP 600 717 or by the method shown in the following Reaction Scheme.

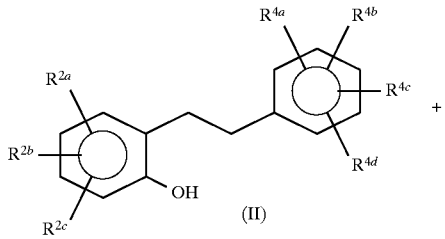

(II)

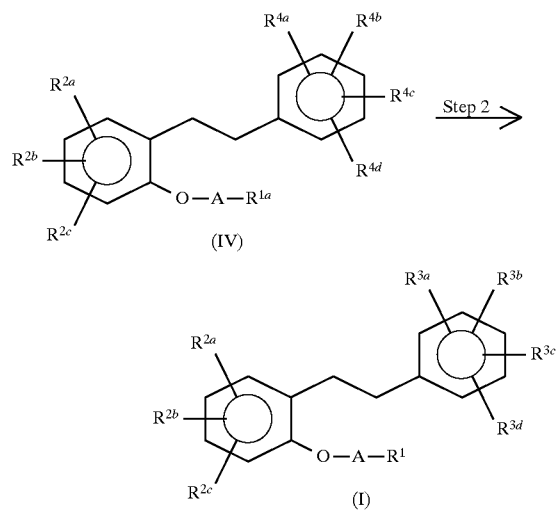

In the above formulae:
$R^1$, $R^{2a}$, $R^{2b}$, $R^{2c}$, $R^{3a}$, $R^{3b}$, $R^{3c}$, $R^{3d}$ and A are as defined above;

$R^{1a}$ represents any of the groups represented by $R^1$, except that any active nitrogen atom (e.g. in the heterocyclic ring or in the amino, alkylamino, carbamoyloxy or alkylcarbamoyloxy groups included in substitutents α) or hydroxy group is protected and excluding the case where substituent α is a carboxy-substituted alkanoyloxy group;

$R^{4a}$, $R^{4b}$, $R^{4c}$ and $R^4d$ are as defined for $R^{3a}$, $R^{3b}$, $R^{3c}$ and $R^{3d}$, respectively, except that any hydroxy group is protected; and Z represents a hydroxy group, a halogen atom (preferably a chlorine, bromine or iodine atom), an alkanesulfonyloxy group having from 1 to 6 carbon atoms, or an arylsulfonyloxy group in which the aryl part is an aromatic carbocyclic ring which has from 6 to 10 ring carbon atoms and which is unsubstituted or is substituted by at least one substitutent selected from the group consisting of substituents γ, defined and exemplified above.

Examples of hydroxy-protecting groups for the groups included in $R^{1a}$, $R^{4a}$, $R^{4b}$, $R^{4c}$, $R^{4d}$ include cyclic ether groups (such as the tetrahydrofuranyl group and the tetrahydropyranyl group), the methoxymethyl group, the methoxymethoxymethyl group, and arylmethyl groups and arylmethoxycarbonyl groups in which the aryl part has from 6 to 10 ring carbon atoms and is unsubstituted or is substituted by at least one substitutent selected from the group consisting of substituents γ, defined and exemplified above. Of these, we prefer the tetrahydropyranyl, methoxymethyl, benzyl, p-methoxybenzyl, p-brombenzyl, benzyloxycarbonyl, p-methoxybenzyloxycarbonyl and p-bromobenzyloxycarbonyl groups.

Examples of protecting groups for the nitrogen atom, amino group, mono-alkylamino group and others of the heterocyclic ring represented by $R^{1a}$ include alkoxycarbonyl groups having from 1 to 6 carbon atoms in the alkoxy part, alkanoyl groups having from 1 to 5 carbon atoms, arylmethyl groups and arylmethoxycarbonyl groups in which the aryl part has from 6 to 10 ring carbon atoms and is unsubstituted or is substituted by at least one substituent selected from the group consisting of substituents γ, defined and exemplified above. Of these, we especially prefer the t-butoxycarbonyl, acetyl, benzyl, p-methoxybenzyl, p-bromobenzyl, benzyloxycarbonyl, p-methoxybenzyloxycarbonyl and p-brombenzyloxycarbonyl groups.

In Step 1 of this reaction scheme, a compound of formula (IV) is prepared by reacting a compound of formula (II) with a compound of formula (III).

Where Z represents a halogen atom, an alkanesulfonyloxy group or an arylsulfonyloxy group, the reaction can be carried out in the presence of a solvent and of a base.

There is no particular restriction on the nature of the bases used, and any base commonly used in reactions of this type may equally be used here. Examples of such bases include: alkali metal carbonates, such as sodium carbonate and potassium carbonate; alkali metal hydrogencarbonates, such as sodium hydrogencarbonate and potassium hydrogencarbonate; alkali metal fluorides, such as sodium fluoride and potassium fluoride; alkali metal hydrides, such as sodium hydride, potassium hydride and lithium hydride; alkali metal alkoxides, such as sodium methoxide, sodium ethoxide, potassium t-butoxide and lithium methoxide; and organic amines, such as pyridine, picoline, triethylamine, N-methylmorpholine and 4-dimethylaminopyridine. Of these, we particularly prefer the alkali metal carbonates, alkali metal fluorides, alkali metal hydrides or alkali metal alkoxides.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as hexane, benzene and toluene; halogenated hydrocarbons, such as methylene chloride, chloroform and 1,2-dichlorethane; ethers, such as diethyl ether, tetrahydrofuran and dioxane; ketones, such as acetone and methyl ethyl ketone; nitriles, such as acetonitrile; amides, such as N,N-dimethylacetamide, dimethylformamide, N-methylpyrrolidone and hexamethylphosphoric triamide; and sulfoxides, such as dimethyl sulfoxide; or a mixture of any two or more of these solvents. Of these, we particularly prefer the ethers, ketones, amides or sulfoxides.

The reaction can take place over a wide range of temperatures, and the precise reaction temperature is not critical to the invention. The preferred reaction temperature will depend upon such factors as the nature of the solvent, and the starting materials and bases used. However, in general, we find it convenient to carry out the reaction at a temperature of from 0° C. to 100° C., more preferably from 10° C. to 80° C. The time required for the reaction may also vary widely, depending on many factors, notably the reaction temperature and the nature of the reagents and solvent employed. However, provided that the reaction is effected under the preferred conditions outlined above, a period of from 30 minutes to 48 hours, more preferably from 1 to 24 hours, will usually suffice.

Where Z represents a hydroxy group, the reaction can be carried out in the presence of a solvent, triphenylphosphine and of a di($C_1$–$C_4$ alkyl) azodicarboxylate, such as dimethyl azodicarboxylate or diethyl azodicarboxylate.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include those mentioned above, of which we prefer the aromatic hydrocarbons, halogenated hydrocarbons or ethers.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 100° C., more preferably from 10° C. to 80° C. The time required for the reaction may also vary widely, depending on many factors, notably the reaction temperature and the nature of the reagents and solvent employed. However, provided that the reaction is effected under the preferred conditions outlined above, a period of from 30 minutes to 48 hours, more preferably from 1 to 24 hours, will usually suffice.

After the reaction is complete, the desired compound of formula (IV) can be collected from reaction mixture by conventional means. For example, if an insoluble substance is present, this is removed by filtration when appropriate, and then the solvent is removed by evaporation under reduced pressure; in other cases, the solvent is removed by evaporation under reduced pressure, water is added to the residue, the mixture is extracted with a water-immiscible organic solvent, such as ethyl acetate, the extract is allowed to dry in the presence of, for example, anhydrous magnesium sulfate, and then the solvent is removed. If necessary, the desired compound can be further purified by conventional methods, for example, by recrystallization or by column chromatography.

Step 2 includes the following optional reactions, which may be carried out in any appropriate order:

Reaction (a): A reaction that removes the hydroxy-protecting group which may be present in $R^{1a}$, $R^{4a}$, $R^{4b}$, $R^{4c}$ or $R^{4d}$;

Reaction (b): A reaction that alkylates, acylates or carbamoylates the hydroxy group formed in reaction (a);

Reaction (c): A reaction that removes a protecting group for the nitrogen atom, amino group and others which may be present in $R^{1a}$;

Reaction (d): A reaction that converts the hydroxy group to an amino group;

Reaction (e): A reaction that converts the alkoxycarbonyl group which may be present in $R^{1a}$ to a methyl group or the alkanoyl group which may be present in $R^{1a}$ to an alkyl group;

Reaction (f): A reaction that alkylates the =NH group which may be present in $R^{1a}$; and Reaction (g): A reaction that converts the cyano group to a carbamoyl group.

Reaction (a):

This reaction removes a hydroxy-protecting group which may be present in $R^{1a}$, $R^{4a}$, $R^{4b}$, $R^{4c}$ or $R^{4d}$. The nature of the reaction varies depending on the type of protecting group, and the reaction can be carried out by methods well known in the field of organic synthesis.

When the hydroxy-protecting group is an arylmethyl group or arylmethoxycarbonyl group, the reaction can be carried out by allowing the protected compound to react with hydrogen (usually under from 1 to 10 atmospheres pressure, and preferably under from 1 to 3 atmospheres pressure) in a solvent in the presence of a hydrogenation catalyst. There is no particular restriction on the nature of the catalysts used, and any catalyst commonly used in reactions of this type may equally be used here. Examples of such catalysts include: palladium-on-carbon, Raney nickel, platinum oxide, platinum black, rhodium-on-aluminum oxide, and palladium-on-barium sulfate.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol, ethanol and isopropanol, ethers; such as diethyl ether, tetrahydrofuran and dioxane; aromatic hydrocarbons, such as toluene, benzene and xylene; aliphatic hydrocarbons, such as hexane and cyclohexane; esters, such as ethyl acetate and butyl acetate; aliphatic acids, such as acetic acid; and mixtures of any one or more of these organic solvents with water.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to 100° C., more preferably from 20° C. to 80° C. The time required for the reaction may also vary widely, depending on many factors, notably the reaction temperature and the nature of the reagents and solvent employed. However, provided that the reaction is effected under the preferred conditions outlined above, a period of from 30 minutes to 48 hours, more preferably from 1 to 24 hours, will usually suffice.

When the hydroxy-protecting group is a methoxymethyl group, a methoxymethoxymethyl group or a cyclic ether group, the reaction can be carried out by allowing the protected compound to react with an acid. There is no particular restriction on the nature of the acids used, and any acid commonly used in reactions of this type may equally be used here. Examples of such acids include: inorganic acids, such as hydrogen chloride, nitric acid, hydrochloric acid and sulfuric acid; organic acids, such as acetic acid, trifluoroacetic acid, methanesulfonic acid and p-toluenesulfonic acid; Lewis acids, such as boron trifluoride; or strongly acidic cation exchange resins, such as Dow X 50W (trade mark). Of these, we prefer the inorganic acids or organic acids; and more prefer hydrochloric acid, sulfuric acid or trifluoroacetic acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as hexane and benzene, halogenated hydrocarbons, such as methylene chloride and chloroform; esters, such as ethyl acetate; ketones, such as acetone and methyl ethyl ketone; alcohols, such as methanol and ethanol; ethers, such as diethyl ether, tetrahydrofuran and dioxane; or a mixture of any one or more of these organic solvents with water. Of these, we prefer the esters, ethers or halogenated hydrocarbons.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10° C. to 100° C., more preferably from −5° C. to 50° C. The time required for the reaction may also vary widely, depending on many factors, notably the reaction temperature and the nature of the reagents and solvent employed. However, provided that the reaction is effected under the preferred conditions outlined above, a period of from 5 minutes to 48 hours, more preferably from 30 minutes to 10 hours, will usually suffice.

If there are two or more hydroxy-protecting groups included in $R^{1a}$, $R^{4a}$, $R^{4b}$, $R^{4c}$ or $R^{4d}$, these can be removed selectively by an appropriate choice of protecting groups and suitable selection of the reaction conditions.

After the reaction is completed, the desired compound can be collected from reaction mixture by a conventional method. For example, one suitable technique comprises: neutralizing the reaction mixture, if appropriate; or, where an insoluble substance is present, removing the insoluble substance by filtration; adding a water-immiscible organic solvent, such as ethyl acetate; washing with water; and removing the solvent. If necessary, the desired compound thus obtained can be further purified by conventional methods, for example, by recrystallization, reprecipitation or chromatography.

Reaction (b):

This reaction alkylates, acylates or carbamoylates the hydroxy group. The reaction can be carried out using methods generally known in the field of organic synthesis. Thus, in general terms, the hydroxy group is allowed to react with an alkylating agent, an acylating agent or a carbamoylating agent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene and toluene; halogenated hydrocarbons, such as methylene chloride and chloroform; esters, such as ethyl acetate; ethers, such as tetrahydrofuran and dioxane; ketones, such as acetone and methyl ethyl ketone; and amides, such as N,N-dimethylacetamide.

The reaction can take place in the presence or absence of a base. There is no particular restriction on the nature of the bases used, and any base commonly used in reactions of this type may equally be used here. Examples of such bases include: organic tertiary amines, such as triethylamine, pyridine, diethylisopropylamine and 4-(N,N-dimethylamino)pyridine.

Examples of alkylating agents, acylating agents and carbamoylating agents which may be used include:

alkyl halides having from 1 to 6 carbon atoms, such as methyl iodide, ethyl iodide, propyl iodide, butyl iodide, pentyl iodide and hexyl iodide;

($C_1$–$C_6$ alkanoyloxy)-($C_1$–$C_6$ alkyl) halides, such as formyloxymethyl chloride, acetoxymethyl chloride, acetoxymethyl iodide, propionyloxymethyl iodide, butyryloxymethyl iodide, valeryloxymethyl iodide, pivaloyloxymethyl chloride, pivaloyloxymethyl bromide and pivaloyloxymethyl iodide;

alkyl halocarbonates having from 1 to 14 carbon atoms in the alkyl part, such as methyl chlorocarbonate, methyl bromocarbonate, ethyl chlorocarbonate, propyl chlorocarbonate, isopropyl chlorocarbonate, butyl chlorocarbonate, t-butyl chlorocarbonate, pentyl chlorocarbonate, hexyl chlorocarbonate, heptyl chlorocarbonate, octyl chlorocarbonate, nonyl chlorocarbonate, decyl chlorocarbonate, undecyl chlorocarbonate, dodecyl chlorocarbonate, tridecyl chlorocarbonate and tetradecyl chlorocarbonate;

aryl and aralkyl halocarbonates having from 6 to 10 carbon atoms in the aryl part (which may be unsubstituted or may be substituted by at least one of substituents γ, as defined and exemplified above), such as phenyl chlorocarbonate, methylphenyl chlorocarbonate, fluorophenyl chlorocarbonate, chlorophenyl chlorocarbonate, methoxyphenyl chlorocarbonate and naphthyl chlorocarbonate;

alkanoyl and alkenoyl halides having from 2 to 20 carbon atoms, such as acetyl chloride, propionyl chloride, butyryl chloride, butyryl bromide, isobutyryl chloride, valeryl chloride, pivaloyl chloride, hexanoyl chloride, 3,3-dimethylbutyryl chloride, heptanoyl chloride, octanoyl chloride, nonanoyl chloride, decanoyl chloride, lauroyl chloride, myristoyl chloride, palmitoyl chloride, stearoyl chloride, icosanoyl chloride, acryloyl chloride, methacryloyl chloride, crotonoyl chloride and linolenoyl chloride;

anhydrides of alkanoic and alkenoic acids having from 2 to 20 carbon atoms, such as the mixed anhydride of formic acid and acetic acid, acetic anhydride, propionic anhydride, butanoic anhydride, valeric anhydride, pivalic anhydride, hexanoic anhydride, heptanoic anhydride, octanoic anhydride, nonanoic anhydride, decanoic anhydride, lauric anhydride, myristic anhydride, palmitic anhydride, acrylic anhydride, methacrylic anhydride, crotonic anhydride and linoleic anhydride;

arylcarboxylic acid halides having from 6 to 10 carbon atoms in the aryl part (which may be unsubstituted or may be substituted by at least one of substituents γ, as defined and exemplified above), such as benzoyl chloride, benzoyl bromide, benzoyl iodide, methylbenzoyl chloride, methoxybenzoyl chloride, fluorobenzoyl chloride, chlorobenzoyl chloride and naphthoyl chloride;

anhydrides of arylcarboxylic acids having from 6 to 10 carbon atoms in the aryl part (which may be unsubstituted or may be substituted by at least one of substituents , as defined and exemplified above), such as benzoic anhydride, methylbenzoic anhydride, methoxybenzoic anhydride, fluorobenzoic anhydride, chlorobenzoic anhydride and naphthoic anhydride;

cyclic acid anhydrides, such as succinic anhydride, glutaric anhydride, adipic anhydride, pimelic anhydride and suberic anhydride;

isocyanic acid and alkyl isocyanates having from 1 to 6 carbon atoms in the alkyl part, such as methyl isocyanate, ethyl isocyanate, propyl isocyanate, butyl isocyanate, pentyl isocyanate and hexyl isocyanate;

aryl and aralkyl isocyanates having from 6 to 10 carbon atoms in the aryl part (which may be unsubstituted or may be substituted by at least one of substituents γ, as defined and exemplified above), such as phenyl isocyanate, methylphenyl isocyanate, methoxyphenyl isocyanate, fluorophenyl isocyanate, chlorophenyl isocyanate and naphthyl isocyanate; and di-($C_1$–$C_6$alkyl)carbamoyl halides, such as N,N-dimethylcarbamoyl chloride, N-ethyl-N-methylcarbamoyl chloride, N,N-diethylcarbamoyl chloride, N,N-dipropylcarbamoyl chloride, N-isopropyl-N-methylcarbamoyl chloride, N,N-dibutylcarbamoyl chloride, N,N-dipentylcarbamoyl chloride and N,N-dihexylcarbamoyl chloride.

The reaction that acylates the hydroxy group can also be carried out by allowing the corresponding hydroxy compound to react with a carboxylic acid. There is no particular restriction on the nature of the carboxylic acids used, and that chosen will depend on the acyl group to be introduced. Examples of such carboxylic acids include: aliphatic carboxylic acids having from 2 to 20 carbon atoms which may be an alkanoic or alkenoic acid, such as acetic acid, propionic acid, butanoic acid, valeric acid, hexanoic acid, 3,3-dimethylbutanoic acid, heptanoic acid, octanoic acid, nonanoic acid, decanoic acid, lauric acid, myristic acid, palmitic acid, stearic acid, icosanoic acid, acrylic acid, methacrylic acid, crotonic acid and linoleic acid; monoalkyl esters of a dicarboxylic acid, such as t-butyl malonate, t-butyl succinate, t-butyl glutarate, t-butyl adipate, t-butyl pimelate and t-butyl suberate; and aryl carboxylic acids having from 6 to 10 carbon atoms in the aryl part (which may be unsubstituted or may be substituted by at least one of substituents γ, as defined and exemplified above), such as benzoic acid, methylbenzoic acid, methoxybenzoic acid, fluorobenzoic acid, chlorobenzoic acid and naphthoic acid). The reaction may be carried out in the same manner as when Z in Step 1 represents a hydroxy group. Where the acylation is carried out using a monoalkyl ester of a dicarboxylic acid, the resulting t-butyl ester compound can be treated with an acid in the same manner as in reaction (a) of Step 2 and thereby converted to the desired $C_2$–$C_7$ alkanoyloxy compound that has been substituted by a carboxy group.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from –10° C. to 50° C., more preferably from 0° C. to 30° C. The time required for the reaction may also vary widely, depending on many factors, notably the reaction temperature and the nature of the reagents and solvent employed. However, provided that the reaction is effected under the preferred conditions outlined above, a period of from 15 minutes to 20 hours, more preferably from 30 minutes to 10 hours, will usually suffice.

After completion of the reaction, the reaction product can be collected from the reaction mixture by conventional means. For example, if an insoluble substance is present, this is, when appropriate, separated from the reaction mixture by filtration; or if the reaction solution is acidic or alkaline, the reaction mixture is, when appropriate, neutralized; thereafter the same procedure as is used in Step 1 may be followed.

Reaction (c):

In this reaction, a protecting group for the nitrogen atom present in the group represented by $R^{1a}$ is removed. This reaction can be carried out by methods well known in the field of organic synthesis, although the nature of the reaction will vary depending on the type of protecting group.

When the protecting group for the nitrogen atom is an arylmethyl group or an arylmethoxycarbonyl group, the reaction can be carried out as described in reaction (a) of Step 2, where the protecting group for the hydroxy group is an arylmethyl group.

When the protecting group for the nitrogen atom is a t-butoxycarbonyl group, the reaction can be carried out as described in reaction (a) of Step 2, where the protecting group for the hydroxy group is a methoxymethyl group.

When the protecting group for the nitrogen atom is an alkoxycarbonyl group, it can be removed by reaction with a base. There is no particular restriction on the nature of the bases used, and any base commonly used in reactions of this type may equally be used here. Examples of such bases include: alkali metal hydroxides, such as lithium hydroxide, sodium hydroxide and potassium hydroxide; and alkali metal carbonates, such as sodium carbonate and potassium carbonate. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol and ethanol; ethers, such as tetrahydrofuran and dioxane; water; and mixtures of water and any one or more of these organic solvents. The product is then hydrolysed.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to 100° C., more preferably from room temperature to 60° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 hour to 16 hours, will usually suffice.

After completion of the reaction, the reaction product can be collected from the reaction mixture by a conventional method, for example as described in Step 1.

Reaction (d):

In this reaction a hydroxy group is converted to an amino group. The reaction can be carried out by the following sequence of steps: convert the hydroxy group to a sulfonyloxy group and then convert the sulfonyloxy group to an azido group; or convert the hydroxy group to a halogen atom (preferably a chlorine, bromine or iodine atom), convert the halogen atom to an azido group, and then reduce the azido group.

The reaction that converts the hydroxy group to a sulfonyloxy group can be carried out in the presence or absence of a base by treatment with a sulfonylating agent, for example an alkanesulfonyl halide having from 1 to 4 carbon atoms, such as methanesulfonyl chloride, methanesulfonyl bromide, ethanesulfonyl chloride and butanesulfonyl chloride; or an arylsulfonyl halide having from 6 to 10 carbon atoms in the aryl part (which may be unsubstituted or may be substituted by at least one of substituents γ, as defined and exemplified above), such as benzenesulfonyl chloride, benzenesulfonyl bromide, p-toluenesulfonyl chloride and naphthalenesulfonyl chloride. Of these, we prefer methanesulfonyl chloride, benzenesulfonyl chloride or p-toluenesulfonyl chloride. This reaction may be carried out in the same manner as reaction (b) of Step 2.

The reaction that converts the hydroxy group to a halogen atom can be carried out in the presence or absence of a base by treatment with a halogenating agent. There is likewise no particular restriction on the nature of the halogenating agents used, and any halogenating agent commonly used in reactions of this type may equally be used here. Examples of such halogenating agents include: thionyl halides, such as thionyl chloride or thionyl bromide; phosphorus oxyhalides, such as phosphorus oxychloride or phosphorus oxybromide; phosphorus halides, such as phosphorus trichloride, phosphorus tribromide, phosphorus triiodide, phosphorus pentachloride or phosphorus pentabromide; arylphosphine dihalides having from 6 to 10 carbon atoms in the aryl part (which may be unsubstituted or may be substituted by at least one of substituents γ, as defined and exemplified above), such as triphenylphosphine dichloride, triphenylphosphine dibromide or triphenylphosphine diiodide; mixtures of a triarylphosphine as defined and exemplified above [for example triphenylphosphine] and a carbon tetrahalide [for example carbon tetrachloride, carbon tetrabromide or carbon tetraiodide]; and mixtures of a triarylphosphine as defined and exemplified above[for example triphenylphosphine] and an N-halosuccinimide [for example N-chlorosuccinimide or N-bromosuccinimide]. Of these, we prefer the thionyl halides, phosphorus halides and arylphosphine dihalides; and most prefer thionyl chloride, phosphorus trichloride, phosphorus tribromide, triphenylphosphine dichloride, triphenylphosphine dibromide and triphenylphosphine diiodide. The reaction may be carried out in the same manner as in reaction (b) of Step 2.

The reaction that converts the sulfonyloxy group or halogen atom to an azido group can be carried out by allowing the corresponding compound to react with an alkali metal azide (preferably sodium azide or potassium azide). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as tetrahydrofuran and dioxane; and amides, such as dimethylformamide and N,N-dimethylacetamide. The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to 150° C., more preferably from room temperature to 100° C. The time required for the reaction may also vary widely, depending on many factors, notably the reaction temperature and the nature of the reagents and solvent employed. However, provided that the reaction is effected under the preferred conditions outlined above, a period of from 30 minutes to 20 hours, more preferably from 1 hour to 10 hours, will usually suffice.

The reaction for reducing the azido group can be carried out in the same manner as the reaction removing the hydroxy-protecting group in reaction (a) of Step 2 where the protecting group is an arylmethyl group or others, or as in reaction (e) of Step 2.

After completion of the reaction, each reaction product can be collected from reaction mixtures by conventional means, for example as described in Step 1.

Reaction (e):

In this reaction, the alkoxycarbonyl group represented by $R^{6a}$ is converted to a methyl group or the alkanoyl group represented by $R^{6a}$ is converted to an alkyl group. The reaction can be carried out by treatment with a reducing agent (preferably an alkali metal aluminum hydride, such as lithium aluminum hydride) in an inactive solvent (preferably an ether, such as diethyl ether, tetrahydrofuran or dioxane). The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to 100° C., more preferably from room temperature to 80° C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 hour to 16 hours, will usually suffice.

After completion of the reaction, each reaction product can be collected from reaction mixtures by conventional means, for example as described in Step 1.

Reaction (f):

In this reaction the =NH group which may be included in the group represented by $R^{1a}$ is alkylated. The reaction can be carried out by treatment with an alkylating agent in the presence of a base in the same manner as in reaction (b) of Step 2. There is no particular restriction on the nature of the alkylating agents used, and any alkylating agent commonly used in reactions of this type may equally be used here. Examples of such alkylating agents include: alkyl halides having from 1 to 6 carbon atoms, such as methyl iodide, ethyl iodide, propyl iodide, butyl iodide, pentyl iodide and hexyl iodide. There is likewise no particular restriction on the nature of the bases used, and any base commonly used in reactions of this type may equally be used here. Examples of such bases include: alkali metal carbonates, such as potassium carbonate and sodium carbonate; and alkali metal hydrides, such as sodium hydride.

Reaction (g):

In this reaction a cyano group is converted to a carbamoyl group. The reaction can be carried out by allowing the corresponding compound to react with a base. There is no particular restriction on the nature of the bases used, and any base commonly used in reactions of this type may equally be used here. Examples of such bases include: alkali metal hydroxides, such as sodium hydroxide and potassium hydroxide; and alkali metal carbonates, such as sodium carbonate and potassium carbonate. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aqueous alcohols, such as aqueous methanol or aqueous ethanol, aqueous ethers, such as aqueous diethyl ether, aqueous tetrahydrofuran or aqueous dioxane; and water. Of these, we prefer the aqueous alcohols.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 10° C. to 200° C., more preferably from 50° C to 150° C. The time required for the reaction may also vary widely, depending on many factors, notably the reaction temperature and the nature of the reagents and solvent employed. However, provided that the reaction is effected under the preferred conditions outlined above, a period of from 30 minutes to 48 hours, more preferably from 1 hour to 20 hours, will usually suffice.

After completion of the reaction, the desired compound can be collected from the reaction mixture by conventional means. For example, one suitable recovery technique comprises: neutralizing the reaction mixture, if appropriate; or if an insoluble substance is present, removing the insoluble substance by filtration; adding a water-immiscible organic solvent, such as ethyl acetate; washing with water; and then removing the solvent. The desired compound thus obtained may, if necessary, be further purified by conventional methods, for example, recrystallization, re-precipitation or chromatography.

Compounds of formula (I) may be converted to salts thereof, preferably the pharmaceutically acceptable salts, by treatment with an acid by conventional means, for example by allowing a compound of formula (I) to react with the corresponding acid in a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran and dioxane; alcohols, such as methanol and ethanol; or halogenated hydrocarbons, such as methylene chloride and chloroform. The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at about room temperature. The time required for the reaction may also vary widely, depending on many factors, notably the reaction temperature and the nature of the reagents and solvent employed. However, provided that the reaction is effected under the preferred conditions outlined above, a period of from 5 minutes to 1 hour will usually suffice.

An alternative method of obtaining the hydrochloride is as follows: allow a compound of formula (I) or a salt thereof to be adsorbed on an acidic resin column (for example CM-Sephadex C-25 [trade mark]), and elute the column with dilute hydrochloric acid.

Esters of the compounds of the present invention may also be prepared by methods well known in the art, and no special techniques are required.

One of the starting materials, the compound of formula (II) can be manufactured by an well known method (EP 1759; EP 398 326; and EP 600 717).

BIOLOGICAL ACTIVITY

The compounds of formula (I) have both serotonin 2 receptor antagonistic action and squalene synthase inhibitory action, which are persistent in effect, and which have a proplonged serotonin 2 receptor antagonistic action in vivo. They also have a minimal adrenaline $\alpha_1$ antagonistic effect, and a very low toxicity. Therefore, the compounds of formula (I) useful for the therapy or prophylaxis (preferably for the therapy) of thrombotic or arteriosclerotic diseases since these compounds are effective to antagonize serotonin 2 receptors distributed in vascular endothelial cells or platelets and to inhibit platelet aggregation. They are also useful for the therapy or prophylaxis (preferably for the therapy) of various diseases (for example coronary artery disease or cerebrovascular disease) resulting from the above diseases. In addition, they are useful for the therapy or prophylaxis of hyperlipidemic and arteriosclerotic diseases since these compounds are effective to reduce cholesterol levels. In particular, they are extremely useful for the therapy or prophylaxis (preferably for the therapy) of arteriosclerotic diseases since these compounds are effective both to antagonize serotonin 2 receptors and to reduce cholesterol levels.

The biological activity of the compounds of the present invention is illustrated by the following Tests.

Test 1

Vasoconstriction experiment

Effects on smooth muscle contraction were examined by the method of Van Neuten et al. [J. Pharmacol. Exp. Ther., 218, 217–230, (1981)]. Male SD rats, each weighing approximately 500 g, were sacrificed by exsanguination, and the tail artery was excised from each animal. Adherent tissues were removed from the artery for preparation of a helical strip of dimensions about 2×20 mm. The strip was suspended in an organ bath kept at 37° C. and containing 10 ml of Tyrode's solution saturated with a mixed gas (95% $O_2$/5% $CO_2$) and equilibrated for 1 hour before used in the experiment. An initial tension of 0.5 g was loaded on the helical strip, and changes in tension were recorded in an isometric manner via a transducer. $3 \times 10^{-6}$M of serotonin was added to the bath as a vasoconstriction inducer, and, after stabilisation of the contractile response of the specimen, a test compound was added to the bath so as to increase the level of test compound in the bath progressively, whilst monitoring the tension in the helical strip. $10^{-4}$M of papaverine was then added. On the assumption that the tension before the addition of each test compound was 100% and that the tension 5 minutes after the addition of papaverine was 0%, the concentration of each test compound required to reduce the tension to 50% ($IC_{50}$) was calculated from the least square regression line. The results are shown in Table 2.

TABLE 2

Test 2

| Compound of Example No. | $IC_{50}$ nM |
|---|---|
| 1 | 1.9 |
| 2 | 2.0 |
| 4 | 2.3 |
| 6 | 2.2 |
| 7 | 2.6 |

Receptor-binding experiment

The method of Leysen et al. [Mol. Pharmacol., 21, 301–314, (1982)] was employed. Male Wistar rats (body weight 280–320 g) were used in this experiment. The head of each animal was severed, and the cerebral cortex and corpus striatum were excised. These organs were frozen on dry ice and stored at −80° C. until used. Binding to serotonin receptors was examined using the cerebral cortex. To prepare a membrane suspension, the frozen brain tissue was homogenised with 50 mM Tris-HCl buffer (pH 7.7) using Polytron PT-20, and the homogenate was centrifuged at 49,000×g for 10 minutes. The resulting pellet was suspending in a Tris buffer, centrifuged, and resuspended in Tris buffer. The content of protein in the membrane suspension thus prepared was determined, and adjusted to 0.57 mg/protein/ml with Tris buffer. The membrane suspension was stored at −80° C.

The receptor-binding reaction was started by adding 440 μl of the membrane suspension to a test tube containing 50 μl of $^3$H-ligand and 10 μl of each test compound (dissolved in dimethyl sulfoxide). After incubation at 30° C. for 1 hour, the reaction was terminated by filtration under reduced pressure using a Whatman GF/B glass filter. The filter was washed with ice-cooled Tris buffer (4 ml×2 times). The filter was then treated with ACS-II, and its radioactivity was determined with a liquid scintillation counter. Non-specific binding was determined in the presence of 20 μM atropine. The percent inhibition of receptorbinding was determined from the percent binding in the presence of each test compound. The concentration of each test compound required to inhibit the binding by 50% ($IC_{50}$) was calculated from the least square regression line. The result are shown in Table 3.

TABLE 3

Test 3

| Compound of Example No. | $IC_{50}$ nM |
|---|---|
| 1 | 1.0 |
| 2 | 0.8 |
| 4 | 0.65 |
| 6 | 3.4 |
| 7 | 0.75 |

Squalene synthase inhibitory activity

Squalene synthase inhibitory activity was determined by the method described in U.S. Pat. No. 5,102,907; Anal. Biochem. 203, 310 (1992).

The reaction to squalene synthase was examined under anaerobic conditions, using a tube of dimensions 16×110 mm, containing a reaction solution having the following composition:

Each 100 μl of reaction solution (one assay) contained 50 mM $KH_2PO_4/K_2HPO_4$ (pH 7.5: potassium dihydrogenphosphate-dipotassium hydrogenphosphate buffer), 10 mM NaF (sodium fluoride), 10 mM $MgCl_2$ (magnesium chloride), 2 mM DTT (dithiothreitol), 50 mM ascorbic acid, 20 units/ml ascorbic acid oxidase, 1 mM NADPH (nicotinamide adenine dinucleotide phosphate), 10 μM [4-$^{14}$C]-FPP (farnesyl pyrophosphoric acid; 58 μCi/μmol), 60 μg/ml rat liver microsome suspension, and a solution of inhibitor (5 μl of each test compound in methanol or water).

The reaction was started by the addition of rat liver microsome suspension. The reaction solution was then incubated in a thermostat at 37° C. for 20 minutes, after which the reaction was terminated by the addition of 100 μl of a 1:1 by volume mixture of 40% KOH (aqueous potassium hydroxide) and 95% EtOH (aqueous ethanol). The reaction solution thus treated was further heated at 65° C. for 30 minutes, and then cooled. Squalene was extracted with 2 ml of hexane. One milliliter of the resulting hexane layer was mixed with 10 ml of scintillator, and radioactivity was determined using a liquid scintillation counter.

The inhibitory activity of each test compound for the enzyme was determined by co-incubation of the sample containing the test compound with the enzyme sample and substrate in the reaction solution.

Table 4 shows the 50% inhibitory concentration of each test compound ($IC_{50}$).

TABLE 4

| Compound of Example No. | $IC_{50}$ μM |
|---|---|
| 4 | 1.6 |
| 5 | 0.74 |
| 6 | 1.1 |
| 12 | 1.5 |

From the above data, it can be seen clearly that the compounds of the present invention have excellent serotonin 2 receptor antagonist activity, combined with the ability to inhibit the activity of squalene synthase.

Compounds of formula (I) and pharmaceutically acceptable salts and esters, when used as a therapeutic or prophylactic drugs for the above-mentioned diseases, may be administered by themselves or in admixture with a pharmaceutically acceptable additive, for example an excipient or diluent by any suitable route, for example the oral route (e.g. in the form of a tablet, capsule, granule, powder or syrup) or the parenteral route (e.g. in the form of an injection).

These dosage forms can be manufactured by a well-known method, using additives such as an excipient (for example, sugar derivatives such as lactose, saccharose, glucose, mannit and sorbit; starch derivatives such as corn starch, potato starch, α-starch, dextrin and carboxymethyl starch; cellulose derivatives such as crystalline cellulose, poorly substituted hydroxypropyl cellulose, hydroxypropylmethyl cellulose, carboxymethyl cellulose, carboxymethyl cellulose calcium and internally cross-linked carboxymethyl cellulose sodium; gum arabic; dextran; pullulan; silicate derivatives such as light silicic acid anhydride, synthetic aluminium silicate and magnesium aluminate metacilicate; phosphate derivatives such as calcium phosphate; carbonate derivatives such as calcium carbonate; sulfate derivatives such as calcium sulfate), a binder (for example said excipients; gelatin; polyvinyl pyrrolidone; macrogol), a disintegrating agent (for example said excipients; chemically modified starch or cellulose derivatives such as cross carmellose sodium, carboxymethyl starch sodium and cross-linked polyvinyl pyrrolidone), a fabricating agent (for example talc; stearic acid; metal stearates such as calcium stearate and magnesium stearate; colloid silica; lax such as bee gum and spermaceti; boric acid; glycol; carboxylic acids such as fumaric acid and adipic acid; sodium carboxylates such as sodium benzoate; sulfates such as sodium sulfate; leucine; lauryl sulfates such as sodium lauryl sulfate and magnesium lauryl sulfate; silicic acids such as silicic acid anhydride and silicic acid hydrate; starch derivatives used in said excipients), an stabilizer (for example paraoxy benzoate esters such as methylparaben and propylparaben; alcohol such as chlorobutanol, benzylalcohol and phenylethylalcohol; benzalkonium chloride; phenols such as phenol and cresol; thimerosal; acetic acid anhydride; sorbic acid), a flavor (for example commonly used edulcorant, acidifier, perfume), a diluent, and a solvent for injection (for example water, ethanol, glycerin). The recommended daily dosage in adults, although depending on symptoms, age and others, ranges from 1 mg (preferably 10 mg) to 2000 mg (preferably 400 mg) for oral administration, and from 0.1 mg (preferably 1 mg) to 500 mg (preferably 300 mg) for intravenous administration. The dosage should be administered in one to six divided doses per day, according to symptoms.

The preparation of the compounds of the present invention is further illustrated by the following non-limiting Examples. The preparation of certain of the starting materials used in these Examples is illustrated by the subsequent Preparations.

EXAMPLE 1

(2R,4R)-2-[2-{4-Fluoro-2-[2-(3 -methoxyphenyl)ethyl] phenoxy}ethyl]-4-hydroxy-1-methylpyrrolidine hydrochloride 1(a) (2R,4R)-1-Ethoxycarbonyl-2-[2-{4-fluoro-2-[2-(3-methoxyphenyl)ethyl]phenoxy}ethyl]-4-hydroxypyrrolidine 399 mg of 4-fluoro-2-[2-(3-methoxyphenyl)ethyl]phenol (prepared as described in Preparation 4) were dissolved in 8 ml of N,N-dimethylacetamide, and then 363 mg of potassium t-butoxide and 718 mg of (2S,4R)-2-(2-chloroethyl)-1-ethoxycarbonyl-4-hydroxypyrrolidine were added, whilst ice-cooling, to the resulting solution. The resulting mixture was then stirred at 40° C. for 5 hours. At the end of this time, 50 ml of ethyl acetate were added, and the reaction mixture was washed with water and with a saturated aqueous solution of sodium chloride, in that order. The ethyl acetate layer was dried over anhydrous magnesium sulfate, and then concentrated by evaporation under reduced pressure. The resulting oily substance was purified by silica gel column chromatography, using a 3:7 by volume mixture of hexane and ethyl acetate as the eluent, to give 535 mg (yield 76%) of the title compound as a colorless oily substance.

Nuclear Magnetic Resonance Spectrum (270 MHz, CDCl$_3$) δ ppm:

1.1–1.35 (3H, multiplet);
1.75–2.3 (3H, multiplet);
2.3–2.6 (1H, multiplet);
2.75–3.0 (4H, multiplet);
3.4–3.8 (1H, multiplet);
3.45 (1H, doublet of doublets, J=4.3 & 11.9 Hz);
3.79 (3H, singlet);
3.9–4.3 (5H, multiplet);
4.35–4.5 (1H, multiplet);
6.8–6.9 (6H, multiplet);
7.15–7.25 (1H, multiplet).

1(b) (2R,4R)-2-[2-{4-Fluoro-2-[2-(3-methoxyphenyl)ethyl] phenoxy}ethyl]-4-hydroxy-1-methylpyrrolidine 201 mg of (2R,4R)-2-[2-{4-fluoro-2-[2-(3-methoxyphenyl)ethyl]phenoxy}-ethyl]-1-ethoxycarbonyl-4-hydroxypyrrolidene [prepared as described in step (a) above] were dissolved in 4 ml of tetrahydrofuran, and the resulting solution was added dropwise to a suspension of 53 mg of lithium aluminum hydride in 4 ml of tetrahydrofuran, whilst ice-cooling and stirring. The mixture was then heated under reflux for 30 minutes. At the end of this time, the reaction mixture was cooled on ice, and sodium sulfate decahydrate was added to decompose the excess hydride. Any insoluble substance was removed by filtration, and the filtrate was concentrated by evaporation under reduced pressure. The concentrate was purified by silica gel column chromatography, using a 4:1 by volume mixture of methylene chloride and methanol as the eluent, to give 139 mg (yield 80%) of the title compound as a colorless oily substance.

Nuclear Magnetic Resonance Spectrum (270 MHz, CDCl$_3$) δ ppm:

1.75–2.2 (3H, multiplet);
2.2–2.4 (1H, multiplet);
2.40 (1H, doublet of doublets, J=4.5 & 10.8 Hz);
2.51 (3H, singlet);
2.75–3.05 (5H, multiplet);
3.62 (1H, doublet of doublets, J=6.0 & 10.8 Hz);
3.79 (3H, singlet);
3.9–4.1 (2H, multiplet);
4.4–4.55 (1H, multiplet);
6.7–6.9 (6H, multiplet);
7.15–7.25 (1H, multiplet).

1(c) (2R,4R)-2-[2-{4-Fluoro-2-[2-(3-methoxyphenyl)ethyl] phenoxy}ethyl]-4-hydroxy-1-methylpylrrolidine hydrochloride 246 mg of (2R,4R)-2-[2-{4-fluoro-2-[2-(3-methoxyphenyl)ethyl]phenoxy}ethyl]-4-hydroxy-1-methylpyrrolidine [prepared as described in step (b) above] were dissolved in 5 ml of ethyl acetate, and 0.25 ml of a 4N solution of hydrogen chloride in ethyl acetate were added to the resulting solution. The mixture was then allowed to stand at room temperature for about 10 minutes. The crystals which precipitated were collected by filtration, and dried in vacuo, to give 210 mg (yield 78%) of the title compound as colorless crystals, melting at 128°–129° C.

Nuclear Magnetic Resonance Spectrum (270 MHz, CDCl$_3$) δ ppm:

2.0–2.2 (1H, multiplet);
2.3–2.65 (2H, multiplet);
2.33 (1H, doublet of doublets, J=5.9 & 13.8 Hz);
2.75–3.0 (4H, multiplet);
2.89 (3H, singlet);
2.99 (1H, doublet, J=12.3 Hz);
3.78 (3H, singlet);
3.8–4.2 (4H, multiplet);
4.55–4.7 (1H, multiplet);
6.65–6.8 (4H, multiplet);
6.8–6.9 (2H, multiplet);
7.21 (1H, triplet, J=7.8 Hz).

EXAMPLE 2

(2R,4R)-2-[2-{4-Fluoro-2-[2-(4-fluorophenyl)ethyl]phenoxy}ethyl]-4-hydroxy-1-methylpyrrolidine hydrochloride 2(a) (2R,4R)-1-t-Butoxycarbonyl-4-t-butyldimethylsilyoxy-2-[2-{4-fluoro-2-[2-(4-fluorophenyl)ethyl]phenoxy}ethyl]pyrrolidine 248 mg of 4-fluoro-2-[2-(4-fluorophenyl)ethyl]phenol (prepared as described in Preparation 6) were dissolved in 10 ml of N,N-dimethylacetamide, and then 125 mg of potassium t-butoxide and 405 mg of (2S,4R)-1-t-butoxycarbonyl-4-t-butyldimethylsilyloxy-2-(2-chloroethyl)pyrrolidine were added to the resulting solution, whilst ice-cooling. The resulting mixture was then stirred at room temperature for 3 hours, after which 150 ml of ethyl acetate were added to the reaction mixture. The reaction mixture was then washed with water and with a saturated aqueous solution of sodium chloride, in that order. The ethyl acetate layer was dried over anhydrous magnesium sulfate, and then concentrated by evaporation under reduced pressure. The resulting oily substance was purified by silica gel column chromatography, using a 4:1 by volume mixture of hexane and ethyl acetate as the eluent, to give 433 mg (yield 73%) of the title compound as a colorless oily substance.

Nuclear Magnetic Resonance Spectrum (270 MHz, CDCl$_3$) δ ppm:

0.02 (3H, singlet);
0.03 (3H, singlet);
0.84 (9H, singlet);
1.46 (9H, singlet);
1.7–1.9 (2H, multiplet);
2.0–2.15 (1H, multiplet);
2.25–2.5 (1H, multiplet);
2.75–2.95 (4H, multiplet);
3.3–3.7 (2H, multiplet);
3.9–4.2 (3H, multiplet);
4.25–4.4 (1H, multiplet);
6.7–7.0 (5H, multiplet);
7.05–7.2 (2H, multiplet).

2(b) (2R,4R)-2-[2-{4-Fluoro-2-[2-(4-fluorophenyl)ethyl]phenoxy}ethyl]-4-hydroxy-1-methylpyrrolidine 398 mg of (2R,4R)-1-t-butoxycarbonyl-4-t-butyldimethylsilyloxy-2-[2-{4-fluoro-2-[2-(4-fluorophenyl)ethyl]phenoxy}ethyl]pyrrolidine [prepared as described in step (a) above] were dissolved in 10 ml of tetrahydrofiran, and the resulting solution was added dropwise to a suspension of 81 mg of lithium aluminum hydride in 10 ml of tetrahydrofuran, whilst ice-cooling and stirring. The resulting mixture was then heated under reflux for 1 hour. At the end of this time, the reaction mixture was cooled on ice, and sodium sulfate decahydrate was added in order to decompose any excess hydride. Insoluble substances were removed by filtration, and the filtrate was concentrated by evaporation under reduced pressure. The concentrate was then purified by silica gel column chromatography, using a 7:3 by volume mixture of methylene chloride and methanol as the eluent, to give 151 mg (yield 59%) of the title compound as a colorless oily substance.

Nuclear Magnetic Resonance Spectrum (270 MHz, CDCl$_3$) δ ppm:

1.6–1.8 (1H, multiplet);
1.8–2.0 (2H, multiplet);
2.1–2.3 (2H, multiplet);
2.34 (3H, singlet);
2.6–2.75 (1H, multiplet);
2.8–2.95 (4H, multiplet);
3.49 (1H, doublet of doublets, J=6.3 & 10.2 Hz);
3.85–4.05 (2H, multiplet);
4.35–4.5 (1H, multiplet);
6.7–6.9 (3H, multiplet);
6.9–7.0 (2H, multiplet);
7.05–7.2 (2H, multiplet).

2(c) (2R,4R)-2-[2-{4-Fluoro-2-[2-(4-fluorophenyl)ethyl]phenoxy}ethyl]-4-hydroxy-1-methylpyrrolidine hydrochloride 138 mg of (2R,4R)-2-[2-{4-fluoro-2-[2-(4-fluorophenyl)ethyl]phenoxy}ethyl]-4-hydroxy-1-methylpyrrolidine [prepared as described in step (b) above] were dissolved in 4 ml of ethyl acetate, and then 0.15 ml of a 4N solution of hydrogen chloride in ethyl acetate was added to the resulting solution, and the solution was concentrated by evaporation under reduced pressure. The resulting oily substance was dissolved in 5 ml of ethyl acetate, and the resulting solution was allowed to stand at room temperature for about 10 minutes. The crystals which precipitated were collected by filtration, and dried in vacuo, to give 66 mg (yield 43%) of the title compound as colorless crystals, melting at 70°–73° C.

Nuclear Magnetic Resonance Spectrum (270 MHz, CDCl$_3$) δ ppm:

2.0–2.2 (1H, multiplet);
2.25–2.65 (3H, multiplet);
2.78 (4H, singlet);
2.84 (3H, singlet);
2.99 (1H, doublet, J=12.4 Hz);
3.7–3.9 (1H, multiplet);
3.9–4.2 (3H, multiplet);
4.55–4.7 (1H, multiplet);
6.7–7.05 (5H, multiplet);
7.05–7.2 (2H, multiplet).

EXAMPLE 3

(2R,4R)-2-[2-{4-Fluoro-2-[2-(4-fluorophenyl)ethyl]phenoxy}ethyl]-4-hydroxypyrrolidine hydrochloride 3(a) (2R,4R)-1-t-Butoxycarbonyl-2-[2-{4-fluoro-2-[2-(4-fluorophenyl)ethyl]phenoxy}ethyl]-4-hydroxypvrrolidine 687 mg of 4-fluoro-2-[2-(4-fluorophenyl)ethyl]phenol (prepared as described in Preparation 6) were dissolved in 12 ml of N,N-dimethylacetamide, and then 212 mg of potassium t-butoxide were added to the resulting solution, whilst ice-cooling. The resulting mixture was then stirred for 10 minutes, after which 687 mg of (2S,4R)-2-(2-chloroethyl)-1-t-butoxycarbonyl-4-t- butyldimethylsilyloxypyrrolidine were added. The resulting mixture was then stirred at room temperature for 14 hours. At the end of this time, 135 mg of potassium t-butoxide were added to the reaction mixture, and the mixture was stirred at 40° C. for 4 hours, after which 300 ml of ethyl acetate were added. The resulting reaction mixture was washed with water and with a saturated aqueous solution of sodium chloride, in that order. The ethyl acetate layer was separated and dried over anhydrous magnesium sulfate. It was then concentrated by evaporation under reduced pressure. The resulting oily substance was purified by silica gel column chromatography, using a 2:3 by volume mixture of hexane and ethyl acetate as the eluent, to give 571 mg (yield 74%) of the title compound as a colorless oily substance.

Nuclear Magnetic Resonance Spectrum (270 MHz, CDCl$_3$) δ ppm:

1.45 (9H, singlet);
1.7–2.05 (2H, multiplet);
2.1–2.25 (1H, multiplet);
2.3–2.55 (1H, multiplet);
2.85 (4H, singlet);
3.4–3.7 (1H, multiplet);
3.42 (1H, doublet of doublets, J=4.4 & 11.9 Hz);
3.9–4.05 (2H, multiplet);
4.1–4.25 (1H, multiplet);
4.35–4.5 (1H, multiplet);
6.7–6.9 (3H, multiplet);
6.9–7.0 (2H, multiplet);
7.05–7.2 (2H, multiplet).

3(b) (2R,4R)-2-[2-{4-Fluoro-2-[2-(4-fluorophenyl)ethyl] phenoxy}ethyl]-4-hydroxyprrolidine hydrochloride 570 mg of (2R,4R)-1-t-butoxycarbonyl-2-[2-{4-fluoro-2-[2-(4-fluorophenyl)ethyl]phenoxy}ethyl]-4-hydroxypyrrolidine [prepared as described in step (a) above] were dissolved in 5 ml of ethyl acetate, and then 5 ml of a 4N solution of hydrogen chloride in ethyl acetate were added to the resulting solution. The resulting mixture was then stirred at room temperature for 30 minutes. At the end of this time, the crystals which precipitated were collected by filtration, washed with ethyl acetate, and dried in vacuo, to give 381 mg (yield 78%) of the title compound as colorless crystals, melting at 186°–187° C.

Nuclear Magnetic Resonance Spectrum (270 MHz, hexadeuterated dimethyl sulfoxide) δ ppm:

1.65–1.85 (1H, multiplet);
2.0–2.4 (3H, multiplet);
2.82 (4H, singlet);
3.01 (1H, doublet, J=12.2 Hz);
3.3–3.45 (1H, multiplet);
3.8–4.0 (1H, multiplet);
4.06 (2H, triplet, J=6.1 Hz);
4.35–4.45 (1H, multiplet);
5.41 (1H, doublet, J=3.0 Hz);
6.9–7.15 (5H, multiplet);
7.2–7.3 (2H, multiplet).

EXAMPLE 4

(2R,4R)-2-[2-{4-Fluoro-2-[2-(4-fluoro-3-methoxyphenyl) ethyl]phenoxy}ethyl]-4-hydroxy-1-methylpyrrolidine hydrochloride 4(a) (2R,4R)-1-Ethoxycarbonyl-2-[2-{4-fluoro-2-[2-(4-fluoro-3-methoxyphenyl)ethyl]phenoxy}ethyl]-4-hydroxypvrrolidine 622 mg of 4-fluoro-2-[2-(4-fluoro-3-methoxyphenyl) ethyl]phenol (prepared as described in Preparation 5) were dissolved in 7 ml of N,N-dimethylacetamide. The resulting solution was allowed to react with 343 mg of potassium t-butoxide and 678 mg of (2S,4R)-2-(2-chloroethyl)-1-ethoxycarbonyl-4-hydroxypyrrolidine and extracted in the same manner as described in step (a) of Example 1. The resulting oily substance was purified by silica gel column chromatography, using a 2:3 by volume mixture of hexane and ethyl acetate as the eluent, to give 552 mg (yield 52%) of the title compound as a colorless oily substance.

Nuclear Magnetic Resonance Spectrum (270 MHz, CDCl$_3$) δ ppm:

1.1–1.35 (3H, multiplet);
1.7–1.95 (1H, multiplet);
1.96 (1H, doublet of doublets, J=4.9 & 7.2 Hz);
2.05–2.25 (1H, multiplet);
2.25–2.65 (1H, multiplet);
2.75–2.95 (4H, multiplet);
3.45 (1H, doublet of doublets, J=4.3 & 12.0 Hz);
3.45–3.8 (1H, multiplet);
3.83 (3H, singlet);
3.85–4.05 (1H, multiplet);
4.05–4.3 (3H, multiplet);
4.35–4.5 (1H, multiplet);
6.6–6.9 (5H, multiplet);
6.96 (1H, doublet of doublets, J=8.0 & 11.3 Hz).

4(b) (2R,4R)-2-[2-{4-Fluoro-2-[2-(4-fluoro-3-methoxyphenyl)ethyl]phenoxy}ethyl]-4-hydroxy-1-methylpyrrolidine 551 mg of (2R,4R)-1-ethoxycarbonyl-2-[2-{4-fluoro-2-[2-(4-fluoro-3-methoxyphenyl)ethyl]phenoxy}ethyl]-4-hydroxypyrrolidine [prepared as described in step (a) above], 20 ml of tetrahydrofuran and 140 mg of lithium aluminum hydride were allowed to react together and subsequently treated in the same manner as described in step (b) of Example 1. The concentrate thus obtained was purified by silica gel column chromatography, using a 3:2 by volume mixture of methylene chloride and methanol as the eluent, to give 405 mg (yield 84%) of the title compound as a colorless oily substance.

Nuclear Magnetic Resonance Spectrum (270 MHz, CDCl$_3$) δ ppm:

1.65–2.1 (3H, multiplet);
2.1–2.3 (1H, multiplet);
2.25 (1H, doublet of doublets, J=5.2 & 10.3 Hz);
2.39 (3H, singlet);
2.6–2.8 (1H, multiplet);
2.8–3.0 (4H, multiplet);
3.50 (1H, doublet of doublets, J=6.2 & 10.3 Hz);
3.84 (3H, singlet);
3.85–4.05 (2H, multiplet);
4.35–4.5 (1H, multiplet);
6.65–7.05 (6H, multiplet).

4(c) (2R,4R)-2-[2-{4-Fluoro-2-[2-(4-fluoro-3-methoxyphenyl)ethyl]phenoxy}ethyl]-4-hydroxy-1-methylpyrrolidine hydrochloride 399 mg of the (2R,4R)-2-[2-{4-fluoro-2-[2-(4-fluoro-3-methoxyphenyl)ethyl]phenoxy}ethyl]-4-hydroxy-1-methylpyrrolidine [prepared as described in step (b) above] were dissolved in 5 ml of ethyl acetate. Addition of 0.38 ml of a 4N solution of hydrogen chloride in ethyl acetate resulted in the precipitation of crystals. The solvent was removed by evaporation under reduced pressure, and the resulting solid substance was dissolved in a small quantity (approximately 0.5 ml) of methylene chloride and then 5 ml of ethyl acetate were added to the resulting solution. The resulting mixture was then allowed to stand at room temperature for about 10 minutes. The crystals which precipitated were collected by filtration, and dried in vacuo, to give 359 mg (yield 82%) of the title compound as colorless crystals, melting at 128–130° C.

Nuclear Magnetic Resonance Spectrum (400 MHz, hexadeuterated dimethyl sulfoxide+$D_2O$) δ ppm:

- 1.8–2.0 (1H, multiplet);
- 2.0–2.2 (1H, multiplet);
- 2.20 (1H, doublet of doublets, J=6.0 & 13.7 Hz);
- 2.4–2.55 (1H, multiplet);
- 2.7–3.0 (4H, multiplet);
- 2.89 (3H, singlet);
- 2.97 (1H, doublet, J=12.5 Hz);
- 3.6–3.9 (2H, multiplet);
- 3.80 (3H, singlet);
- 3.95–4.15 (2H, multiplet);
- 4.3–4.45 (1H, multiplet);
- 6.7–6.8(1H, multiplet);
- 6.9–7.15 (5H, multiplet).

EXAMPLE 5
(2R,4R)-2-{2-[4-Fluoro-2-(2-phenylethyl)phenoxy]ethyl}-4-hydroxypyrrolidine hydrochloride 5(a) (2R,4R)-1-t-Butoxycarbonyl-4-t-butyldimethylsilyloxy-2-{2-[4-fluoro-2-(2-phenylethyl)phenoxy]ethyl}pyrrolidine 1090 mg of 4-fluoro-2-(2-phenylethyl)phenol (prepared as described in Preparation 3), 1870 mg of (2S,4R)-2-(2-bromoethyl)-1-t-butoxycarbonyl-4-t-butyldimethylsilyloxypyrrolidine and 566 mg of potassium t-butoxide were allowed to react together in 10 ml of N,N-dimethylacetamide, and the resulting mixture was extracted in the same manner as described in step (a) of Example 2. The resulting oily substance was purified by silica gel column chromatography, using a 5:1 by volume mixture of hexane and ethyl acetate as the eluent, to give 2090 mg (yield 84%) of the title compound as a colorless oily substance.

Nuclear Magnetic Resonance Spectrum (270 MHz, $CDCl_3$) δ ppm:

- 0.02 (3H, singlet);
- 0.03 (3H, singlet);
- 0.84 (9H, singlet);
- 1.45 (9H, singlet);
- 1.7–1.95 (2H, multiplet);
- 2.0–2.15 (1H, multiplet);
- 2.25–2.5 (1H, multiplet);
- 2.8–2.95 (4H, multiplet);
- 3.3–3.65 (1H, multiplet);
- 3.35 (1H, doublet of doublets, J=4.5 & 11.0 Hz);
- 3.85–4.2 (3H, multiplet);
- 4.25–4.4 (1H, multiplet);
- 6.7–6.9 (3H, multiplet);
- 7.15–7.35 (5H, multiplet).

5(b) (2R,4R)-2-{2-[4-fluoro-2-(2-phenylethyl)phenoxy]ethyl}-4-hydroxypyrrolidine hydrochloride 600 mg of (2R,4R)-1-t-butoxycarbonyl-4-t-butyldimethylsilyloxy-2-{2-[4-fluoro-2-(2-phenylethyl)phenoxy]ethyl}pyrrolidine [prepared as described in step (a) above] were dissolved in 5 ml of dioxane, and then 5 ml of a 4N solution of hydrogen chloride in dioxane were added to the resulting solution. The resulting mixture was then allowed to stand at room temperature for 1 hour. At the end of this time, the solvent was removed by evaporation under reduced pressure. The resulting solid substance was dissolved in a small quantity of a mixture of methylene chloride and methanol, and then 10 ml of ethyl acetate were added thereto, and the solution was allowed to stand at room temperature for about 10 minutes. The crystals which precipitated were collected by filtration, and dried in vacuo, to give 270 mg (yield 67%) of the title compound as colorless crystals, melting at 151–152° C.

Nuclear Magnetic Resonance Spectrum (270 MHz, $CD_3OD$) δ ppm:

- 1.8–2.0 (1H, multiplet);
- 2.1–2.4 (3H, multiplet);
- 2.8–3.0 (4H, multiplet);
- 3.22 (1H, doublet, J=12.4 Hz);
- 3.46 (1H, doublet of doublets, J=4.1 & 12.4 Hz);
- 4.0–4.2 (3H, multiplet);
- 4.5–4.6 (1H, multiplet);
- 6.8–7.0 (3H, multiplet);
- 7.1–7.3 (5H, multiplet).

EXAMPLE 6
(2R,4R)-2-{2-[4-Fluoro-2-(2-phenylethyl)phenoxy]ethyl}-4-hydroxy-1-methylpyrrolidine hydrochloride 6(a) (2R,4R)-1-t-Butoxycarbonyl-2-{2-[4-fluoro-2-(2-phenylethyl)phenoxy]ethyl}-4-hydroxypyrrolidine 1490 mg of (2R,4R)-1-t-butoxycarbonyl-4-t-butyldimethylsilyloxy-2-{2-[4-fluoro-2-(2-phenylethyl)phenoxy]ethyl}pyrrolidine [prepared as described in Example 5(a)] were dissolved in 15 ml of tetrahydrofuran, and then 0.79 ml of tetrabutylammonium fluoride were added to the resulting solution. The resulting mixture was then stirred at room temperature for 0.5 hours. At the end of this time, the reaction solution was concentrated by evaporation under reduced pressure, and the resulting concentrated oily substance was purified by silica gel column chromatography, using a 1:1 by volume mixture of hexane and ethyl acetate as the eluent, to give 1115 mg (yield 95%) of the title compound as a colorless solid substance.

Nuclear Magnetic Resonance Spectrum (270 MHz, $CDCl_3$) δ ppm:

- 1.45 (9H, singlet);
- 1.7–2.05 (2H, multiplet);
- 2.05–2.25 (1H, multiplet);
- 2.3–2.55 (1H, multiplet);
- 2.88 (4H, singlet);
- 3.4–3.75 (1H, multiplet);
- 3.42 (1H, doublet of doublets, J=4.4 & 11.9 Hz);
- 3.9–4.05 (2H, multiplet);
- 4.05–4.25 (1H, multiplet);
- 4.3–4.45 (1H, multiplet);
- 6.7–6.9 (3H, multiplet);
- 7.1–7.35 (5H, multiplet).

6(b) (2R,4R)-2-{2-[4-Fluoro-2-(2-phenylethyl)phenoxy]ethyl}-4-hydrox-1-methylpyrrolidine 1115 mg of (2R,4R)-1-t-butoxycarbonyl-2-{2-[4-fluoro-2-(2-phenylethyl)-phenoxy]ethyl}-4-hydroxypyrrolidine

[prepared as described in step (a) above], 20 ml of tetrahydrofuran and 200 mg of lithium aluminum hydride were allowed to react together and subsequently treated in the same manner as described in step (b) of Example 1. The concentrated substance thus obtained was purified by silica gel column chromatography, using a 5:1 by volume mixture of methylene chloride and methanol as the eluent, to give 540 mg (yield 61%) of the title compound as a colorless solid substance.
Nuclear Magnetic Resonance Spectrum (270 MHz, CDCl$_3$) δ ppm:

1.65–2.3 (4H, multiplet);
2.30 (1H, doublet of doublets, J=4.8 & 10.5 Hz);
2.44 (3H, singlet);
2.7–2.95 (1H, multiplet);
2.88 (4H, singlet);
3.55 (1H, doublet of doublets, J=6.1 & 10.5 Hz);
3.85–4.1 (2H, multiplet);
4.35–4.5 (1H, multiplet);
6.7–6.9 (3H, multiplet);
7.1–7.25 (5H, multiplet).

6(c) (2R,4R)-2-{2-[4-Fluoro-2-(2-phenylethyl)phenoxy]ethyl}-4-hydroxy1-methylpyrrolidine hydrochloride 540 mg of (2R,4R)-2-{2-[4-fluoro-2-(2-phenylethyl)phenoxy]ethyl}-4-hydroxy-1-methylpyrrolidine [prepared as described in step (b) above] were dissolved in 5 ml of ethyl acetate, and then 0.60 ml of a 4N solution of hydrogen chloride in ethyl acetate were added to the resulting solution. The crystals which precipitated were collected by filtration, and dried in vacuo, to give 515 mg (yield 86%) of the title compound as colorless crystals, melting at 121°–122° C.
Nuclear Magnetic Resonance Spectrum (270 MHz, CDCl$_3$) δ ppm:

2.0–2.15 (1H, multiplet);
2.25–2.6 (2H, multiplet);
2.33 (1H, doublet of doublets, J=5.8 & 13.9 Hz);
2.85 (4H, singlet);
2.87 (3H, singlet);
3.00 (1H, doublet, J=12.5 Hz);
3.7–4.2 (4H, multiplet);
4.5–4.65 (1H, multiplet);
6.7–6.9 (3H, multiplet);
7.1–7.35 (5H, multiplet).

EXAMPLE 7

(2R,4R)-2-[2-{2-[2-(3,4-Difluorophenyl)ethyl]-4-fluorophenoxy}ethyl]-4-hydroxy-1-methylpyrrolidine hydrochloride 7(a) (2R,4R)-1-t-Butoxycarbonyl-4-t-butyldimethylsilyloxy-2-[2-{2-[2-(3,4-difluorophenyl)ethyl]-4-fluorophenoxy}ethyl]pyrrolidine 400 mg of 2-[2-(3,4-difluorophenyl)ethyl]-4-fluorophenol (prepared as described in Preparation 7), 690 mg of (2S,4R)-2-(2-bromoethyl)-1-t-butoxycarbonyl-4-t-butyldimethylsilyloxypyrrolidine and 208 mg of potassium t-butoxide were allowed to react together in 5 ml of N,N-dimethylacetamide and extracted in the same manner as described in step (a) of Example 2. The resulting oily substance was purified by silica gel column chromatography, using a 5:1 by volume mixture of hexane and ethyl acetate as the eluent, to give 580 mg (yield 63%) of the title compound as a colorless oily substance.
Nuclear Magnetic Resonance Spectrum (270 MHz, CDCl$_3$) δ ppm:

0.02 (3H, singlet);
0.04 (3H, singlet);
0.84 (9H, singlet);
1.45 (9H, singlet);
1.7–1.95 (2H, multiplet);
1.95–2.15 (1H, multiplet);
2.2–2.55 (1H, multiplet);
2.7–3.0 (4H, multiplet);
3.25–3.65 (2H, multiplet);
3.85–4.05 (2H, multiplet);
4.05–4.25 (1H, multiplet);
4.25–4.4 (1H, multiplet);
6.7–7.1 (6H, multiplet).

7(b) (2R,4R)-1-t-Butoxycarbonyl-2-[2-{2-[2-(3,4-difluorophenyl)ethyl]-4-fluorophenoxy}ethyl]-4-hydroxypyrrolidine 580 mg of (2R,4R)-1-t-butoxycarbonyl-4-t-butyldimethylsilyloxy-2-[2-{2-[2-(3,4-difluorophenyl)ethyl]-4-fluorophenoxy}ethyl]pyrrolidine [prepared as described in step (a) above] were dissolved in 5 ml of tetrahydrofuran, and then 0.31 ml of tetrabutylammonium fluoride were added to the resulting solution. The resulting mixture was then stirred at room temperature for 1 hour. At the end of this time, the reaction mixture was concentrated by evaporation under reduced pressure, and the concentrated oily substance was purified by silica gel column chromatography, using a 1:1 by volume mixture of hexane and ethyl acetate as the eluent, to give 280 mg (yield 61%) of the title compound as a colorless solid substance.
Nuclear Magnetic Resonance Spectrum (270 MHz, CDCl$_3$) δ ppm:

1.46 (9H, singlet);
1.7–2.0 (2H, multiplet);
2.05–2.3 (1H, multiplet);
2.3–2.55 (1H, multiplet);
2.84 (4H, singlet);
3.4–3.7 (1H, multiplet);
3.43 (1H, doublet of doublets, J=4.2 & 11.9 Hz);
3.85–4.05 (2H, multiplet);
4.05–4.25 (1H, multiplet);
4.35–4.5 (1H, multiplet);
6.7–7.1 (6H, multiplet).

7(c) (2R,4R)-2-[2-{2-[2-(3,4-Difluorophenyl)ethyl]-4-fluorophenoxy}ethyl]-4-hydroxy-1-methylpyrrolidine 280 mg of (2R,4R)-1-t-butoxycarbonyl-2-[2-{2-[2-(3,4-difluorophenyl)-ethyl]-4-fluorophenoxy}ethyl]-4-hydroxypyrrolidine [prepared as described in step (b) above], 5 ml of tetrahydrofuran and 50 mg of lithium aluminum hydride were allowed to react together and subsequently treated in the same manner as described in step (b) of Example 1. The concentrated substance thus obtained was purified by silica gel column chromatography, using a 10:1 by volume mixture of methylene chloride and methanol as the eluent, to give 140 mg (yield 63%) of the title compound as a colorless solid substance.
Nuclear Magnetic Resonance Spectrum (270 MHz, CDCl$_3$) δ ppm:

1.75–2.5 (4H, multiplet);
2.41 (1H, doublet of doublets, J=4.3 & 10.8 Hz);
2.51 (3H, singlet);
2.8–3.05 (1H, multiplet);
2.84 (4H, singlet);

3.64 (1H, doublet of doublets, J=6.0 & 10.8 Hz);

3.85–4.1 (2H, multiplet);

4.4–4.55 (1H, multiplet);

6.8–6.9 (4H, multiplet);

6.9–7.1 (2H, multiplet).

7(d) (2R,4R)-2-[2-{2-[2-(3,4-Difluorophenyl)ethyl]-4-fluorophenoxy}ethyl]-4-hydroxy-1-methylpyrrolidine hydrochloride 140 mg of (2R,4R)-2-[2-{2-[2-(3,4-difluorophenyl)ethyl]-4-fluorophenoxy}-ethyl]-4-hydroxy-1-methylpyrrolidine [prepared as described in step (c) above] were dissolved in 5 ml of ethyl acetate, and then 0.15 ml of a 4N solution of hydrogen chloride in ethyl acetate were added to the resulting solution. The crystals which precipitated were collected by filtration, and dried in vacuo, to give 113 mg (yield 73%) of the title compound as colorless crystals, melting at 93°–94° C.

Nuclear Magnetic Resonance Spectrum (270 MHz, CDCl$_3$) δ ppm:

2.05–2.25 (1H, multiplet);

2.25–2.7 (3H, multiplet);

2.83 (4H, singlet);

2.9–3.15 (1H, multiplet);

2.91 (3H, singlet);

3.75–4.3 (4H, multiplet);

4.55–4.75 (1H, multiplet);

6.7–7.15 (6H, multiplet).

EXAMPLE 8

(2R,4R)-2-[2-{2-[2-(3,4-Difluorophenyl)ethyl]-4-fluorophenoxy}ethyl]-4-hydroxypyrrolidine hydrochloride 83 mg of (2R,4R)-1-t-butoxycarbonyl-2-[2-{2-[2-(3,4-difluorophenyl)ethyl]-4-fluorophenoxy}ethyl]-4-hydroxypyrrolidine [prepared as described in Example 7(b)] were dissolved in 2 ml of dioxane, and then 2 ml of a 4N solution of hydrogen chloride in dioxane were added to the resulting solution. The resulting mixture was then allowed to stand at room temperature for 1 hour. At the end of this time, the crystals which precipitated were collected by filtration, and dried in vacuo, to give 55 mg (yield 77%) of the title compound as colorless crystals, melting at 170°–171° C.

Nuclear Magnetic Resonance Spectrum (270 MHz, CD$_3$OD) δ ppm:

1.75–1.95 (1H, multiplet);

2.15–2.35 (2H, multiplet);

2.35–2.55 (1H, multiplet);

2.85 (4H, singlet);

3.24 (1H, doublet, J=12.6 Hz);

3.49 (1H, doublet of doublets, J=4.4 & 12.6 Hz);

3.95–4.2 (3H, multiplet);

4.5–4.6 (1H, multiplet);

6.7–7.15 (6H, multiplet).

EXAMPLE 9

(2R,4R)-2-{2-[4-Chloro-2-(2-phenylethyl)phenoxy]ethyl}-4-hydroxy-1-methylpyrrolidine 9(a) (2R,4R)-2-{2-[4-Chloro-2-(2-phenylethyl)phenoxy]ethyl}-1-ethoxycarbonyl-4-hydroxypyrrolidine 500 mg of 4-chloro-2-(2-phenylethyl)phenol were dissolved in 10 ml of N,N-dimethylacetamide, allowed to react with 270 mg of potassium t-butoxide and 520 mg of (2S,4R)-2-(2-chloroethyl)-1-ethoxycarbonyl-4-hydroxypyrrolidine and extracted in the same manner as described in step (a) of Example 1. The resulting oily substance was purified by silica gel column chromatography, using a 1:2 by volume mixture of hexane and ethyl acetate as the eluent, to give 260 mg (yield 29%) of the title compound as an oily substance.

Nuclear Magnetic Resonance Spectrum (270 MHz, CDCl$_3$) δ ppm:

1.1–1.35 (3H, multiplet);

1.75–2.0 (2H, multiplet);

2.05–2.55 (2H, multiplet);

2.85 (4H, singlet);

3.4–3.75 (1H, multiplet);

3.41 (1H, doublet of doublets, J=4.2 & 11.9 Hz);

3.9–4.3 (5H, multiplet);

4.3–4.4 (1H, multiplet);

6.73 (1H, doublet, J=8.6 Hz);

7.05–7.35 (7H, multiplet).

9(b) (2R,4R)-2-{2-[4-Chloro-2-(2-phenylethyl)phenoxy]ethyl}-4-hydroxy-1-methylpyrrolidine 260 mg of (2R,4R)-2-{2-[4-chloro-2-(2-phenylethyl)phenoxy]ethyl}-1-ethoxycarbonyl-4-hydroxypyrrolidine [prepared as described in step (a) above], 10 ml of tetrahydrofuran and 70 mg of lithium aluminum hydride were allowed to react together and subsequently treated in the same manner as described in step (b) of Example 1. The concentrated substance thus obtained was purified by silica gel column chromatography, using a 5:1 by volume mixture of methylene chloride and methanol as the eluent, to give 103 mg (yield 46%) of the title compound as a colorless solid substance, melting at 65°–68° C.

Nuclear Magnetic Resonance Spectrum (270 MHz, CDCl$_3$) δ ppm:

1.7–2.05 (3H, multiplet);

2.15–2.4 (1H, multiplet);

2.31 (1H, doublet of doublets, J=4.9 & 10.5 Hz);

2.44 (3H, singlet);

2.75–2.95 (1H, multiplet);

2.86 (4H, singlet);

3.55 (1H, doublet of doublets, J=6.1 & 10.5 Hz);

3.85–4.1 (2H, multiplet);

4.35–4.5 (1H, multiplet);

6.74 (1H, doublet, J=8.4 Hz);

7.05–7.35 (7H, multiplet).

EXAMPLE 10

(2R,4R)-2-{2-[4-Bromo-2-(2-phenylethyl)phenoxy]ethyl}-4-hydroxy-1-methylpyrrolidine 10(a) (2R,4R)-2-{2-[4-Bromo-2-(2-phenylethyl)phenoxy]ethyl}-1-ethoxycarbonyl-4-hydroxypyrrolidine 500 mg of 4-bromo-2-(2-phenylethyl)phenol were dissolved in 10 ml of N,N-dimethylacetamide, allowed to react with 220 mg of potassium t-butoxide and 440 mg of (2S,4R)-2-(2-chloroethyl)-1-ethoxycarbonyl-4-hydroxypyrrolidine and extracted in the same manner as described in step (a) of Example 1. The resulting oily substance was purified by silica gel column chromatography, using a 1:2 by volume mixture of hexane and ethyl acetate as the eluent, to give 280 mg (yield 34%) of the title compound as an oily substance.

Nuclear Magnetic Resonance Spectrum (270 MHz, CDCl$_3$) δ ppm:

1.1–1.35 (3H, multiplet);

1.75–2.6 (4H, multiplet);

2.85 (4H, singlet);
3.4–3.75 (1H, multiplet);
3.42 (1H, doublet of doublets, J=4.2 & 11.9 Hz);
3.9–4.3 (5H, multiplet);
4.3–4.45 (1H, multiplet);
6.69 (1H, doublet, J=8.5 Hz);
7.15–7.35 (7H, multiplet).

10(b) (2R,4R)-2-{2-[4-Bromo-2-(2-phenylethyl)phenoxy]ethyl}-4-hydroxy-1-methylpyrrolidine 280 mg of (2R,4R)-2-{2-[4-bromo-2-(2-phenylethyl)phenoxy]ethyl}-1-ethoxycarbonyl-4-hydroxypyrrolidine [prepared as described in step (a) above], 10 ml of tetrahydrofuran and 70 mg of lithium aluminum hydride were allowed to react together and subsequently treated in the same manner as described in step (b) of Example 1. The concentrated substance thus obtained was purified by silica gel column chromatography, using a 5:1 by volume mixture of methylene chloride and methanol as the eluent, to give 113 mg (yield 46%) of the title compound as a colorless solid substance, melting at 63°–66° C.

Nuclear Magnetic Resonance Spectrum (270 MHz, CDCl$_3$) δ ppm:

1.7–2.05 (3H, multiplet);
2.1–2.35 (1H, multiplet);
2.29 (1H, doublet of doublets, J=4.9 & 10.4 Hz);
2.42 (3H, singlet);
2.7–2.95 (1H, multiplet);
2.86 (4H, singlet);
3.52 (1H, doublet of doublets, J=6.1 & 10.4 Hz);
3.9–4.05 (2H, multiplet);
4.35–4.5 (1H, multiplet);
6.70 (1H, doublet, J=8.4 Hz);
7.15–7.35 (7H, multiplet).

EXAMPLE 11

(2R,4R)-4-Hydroxy-1-methyl-2-{2-[5-methyl-2-(2-phenylethyl)-phenoxy]ethyl}pyrrolidine hydrochloride 11 (a) (2R,4R)-1-Ethoxycarbonyl-4-benzyloxy-2-{2-[5-methyl-2-(2-phenylethyl)-phenoxy]ethyl}pyrrolidine 1000 mg of 5-methyl-2-(2-phenylethyl)phenol were dissolved in 10 ml of N,N-dimethylacetamide, allowed to react with 580 mg of potassium t-butoxide and 1620 mg of (2-S,4R)-4-benzyloxy-2-(2-chloroethyl)-1-ethoxycarbonylpyrrolidine and extracted in the same manner as described in step (a) of Example 2. The resulting oily substance was purified by silica gel column chromatography, using a 3:1 by volume mixture of hexane and ethyl acetate as the eluent, to give 1680 mg (yield 73%) of the title compound as an oily substance.

Nuclear Magnetic Resonance Spectrum (270 MHz, CDCl$_3$) δ ppm:

1.1–1.35 (3H, multiplet);
1.75–2.1 (2H, multiplet);
2.15–2.6 (2H, multiplet);
2.32 (3H, singlet);
2.86 (4H, singlet);
3.42 (1H, doublet of doublets, J=4.7 & 11.9 Hz);
3.55–4.3 (7H, multiplet);
4.44 (2H, singlet);
6.6–6.75 (2H, multiplet);
6.99 (1H, doublet, J=7.4 Hz);
7.1–7.4 (10H, multiplet).

11 (b) (2R,4R)-1-Ethoxycarbonyl-4-hydroxy-2-{2-[5-methyl-2-(2-phenylethyl)-phenoxy]ethyl}pyrrolidine 1680 mg of (2R,4R)-1-ethoxycarbonyl-4-benzyloxy-2-{2-[5-methyl-2-(2-phenylethyl)phenoxy]ethyl}pyrrolidine [prepared as described in step (a) above] were dissolved in 15 ml of ethanol, and then 200 mg of a 10% w/w palladium-on-carbon catalyst were added to the resulting solution. The resulting suspension was then stirred under a hydrogen atmosphere at atmospheric pressure and at 60° C. for 1.5 hours. At the end of this time, the catalyst was removed by filtration, and the reaction solution was concentrated by evaporation under reduced pressure. The resulting concentrate was purified by silica gel column chromatography, using a 1:2 by volume mixture of hexane and ethyl acetate as the eluent, to give 1150 mg (yield 85%) of the title compound as an oily substance.

Nuclear Magnetic Resonance Spectrum (270 MHz, CDCl$_3$) δ ppm:

1.1–1.35 (3H, multiplet);
1.7–2.25 (3H, multiplet);
2.25–2.65 (1H, multiplet);
2.32 (3H, singlet);
2.86 (4H, singlet);
3.4–3.8 (1H, multiplet);
3.44 (1H, doublet of doublets, J=4.4 & 11.9 Hz);
3.95–4.3 (3H, multiplet);
4.01 (2H, triplet, J=5.9 Hz);
4.3–4.45 (1H, multiplet);
6.6–6.75 (2H, multiplet);
6.99 (1H, doublet, J=7.5 Hz);
7.1–7.35 (5H, multiplet).

11(c) (2R,4R)-4-Hydroxy-1-methyl-2-{2-[5-methyl-2-(2-phenylethyl)phenoxy]ethyl}pyrrolidine 1150 mg of (2R,4R)-1-ethoxycarbonyl-4-hydroxy-2-{2-[5-methyl-2-(2-phenylethyl)phenoxy]ethyl}pyrrolidine [prepared as described in step (b) above], 18 ml of tetrahydrofuran and 330 mg of lithium aluminum hydride were allowed to react together and subsequently treated in the same manner as described in step (b) of Example 1. The concentrated substance thus obtained was purified by silica gel column chromatography, using a 10:1 by volume mixture of methylene chloride and methanol as the eluent, to give 776 mg (yield 80%) of the title compound as a colorless solid substance.

Nuclear Magnetic Resonance Spectrum (270 MHz, CDCl$_3$) δ ppm:

1.6–1.8 (1H, multiplet);
1.85–2.0 (2H, multiplet);
2.15–2.35 (1H, multiplet);
2.20 (1H, doublet of doublets, J=5.4 & 10.0 Hz);
2.33 (3H, singlet);
2.38 (3H, singlet);
2.6–2.8 (1H, multiplet);
2.87 (4H, singlet);
3.47 (1H, doublet of doublets, J=6.4 & 10.0 Hz);
3.9–4.1 (2H, multiplet);
4.35–4.5 (1H, multiplet);
6.6–7.75 (2H, multiplet);
7.00 (1H, doublet, J=7.4 Hz);
7.15–7.35 (5H, multiplet).

11 (d) (2R,4R)-4-Hydroxy-1-methyl-2-{2-[5-methyl-2-(2-phenylethyl)phenoxy]ethyl}pyrrolidine hydrochloride 776 mg of (2R,4R)-4-hydroxy-1-methyl-2-{2-[5-methyl-2-(2-phenylethyl)phenoxy]ethyl}pyrrolidine [prepared as described in step (c) above] were dissolved in 10 ml of ethyl acetate, and then 0.57 ml of a 4N solution of hydrogen chloride in ethyl acetate were added to the resulting solution. The solvent was then removed by evaporation under reduced pressure. The resulting solid substance was dissolved in a small quantity (approximately 0.5 ml) of methylene chloride, and, after the addition of 5 ml of diethyl ether, the resulting solution was allowed to stand at room temperature for about 10 minutes. The crystals which precipitated were collected by filtration, and dried in vacuo, to give 788 mg (yield 92%) of the title compound as colorless crystals, melting at 97°–100° C.

Nuclear Magnetic Resonance Spectrum (270 MHz, CDCl$_3$) δ ppm:

2.0–2.2 (1H, multiplet);
2.25–2.65 (3H, multiplet);
2.33 (3H, singlet);
2.84 (4H, singlet);
2.85 (3H, singlet);
2.98 (1H, doublet, J=12.6 Hz);
3.75–4.1 (3H, multiplet);
4.1–4.25 (1H, multiplet);
4.55–4.65 (1H, multiplet);
6.66 (1H, singlet);
6.73 (1H, doublet, J=7.4 Hz);
7.01 (1H, doublet, J=7.4 Hz);
7.1–7.35 (5H, multiplet).

EXAMPLE 12

(2R,4R)-4-Hydroxy-1-methyl-2-{2-[4-methyl-2-(2-phenylethyl)phenoxy]ethyl}pyrrolidine hydrochloride 12(a) (2R,4R)-1-Ethoxycarbonyl-4-benzyloxy-2-{2-[4-methyl-2-(2-phenylethyl)phenoxy]ethyl}pyrrolidine 1200 mg of 4-methyl-2-(2-phenylethyl)phenol were dissolved in 10 ml of N,N-dimethylacetamide, allowed to react with 700 mg of potassium t-butoxide and 1600 mg of (2S,4R)-4-benzyloxy-2-(2-chloroethyl)-1-ethoxycarbonylpyrrolidine and extracted in the same manner as described in step (a) of Example 2. The resulting oily substance was purified by silica gel column chromatography, using a 3:1 by volume mixture of hexane and ethyl acetate as the eluent, to give 1820 mg (yield 73%) of the title compound as an oily substance.

Nuclear Magnetic Resonance Spectrum (270 MHz, CDCl$_3$) δ ppm:

1.1–1.35 (3H, multiplet);
1.7–2.1 (2H, multiplet);
2.2–2.6 (2H, multiplet);
2.26 (3H, singlet);
2.87 (4H, singlet);
3.42 (1H, doublet of doublets, J=4.7 & 11.9 Hz);
3.55–4.3 (7H, multiplet);
4.44 (2H, singlet);
6.72 (1H, doublet, J=7.8 Hz);
6.9–7.0 (2H, multiplet);
7.1–7.4 (10H, multiplet).

12(b) (2R,4R)-1-Ethoxycarbonyl-4-hydroxy-2-{2-[4-methyl-2-(2-phenylethyl)-phenoxy]ethyl}pyrrolidine 1820 mg of (2R,4R)-1-ethoxycarbonyl-4-benzyloxy-2-{2-[4-methyl-2-(2-phenylethyl)phenoxy]ethyl}pyrrolidine [prepared as described in step (a) above] were dissolved in 20 ml of ethanol, and then 200 mg of a 10% w/w palladium-on-carbon catalyst were added to the resulting solution. The resulting mixture was then stirred under a hydrogen atmosphere at atmospheric pressure and at 60° C. for 2 hours. At the end of this time, the catalyst was removed by filtration, and the reaction mixture was concentrated by evaporation under reduced pressure. The resulting concentrate was purified by silica gel column chromatography, using a 1:2 by volume mixture of hexane and ethyl acetate as the eluent, to give 1410 mg (yield 95%) of the title compound as an oily substance.

Nuclear Magnetic Resonance Spectrum (270 MHz, CDCl$_3$) δ ppm:

1.1–1.35 (3H, multiplet);
1.75–2.3 (3H, multiplet);
2.25 (3H, singlet);
2.3–2.6 (1H, multiplet);
2.86 (4H, singlet);
3.4–3.8 (1H, multiplet);
3.42 (1H, doublet of doublets, J=4.4 & 11.9 Hz);
3.98 (2H, triplet, J=5.9 Hz);
4.05–4.3 (1H, multiplet);
4.12 (2H, quartet, J=7.1 Hz);
4.3–4.45 (1H, multiplet);
6.72 (1H, doublet, J=7.9 Hz);
6.9–7.0 (2H, multiplet);
7.15–7.35 (5H, multiplet).

12(c) (2R,4R)-4-Hydroxy-1-methyl-2-{2-[4-methyl-2-(2-phenylethyl)phenoxy]ethyl}pyrrolidine 1410 mg of (2R,4R)-1-ethoxycarbonyl-4-hydroxy-2-{2-[4-methyl-2-(2-phenylethyl)phenoxy]ethyl}pyrrolidine [prepared as described in step (b) above], 20 ml of tetrahydrofuran and 400 mg of lithium aluminum hydride were allowed to react together and subsequently treated in the same manner as described in step (b) of Example 1. The concentrated substance thus obtained was purified by silica gel column chromatography, using a 5:1 by volume mixture of methylene chloride and methanol as the eluent, to give 884 mg (yield 73%) of the title compound as a colorless solid substance.

Nuclear Magnetic Resonance Spectrum (270 MHz, CDCl$_3$) δ ppm:

1.55–1.8 (1H, multiplet);
1.8–2.0 (2H, multiplet);
2.15–2.3 (1H, multiplet);
2.20 (1H, doublet of doublets, J=5.5 & 10.1 Hz);
2.26 (3H, singlet);
2.38 (3H, singlet);
2.6–2.8 (1H, multiplet);
2.87 (4H, singlet);
3.47 (1H, doublet of doublets, J=6.3 & 10.1 Hz);
3.9–4.1 (2H, multiplet);
4.35–4.5 (1H, multiplet);
6.74 (1H, doublet, J=8.9 Hz);
6.9–7.0 (2H, multiplet);
7.15–7.35 (5H, multiplet).

12(d) (2R,4R)-4-Hydroxy-1-methyl-2-{2-[4-methyl-2-(2-phenylethyl)phenoxy]ethyl}prrolidine hydrochloride 884 mg of (2R,4R)-4-hydroxy-1-methyl-2-{2-[4-methyl-2-(2-phenylethyl)phenoxy]ethyl}pyrrolidine [prepared as described in step (c) above] were dissolved in 10 ml of ethyl acetate, and then 0.65 ml of a 4N solution of hydrogen chloride in ethyl acetate were added to the resulting solution. The solvent was then removed from the resulting solution by evaporation under reduced pressure. The resulting solid substance was dissolved in a small quantity of methylene chloride, and, after the addition of 10 ml of ethyl acetate, allowed to stand at room temperature for about 10 minutes. The crystals which precipitated were collected by filtration, and dried in vacuo, to give 905 mg (yield 92%) of the title compound as colorless crystals, melting at 136°–138° C.

Nuclear Magnetic Resonance Spectrum (270 MHz, CDCl$_3$) δ ppm:

2.0–2.2 (1H, multiplet);
2.25–2.65 (3H, multiplet);
2.27 (3H, singlet);
2.83 (3H, singlet);
2.86 (4H, singlet);
2.94 (1H, doublet, J=12.7 Hz);
3.7–3.9 (1H, multiplet);
3.9–4.1 (2H, multiplet);
4.1–4.25 (1H, multiplet);
4.55–4.65 (1H, multiplet);
6.73 (1H, doublet, J=7.9 Hz);
6.95–7.05 (2H, multiplet);
7.1–7.35 (5H, multiplet).

EXAMPLE 13

(2R,4R)-4-Hydroxy-1-methyl-2-{2-[6-methyl-2-(2-phenylethyl)phenoxy]ethyl}pyrrolidine hydrochloride 13(a) (2R,4R)-1-Ethoxycarbonyl-4-benzyloxy-2- {2-[6-methyl-2-(2-phenylethyl)phenoxy]ethyl}pyrrolidine 1200 mg of 6-methyl-2-(2-phenylethyl)phenol were dissolved in 10 ml of N,N-dimethylacetamide, allowed to react with 700 mg of potassium t-butoxide and 1600 mg of (2S,4R)-4-benzyloxy-2-(2-chloroethyl)-1-ethoxycarbonylpyrrolidine and extracted in the same manner as described in step (a) of Example 2. The resulting oily substance was purified by silica gel column chromatography, using a 3:1 by volume mixture of hexane and ethyl acetate as the eluent, to give 2260 mg (yield 90%) of the title compound as an oily substance.

Nuclear Magnetic Resonance Spectrum (270 MHz, CDCl$_3$) δ ppm:

1.23 (3H, triplet, J=7.0 Hz);
1.75–2.1 (2H, multiplet);
2.2–2.6 (2H, multiplet);
2.28 (3H, singlet);
2.90 (4H, singlet);
3.42 (1H, doublet of doublets, J=4.5 & 11.9 Hz);
3.55–3.9 (3H, multiplet);
4.05–4.3 (2H, multiplet);
4.12 (2H, quartet, J=7.0 Hz);
4.35–4.6 (2H, multiplet);
6.9–7.1 (3H, multiplet);
7.1–7.4 (10H, multiplet).

13(b) (2R,4R)-1-Ethoxycarbonyl-4-hydroxy-2-{2-[6-methyl-2-(2-phenylethyl)phenoxy]ethyl}pyrrolidine 2260 mg of (2R,4R)-1-ethoxycarbonyl-4-benzyloxy-2-{2-[6-methyl-2-(2-phenylethyl)phenoxy]ethyl}pyrrolidine [prepared as described in step (a) above] were dissolved in 20 ml of ethanol, and then 300 mg of a 10% w/w palladium-on-carbon catalyst were added to the resulting solution. The resulting mixture was stirred under a hydrogen atmosphere at atmospheric pressure and at 60° C. for 1.5 hours. At the end of this time, the catalyst was removed by filtration, and the reaction mixture was concentrated by evaporation under reduced pressure. The resulting concentrate was purified by silica gel column chromatography, using a 1:2 by volume mixture of hexane and ethyl acetate as the eluent, to give 1840 mg (a quantitative yield) of the title compound as an oily substance.

Nuclear Magnetic Resonance Spectrum (270 MHz, CDCl$_3$) δ ppm:

1.15–1.2 (3H, multiplet);
1.75–2.05 (2H, multiplet);
2.05–2.25 (1H, multiplet);
2.28 (3H, singlet);
2.35–2.6 (1H, multiplet);
2.90 (4H, singlet);
3.4–3.9 (3H, multiplet);
3.42 (1H, doublet of doublets, J=4.2 & 11.9 Hz);
4.0–4.25 (3H, multiplet);
4.3–4.45 (1H, multiplet);
6.9–7.1 (3H, multiplet);
7.05–7.35 (5H, multiplet).

13(c) (2R,4R)-4-Hydroxy-1-methyl-2-{2-[6-methyl-2-(2-phenylethyl)phenoxy]ethyl}pyrrolidine 1840 mg of (2R,4R)-1-ethoxycarbonyl-4-hydroxy-2-{2-[6-methyl-2-(2-phenylethyl)phenoxy]ethyl}pyrrolidine [prepared as described in step (b) above], 20 ml of tetrahydrofuran and 530 mg of lithium aluminum hydride were allowed to react together and subsequently treated in the same manner as described in step (b) of Example 1. The concentrated substance thus obtained was purified by silica gel column chromatography, using a 5:1 by volume mixture of methylene chloride and methanol as the eluent, to give 1050 mg (yield 67%) of the title compound as a colorless solid substance.

Nuclear Magnetic Resonance Spectrum (270 MHz, CDCl$_3$) δ ppm:

1.55–1.75 (1H, multiplet);
1.8–2.0 (2H, multiplet);
2.18 (1H, doublet of doublets, J=5.6 & 10.0 Hz);
2.2–2.35 (1H, multiplet);
2.30 (3H, singlet);
2.37 (3H, singlet);
2.6–2.75 (1H, multiplet);
2.91 (4H, singlet);
3.43 (1H, doublet of doublets, J=6.3 & 10.0 Hz);
3.78 (2H, triplet, J=6.6 Hz);
4.3–4.55 (1H, multiplet);
6.95 (1H, doublet of doublets, J=6.0 & 8.6 Hz);
7.0–7.1 (2H, multiplet);
7.15–7.35 (5H, multiplet).

13(d) (2R,4R)-4-Hydroxy-1-methyl-2-{2-[6-methyl-2-(2-phenylethyl)phenoxy]ethyl}pyrrolidine hydrochloride 1050 mg of (2R,4R)-4-hydroxy-1-methyl-2-{2-[6-methyl-2-(2-phenylethyl)phenoxy]ethyl}pyrrolidine [prepared as described in step (c) above] were dissolved in 10 ml of ethyl acetate, and then 0.77 ml of a 4N solution of hydrogen chloride in ethyl acetate were added to the resulting solution. The solvent was then removed by evaporation under reduced pressure. 20 ml of ethyl acetate were added to the resulting solid substance, and the mixture was allowed to stand at room temperature for about 10 minutes. The crystals which precipitated were collected by filtration, and dried in vacuo, to give 1024 mg (yield 88%) of the title compound as colorless crystals, melting at 114°–115° C.

Nuclear Magnetic Resonance Spectrum (270 MHz, CDCl$_3$) δ ppm:

2.0–2.1 (1H, multiplet);
2.25–2.45 (1H, multiplet);
2.27 (3H, multiplet);
2.35 (1H, doublet of doublets, J=5.7 & 13.7 Hz);
2.45–2.65 (1H, multiplet);
2.7–3.1 (5H, multiplet);
2.90 (3H, singlet);
3.7–4.0 (3H, multiplet);
4.0–4.2 (1H, multiplet);
4.5–4.65 (1H, multiplet);
6.9–7.1 (3H, multiplet);
7.15–7.35 (5H, multiplet).

EXAMPLE 14

(2R,4R)-4-Hydroxy-2-{2-[4-methoxy-2-(2-phenylethyl)phenoxy]ethyl}-1-methylpyrrolidine hydrochloride 14(a) (2R,4R)-1-Ethoxycarbonyl-4-hydroxy-2-{2-[4-methoxy-2-(2-phenylethyl)phenoxy]ethyl}pyrrolidine 1130 mg of 4-methoxy-2-(2-phenylethyl)phenol were dissolved in 10 ml of N,N-dimethylacetamide, allowed to react with 610 mg of potassium t-butoxide and 1000 mg of (2S,4R)-2-(2-chloroethyl)-1-ethoxycarbonyl-4-hydroxypyrrolidine and extracted in the same manner as described in step (a) of Example 2. The resulting oily substance was purified by silica gel column chromatography, using a 1:2 by volume mixture of hexane and ethyl acetate as the eluent, to give 448 mg (yield 24%) of the title compound as an oily substance.

Nuclear Magnetic Resonance Spectrum (270 MHz, CDCl$_3$) δ ppm:

1.1–1.35 (3H, multiplet);
1.7–2.1 (2H, multiplet);
2.1–2.25 (1H, multiplet);
2.25–2.6 (1H, multiplet);
2.88 (4H, singlet);
3.44 (1H, doublet of doublets, J=4.4 & 11.9 Hz);
3.45–3.75 (1H, multiplet);
3.73 (3H, singlet);
3.97 (2H, triplet, J=6.1 Hz);
4.05–4.3 (3H, multiplet);
4.35–4.5 (1H, multiplet);
6.65–6.85 (3H, multiplet);
7.1–7.35 (5H, multiplet).

14(b) (2R,4R)-4-Hydroxy-2-{2-[4-methoxy-2-(2-phenylethyl)phenoxy]ethyl}-1-methylpyrrolidine 448 mg of (2R,4R)-1-ethoxycarbonyl-4-hydroxy-2-{2-[4-methoxy-2-(2-phenylethyl)phenoxy]ethyl}pyrrolidine [prepared as described in step (a) above], 10 ml of tetrahydrofuran and 120 mg of lithium aluminum hydride were allowed to react together and subsequently treated in the same manner as described in step (b) of Example 1. The concentrated substance thus obtained was purified by silica gel column chromatography, using a 5:1 by volume mixture of methylene chloride and methanol as the eluent, to give 144 mg (yield 37%) of the title compound as a colorless solid substance.

Nuclear Magnetic Resonance Spectrum (270 MHz, CDCl$_3$) δ ppm:

1.6–1.8 (1H, multiplet);
1.85–2.0 (2H, multiplet);
2.1–2.3 (1H, multiplet);
2.22 (1H, doublet of doublets, J=5.1 & 10.2 Hz);
2.39 (3H, singlet);
2.6–2.8 (1H, multiplet);
2.88 (4H, singlet);
3.48 (1H, doublet of doublets, J=6.3 & 10.2 Hz);
3.74 (3H, singlet);
3.85–4.05 (2H, multiplet);
4.35–4.5 (1H, multiplet);
6.65–6.85 (3H, multiplet);
7.1–7.35 (5H, multiplet).

14(c) (2R,4R)-4-Hydroxy-2-{2-[4-methoxy-2-(2-phenylethyl)phenoxy]ethyl}-1-methylpyrrolidine hydrochloride 144 mg of (2R,4R)-4-hydroxy-2-{2-[4-methoxy-2-(2-phenylethyl)phenoxy]ethyl}-1-methylpyrrolidine [prepared as described in step (b) above] were dissolved in 5 ml of ethyl acetate, and then 0.10 ml of a 4N solution of hydrogen chloride in ethyl acetate was added to the resulting solution. The solvent was then removed by evaporation under reduced pressure. The resulting oily substance was dissolved in 1 ml of methylene chloride, and diethyl ether was added to the solution until it became turbid. The turbid mixture was then allowed to stand at room temperature for about 10 minutes. The crystals which precipitated were collected by filtration, and dried in vacuo, to give 137 mg (yield 86%) of the title compound as colorless crystals, melting at 63°–65° C.

Nuclear Magnetic Resonance Spectrum (270 MHz, CDCl$_3$) δ ppm:

2.05–2.2 (1H, multiplet);
2.30 (1H, doublet of doublets, J=5.8 & 13.9 Hz);
2.35–2.65 (2H, multiplet);
2.8–3.0 (1H, multiplet);
2.85 (3H, singlet);
2.87 (4H, singlet);
3.74 (3H, singlet);
3.7–4.2 (4H, multiplet);
4.55–4.65 (1H, multiplet);
6.65–6.85 (2H, multiplet);
6.72 (1H, singlet);
7.1–7.35 (5H, multiplet).

EXAMPLE 15

(2R,4R)-4-Hydroxy-2-{2-[5-methoxy-2-(2-phenylethyl)phenoxy]ethyl}-1-methylpyrrolidine hydrochloride 15(a) (2R,4R)-4-Dimethylcarbamoyloxy-2-{2-[5-methoxy-2-(2-phenylethyl)phenoxy]ethyl}-1-octyloxycarbonylpyrrolidine 670 mg of 5-methoxy-2-(2-phenylethyl)phenol (prepared as described in Preparation 1) were dissolved in 10 ml of N,N-dimethylacetamide, allowed to react with 360 mg of potassium t-butoxide and 1000 mg of (2S,4R)-2-(2-chloroethyl)-4-dimethylcarbamoyloxy-1-octyloxycarbonylpyrrolidine and extracted in the same manner as described in step (a) of Example 2. The resulting oily substance was purified by silica gel column chromatography, using a 1:1 by volume mixture of hexane and ethyl acetate as the eluent, to give 1500 mg (yield 99%) of the title compound as an oily substance.

Nuclear Magnetic Resonance Spectrum (270 MHz, CDCl$_3$) δ ppm:
- 0.8–0.95 (3H, multiplet);
- 1.15–1.45 (10H, multiplet);
- 1.5–1.75 (2H, multiplet);
- 1.75–2.15 (2H, multiplet);
- 2.25–2.8 (2H, multiplet);
- 2.7–3.0 (4H, multiplet);
- 2.83 (6H, singlet);.
- 3.5–3.9 (1H, multiplet);
- 3.53 (1H, doublet of doublets, J=4.3 & 12.6 Hz);
- 3.78 (3H, singlet);
- 3.9–4.3 (5H, multiplet);
- 5.1–5.25 (1H, multiplet);
- 6.35–6.5 (2H, multiplet);
- 6.98 (1H, doublet, J=8.1 Hz);
- 7.1–7.3 (5H, multiplet).

15(b) (2R,4R)-4-Hydroxy-2-{2-[5-methoxy-2-(2-phenylethyl)phenoxy]ethyl}-1-methylpyrrolidine 1500 mg of (2R,4R)-4-dimethylcarbamoyloxy-2-{2-[5-methoxy-2-(2-phenylethyl)phenoxy]ethyl}-1-octyloxycarbonylpyrrolidine [prepared as described in step (a) above], 25 ml of tetrahydrofuran and 310 mg of lithium aluminum hydride were allowed to react together and subsequently treated in the same manner as described in step (b) of Example 1. The concentrated substance thus obtained was purified by silica gel column chromatography, using a 5:1 by volume mixture of methylene chloride and methanol as the eluent, to give 385 mg (yield 41%) of the title compound as a colorless solid substance.

Nuclear Magnetic Resonance Spectrum (270 MHz, CDCl$_3$) δ ppm:
- 1.6–1.8 (1H, multiplet);
- 1.8–2.0 (2H, multiplet);
- 2.15–2.3 (1H, multiplet);
- 2.20 (1H, doublet of doublets, J=5.5 & 10.1 Hz);
- 2.38 (3H, singlet);
- 2.6–2.75 (1H, multiplet);
- 2.84 (4H, singlet);
- 3.46 (1H, doublet of doublets, J=6.4 & 10.1 Hz);
- 3.79 (3H, singlet);
- 3.9–4.1 (2H, multiplet);
- 4.35–4.5 (1H, multiplet);
- 6.35–6.5 (2H, multiplet);
- 7.00 (1H, doublet, J=8.0 Hz);
- 7.05–7.35 (5H, multiplet).

15(c) (2R,4R)-4-Hydroxy-2-{2-[5-methoxy-2-(2-phenylethyl)phenoxy]ethyl}-1-methylpyrrolidine hydrochloride 385 mg of (2R,4R)-4-hydroxy-2-{2-[5-methoxy-2-(2-phenylethyl)phenoxy]ethyl}-1-methylpyrrolidine [prepared as described in step (b) above] were dissolved in 5 ml of dioxane, and then 0.27 ml of a 4N solution of hydrogen chloride in dioxane were added to the resulting solution. The solvent was then removed by evaporation under reduced pressure. The resulting oily substance was dissolved in 10 ml of ethyl acetate, and allowed to stand at room temperature for about 10 minutes. The crystals which precipitated were collected by filtration, and dried in vacuo, to give 385 mg (yield 91%) of the title compound as colorless crystals, melting at 108°–110° C.

Nuclear Magnetic Resonance Spectrum (270 MHz, CDCl$_3$) δ ppm:
- 2.0–2.2 (1H, multiplet);
- 2.3–2.65 (2H, multiplet);
- 2.31 (1H, doublet of doublets, J=5.9 & 13.8 Hz);
- 2.83 (4H, singlet);
- 2.84 (3H, singlet);
- 2.96 (1H, doublet, J=12.3 Hz);
- 3.75–3.9 (1H, multiplet);
- 3.79 (3H, singlet);
- 3.9–4.2 (3H, multiplet);
- 4.55–4.65 (1H, multiplet);
- 6.4–6.5 (2H, multiplet);
- 7.01 (1H, doublet, J=7.9 Hz);
- 7.1–7.35 (5H, multiplet).

EXAMPLE 16

(2R,4R)-4-Hydroxy-2-{2-[6-methoxy-2-(2-phenylethyl)phenoxy]ethyl}-1-methylpyrrolidine hydrochloride 16(a) (2R,4R)-4-Dimethylcarbamoyloxy-2-{2-[6-methoxy-2-(2-phenylethyl)phenoxy]ethyl}-1-octyloxycarbonylpyrrolidine 670 mg of 6-methoxy-2-(2-phenylethyl)phenol were dissolved in 10 ml of N,N-dimethylacetamide, allowed to react with 360 mg of potassium t-butoxide and 1000 mg of (2S,4R)-2-(2-chloroethyl)-4-dimethylcarbamoyloxy-1-octyloxycarbonylpyrrolidine and extracted in the same manner as described in step (a) of Example 2. The resulting oily substance was purified by silica gel column chromatography, using a 1:1 by volume mixture of hexane and ethyl acetate as the eluent, to give 1500 mg (99% yield) of the title compound as an oily substance.

Nuclear Magnetic Resonance Spectrum (270 MHz, CDCl$_3$) δ ppm:
- 0.8–0.95 (3H, multiplet);
- 1.15–1.45 (I OH, multiplet);
- 1.5–1.7 (2H, multiplet);
- 1.75–2.05 (1H, multiplet);
- 2.05–2.2 (1H, multiplet);
- 2.25–2.6 (2H, multiplet);
- 2.75–3.0 (4H, multiplet);
- 2.90 (6H, singlet);
- 3.5–3.9 (1H, multiplet);
- 3.55 (1H, doublet of doublets, J=4.3 & 12.6 Hz);
- 3.83 (3H, singlet);
- 3.9–4.3 (5H, multiplet);
- 5.1–5.25 (1H, multiplet);
- 6.7–6.8 (2H, multiplet);
- 6.96 (1H, triplet, J=7.9 Hz);
- 7.1–7.35 (5H, multiplet).

16(b) (2R,4R)-4-Hydroxy-2-{2-[6-methoxy-2-(2-phenylethyl)phenoxy]ethyl}-1-methylpyrrolidine 1500 mg of (2R,4R)-4-dimethylcarbamoyloxy-2-{2-[6-methoxy-2-(2-phenylethyl)phenoxy]ethyl}-1-octyloxycarbonylpyrrolidine [prepared as described in step (a) above], 25 ml of tetrahydrofuran and 300 mg of lithium aluminum hydride were allowed to react together and subsequently treated in the same manner as described in step (b) of Example 1. The concentrated substance thus obtained was purified by silica gel column chromatography, using a 5:1 by volume mixture of methylene chloride and methanol as the eluent, to give 552 mg (yield 59%) of the title compound as a colorless solid substance.

Nuclear Magnetic Resonance Spectrum (270 MHz, CDCl₃) δ ppm:

1.55–1.75 (1H, multiplet);
   1.8–2.0 (2H, multiplet);
   2.15–2.4 (1H, multiplet);
   2.18 (1H, doublet of doublets, J=5.4 & 10.1 Hz);
   2.37 (3H, singlet);
   2.6–2.75 (1H, multiplet);
   2.8–3.0 (4H, multiplet);
   3.45 (1H, doublet of doublets, J=6.4 & 10.1 Hz);
   3.84 (3H, singlet);
   3.85–4.05 (2H, multiplet);
   4.3–4.45 (1H, multiplet);
   6.7–6.85 (2H, multiplet);
   6.97 (1H, triplet, J=7.8 Hz);
   7.1–7.35 (5H, multiplet).

16(c) (2R,4R)-4-Hydroxy-2-{2-[6-methoxy-2-(2-phenylethyl)phenoxy]ethyl}-1-methylpyrrolidine hydrochloride 552 mg of (2R,4R)-4-hydroxy-2-{2-[6-methoxy-2-(2-phenylethyl)phenoxy]ethyl}-1-methylpyrrolidine [prepared as described in step (b) above] were dissolved in 10 ml of ethyl acetate, and then 0.39 ml of a 4N solution of hydrogen chloride in ethyl acetate were added to the resulting solution. The solvent was then removed by evaporation under reduced pressure. The resulting oily substance was dissolved in 10 ml of ethyl acetate, and allowed to stand at room temperature for about 10 minutes. The crystals which precipitated were collected by filtration, and dried in vacuo, to give 424 mg (yield 70%) of the title compound as colorless crystals, melting at 70°–72° C.

Nuclear Magnetic Resonance Spectrum (270 MHz, CDCl₃) δ ppm:

2.05–2.2 (1H, multiplet);
   2.2–2.6 (2H, multiplet);
   2.44 (1H, doublet of doublets, J=5.7 & 13.9 Hz);
   2.8–3.1 (1H, multiplet);
   2.89 (4H, singlet);
   2.93 (3H, singlet);
   3.75–3.9 (1H, multiplet);
   3.84 (3H, singlet);
   3.9–4.2 (3H, multiplet);
   4.55–4.65 (1H, multiplet);
   6.75–6.85 (2H, multiplet);
   7.01 (1H, triplet, J=7.9 Hz);
   7.1–7.35 (5H, multiplet).

EXAMPLE 17

(2R,4R)-2-{2-[5-Chloro-2-(2-phenylethyl)phenoxy]ethyl}-4-hydroxy-1-methylpyrrolidine hydrochloride 17(a) (2R,4R)-2-{2-[5-Chloro-2-(2-phenylethyl)phenoxy]ethyl}-4-dimethylcarbamoyloxy-1-octyloxycarbonylpyrrolidine 680 mg of 5-chloro-2-(2-phenylethyl)phenol (prepared as described in Preparation 9) were dissolved in 10 ml of N,N-dimethylacetamide, allowed to react with 360 mg of potassium t-butoxide and 1000 mg of (2S,4R)-2-(2-chloroethyl)-4-dimethylcarbamoyloxy-1-octyloxycarbonylpyrrolidine and extracted in the same manner as described in step (a) of Example 2. The resulting oily substance was purified by silica gel column chromatography, using a 1:1 by volume mixture of hexane and ethyl acetate as the eluent, to give 1.38 g (yield 91%) of the title compound as an oily substance.

Nuclear Magnetic Resonance Spectrum (270 MHz, CDCl₃) δ ppm:

0.8–1.0 (3H, multiplet);
   1.15–1.45 (10H, multiplet);
   1.45–1.7 (2H, multiplet);
   1.75–2.15 (2H, multiplet);
   2.25–2.7 (2H, multiplet);
   2.7–3.0 (4H, multiplet);
   2.85 (3H, singlet);
   2.87 (3H, singlet);
   3.53 (1H, doublet of doublets, J=4.1 & 12.6 Hz);
   3.6–3.9 (1H, multiplet);
   3.9–4.3 (5H, multiplet);
   5.1–5.3 (1H, multiplet);
   6.7–6.9 (2H, multiplet);
   6.97 (1H, doublet, J=7.9 Hz);
   7.1–7.35 (5H, multiplet).

17(b) (2R,4R)-2-{2-[5-Chloro-2-(2-phenylethyl)phenoxy]ethyl}-4-hydroxy-1-methylpyrrolidine 1380 mg of (2R,4R)-2-{2-[5-chloro-2-(2-phenylethyl)phenoxy]ethyl}-4-dimethylcarbamoyloxy-1-octyloxycarbonylpyrrolidine [prepared as described in step (a) above], 20 ml of tetrahydrofuran and 450 mg of lithium aluminum hydride were allowed to react together and subsequently treated in the same manner as described in step (b) of Example 1. The concentrated substance thus obtained was purified by silica gel column chromatography, using a 5:1 by volume mixture of methylene chloride and methanol as the eluent, to give 256 mg (yield 30%) of the title compound as a colorless solid substance.

Nuclear Magnetic Resonance Spectrum (270 MHz, CDCl₃) δ ppm:

1.6–1.8 (1H, multiplet);
   1.8–2.05 (2H, multiplet);
   2.1–2.3 (1H, multiplet);
   2.22 (1H, doublet of doublets, J=5.4 & 10.1 Hz);
   2.39 (3H, singlet);
   2.6–2.75 (1H, multiplet);
   2.8–2.95 (4H, multiplet);
   3.48 (1H, doublet of doublets, J=6.3 & 10.1 Hz);
   3.9–4.1 (2H, multiplet);
   4.35–4.5 (1H, multiplet);
   6.75–6.9 (2H, multiplet);
   6.99 (1H, doublet, J=7.8 Hz);
   7.1–7.35 (5H, multiplet).

17(c) (2R,4R)-2-{2-[5-Chloro-2-(2-phenylethyl)phenoxy]ethyl}-4-hydroxy-1-methylpyrrolidine hydrochloride 256 mg of (2R,4R)-2-{2-[5-chloro-2-(2-phenylethyl)phenoxy]ethyl}-4-hydroxy-1-methylpyrrolidine [prepared as described in step (b) above] were dissolved in 5 ml of ethyl acetate, and then 0.18 ml of a 4N solution of hydrogen chloride in ethyl acetate was added to the resulting solution. The solvent was then removed by evaporation under reduced pressure. The resulting oily substance was dissolved in 10 ml of ethyl acetate, and allowed to stand at room temperature. The crystals which precipitated were collected by filtration and dried in vacuo, to give 183 mg (yield 65%) of the title compound as colorless crystals, melting at 99°–102° C.

Nuclear Magnetic Resonance Spectrum (270 MHz, CDCl$_3$) δ ppm:

2.05–2.25 (1H, multiplet);
2.31 (1H, doublet of doublets, J=5.9 & 13.8 Hz);
2.35–2.65 (2H, multiplet);
2.8–3.0 (5H, multiplet);
2.86 (3H, singlet);.
3.7–3.9 (1H, multiplet);
3.9–4.25 (3H, multiplet);
4.55–4.7 (1H, multiplet);
6.82 (1H, doublet, J=1.9 Hz);
6.85–7.0 (1H, multiplet);
7.02 (1H, doublet, J=8.0 Hz);
7.1–7.35 (5H, multiplet).

EXAMPLE 18

(2R,4R)-2-{2-[6-Fluoro-2-(2-phenylethyl)phenoxy]ethyl}-4-hydroxy-1-methylpyrrolidine hydrochloride 18(a) (2R,4R)-4-Dimethylcarbamoyloxy-2-{2-[6-fluoro-2-(2-phenylethyl)phenoxy]ethyl}-1-octyloxycarbonylpyrrolidine 520 mg of 6-fluoro-2-(2-phenylethyl)phenol (prepared as described in Preparation 10) were dissolved in 10 ml of N,N-dimethylacetamide, allowed to react with 300 mg of potassium t-butoxide and 820 mg of (2S,4R)-2-(2-chloroethyl)-4-dimethylcarbamoyloxy-1-octyloxycarbonylpyrrolidine and extracted in the same manner as described in step (a) of Example 2. The resulting oily substance was purified by silica gel column chromatography, using a 2:1 by volume mixture of hexane and ethyl acetate as the eluent, to give 984 mg (yield 81 %) of the title compound as an oily substance.

Nuclear Magnetic Resonance Spectrum (270 MHz, CDCl$_3$) δ ppm:

0.8–0.95 (3H, multiplet);
1.1 5–1.45 (10H, multiplet);
1.55–1.7 (2H, multiplet);
1.7–2.0 (1H, multiplet);
2.0–2.15 (1H, multiplet);
2.25–2.6 (2H, multiplet);
2.75–3.0 (4H, multiplet);
2.89 (6H, singlet);
3.54 (1H, doublet of doublets, J=4.3 & 12.5 Hz);
3.6–3.9 (1H, multiplet);
3.95–4.25 (5H, multiplet);
5.1–5.3 (1H, multiplet);
6.8–7.0 (3H, multiplet);
7.1–7.3 (5H, multiplet).

18(b) (2R,4R)-2-{2-[6-Fluoro-2-(2-phenylethyl)phenoxy]ethyl}-4-hydroxy-1-methylpyrrolidine 984 mg of (2R,4R)-4-dimethylcarbamoyloxy-2-{2-[6-fluoro-2-(2-phenylethyl)phenoxy]ethyl}-1-octyloxycarbonylpyrrolidine [prepared as described in step (a) above], 20 ml of tetrahydrofuran and 200 mg of lithium aluminum hydride were allowed to react together and subsequently treated in the same manner as described in step (b) of Example 1. The concentrated substance thus obtained was purified by silica gel column chromatography, using a 5:1 by volume mixture of methylene chloride and methanol as the eluent, to give 319 mg (yield 53%) of the title compound as an oily substance.

Nuclear Magnetic Resonance Spectrum (270 MHz, CDCl$_3$) δ ppm:

1.55–1.75 (1H, multiplet);
1.8–2.0 (2H, multiplet);
2.15–2.35 (1H, multiplet);
2.19 (1H, doublet of doublets, J=5.4 & 10.1 Hz);
2.37 (3H, singlet);
2.6–2.75 (1H, multiplet);
2.8–3.0 (4H, multiplet);
3.45 (1H, doublet of doublets, J=6.3 & 10.1 Hz);
3.95–4.15 (2H, multiplet);
4.35–4.45 (1H, multiplet);
6.85–7.0 (3H, multiplet);
7.15–7.35 (5H, multiplet).

18(c) (2R,4R)-2-{2-[6-Fluoro-2-(2-phenylethyl)phenoxy]ethyl}-4-hydroxy-1-methylpyrrolidine hydrochloride.

319 mg of (2R,4R)-2-{2-[6-fluoro-2-(2-phenylethyl)phenoxy]ethyl}-4-hydroxy-1-methylpyrrolidine [prepared as described in step (b) above] were dissolved in 10 ml of ethyl acetate, and then 0.23 ml of a 4N solution of hydrogen chloride in ethyl acetate was added to the resulting solution. The solvent was then removed by evaporation under reduced pressure. The resulting oily substance was dissolved in ethyl acetate, and allowed to stand at room temperature. The crystals which precipitated were collected by filtration and dried in vacuo, to give 320 mg (yield 91%) of the title compound as colorless crystals, melting at 136°–138° C.

Nuclear Magnetic Resonance Spectrum (270 MHz, CDCl$_3$) δ ppm:

2.0–2.2 (1H, multiplet),
2.2–2.6 (3H, multiplet);
2.8–3.1 (5H, multiplet);
2.92 (3H, singlet),
3.8–4.25 (4H, multiplet);
4.55–4.7 (1H, multiplet);
6.85–7.05 (3H, multiplet);
7.1–7.4 (5H, multiplet).

EXAMPLE 19

(2R,4R)-2-[2-{4-Fluoro-2-[2-(4-fluoro-3-methoxyphenyl)ethyl]phenoxy}ethyl]-4-lauroyloxy-1-methylpyrrolidine hydrochloride 19(a) (2R,4R)-2-[2-{4-Fluoro-2-[2-(4-fluoro-3-methoxyphenyl)ethyl]phenoxy}ethyl]-4-lauroyloxy-1-methylpyrrolidine 513 mg of (2R,4R)-2-[2-{4-fluoro-2-[2-(4-fluoro-3-methoxyphenyl)ethyl]phenoxy}ethyl]-4-hydroxy-1-methylpyrrolidine [prepared as described in step (b) of Example 4] were dissolved in 10 ml of pyridine, and then 652 mg of lauric anhydride and 48 mg of 4-dimethylaminopyridine were added to the resulting solution, whilst stirring at room temperature. The resulting mixture was then stirred at room temperature for 30 minutes, and then stirred at 40° C. for 1 hour. At the end of this time, about 100 ml of ethyl acetate were added, and the reaction mixture was washed twice, each time with 1N hydrochloric acid, and then once with a saturated aqueous solution of sodium chloride, in that order. The ethyl acetate layer was dried over anhydrous magnesium sulfate, and then concentrated by evaporation under reduced pressure. The resulting oily substance was purified by silica gel column chromatography, using a 5:1 by volume mixture of methylene chloride and methanol as the eluent, to give 684 mg (yield 91%) of the title compound as a colorless oily substance.

Nuclear Magnetic Resonance Spectrum (270 MHz, CDCl$_3$) δ ppm:

0.88 (3H, triplet, J=6.6 Hz);
1.15–1.4 (16H, multiplet);
1.45–1.85 (3H, multiplet);
1.85–2.1 (2H, multiplet);
2.15–2.3 (2H, multiplet);
2.22 (2H, triplet, J=7.6 Hz);
2.38 (3H, singlet);
2.55–2.7 (1H, multiplet);
2.7–3.0 (4H, multiplet);
3.60 (1H, doublet of doublets, J=6.6 & 10.7 Hz);
3.83 (3H, singlet);
3.85–4.05 (2H, multiplet);
5.05–5.2 (1H, multiplet);
6.6–7.05 (6H, multiplet).

19(b) (2R,4R)-2-[2-{4-Fluoro-2-[2-(4-fluoro-3-methoxyphenyl)ethyl]phenoxy}ethyl]-4-lauroyloxy-1-methylpyrrolidine hydrochloride 684 mg of (2R,4R)-2-[2-{4-fluoro-2-[2-(4-fluoro-3-methoxyphenyl)ethyl]phenoxy}ethyl]-4-lauroyloxy-1-methylpyrrolidine [prepared as described in step (a) above] were dissolved in 10 ml of dioxane, and 0.45 ml of a 4N solution of hydrogen chloride in dioxane was added to the resulting solution. The solution was then concentrated by evaporation under reduced pressure. Hexane was added to the residue, and the crystals which precipitated were collected by filtration, and dried in vacuo, to give 485 mg (yield 67%) of the title compound as colorless crystals, melting at 49°–53° C.

Nuclear Magnetic Resonance Spectrum (270 MHz, CDCl$_3$) δ ppm:

0.88 (3H, triplet, J=6.6 Hz);
1.1–1.4 (16H, multiplet);
1.4–1.7 (2H, multiplet);
2.21 (2H, triplet, J=7.6 Hz);
2.3–2.5 (2H, multiplet);
2.5–2.7 (2H, multiplet);
2.75–3.0 (5H, multiplet);
2.86 (3H, singlet);
3.45–3.7 (1H, multiplet);
3.83 (3H, singlet);
3.9–4.05 (1H, multiplet);
4.1–4.25 (1H, multiplet);
4.25–4.45 (1H, multiplet);
5.3–5.4 (1H, multiplet);
6.55–7.05 (6H, multiplet).

EXAMPLE 20

(2R,4R)-2-[2-{4-Fluoro-2-[2-(3-methoxyphenyl)ethyl]phenoxy}ethyl]-4-lauroyloxy-1-methylpyrrolidine hydrochloride 20(a) (2R,4R)-2-[2-{4-Fluoro-2-[2-(3-methoxyphenyl)ethyl]phenoxy}ethyl]-4-lauroyloxy-1-methylpyrrolidine.

1.13 g of (2R,4R)-2-[2-{4-fluoro-2-[2-(3-methoxyphenyl)ethyl]phenoxy}ethyl]-4-hydroxy-1-methylpyrrolidine [prepared as described in step (b) of Example 1], 1.50 g of lauric anhydride and 0.11 g of 4-dimethylaminopyridine were allowed to react together in 20 ml of pyridine and extracted in the same manner as described in step (a) of Example 21. The resulting oily substance was purified by silica gel column chromatography, using a 5:1 by volume mixture of methylene chloride and methanol as the eluent, to give 1.34 g (yield 80%) of the title compound as a colorless oily substance.

Nuclear Magnetic Resonance Spectrum (270 MHz, CDCl$_3$) δ ppm:

0.88 (3H, triplet, J=6.6 Hz);
1.15–1.4 (16H, multiplet);
1.45–1.8 (3H, multiplet);
1.85–2.1 (2H, multiplet);
2.15–2.3 (2H, multiplet);
2.21 (2H, triplet, J=7.6 Hz);
2.39 (3H, singlet);
2.6–2.75 (1H, multiplet);
2.75–3.0 (4H, multiplet);
3.62 (1H, doublet of doublets, J=6.6 & 10.8 Hz);
3.78 (3H, singlet);
3.85–4.1 (2H, multiplet);
5.05–5.2 (1H, multiplet);
6.7–6.9 (6H, multiplet);
7.15–7.25 (1H, multiplet).

20(b) (2R,4R)-2-[2-{4-Fluoro-2-[2-(3-methoxyphenyl)ethyl]phenoxy}ethyl]-4-lauroyloxy-1-methylpyrrolidine hydrochloride 1.34 g of (2R,4R)-2-[2-{4-fluoro-2-[2-(3-methoxyphenyl)ethyl]phenoxy}-ethyl]-4-lauroyloxy-1-methylpyrrolidine [prepared as described in step (a) above] were dissolved in 15 ml of dioxane, and 0.90 ml of a 4N solution of hydrogen chloride in dioxane was added to the resulting solution. The solution was then concentrated by evaporation under reduced pressure. The resulting residue was purified by decantation three times with hexane, and the resulting oily substance was dried in vacuo, to give 1.39 g (yield 97%) of the title compound as a colorless oily substance.

Infrared Absorption Spectrum (film) ν$_{max}$cm$^{-1}$: 1739, 1601, 1584, 1499, 1468, 1456, 1258, 1216, 1156.

Nuclear Magnetic Resonance Spectrum (270 MHz, CDCl$_3$) δ ppm:

0.88 (3H, triplet, J=6.6 Hz);
1.1–1.4 (16H, multiplet);
1.4–1.8 (2H, multiplet);
2.15 (2H, triplet, J=7.5 Hz);
2.25–2.5 (2H, multiplet);
2.5–2.7 (2H, multiplet);
2.75–3.0 (5H, multiplet);
2.86 (3H, singlet);
3.6–3.85 (1H, multiplet);
3.78 (3H, singlet);
3.85–4.05 (1H, multiplet);
4.1–4.3 (1H, multiplet);
4.35 (1H, doublet of doublets, J=5.7 & 13.6 Hz);
5.3–5.4 (1H, multiplet);
6.65–7.0 (6H, multiplet);
7.21 (1H, triplet, J=7.8 Hz).

PREPARATION 1

5-Methoxy-2-(2-phenylethyl)phenol 3.0 g of 2-hydroxy-4-methoxybenzaldehyde were dissolved in 30 ml of acetonitrile, and then 9.2 g of benzyltriphenylphosphonium chloride were added to the resulting solution. The resulting mixture was stirred at 80° C. for 30 minutes, and then 3.53 ml of 1,8-diazabicyclo [5.4.0]-7-undecene (DBU) were added. The reaction mixture was then heated under reflux for 1 hour. At the end of this time, the solvent was removed by evaporation under reduced pressure. Ethyl acetate and water were added to the residue. The ethyl acetate layer was separated and concentrated by evaporation under reduced pressure. The residue was then purified by silica gel column chromatography, using a 2:1 by volume mixture of hexane and ethyl acetate as the eluent, to give 4.37 g of a solid substance. This solid substance was dissolved in 50 ml of ethanol, and then 0.5 g of 5% w/w palladium black were added to the resulting solution. The reaction mixture was then stirred under a hydrogen atmosphere at atmospheric pressure and at 60° C. for 2 hours. At the end of this time, the catalyst was removed by filtration. The filtrate was concentrated by evaporation under reduced pressure, and purified by silica gel column chromatography, using a 3:1 by volume mixture of hexane and ethyl acetate as the eluent, to give 1.60 g (yield 36%) of the title compound as a colorless solid substance.

Nuclear Magnetic Resonance Spectrum (270 MHz, CDCl$_3$) δ ppm:

2.75–2.95 (4H, multiplet);

3.74 (3H, singlet);

4.87 (1H, singlet);

6.33 (1H, doublet, J=2.5 Hz);

6.42 (1H, doublet of doublets, J=2.5 & 8.3 Hz);

6.97 (1H, doublet, J=8.3 Hz);

7.15–7.35 (5H, multiplet).

PREPARATION 2
4-Bromo-2-(2-phenylethyl)phenol 6.0 g of 2-hydroxy-5-bromobenzaldehyde were dissolved in 70 ml of acetonitrile, and then 13.9 g of benzyltriphenylphosphonium chloride were added to the resulting solution. The resulting mixture was stirred at 80° C. for 15 minutes, and then 5.3 ml of DBU were added. The reaction mixture was then heated under reflux for 1 hour. At the end of this time, the solvent was removed by evaporation under reduced pressure. Ethyl acetate and water were then added to the residue. The ethyl acetate layer was separated and concentrated by evaporation under reduced pressure. It was then purified by silica gel column chromatography, using a 2:1 by volume mixture of hexane and ethyl acetate as the eluent, to give 7.44 g of a solid substance. This solid substance was dissolved in 150 ml of ethanol, and then 0.8 g of tris(triphenylphosphine)rhodium(I) chloride were added to the resulting solution. The reaction mixture was then stirred under a hydrogen atmosphere at atmospheric pressure and at 50° C. for 24 hours. A saturated aqueous solution of sodium hydrogen sulfite was then added to the reaction mixture and the mixture was then stirred for about 10 minutes. The resulting insoluble substances were then removed by filtration using a Celite (trade mark) filter aid. The filtrate was concentrated by evaporation under reduced pressure, and purified by silica gel column chromatography, using a 3:1 by volume mixture of hexane and ethyl acetate as the eluent, to give 7.13 g (yield 86%) of the title compound as an oily substance.

Nuclear Magnetic Resonance Spectrum (270 MHz, CDCl$_3$) δ ppm:

2.75–3.0 (4H, multiplet);

5.13 (1H, singlet);

6.61 (1H, doublet, J=8.5 Hz);

7.1–7.35 (7H, multiplet).

PREPARATION 3
4-Fluoro-2-(2-phenylethyl)phenol 0.91 g of benzaldehyde, 4.00 g of 5-fluoro-2-methoxymethoxybenzyl-triphenylphosphonium chloride (prepared as described in Preparation 8) and 1.28 ml of DBU were allowed to react together in 40 ml of acetonitrile, subsequently treated, and purified by silica gel column chromatography, using a 10:1 by volume mixture of hexane and ethyl acetate as the eluent, in the same manner as described in Preparation 2, to give 2.04 g of an oily substance. 2.03 g of this oily substance were dissolved in 12 ml of a 1:2 by volume mixture of benzene and ethanol, and then 0.30 g of tris-(triphenylphosphine)rhodium(I) chloride were added to the resulting solution. The resulting mixture was stirred under a hydrogen atmosphere at atmospheric pressure and at 60° C. for 8 hours. At the end of this time, the reaction solution was filtered with a Celite (trade mark) filter aid. The filtrate was concentrated by evaporation under reduced pressure, and purified by silica gel column chromatography, using a 10:1 by volume mixture of hexane and ethyl acetate as the eluent. The purified substance was then dissolved in 10 ml of ethyl acetate, and then 10 ml of a 4N solution of hydrogen chloride in ethyl acetate were added to the resulting solution, with ice-cooling. The resulting mixture was allowed to stand at room temperature for 2 hours, after which it was concentrated by evaporation under reduced pressure, and purified by silica gel column chromatography, using a 5:1 by volume mixture of hexane and ethyl acetate as the eluent, to give 1.45 g (yield 79%) of the title compound as a solid substance.

Nuclear Magnetic Resonance Spectrum (270 MHz, CDCl$_3$) δ ppm:

2.8–3.0 (4H, multiplet);

4.43 (1H, singlet);

6.6–6.9 (3H, multiplet);

7.15–7.35 (5H, multiplet).

PREPARATION 4
4-Fluoro-2-[2-(3-methoxyphenyl)ethyl]phenol 312 mg of 2-hydroxy-5-fluorobenzaldehyde, 1110 mg of 3-methoxybenzyl-triphenylphosphonium chloride and 0.37 ml of DBU were allowed to react together in 20 ml of acetonitrile, subsequently treated, and purified by silica gel column chromatography, using a 2:1 by volume mixture of hexane and ethyl acetate as the eluent, in the same manner as described in Preparation 2, to give 526 mg of a solid substance. This solid substance was dissolved in 12 ml of a 1:2 by volume mixture of benzene and ethanol, and then 52 mg of tris-(triphenylphosphine)-rhodium(I) chloride were added to the resulting solution. The reaction mixture was then stirred under a hydrogen atmosphere at atmospheric pressure and at room temperature for 7 hours. A saturated aqueous solution of sodium hydrogen sulfite was then added to the reaction mixture and the mixture was then stirred for about 10 minutes. The resulting insoluble substances were then removed by filtration using a Celite (trade mark) filter aid. The filtrate was concentrated by evaporation under reduced pressure, and purified by silica gel column chromatography, using a 2:1 by volume mixture of hexane and ethyl acetate as the eluent, to give 404 mg (yield 75%) of the title compound as an oily substance.

Nuclear Magnetic Resonance Spectrum (270 MHz, CDCl$_3$) δ ppm:

2.88 (4H, singlet);

3.78 (3H, singlet);

4.52 (1H, singlet);

6.65–6.85 (6H, multiplet);

7.21 (1H, triplet, J=7.5 Hz).

PREPARATION 5

4-Fluoro-2-[2-(4-fluoro-3-methoxyphenyl)ethyl]phenol 5 (a) Methoxymethyl {4-fluoro-2-[2-(4-fluoro-3-methoxyphenyl)ethyl]phenyl} ether 547 mg of 4-fluoro-3-methoxybenzaldehyde, 1990 mg of 5-fluoro-2-methoxymethoxybenzyltriphenylphosphonium chloride (prepared as described in Preparation 8) and 0.58 ml of DBU were allowed to react together in 30 ml of acetonitrile, subsequently treated, and purified by silica gel column chromatography, using a 4:1 by volume mixture of hexane and ethyl acetate as the eluent, in the same manner as described in Preparation 2, to give 948 mg of an oily substance. 936 mg of this oily substance were dissolved in 9 ml of a 1:2 by volume mixture of benzene and ethanol, and then 155 mg of tris-(triphenylphosphine)rhodium(I)chloride were added to the resulting solution. The resulting mixture was then stirred under a hydrogen atmosphere at atmospheric pressure and at 60° C. for 14 hours. A saturated aqueous solution of sodium hydrogen sulfite was then added to the reaction mixture and the mixture was then stirred for about 10 minutes. The resulting insoluble substances were then removed by filtration using a Celite (trade mark) filter aid. The filtrate was concentrated by evaporation under reduced pressure, and purified by silica gel column chromatography, using a 4:1 by volume mixture of hexane and ethyl acetate as the eluent, to give 785 mg (yield 73%) of the title compound as an oily substance.

Nuclear Magnetic Resonance Spectrum (270 MHz, CDCl$_3$) δ ppm:

2.75–3.0 (4H, multiplet);

3.47 (3H, singlet);

3.84 (3H, singlet);

5.12 (2H, singlet);

6.65–6.75 (2H, multiplet);

6.75–6.9 (2H, multiplet);

6.9–7.1 (2H, multiplet).

5(b) 4-Fluoro-2-[2-(4-fluoro-3-methoxyphenyl)ethyl]phenol 770 mg of methoxymethyl {4-fluoro-2-[2-(4-fluoro-3-methoxyphenyl)ethyl]phenyl} ether [prepared as described in step (a) above] were dissolved in 4 ml of ethyl acetate, and then 4 ml of a 4N solution of hydrogen chloride in ethyl acetate were added to the resulting solution, whilst ice-cooling. The resulting mixture was then allowed to stand at room temperature for 2 hours. At the end of this time, the reaction mixture was concentrated by evaporation under reduced pressure, and purified by silica gel column chromatography, using a 3:2 by volume mixture of hexane and ethyl acetate as the eluent, to give 631 mg (yield 96%) of the title compound as an oily substance.

Nuclear Magnetic Resonance Spectrum (270 MHz, CDCl$_3$) δ ppm:

2.87 (4H, singlet);

3.83 (3H, singlet);

4.60 (1H, singlet);

6.6–6.85 (5H, multiplet);

6.98 (1H, doublet of doublets, J=8.5 & 11.3 Hz).

PREPARATION 6

4-Fluoro-2-[2-(4-fluorophenyl)ethyl]phenol

6(a) Methoxymethyl {4-fluoro-2-[2-(4-fluorophenyl)ethyl]phenyl} ether 950 mg of 4-fluorobenzaldehyde, 3860 mg of 5-fluoro-2-methoxymethoxybenzyltriphenylphosphonium chloride (prepared as described in Preparation 8) and 1.26 ml of DBU were allowed to react together in 60 ml of acetonitrile, subsequently treated, and purified by silica gel column chromatography, using a 9:1 by volume mixture of hexane and ethyl acetate as the eluent, in the same manner as described in Preparation 2, to give 2030 mg of an oily substance. 1980 mg of this oily substance were dissolved in 12 ml of a 1:2 by volume mixture of benzene and ethanol, and then 155 mg of tris-(triphenylphosphine)rhodium(I) chloride were added to the resulting solution. The mixture was then stirred under a hydrogen atmosphere at atmospheric pressure and at 60° C. for 20 hours. At the end of this time, the reaction solution was filtered with diatomaceous earth. The filtrate was concentrated by evaporation under reduced pressure, and purified by silica gel column chromatography, using a 9:1 by volume mixture of hexane and ethyl acetate as the eluent, to give 1816 mg (yield 87%) of the title compound as an oily substance.

Nuclear Magnetic Resonance Spectrum (270 MHz, CDCl$_3$) δ ppm:

2.75–3.0 (4H, multiplet);

3.47 (3H, singlet);

5.11 (2H, singlet);

6.75–6.9 (2H, multiplet);

6.9–7.2 (5H, multiplet).

6(b) 4-Fluoro-2-[2-(4-fluorophenyl)ethyl]phenol 1785 mg of methoxymethyl {4-fluoro-2-[2-(4-fluorophenyl)ethyl]phenyl} ether [prepared as described in step (a) above] were dissolved in 8 ml of ethyl acetate, and then 8 ml of a 4N solution of hydrogen chloride in ethyl acetate were added to the resulting solution, whilst ice-cooling. The resulting mixture was allowed to stand at room temperature for 2 hours, after which it was concentrated by evaporation under reduced pressure, and purified by silica gel column chromatography, using a 4:1 by volume mixture of hexane and ethyl acetate as the eluent, to give 1483 mg (yield 99%) of the title compound as an oily substance.

Nuclear Magnetic Resonance Spectrum (270 MHz, CDCl$_3$) δ ppm:

2.75–3.0 (4H, multiplet);

4.57 (1H, singlet);

6.6–6.85 (3H, multiplet);

6.9–7.05 (2H, multiplet);

7.05–7.2 (2H, multiplet).

PREPARATION 7

2-[2-(3,4-Difluorophenyl)ethyl]-4-fluorophenol 610 mg of 3,4-difluorobenzaldehyde, 2000 mg of 5-fluoro-2-methoxymethoxybenzyltriphenylphosphonium chloride and 0.64 ml of DBU were allowed to react together in 20 ml of acetonitrile, subsequently treated, and purified by silica gel column chromatography, using a 15:1 by volume mixture of hexane and ethyl acetate as the eluent, in the same manner as described in Preparation 2, to give 1230 mg of an oily substance. This oily substance was dissolved in 10 ml of ethanol, and 300 mg of tris-(triphenylphosphine)rhodium (I) chloride were added to the resulting solution. The resulting mixture was then stirred under a hydrogen atmosphere at atmospheric pressure and at 60° C. for 14 hours. At the end of this time, the reaction solution was filtered with a Celite (trade mark) filter aid. The filtrate was concentrated by evaporation under reduced pressure, and allowed to adsorb on a silica gel column for some time. The filtrate was then allowed to elute slowly, using a 4:1 by volume mixture of hexane and ethyl acetate as the eluent, to give an eluate containing the title compound. This eluate was concentrated by evaporation under reduced pressure, and dried in vacuo, to give 1010 mg (yield 93%) of the title compound as a solid substance.
Nuclear Magnetic Resonance Spectrum (270 MHz, CDCl$_3$) δ ppm:

2.86 (4H, singlet);
4.60 (1H, singlet);
6.6–7.15 (6H, multiplet).

PREPARATION 8
5-Fluoro-2-mehoxymethoxybenzyltriphenylphosphonium chloride
8(a) 5-Fluoro-2-hydroxybenzyl alcohol 1.98 g of lithium aluminum hydride were added to 50 ml of tetrahydrofuran, and a solution of 5.44 g of 5-fluorosalicylic acid in 50 ml of tetrahydrofuran was then added dropwise at room temperature to the resulting solution. The resulting mixture was then heated under reflux for 1 hour. At the end of this time, it was cooled, and sodium sulfate decahydrate was added in order to decompose any excess hydride. Insoluble substances were removed by filtration. The filtrate was concentrated by evaporation under reduced pressure, and purified by silica gel column chromatography, using a 2:1 by volume mixture of hexane and ethyl acetate as the eluent, to give 4.72 g (yield 95%) of the title compound as a solid substance.
Nuclear Magnetic Resonance Spectrum (270 MHz, CDCl$_3$) δ ppm:

1.69 (1H, triplet, J=3.2 Hz);
4.82 (2H, doublet, J=3.2 Hz);
6.7–7.0 (3H, multiplet);
7.17 (1H, singlet).

8(b) 5-Fluoro-2-methoxymethoxybenzal alcohol 4.71 g of 5-fluoro-2-hydroxybenzyl alcohol [prepared as described in step (a) above] were dissolved in 100 ml of N,N-dimethylacetamide, and then 3.72 g of potassium t-butoxide were added to the resulting solution, whilst ice-cooling. The resulting mixture was then stirred at the same temperature for 10 minutes, and then 2.74 ml of methoxymethyl chloride were added at the same temperature. The mixture was then allowed to stand until the temperature returned to room temperature, after which it was stirred for 1 hour. 60 ml of water and 300 ml of ethyl acetate were then added to the reaction solution. The ethyl acetate layer was separated, washed with a saturated aqueous solution of sodium chloride, dried over anhydrous magnesium sulfate, and concentrated by evaporation under reduced pressure. The concentrated substance was purified by silica gel column chromatography, using a 3:2 by volume mixture of hexane and ethyl acetate as the eluent, to give 4.25 g (yield 69%) of the title compound as an oily substance.
Nuclear Magnetic Resonance Spectrum (270 MHz, CDCl$_3$) δ ppm:

2.30 (1H, triplet, J=6.2 Hz);
3.49 (3H, singlet);
4.67 (2H, doublet, J=6.2 Hz);
5.19 (2H, singlet);
6.85–7.0 (1H, multiplet);
7.0–7.15 (2H, multiplet).

8(c) 5-Fluoro-2-methoxymethoxybenzyl chloride 4.15 g of 5-fluoro-2-methoxymethoxybenzyl alcohol [prepared as described in step (b) above] were dissolved in 70 ml of tetrahydrof tiran, and then 6.86 g of carbon tetrachloride and 11.69 g of triphenylphosphine were added to the resulting solution, in that order. The resulting mixture was then stirred at room temperature for 1 hour, and then heated under reflux for 5 hours. At the end of this time, insoluble substances were removed by filtration. The filtrate was concentrated by evaporation under reduced pressure, and purified by silica gel column chromatography, using a 9:1 by volume mixture of hexane and ethyl acetate as the eluent, to give 3.27 g (yield 71%) of the title compound as an oily substance.
Nuclear Magnetic Resonance Spectrum (270 MHz, CDCl$_3$) δ ppm:

3.50 (3H, singlet);
4.62 (2H, singlet);
5.21 (2H, singlet);
6.9–7.05 (1H, multiplet);
7.05–7.2 (2H, multiplet).

8(d) 5-Fluoro-2-methoxymethoxybenzyltriphenylphosphonium chloride 3.25 g of 5-fluoro-2-methoxymethoxybenzyl chloride [prepared as described in step (c) above] were dissolved in 50 ml of toluene, and then 6.25 g of triphenylphosphine were added to the resulting solution. The resulting mixture was then heated under reflux for 6 hours. At the end of this time, the reaction solution was cooled. The resulting crystals were collected by filtration, and dried in vacuo, to give 5.16 g (yield 70%) of the title compound. Separately, the filtrate was concentrated by evaporation under reduced pressure, and the crystals which precipitated were collected by filtration, to give an additional 0.75 g (total yield: 80%) of the title compound.
Nuclear Magnetic Resonance Spectrum (270 MHz, CDCl$_3$) δ ppm:

3.18 (3H, singlet);
4.51 (2H, singlet);
5.60 (2H, doublet, J=14.6 Hz);
6.85–6.95 (2H, multiplet);
7.05–7.15 (1H, multiplet);
7.55–7.85 (15H, multiplet).

PREPARATION 9
5-Chloro-2-(2-phenylethyl)phenol.

1.10 g of benzaldehyde, 6.02g of 4-chloro-2-methoxybenzyltriphenyl-phosphonium chloride and 1.85 ml of DBU were allowed to react together in 20 ml of acetonitrile and were subsequently treated and purified by silica gel column chromatography, using a 10: 1 by volume mixture of hexane and ethyl acetate as the eluent, in the same manner as described in Preparation 2, to give 2.85 g of an oily substance. This oily substance was dissolved in 50 ml of ethanol, and 0.40 g of tris(triphenylphosphine)rhodium(I) chloride was added to the resulting solution. The resulting mixture was then stirred under a hydrogen atmosphere at atmospheric pressure and at 50° C. for 14 hours. At the end of this time, the reaction solution was filtered using a Celite (trade mark) filter aid. The filtrate was concentrated by evaporation under reduced pressure, and purified by silica gel column chromatography, using a 5:1 by volume mixture of hexane and ethyl acetate as the eluent, to give an intermediate compound. This intermediate compound was dissolved in 10 ml of ethyl acetate, and 10 ml of a 4N solution of hydrogen chloride in ethyl acetate were added to the resulting solution, whilst ice-cooling. The reaction mixture was then allowed to stand at room temperature for 1 hour. At the end of this time, the solvent was removed by evaporation under reduced pressure. The residue was purified by silica gel column chromatography, using a 5:1 by volume mixture of hexane and ethyl acetate as the eluent, to give 2.40 g (a quantitative yield) of the title compound as a colorless oily substance.

Nuclear Magnetic Resonance Spectrum (270 MHz, CDCl$_3$) δ ppm:

2.75–3.0 (4H, multiplet);
6.7–6.9 (2H, multiplet);
6.96 (1H, doublet, J=8.1 Hz);
5 7.1–7.35 (5H, multiplet).

PREPARATION 10
6-Fluoro-2-(2-phenylethyl)phenol.

3.00 g of 3-fluoro-2-hydroxybenzaldehyde, 9.99 g of benzyltriphenyl-phosphonium chloride and 3.83 ml of DBU were allowed to react together in 30 ml of acetonitrile and were subsequently treated and purified by silica gel column chromatography, using a 5:1 by volume mixture of hexane and ethyl acetate as the eluent, in the same manner as described in Preparation 2, to give 4.58 g of a colorless solid substance. This solid substance was dissolved in 50 ml of ethanol, and 0.50 g of tris(triphenylphosphine)rhodium(I) chloride was added to the resulting solution. The resulting mixture was then stirred under a hydrogen atmosphere at atmospheric pressure and at 50° C. for 48 hours. At the end of this time, the reaction solution was filtered using a Celite (trade mark) filter aid. The filtrate was concentrated by evaporation under reduced pressure, and purified by silica gel column chromatography, using a 5:1 by volume mixture of hexane and ethyl acetate as the eluent, to give 3.15 g (yield 68%) of the title compound as a colorless solid substance.

Nuclear Magnetic Resonance Spectrum (270 MHz, CDCl$_3$) δ ppm:

2.8–3.05 (4H, multiplet);
6.65–7.0 (3H, multiplet);
7.1–7.35 (5H, multiplet).

PREPARATION 11
4-Chloro-2-methoxymethoxybenzyltriphenylphosphonium chloride.

11(a) 4-Chloro-2-hydroxybenzyl alcohol.

1.65 g of lithium aluminum hydride were suspended in 100 ml of tetrahydrofuran, and then 5.00 g of 4-chlorosalicylic acid in 50 ml of tetrahydrofuran were added dropwise to the resulting suspension, whilst stirring and ice-cooling. The resulting mixture was then heated under reflux for 1 hour. At the end of this time, the reaction mixture was cooled on ice, and sodium sulfate decahydrate was added to decompose the excess hydride. Insoluble substances were removed by filtration, and the filtrate was concentrated by evaporation under reduced pressure. The residue was then purified by silica gel column chromatography, using a 1:1 by volume mixture of hexane and ethyl acetate as the eluent, to give 4.00 g (yield 87%) of the title compound as a colorless solid substance.

Nuclear Magnetic Resonance Spectrum (270 MHz, hexadeuterated dimethyl sulfoxide) δ ppm:

4.43 (2H, singlet);
6.75–6.9 (2H, multiplet);
7.28 (1H, doublet, J=8.0 Hz).

11(b) 4-Chloro-2-methoxymethoxybenzyl alcohol.

4.00 g of 4-chloro-2-hydroxybenzyl alcohol [prepared as described in step (a) above] were dissolved in 80 ml of N,N-dimethylacetamide, and then 2.83 g of potassium t-butoxide were added to the resulting solution, whilst ice-cooling, and the mixture was stirred for 10 minutes. 2.09 ml of methoxymethyl chloride were then added to the reaction mixture, whilst ice-cooling, and the mixture was then stirred at room temperature for 1 hour. At the end of this time, 60 ml of water and 300 ml of ethyl acetate were added, and the ethyl acetate layer was separated and washed with a saturated aqueous solution of sodium chloride, and then dried over anhydrous magnesium sulfate. It was then concentrated by evaporation under reduced pressure. The residue was purified by silica gel column chromatography, using a 2:1 by volume mixture of hexane and ethyl acetate as the eluent, to give 4.69 g (yield 92%) of the title compound as an oily substance.

Nuclear Magnetic Resonance Spectrum (270 MHz, CDCl$_3$) δ ppm:

3.48 (3H, singlet);
4.65 (2H, singlet);
5.20 (2H, singlet);
6.98 (1H, doublet of doublets, J=1.9 & 8.2 Hz);
7.12 (1H, doublet, J=1.9 Hz);
7.24 (1H, doublet, J=8.2 Hz).

11(c) 4-Chloro-2-methox ymethoxybenzyl chloride.

4.69 g of 4-chloro-2-methoxymethoxybenzyl alcohol [prepared as described in step (b) above] were dissolved in 80 ml of tetrahydrofuran, and then 7.11 g of carbon tetrachloride and 12.14 g of triphenylphosphine were added to the resulting solution. The resulting mixture was stirred at room temperature for 1 hour and then heated under reflux for 2.5 hours. At the end of this time, any insoluble substance was removed by filtration, and the filtrate was concentrated by evaporation under reduced pressure. The residue was purified by silica gel column chromatography, using a 10:1 by volume mixture of hexane and ethyl acetate as the eluent, to give 3.38 g (yield 66%) of the title compound as an oily substance.

Nuclear Magnetic Resonance Spectrum (270 MHz, CDCl$_3$) δ ppm:

3.50 (3H, singlet);
4.61 (2H, singlet);
5.24 (2H, singlet);
6.98 (1H, doublet of doublets, J=2.0 & 8.2 Hz);
7.14 (1H, doublet, J=2.0 Hz);
7.26 (1H, doublet, J=8.2 Hz).

11(d) 4-Chloro-2-methoxymethoxybenzyltriphenylphosphonium chloride.

3.38 g of 4-chloro-2-methoxymethoxybenzyl chloride [prepared as described in step (c) above] were dissolved in 50 ml of toluene, and then 6.02 g of triphenylphosphine were added to the resulting solution. The resulting mixture was heated under reflux for 15.5 hours. At the end of this time, the reaction mixture was cooled on ice, and the crystals which precipitated were collected by filtration, and dried in vacuo, to give 6.02 g (yield 82%) of the title compound.

Nuclear Magnetic Resonance Spectrum (270 MHz, CDCl$_3$) δ ppm:

3.19 (3H, singlet);
4.52 (2H, singlet);
5.58 (2H, doublet, J=14.3 Hz);
6.8–6.9 (1H, multiplet);

6.9–6.95 (1H, multiplet);
7.39 (1H, doublet of doublets, J=3.0 & 8.2 Hz);
7.6–7.9 (15H, multiplet).

FORMULATION 1
Capsules

The components used were as follows:

| | |
|---|---|
| Compound of Example 4 | 20.0 mg |
| Lactose | 158.7 |
| Corn starch | 70.0 |
| Magnesium stearate | 1.3 |
| | 250 mg |

Powders of the above substances were blended, and the blended powder was sieved through a 60-mesh screen (Tyler standard mesh). The sieved powder was then charged into a 250 mg No. 3 gelatine capsule to make a capsule preparation.

FORMULATION 2
Tablets

The components used were as follows:

| | |
|---|---|
| Compound of Example 4 | 20.0 mg |
| Lactose | 154.0 |
| Corn starch | 25.0 |
| Magnesium stearate | 1.0 |
| | 200 mg |

Powder of the above substances was blended. The blended powder was then compressed with a tabletting machine to make a 200 mg tablet. The tablet may be sugar-coated, if necessary.

We claim:

1. A compound of formula (I):

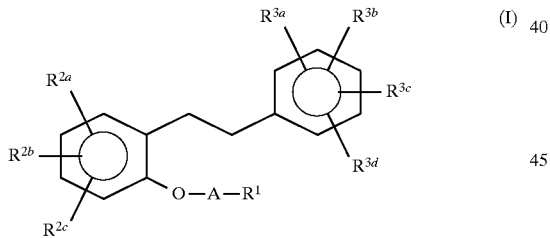

wherein:
$R^1$ represents a saturated heterocyclic group attached to the bond or group represented by A through a ring carbon atom, said saturated heterocyclic group having from 3 to 6 ring atoms, of which one or two are hetero-atoms selected from the group consisting of nitrogen, oxygen and sulfur hetero-atoms, and being substituted on at least one carbon atom by at least one substituent selected from the group consisting of substituents α defined below or being unsubstituted on a nitrogen atom or being substituted on a nitrogen atom by at least one substituent selected from the group consisting of substituents β defined below;

$R^{2a}$ and $R^{2b}$ are the same as or different from each other and each represents a hydrogen atom, a fluorine atom or a chlorine atom and $R^{2c}$ is a hydrogen atom, wherein at least one of $R^{2a}$ and $R^{2b}$ is not a hydrogen atom;

$R^{3a}$, $R^{3b}$, $R^{3c}$ and $R^{3d}$ are the same as or different from each other and each represents a hydrogen atom, an alkyl group having from 1 to 6 carbon atoms, a haloalkyl group having from 1 to 6 carbon atoms, an alkenyl group having from 2 to 6 carbon atoms, an alkynyl group having from 2 to 6 carbon atoms, a hydroxy group, an alkoxy group having from 1 to 6 carbon atoms, a haloalkoxy group having from 1 to 6 carbon atoms, an alkoxycarbonyloxy group having from 2 to 6 carbon atoms, an alkanoyloxy group having from 1 to 6 carbon atoms, a carbamoyloxy group, an alkylcarbamoyloxy group in which the alkyl part has from 1 to 6 carbon atoms, a dialkylcarbamoyloxy group in which each alkyl part has from 1 to 6 carbon atoms, a halogen atom, a cyano group, a nitro group or an aryl group as defined below;

A represents a single bond or an alkylene group having from 1 to 6 carbon atoms;

said substituents α are selected from the group consisting of hydroxy groups, alkoxycarbonyloxy groups in which the alkoxy part has from 1 to 20 carbon atoms, alkanoyloxy groups having from 1 to 20 carbon atoms, alkanoyloxy groups having from 2 to 7 carbon atoms and substituted by a carboxy group, carbamoyloxy groups, alkylcarbamoyloxy groups having from 1 to 6 carbon atoms, and dialkylcarbamoyloxy groups in which each alkyl part has from 1 to 10 carbon atoms;

said substituents β are selected from the group consisting of alkyl groups having from 1 to 6 carbon atoms, alkyl groups having from 1 to 6 carbon atoms and substituted by at least one aryl group as defined below, aryl groups as defined below, and alkoxycarbonyl groups having from 2 to 10 carbon atoms;

said aryl groups are carbocyclic aromatic groups which have from 6 to 10 ring carbon atoms and which are unsubstituted or are substituted by at least one substituent selected from the group consisting of substituents γ, defined below;

said substituents γ are selected from the group consisting of alkyl groups having from 1 to 6 carbon atoms, alkoxy groups having from 1 to 6 carbon atoms, and halogen atoms;

or pharmaceutically acceptable salts or esters thereof.

2. The compound of claim 1, wherein $R^1$ represents a pyrrolidinyl group, a piperidyl group, a morpholinyl group, a thiomorpholinyl group or a piperazinyl group, which is substituted on a carbon atom by at least one of substituents $\alpha^1$ and is unsubstituted or is substituted on a nitrogen atom by at least one of substituents $\beta^1$, said substituents $\alpha^1$ are selected from the group consisting of hydroxy groups, alkoxycarbonyloxy groups having from 1 to 6 or from 8 to 18 carbon atoms in the alkoxy part, alkanoyloxy groups having from 1 to 20 carbon atoms, carboxy-substituted alkanoyloxy groups having from 3 to 6 carbon atoms in the alkanoyl part, carbamoyloxy groups, and mono- or di- alkylcarbamoyloxy groups having 1 or 2 carbon atoms in the or each alkyl part; and said substituents $\beta^1$ are selected from the group consisting of alkyl groups having from 1 to 4 carbon atoms, and phenyl groups which are unsubstituted or are substituted by at least one substituent selected from the group consisting of methyl groups, methoxy groups, fluorine atoms and chlorine atoms.

3. The compound of claim 1, wherein $R^1$ represents a pyrrolidinyl group, a piperidyl group, a morpholinyl group or a thiomorpholinyl group, which is substituted on a carbon atom by at least one of substituents $\alpha^2$ and is unsubstituted or is substituted on a nitrogen atom by at least one of substituents β², said substituents α² are selected from the group consisting of hydroxy groups, alkoxycarbonyloxy groups having from 1 to 4 or from 8 to 18 carbon atoms in the alkoxy part, alkanoyloxy groups having from 2 to 5 carbon atoms, alkanoyloxy groups having from 10 to 18 carbon atoms, carboxy-substituted alkanoyloxy groups having from 3 to 6 carbon atoms in the alkanoyl part, carbamoyloxy groups, and mono- or di-alkylcarbamoyloxy groups having 1 or 2 carbon atoms in the or each alkyl part; and said substituents β² are selected from the group consisting of alkyl groups having from 1 to 4 carbon atoms.

4. The compound of claim 1, wherein R¹ represents a pyrrolidinyl group, a piperidyl group, a morpholinyl group or a thiomorpholinyl group, which is substituted on a carbon atom by at least one of substituents α³ and is unsubstituted or is substituted on a nitrogen atom by at least one of substituents β³, said substituents α³ are selected from the group consisting of hydroxy, methoxycarbonyloxy, ethoxycarbonyloxy, isopropoxycarbonyloxy, t-butoxycarbonyloxy, octyloxycarbonyloxy, decyloxycarbonyloxy, hexadecyloxycarbonyloxy, octadecyloxycarbonyloxy, acetoxy, propionyloxy, butyryloxy, valeryloxy, pivaloyloxy, decanoyloxy, undecanoyloxy, lauroyloxy, myristoyloxy, palmitoyloxy, stearoyloxy, succinyloxy, glutaryloxy, carbamoyloxy, N-methylcarbamoyloxy, N-ethylcarbamoyloxy and N,N-dimethylcarbamoyloxy groups; and said substituents β³ are selected from the group consisting of methyl and ethyl groups.

5. The compound of claim 1, wherein R¹ represents a pyrrolidinyl group, a piperidyl group or a morpholinyl group, which is substituted on a carbon atom by at least one of substituents α⁴ and is unsubstituted or is substituted on a nitrogen atom by at least one of substituents β³, said substituents α⁴ are selected from the group consisting of hydroxy, ethoxycarbonyloxy, isopropoxycarbonyloxy, t-butoxycarbonyloxy, octyloxycarbonyloxy, hexadecyloxycarbonyloxy, octadecyloxycarbonyloxy, decanoyloxy, lauroyloxy, palmitoyloxy, stearyloxy, succinyloxy, carbamoyloxy and N,N-dimethylcarbamoyloxy groups; and said substituents β⁴ are selected from the group consisting of methyl and ethyl groups.

6. The compound of claim 1, wherein R¹ represents a 4-hydroxy-2-pyrrolidinyl group, a 4-ethoxycarbonyloxy-2-pyrrolidinyl group, a 4-isopropoxycarbonyloxy-2-pyrrolidinyl group, a 4-t-butoxycarbonyloxy-2-pyrrolidinyl group, a 4-octyloxy-carbonyloxy-2-pyrrolidinyl group, a 4-hexadecyloxycarbonyloxy-2-pyrrolidinyl group, a 4-octadecyloxycarbonyloxy-2-pyrrolidinyl group, a 4-acetoxy-2-pyrrolidinyl group, a 4-decanoyloxy-2-pyrrolidinyl group, a 4-lauroyloxy-2-pyrrolidinyl group, a 4-myristoyloxy-2-pyrrolidinyl group, a 4-palmitoyloxy-2-pyrrolidinyl group, a 4-stearoyloxy-2-pyrrolidinyl group, a 4-succinyloxy-2-pyrrolidinyl group, a 4-carbamoyloxy-2-pyrrolidinyl group, a 1-methyl-4-hydroxy-2-pyrrolidinyl group, a 1-methyl-4-ethoxycarbonyloxy-2-pyrrolidinyl group, a 1-methyl-4-isopropoxycarbonyloxy-2-pyrrolidinyl group, a 1-methyl-4-t-butoxycarbonyloxy-2-pyrrolidinyl group, a 1-methyl-4-octyloxycarbonyloxy-2-pyrrolidinyl group, a 1-methyl-4-hexadecyloxycarbonyloxy-2-pyrrolidinyl group, a 1-methyl-4-octadecyloxycarbonyloxy-2-pyrrolidinyl group, a 1-methyl-4-acetoxy-2-pyrrolidinyl group, a 1-methyl-4-decanoyloxy-2-pyrrolidinyl group, a 1-methyl-4-lauroyloxy-2-pyrrolidinyl group, a 1-methyl-4-myristoyloxy-2-pyrrolidinyl group, a 1-methyl-4-palmitoyloxy-2-pyrrolidinyl group, a 1-methyl-4-stearoyloxy-2-pyrrolidinyl group, or a 1-methyl-4-succinyloxy-2-pyrrolidinyl group.

7. The compound of claim 1, wherein R¹ represents a 4-hydroxy-2-pyrrolidinyl group, a 4-ethoxycarbonyloxy-2-pyrrolidinyl group, a 4-t-butoxycarbonyloxy-2-pyrrolidinyl group, a 4-octyloxycarbonyloxy-2-pyrrolidinyl group, a 4-hexadecyloxycarbonyloxy-2-pyrrolidinyl group, a 4-octadecyloxycarbonyloxy-2-pyrrolidinyl group, a 4-decanoyloxy-2-pyrrolidinyl group, a 4-lauroyloxy-2-pyrrolidinyl group, a 4-myristoyloxy-2-pyrrolidinyl group, a 4-palmitoyloxy-2-pyrrolidinyl group, a 4-stearoyloxy-2-pyrrolidinyl group, a 1-methyl-4-hydroxy-2-pyrrolidinyl group, a 1-methyl-4-ethoxycarbonyloxy-2-pyrrolidinyl group, a 1-methyl-4-t-butoxycarbonyloxy-2-pyrrolidinyl group, a 1-methyl-4-octyloxycarbonyloxy-2-pyrrolidinyl group, a 1-methyl-4-hexadecyloxycarbonyloxy-2-pyrrolidinyl group, a 1-methyl-4-octadecyloxycarbonyloxy-2-pyrrolidinyl group, a 1-methyl-4-decanoyloxy-2-pyrrolidinyl group, a 1-methyl-4-lauroyloxy-2-pyrrolidinyl group, a 1-methyl-4-myristoyloxy-2-pyrrolidinyl group, a 1-methyl-4-palmitoyloxy-2-pyrrolidinyl group or a 1-methyl-4-stearoyloxy-2-pyrrolidinyl group.

8. The compound of claim 1, wherein R¹ represents a 4-hydroxy-2-pyrrolidinyl group, a 4-decanoyloxy-2-pyrrolidinyl group, a 4-lauroyloxy-2-pyrrolidinyl group, a 4-myristoyloxy-2-pyrrolidinyl group, a 4-palmitoyloxy-2-pyrrolidinyl group, a 4-stearoyloxy-2-pyrrolidinyl group, a 1-methyl-4-hydroxy-2-pyrrolidinyl group, a 1-methyl-4-decanoyloxy-2-pyrrolidinyl group, a 1-methyl-4-lauroyloxy-2-pyrrolidinyl group, a 1-methyl-4-myristoyloxy-2-pyrrolidinyl group, a 1-methyl-4-palmitoyloxy-2-pyrrolidinyl group or a 1-methyl-4-stearoyloxy-2-pyrrolidinyl group.

9. The compound of claim 1, wherein $R^{2a}$ a represents a fluorine atom, and $R^{2b}$ and $R^{2c}$ both represent hydrogen atoms.

10. The compound of claim 1, wherein $R^{3a}$, $R^{3b}$ and $R^{3c}$, which are the same as or different from each other, each represents a hydrogen atom, an alkyl group having from 1 to 4 carbon atoms, a halogen-substituted alkyl group having 1 or 2 carbon atoms, an alkenyl group having 3 or 4 carbon atoms, an alkynyl group having 3 or 4 carbon atoms, a hydroxy group, an alkoxy group having from 1 to 4 carbon atoms, a halogen-substituted alkoxy group having 1 or 2 carbon atoms, an alkoxycarbonyl group having from 1 to 4 carbon atoms in the alkoxy part, an alkanoyloxy group having from 2 to 5 carbon atoms, a carbamoyl group, a mono- or di-alkylcarbamoyl group having 1 or 2 carbon atoms in the or each alkyl part, a halogen atom, a cyano group, a nitro group, or a phenyl group which is unsubstituted or is substituted by at least one of substituents $\gamma^1$, defined below, and $R^{3d}$ represents a hydrogen atom;

said substituents $\gamma^1$ are selected from the group consisting of methyl, ethyl, methoxy and ethoxy groups and halogen atoms.

11. The compound of claim 1, wherein $R^{3a}$, $R^{3b}$ and $R^{3c}$, which are the same as or different from each other, each represents a hydrogen atom, a methyl or ethyl group, a fluorine- or chlorine-substituted alkyl group having 1 or 2 carbon atoms, an allyl group, a propargyl group, a hydroxy group, a methoxy group, an ethoxy group, a fluoromethoxy group, a difluoromethoxy group, a chloromethoxy group, a 2-fluoroethoxy group, a 2-chloroethoxy group, a methoxycarbonyl group, an ethoxycarbonyl group, an alkanoyloxy group having 2 or 3 carbon atoms, a carbamoyl group, a methylcarbamoyl group, a dimethylcarbamoyl group, a fluorine atom, a chlorine atom, a bromine atom, a cyano group, a nitro group, or a phenyl group which is unsubstituted or is substituted by at least one of substituents $\gamma^2$, defined below, and $R^{3d}$ represents a hydrogen atom;

said substituents $\gamma^2$ are selected from the group consisting of methyl and methoxy groups and fluorine and chlorine atoms.

12. The compound of claim 1, wherein $R^{3a}$, $R^{3b}$ and $R^{3c}$, which are the same as or different from each other, each represents a hydrogen atom, a methyl group, an ethyl group, a fluoromethyl group, a trifluoromethyl group, a chloromethyl group, a hydroxy group, a methoxy group, an ethoxy group, a fluoromethoxy group, a difluoromethoxy group, a 2-fluoroethoxy group, a fluorine atom, a chlorine atom, a bromine atom, a cyano group, a carbamoyl group or a phenyl group, and $R^{3d}$ represents a hydrogen atom.

13. The compound of claim 1, wherein $R^{3a}$ and $R^{3b}$, which are the same as or different from each other, each represents a hydrogen atom, a methyl group, a hydroxy group, a methoxy group, an ethoxy group, a fluoromethoxy group, a difluoromethoxy group, a fluorine atom, a chlorine atom, a bromine atom or a cyano group, and $R^{3c}$ and $R^{3d}$ both represent hydrogen atoms.

14. The compound of claim 1, wherein $R^{3a}$ and $R^{3b}$, which are the same as or different from each other, each represents a hydrogen atom, a methoxy group or a fluorine atom, and $R^{3c}$ and $R^{3d}$ both represent hydrogen atoms.

15. The compound of claim 1, wherein A represents a single bond or an alkylene group having from 1 to 4 carbon atoms.

16. The compound of claim 1, wherein A represents a single bond, a methylene group, an ethylene group or a trimethylene group.

17. The compound of claim 1, wherein A represents a single bond, a methylene group or an ethylene group.

18. The compound of claim 1, wherein A represents an ethylene group.

19. The compound of claim 1, wherein:

$R^1$ represents a pyrrolidinyl group, a piperidyl group, a morpholinyl group, a thiomorpholinyl group or a piperazinyl group, which is substituted on a carbon atom by at least one of substituents $\alpha^1$ and is unsubstituted or is substituted on a nitrogen atom by at least one of substituents $\beta^1$, defined below;

said substituents $\alpha^1$ are selected from the group consisting of hydroxy groups, alkoxycarbonyloxy groups having from 1 to 6 or from 8 to 18 carbon atoms in the alkoxy part, alkanoyloxy groups having from 1 to 20 carbon atoms, carboxy-substituted alkanoyloxy groups having from 3 to 6 carbon atoms in the alkanoyl part, carbamoyloxy groups, and mono- or di-alkylcarbamoyloxy groups having 1 or 2 carbon atoms in the or each alkyl part; and said substituents $\beta^1$ are selected from the group consisting of alkyl groups having from 1 to 4 carbon atoms, and phenyl groups which are unsubstituted or are substituted by at least one substituent selected from the group consisting of methyl groups, methoxy groups, fluorine atoms and chlorine atoms;

$R^{3a}$, $R^{3b}$ and $R^{3c}$, which are the same as or different from each other, each represents a hydrogen atom, an alkyl group having from 1 to 4 carbon atoms, a halogen-substituted alkyl group having 1 or 2 carbon atoms, an alkenyl group having 3 or 4 carbon atoms, an alkynyl group having 3 or 4 carbon atoms, a hydroxy group, an alkoxy group having from 1 to 4 carbon atoms, a halogen-substituted alkoxy group having 1 or 2 carbon atoms, an alkoxycarbonyl group having from 1 to 4 carbon atoms in the alkoxy part, an alkanoyloxy group having from 2 to 5 carbon atoms, a carbamoyl group, a mono- or di-alkylcarbamoyl group having 1 or 2 carbon atoms in the or each alkyl part, a halogen atom, a cyano group, a nitro group, or a phenyl group which is unsubstituted or is substituted by at least one of substituents $\gamma^1$, defined below, and $R^{3d}$ represents a hydrogen atom;

said substituents $\gamma^1$ are selected from the group consisting of methyl, ethyl, methoxy and ethoxy groups and halogen atoms; and A represents a single bond or an alkylene group having from 1 to 4 carbon atoms.

20. The compound of claim 1, wherein:

$R^1$ represents a pyrrolidinyl group, a piperidyl group, a morpholinyl group or a thiomorpholinyl group, which is substituted on a carbon atom by at least one of substituents $\alpha^2$ and is unsubstituted or is substituted on a nitrogen atom by at least one of substituents $\beta^2$, defined below;

said substituents $\alpha^2$ are selected from the group consisting of hydroxy groups, alkoxycarbonyloxy groups having from 1 to 4 or from 8 to 18 carbon atoms in the alkoxy part, alkanoyloxy groups having from 2 to 5 carbon atoms, alkanoyloxy groups having from 10 to 18 carbon atoms, carboxy-substituted alkanoyloxy groups having from 3 to 6 carbon atoms in the alkanoyl part, carbamoyloxy groups, and mono- or di-alkylcarbamoyloxy groups having 1 or 2 carbon atoms in the or each alkyl part; and said substituents $\beta^2$ are selected from the group consisting of alkyl groups having from 1 to 4 carbon atoms;

$R^{3a}$, $R^{3b}$ and $R^{3c}$, which are the same as or different from each other, each represents a hydrogen atom, an alkyl group having from 1 to 4 carbon atoms, a halogen-substituted alkyl group having 1 or 2 carbon atoms, an alkenyl group having 3 or 4 carbon atoms, an alkynyl group having 3 or 4 carbon atoms, a hydroxy group, an alkoxy group having from 1 to 4 carbon atoms, a halogen-substituted alkoxy group having 1 or 2 carbon atoms, an alkoxycarbonyl group having from 1 to 4 carbon atoms in the alkoxy part, an alkanoyloxy group having from 2 to 5 carbon atoms, a carbamoyl group, a mono- or di-alkylcarbamoyl group having 1 or 2 carbon atoms in the or each alkyl part, a halogen atom, a cyano group, a nitro group, or a phenyl group which is unsubstituted or is substituted by at least one of substituents $\gamma^1$, defined below, and $R^{3d}$ represents a hydrogen atom;

said substituents $\gamma^1$ are selected from the group consisting of methyl, ethyl, methoxy and ethoxy groups and halogen atoms; and A represents a single bond or an alkylene group having from 1 to 4 carbon atoms.

21. The compound of claim 1, wherein:

$R^1$ represents a pyrrolidinyl group, a piperidyl group, a morpholinyl group or a thiomorpholinyl group, which is substituted on a carbon atom by at least one of substituents $\alpha^3$ and is unsubstituted or is substituted on a nitrogen atom by at least one of substituents $\beta^3$, defined below;

said substituents α³ are selected from the group consisting of hydroxy, methoxycarbonyloxy, ethoxycarbonyloxy, isopropoxycarbonyloxy, t-butoxycarbonyloxy, octyloxycarbonyloxy, decyloxycarbonyloxy, hexadecyloxycarbonyloxy, octadecyloxycarbonyloxy, acetoxy, propionyloxy, butyryloxy, valeryloxy, pivaloyloxy, decanoyloxy, undecanoyloxy, lauroyloxy, myristoyloxy, palmitoyloxy, stearoyloxy, succinyloxy, glutaryloxy, carbamoyloxy, N-methylcarbamoyloxy, N-ethylcarbamoyloxy and N,N-dimethylcarbamoyloxy groups; and said substituents β³ are selected from the group consisting of methyl and ethyl groups;

$R^{3a}$, $R^{3b}$ and $R^{3c}$, which are the same as or different from each other, each represents a hydrogen atom, a methyl group, an ethyl group, a fluorine- or chlorine-substituted alkyl group having 1 or 2 carbon atoms, an allyl group, a propargyl group, a hydroxy group, a methoxy group, an ethoxy group, a fluoromethoxy group, a difluoromethoxy group, a chloromethoxy group, a 2-fluoroethoxy group, a 2-chloroethoxy group, a methoxycarbonyl group, an ethoxycarbonyl group, an alkanoyloxy group having 2 or 3 carbon atoms, a carbamoyl group, a methylcarbamoyl group, a dimethylcarbamoyl group, a fluorine atom, a chlorine atom, a bromine atom, a cyano group, a nitro group, or a phenyl group which is unsubstituted or is substituted by at least one of substituents γ², defined below, and $R^{3d}$ represents a hydrogen atom;

said substituents γ² are selected from the group consisting of methyl and methoxy groups and fluorine and chlorine atoms; and A represents a single bond, a methylene group, an ethylene group or a trimethylene group.

22. The compound of claim 1, wherein:

$R^1$ represents a pyrrolidinyl group, a piperidyl group or a morpholinyl group, which is substituted on a carbon atom by at least one of substituents α⁴ and is unsubstituted or is substituted on a nitrogen atom by at least one of substituents β³, defined below;

said substituents α⁴ are selected from the group consisting of hydroxy, ethoxycarbonyloxy, isopropoxycarbonyloxy, t-butoxycarbonyloxy, octyloxycarbonyloxy, hexadecyloxycarbonyloxy, octadecyloxycarbonyloxy, decanoyloxy, lauroyloxy, palmitoyloxy, stearyloxy, succinyloxy, carbamoyloxy and N,N-dimethylcarbamoyloxy groups; and said substituents β³ are selected from the group consisting of methyl and ethyl groups;

$R^{3a}$, $R^{3b}$ and $R^{3c}$, which are the same as or different from each other, each represents a hydrogen atom, a methyl group, an ethyl group, a fluoromethyl group, a trifluoromethyl group, a chloromethyl group, a hydroxy group, a methoxy group, an ethoxy group, a fluoromethoxy group, a difluoromethoxy group, a 2-fluoroethoxy group, a fluorine atom, a chlorine atom, a bromine atom, a cyano group, a carbamoyl group or a phenyl group, and $R^{3d}$ represents a hydrogen atom; and A represents a single bond, a methylene group, an ethylene group or a trimethylene group.

23. The compound of claim 1, wherein:

$R^1$ represents a 4-hydroxy-2-pyrrolidinyl group, a 4-ethoxycarbonyloxy-2-pyrrolidinyl group, a 4-isopropoxycarbonyloxy-2-pyrrolidinyl group, a 4-t-butoxycarbonyloxy-2-pyrrolidinyl group, a 4-octyloxycarbonyloxy-2-pyrrolidinyl group, a 4-hexadecyloxycarbonyloxy-2-pyrrolidinyl group, a 4-octadecyloxycarbonyloxy-2-pyrrolidinyl group, a 4-acetoxy-2-pyrrolidinyl group, a 4-decanoyloxy-2-pyrrolidinyl group, a 4-lauroyloxy-2-pyrrolidinyl group, a 4-myristoyloxy-2-pyrrolidinyl group, a 4-palmitoyloxy-2-pyrrolidinyl group, a 4-stearoyloxy-2-pyrrolidinyl group, a 4-succinyloxy-2-pyrrolidinyl group, a 4-carbamoyloxy-2-pyrrolidinyl group, a 1-methyl-4-hydroxy-2-pyrrolidinyl group, a 1-methyl-4-ethoxycarbonyloxy-2-pyrrolidinyl group, a 1-methyl-4-isopropoxycarbonyloxy-2-pyrrolidinyl group, a 1-methyl-4-t-butoxycarbonyloxy-2-pyrrolidinyl group, 1-methyl-4-octyloxycarbonyloxy-2-pyrrolidinyl group, a 1-methyl-4-hexadecyloxycarbonyloxy-2-pyrrolidinyl group, a 1-methyl-4-octadecyloxycarbonyloxy-2-pyrrolidinyl group, a 1-methyl-4-acetoxy-2-pyrrolidinyl group, a 1-methyl-4-decanoyloxy-2-pyrrolidinyl group, a 1-methyl-4-lauroyloxy-2-pyrrolidinyl group, a 1-methyl-4-myristoyloxy-2-pyrrolidinyl group, a 1-methyl-4-palmitoyloxy-2-pyrrolidinyl group, a 1-methyl-4-stearoyloxy-2-pyrrolidinyl group, or a 1-methyl-4-succinyloxy-2-pyrrolidinyl group;

$R^{3a}$ and $R^{3b}$, which are the same as or different from each other, each represents a hydrogen atom, a methyl group, a hydroxy group, a methoxy group, an ethoxy group, a fluoromethoxy group, a difluoromethoxy group, a fluorine atom, a chlorine atom, a bromine atom or a cyano group, and $R^{3c}$ and $R^{3d}$ both represent hydrogen atoms; and A represents a single bond, a methylene group or an ethylene group.

24. The compound of claim 1, wherein:

$R^1$ represents a 4-hydroxy-2-pyrrolidinyl group, a 4-ethoxycarbonyloxy-2-pyrrolidinyl group, a 4-t-butoxycarbonyloxy-2-pyrrolidinyl group, a 4-octyloxycarbonyloxy-2-pyrrolidinyl group, a 4-hexadecyloxycarbonyloxy-2-pyrrolidinyl group, a 4-octadecyloxycarbonyloxy-2-pyrrolidinyl group, a 4-decanoyloxy-2-pyrrolidinyl group, a 4-lauroyloxy-2-pyrrolidinyl group, a 4-myristoyloxy-2-pyrrolidinyl group, a 4-palmitoyloxy-2-pyrrolidinyl group, a 4-stearoyloxy-2-pyrrolidinyl group, a 1-methyl-4-hydroxy-2-pyrrolidinyl group, a 1-methyl-4-ethoxycarbonyloxy-2-pyrrolidinyl group, a 1-methyl-4-t-butoxycarbonyloxy-2-pyrrolidinyl group, 1-methyl-4-octyloxycarbonyloxy-2-pyrrolidinyl group, a 1-methyl-4-hexadecyloxycarbonyloxy-2-pyrrolidinyl group, a 1-methyl-4-octadecyloxycarbonyloxy-2-pyrrolidinyl group, a 1-methyl-4-decanoyloxy-2-pyrrolidinyl group, a 1-methyl-4-lauroyloxy-2-pyrrolidinyl group, a 1-methyl- 4-myristoyloxy-2-pyrrolidinyl group, a 1-methyl-4-palmitoyloxy-2-pyrrolidinyl group or a 1-methyl-4-stearoyloxy-2-pyrrolidinyl group;

$R^{2a}$ represents a fluorine atom, and $R^{2b}$ and $R^{2c}$ both represent hydrogen atoms;

$R^{3a}$ and $R^{3b}$, which are the same as or different from each other, each represents a hydrogen atom, a methoxy group or a fluorine atom, and $R^{3c}$ and $R^{3d}$ both represent hydrogen atoms; and A represents an ethylene group.

25. The compound of claim 1, wherein:

$R^1$ represents a 4-hydroxy-2-pyrrolidinyl group, a 4-decanoyloxy-2-pyrrolidinyl group, a 4-lauroyloxy-2- pyrrolidinyl group, a 4-myristoyloxy-2-pyrrolidinyl group, a 4-palmitoyloxy-2-pyrrolidinyl group, a 4-stearoyloxy-2-pyrrolidinyl group, a 1-methyl-4-hydroxy-2-pyrrolidinyl group, a 1-methyl-4-decanoyloxy-2-pyrrolidinyl group, a 1-methyl-4-lauroyloxy-2-pyrrolidinyl group, a 1-methyl-4-myristoyloxy-2-pyrrolidinyl group, a 1-methyl-4-palmitoyloxy-2-pyrrolidinyl group or a 1-methyl-4-stearoyloxy-2-pyrrolidinyl group;

$R^{2a}$ represents a fluorine atom, and $R^{2b}$ and $R^{2c}$ both represent hydrogen atoms;

$R^{3a}$ and $R^{3b}$, which are the same as or different from each other, each represents a hydrogen atom, a methoxy group or a fluorine atom, and $R^{3c}$ and $R^{3d}$ both represent hydrogen atoms; and A represents an ethylene group.

26. The compound of claim 1, selected from the group consisting of 2-{2-[4-fluoro-2-(2-phenylethyl)phenoxy]ethyl}-4-hydroxy-1-methylpyrrolidine and pharmaceutically acceptable salts thereof.

27. The compound of claim 1, selected from the group consisting of 2-{2-[4-fluoro-2-(2-phenylethyl)phenoxy]ethyl}-4-hydroxypyrrolidine and pharmaceutically acceptable salts thereof.

28. The compound of claim 1, selected from the group consisting of 2-{2-[4-fluoro-2-(2-phenylethyl)phenoxy]ethyl}-4-lauroyloxy-1-methylpyrrolidine and pharmaceutically acceptable salts thereof.

29. The compound of claim 1, selected from the group consisting of 2-{2-[4-fluoro-2-(2-phenylethyl)phenoxy]ethyl}-1-methyl-4-succinyloxypyrrolidine and pharmaceutically acceptable salts thereof.

30. The compound of claim 1, selected from the group consisting of 2-[2-{4-fluoro-2-[2-(3-methoxyphenyl)ethyl]phenoxy}ethyl]-4-hydroxy-1-methylpyrrolidine and pharmaceutically acceptable salts thereof.

31. The compound of claim 1, selected from the group consisting of 2-[2-{4-fluoro-2-[2-(3-methoxyphenyl)ethyl]phenoxy}ethyl]-4-lauroyloxy-1-methylpyrrolidine and pharmaceutically acceptable salts thereof.

32. The compound of claim 1, selected from the group consisting of 2-[2-{4-fluoro-2-[2-(3-methoxyphenyl)ethyl]phenoxy}ethyl]-1-methyl-4-succinyloxypyrrolidine and pharmaceutically acceptable salts thereof.

33. The compound of claim 1, selected from the group consisting of 2-[2-{4-fluoro-2-[2-(4-fluorophenyl)ethyl]phenoxy}ethyl]-4-hydroxy-1-methylpyrrolidine and pharmaceutically acceptable salts thereof.

34. The compound of claim 1, selected from the group consisting of 2-[2-{4-fluoro-2-[2-(4-fluorophenyl)ethyl]phenoxy}ethyl]-4-hydroxypyrrolidine and pharmaceutically acceptable salts thereof.

35. The compound of claim 1, selected from the group consisting of 2-[2-{4-fluoro-2-[2-(4-fluorophenyl)ethyl]phenoxy}ethyl]-1-methyl-4-palmitoyloxypyrrolidine and pharmaceutically acceptable salts thereof.

36. The compound of claim 1, selected from the group consisting of 2-[2-{4-fluoro-2-[2-(4-fluorophenyl)ethyl]phenoxy}ethyl]-1-methyl-4-succinyloxypyrrolidine and pharmaceutically acceptable salts thereof.

37. The compound of claim 1, selected from the group consisting of 2-[2-{4-fluoro-2-[2-(4-fluoro-3-methoxyphenyl)ethyl]phenoxy}ethyl]-4-hydroxy-1-methylpyrrolidine and pharmaceutically acceptable salts thereof.

38. The compound of claim 1, selected from the group consisting of 2-[2-{4-fluoro-2-[2-(4-fluoro-3-methoxyphenyl)ethyl]phenoxy}ethyl]-4-hydroxypyrrolidine and pharmaceutically acceptable salts thereof.

39. The compound of claim 1, selected from the group consisting of 2-[2-{4-fluoro-2-[2-(4-fluoro-3-methoxyphenyl)ethyl]phenoxy}ethyl]-4-lauroyloxy-1-methyl-pyrrolidine and pharmaceutically acceptable salts thereof.

40. The compound of claim 1, selected from the group consisting of 2-[2-{4-fluoro-2-[2-(4-fluoro-3-methoxyphenyl)ethyl]phenoxy}ethyl]-1-methyl-4-succinyloxypyrrolidine and pharmaceutically acceptable salts thereof.

41. The compound of claim 1, selected from the group consisting of 2-[2-{2-[2-(3,4-difluorophenyl)ethyl]-4-fluorophenoxy}ethyl]-4-hydroxy-1-methylpyrrolidine and pharmaceutically acceptable salts thereof.

42. The compound of claim 1, selected from the group consisting of 2-[2-{2-[2-(3,4-difluorophenyl)ethyl]-4-fluorophenoxy}ethyl]-4-hydroxypyrrolidine and pharmaceutically acceptable salts thereof.

43. The compound of claim 1, selected from the group consisting of 2-[2-{2-[2-(3,4-difluorophenyl)ethyl]-4-fluorophenoxy}ethyl]-4-lauroyloxy-1-methylpyrrolidine and pharmaceutically acceptable salts thereof.

44. The compound of claim 1, selected from the group consisting of 2-[2-{2-[2-(3,4-difluorophenyl)ethyl]-4-fluorophenoxy}ethyl]-1-methyl-4-succinyloxypyrrolidine and pharmaceutically acceptable salts thereof.

45. A composition for the prevention and treatment of cardiovascular diseases comprising a serotonin 2 receptor antagonist, wherein said serotonin 2 receptor antagonist also has squalene synthase inhibitory activity and is an active compound selected from the group consisting of compounds of formula (I) and pharmaceutically acceptable salts thereof, as claimed in claim 1.

46. The composition of claim 45, wherein:

$R^1$ represents a pyrrolidinyl group, a piperidyl group, a morpholinyl group, a thiomorpholinyl group or a piperazinyl group, which is substituted on a carbon atom by at least one of substituents $\alpha^1$ and is unsubstituted or is substituted on a nitrogen atom by at least one of substituents $\beta^1$, defined below;

said substituents $\alpha^1$ are selected from the group consisting of hydroxy groups, alkoxycarbonyloxy groups having from 1 to 6 or from 8 to 18 carbon atoms in the alkoxy part, alkanoyloxy groups having from 1 to 20 carbon atoms, carboxy-substituted alkanoyloxy groups having from 3 to 6 carbon atoms in the alkanoyl part, carbamoyloxy groups, and mono- or di-alkylcarbamoyloxy groups having 1 or 2 carbon atoms in the or each alkyl part; and said substituents $\beta^1$ are selected from the group consisting of alkyl groups having from 1 to 4 carbon atoms, and phenyl groups which are unsubstituted or are substituted by at least one substituent selected from the group consisting of methyl groups, methoxy groups, fluorine atoms and chlorine atoms;

$R^{3a}$, $R^{3b}$ and $R^{3c}$, which are the same as or different from each other, each represents a hydrogen atom, an alkyl group having from 1 to 4 carbon atoms, a halogen-substituted alkyl group having 1 or 2 carbon atoms, an alkenyl group having 3 or 4 carbon atoms, an alkynyl group having 3 or 4 carbon atoms, a hydroxy group, an alkoxy group having from 1 to 4 carbon atoms, a halogen-substituted alkoxy group having 1 or 2 carbon atoms, an alkoxycarbonyl group having from 1 to 4 carbon atoms in the alkoxy part, an alkanoyloxy group having from 2 to 5 carbon atoms, a carbamoyl group, a mono- or di-alkylcarbamoyl group having 1 or 2 carbon atoms in the or each alkyl part, a halogen atom, a cyano group, a nitro group, or a phenyl group which is unsubstituted or is substituted by at least one of substituents $\gamma^1$, defined below, and $R^{3d}$ represents a hydrogen atom;

said substituents $\gamma^1$ are selected from the group consisting of methyl, ethyl, methoxy and ethoxy groups and halogen atoms; and A represents a single bond or an alkylene group having from 1 to 4 carbon atoms.

47. The composition of claim 45, wherein:

$R^1$ represents a pyrrolidinyl group, a piperidyl group, a morpholinyl group or a thiomorpholinyl group, which is substituted on a carbon atom by at least one of substituents $\alpha^2$ and is unsubstituted or is substituted on a nitrogen atom by at least one of substituents $\beta^2$, defined below;

said substituents $\alpha^2$ are selected from the group consisting of hydroxy groups, alkoxycarbonyloxy groups having from 1 to 4 or from 8 to 18 carbon atoms in the alkoxy part, alkanoyloxy groups having from 2 to 5 carbon atoms, alkanoyloxy groups having from 10 to 18 carbon atoms, carboxy-substituted alkanoyloxy groups having from 3 to 6 carbon atoms in the alkanoyl part, carbamoyloxy groups, and mono- or di-alkylcarbamoyloxy groups having 1 or 2 carbon atoms in the or each alkyl part; and said substituents $\beta^2$ are selected from the group consisting of alkyl groups having from 1 to 4 carbon atoms;

$R^{3a}$, $R^{3b}$ and $R^{3c}$, which are the same as or different from each other, each represents a hydrogen atom, an alkyl group having from 1 to 4 carbon atoms, a halogen-substituted alkyl group having 1 or 2 carbon atoms, an alkenyl group having 3 or 4 carbon atoms, an alkynyl group having 3 or 4 carbon atoms, a hydroxy group, an alkoxy group having from 1 to 4 carbon atoms, a halogen-substituted alkoxy group having 1 or 2 carbon atoms, an alkoxycarbonyl group having from 1 to 4 carbon atoms in the alkoxy part, an alkanoyloxy group having from 2 to 5 carbon atoms, a carbamoyl group, a mono- or di-alkylcarbamoyl group having 1 or 2 carbon atoms in the or each alkyl part, a halogen atom, a cyano group, a nitro group, or a phenyl group which is unsubstituted or is substituted by at least one of substituents $\gamma^1$, defined below, and $R^{3d}$ represents a hydrogen atom;

said substituents $\gamma^1$ are selected from the group consisting of methyl, ethyl, methoxy and ethoxy groups and halogen atoms; and A represents a single bond or an alkylene group having from 1 to 4 carbon atoms.

48. The composition of claim 45, wherein:

$R^1$ represents a pyrrolidinyl group, a piperidyl group, a morpholinyl group or a thiomorpholinyl group, which is substituted on a carbon atom by at least one of substituents $\alpha^3$ and is unsubstituted or is substituted on a nitrogen atom by at least one of substituents $\beta^3$, defined below;

said substituents $\alpha^3$ are selected from the group consisting of hydroxy, methoxycarbonyloxy, ethoxycarbonyloxy, isopropoxycarbonyloxy, t-butoxycarbonyloxy, octyloxycarbonyloxy, decyloxycarbonyloxy, hexadecyloxycarbonyloxy, octadecyloxycarbonyloxy, acetoxy, propionyloxy, butyryloxy, valeryloxy, pivaloyloxy, decanoyloxy, undecanoyloxy, lauroyloxy, myristoyloxy, palmitoyloxy, stearoyloxy, succinyloxy, glutaryloxy, carbamoyloxy, N-methylcarbamoyloxy, N-ethylcarbamoyloxy and N,N-dimethylcarbamoyloxy groups; and said substituents $\beta^3$ are selected from the group consisting of methyl and ethyl groups;

$R^{3a}$, $R^{3b}$ and $R^{3c}$, which are the same as or different from each other, each represents a hydrogen atom, a methyl group, an ethyl group, a fluorine- or chlorine-substituted alkyl group having 1 or 2 carbon atoms, an allyl group, a propargyl group, a hydroxy group, a methoxy group, an ethoxy group, a fluoromethoxy group, a difluoromethoxy group, a chloromethoxy group, a 2-fluoroethoxy group, a 2-chloroethoxy group, a methoxycarbonyl group, an ethoxycarbonyl group, an alkanoyloxy group having 2 or 3 carbon atoms, a carbamoyl group, a methylcarbamoyl group, a dimethylcarbamoyl group, a fluorine atom, a chlorine atom, a bromine atom, a cyano group, a nitro group, or a phenyl group which is unsubstituted or is substituted by at least one of substituents $\gamma^2$, defined below, and $R^{3d}$ represents a hydrogen atom;

said substituents $\gamma^2$ are selected from the group consisting of methyl and methoxy groups and fluorine and chlorine atoms; and A represents a single bond, a methylene group, an ethylene group or a trimethylene group.

49. The composition of claim 45, wherein:

$R^1$ represents a pyrrolidinyl group, a piperidyl group or a morpholinyl group, which is substituted on a carbon atom by at least one of substituents $\alpha^4$ and is unsubstituted or is substituted on a nitrogen atom by at least one of substituents $\beta^3$, defined below;

said substituents $\alpha^4$ are selected from the group consisting of hydroxy, ethoxycarbonyloxy, isopropoxycarbonyloxy, t-butoxycarbonyloxy, octyloxycarbonyloxy, hexadecyloxycarbonyloxy, octadecyloxycarbonyloxy, decanoyloxy, lauroyloxy, palmitoyloxy, stearyloxy, succinyloxy, carbamoyloxy and N,N-dimethylcarbamoyloxy groups; and said substituents $\beta^3$ are selected from the group consisting of methyl and ethyl groups;

$R^{3a}$, $R^{3b}$ and $R^{3c}$, which are the same as or different from each other, each represents a hydrogen atom, a methyl group, an ethyl group, a fluoromethyl group, a trifluoromethyl group, a chloromethyl group, a hydroxy group, a methoxy group, an ethoxy group, a fluoromethoxy group, a difluoromethoxy group, a 2-fluoroethoxy group, a fluorine atom, a chlorine atom, a bromine atom, a cyano group, a carbamoyl group or a phenyl group, and $R^{3d}$ represents a hydrogen atom; and A represents a single bond, a methylene group, an ethylene group or a trimethylene group.

50. The composition of claim 45, wherein:

$R^1$ represents a 4-hydroxy-2-pyrrolidinyl group, a 4-ethoxycarbonyloxy-2-pyrrolidinyl group, a 4-isopropoxycarbonyloxy-2-pyrrolidinyl group, a 4-t-butoxycarbonyloxy-2-pyrrolidinyl group, a 4-octyloxycarbonyloxy-2-pyrrolidinyl group, a 4-hexadecyloxycarbonyloxy-2-pyrrolidinyl group, a 4-octadecyloxy-carbonyloxy-2-pyrrolidinyl group, a 4-acetoxy-2-pyrrolidinyl group, a 4-decanoyloxy-2-pyrrolidinyl group, a 4-lauroyloxy-2-pyrrolidinyl group, a 4-myristoyloxy-2-pyrrolidinyl group, a 4-palmitoyloxy-2-pyrrolidinyl group, a 4-stearoyloxy-2-pyrrolidinyl group, a 4-succinyltoxy-2-pyrrolidinyl croup, a 4-carbamoyloxy-2-pyrrolidinyl group, a 1-methyl-4-hydroxy-2-pyrrolidinyl group, a 1-methyl-4-ethoxycarbonyloxy-2-pyrrolidinyl group, a 1-methyl-4-isopropoxycarbonyloxy-2-pyrrolidinyl group, a 1-methyl-4-t-butoxycarbonyloxy-2-pyrrolidinyl group, 1-methyl-4-octyloxycarbonyloxy-2-pyrrolidinyl group, a 1-methyl-4-hexadecyloxycarbonyloxy-2-pyrrolidinyl group, a 1-methyl-4-octadecyloxycarbonyloxy-2-pyrrolidinyl group, a 1-methyl-4-acetoxy-2-pyrrolidinyl group, a 1-methyl-4-decanoyloxy-2-pyrrolidinyl group, a 1-methyl-4-lauroyloxy-2-pyrrolidinyl group, a 1-methyl-4-myristoyloxy-2-pyrrolidinyl group, a 1-methyl-4-palmitoyloxy-2-pyrrolidinyl group, a 1-methyl-4-stearoyloxy-2-pyrrolidinyl group, or a 1-methyl-4-succinyloxy-2-pyrrolidinyl group;

$R^{3a}$ and $R^{3b}$, which are the same as or different from each other, each represents a hydrogen atom, a methyl group, a hydroxy group, a methoxy group, an ethoxy group, a fluoromethoxy group, a difluoromethoxy group, a fluorine atom, a chlorine atom, a bromine atom or a cyano group, and $R^{3c}$ and $R^{3d}$ both represent hydrogen atoms; and A represents a single bond, a methylene group or an ethylene group.

51. The composition of claim 45, wherein:

$R^1$ represents a 4-hydroxy-2-pyrrolidinyl group, a 4-ethoxycarbonyloxy-2-pyrrolidinyl group, a 4-t-butoxycarbonyloxy-2-pyrrolidinyl group, a 4-octyloxycarbonyloxy-2-pyrrolidinyl group, a 4-hexadecyloxycarbonyloxy-2-pyrrolidinyl group, a 4-octadecyloxycarbonyloxy-2-pyrrolidinyl group, a 4-decanoyloxy-2-pyrrolidinyl group, a 4-lauroyloxy-2-pyrrolidinyl group, a 4-myristoyloxy-2-pyrrolidinyl group, a 4-palmitoyloxy-2-pyrrolidinyl group, a 4-stearoyloxy-2-pyrrolidinyl group, a 1-methyl-4-hydroxy-2-pyrrolidinyl group, a 1-methyl-4-ethoxycarbonyloxy-2-pyrrolidinyl group, a 1-methyl-4-t-butoxycarbonyloxy-2-pyrrolidinyl group, 1-methyl-4-octyloxycarbonyloxy-2-pyrrolidinyl group, a 1-methyl-4-hexadecyloxycarbonyloxy-2-pyrrolidinyl group, a 1-methyl-4-octadecyloxycarbonyloxy-2-pyrrolidinyl group, a 1-methyl-4-decanoyloxy-2-pyrrolidinyl group, a 1-methyl-4-lauroyloxy-2-pyrrolidinyl group, a 1-methyl-4-myristoyloxy-2-pyrrolidinyl group, a 1-methyl-4-palmitoyloxy-2-pyrrolidinyl group or a 1-methyl-4-stearoyloxy-2-pyrrolidinyl group;

$R^{2a}$ represents a fluorine atom, and $R^{2b}$ and $R^{2c}$ both represent hydrogen atoms;

$R^{3a}$ and $R^{3b}$, which are the same as or different from each other, each represents a hydrogen atom, a methoxy group or a fluorine atom, and $R^{3c}$ and $R^{3d}$ both represent hydrogen atoms; and A represents an ethylene group.

52. The composition of claim 45, wherein:

$R^1$ represents a 4-hydroxy-2-pyrrolidinyl group, a 4-decanoyloxy-2-pyrrolidinyl group, a 4-lauroyloxy-2-pyrrolidinyl group, a 4-myristoyloxy-2-pyrrolidinyl group, a 4-palmitoyloxy-2-pyrrolidinyl group, a 4-stearoyloxy-2-pyrrolidinyl group, a 1-methyl-4-hydroxy-2-pyrrolidinyl group, a 1-methyl-4-decanoyloxy-2-pyrrolidinyl group, a 1-methyl-4-lauroyloxy-2-pyrrolidinyl group, a 1-methyl-4-myristoyloxy-2-pyrrolidinyl group, a 1-methyl-4-palmitoyloxy-2-pyrrolidinyl group or a 1-methyl-4-stearoyloxy-2-pyrrolidinyl group;

$R^{2a}$ represents a fluorine atom, and $R^{2b}$ and $R^{2c}$ both represent hydrogen atoms;

$R^{3a}$ and $R^{3b}$, which are the same as or different from each other, each represents a hydrogen atom, a methoxy group or a fluorine atom, and $R^{3c}$ and $R^{3d}$ both represent hydrogen atoms; and A represents an ethylene group.

53. The composition of claim 45, wherein said active compound is selected from the group consisting of:

2-{2-[4-fluoro-2-(2-phenylethyl)phenoxy]ethyl}-4-hydroxy-1-methylpyrrolidine;

2-{2-[4-fluoro-2-(2-phenylethyl)phenoxy]ethyl}-4-hydroxypyrrolidine;

2-{2-[4-fluoro-2-(2-phenylethyl)phenoxy]ethyl}-4-lauroyloxy-1-methylpyrrolidine;

2-{2-[4-fluoro-2-(2-phenylethyl)phenoxy]ethyl}-1-methyl-4-succinyloxypyrrolidine;

2-[2-{4-fluoro-2-[2-(3-methoxyphenyl)ethyl]phenoxy}ethyl]-4-hydroxy-1-methylpyrrolidine;

2-[2-{4-fluoro-2-[2-(3-methoxyphenyl)ethyl]phenoxy}ethyl]-4-lauroyloxy-1-methylpyrrolidine;

2-[2-{4-fluoro-2-[2-(3-methoxyphenyl)ethyl]phenoxy}ethyl]-1-methyl-4-succinyloxypyrrolidine;

2-[2-{4-fluoro-2-[2-(4-fluorophenyl)ethyl]phenoxy}ethyl]-4-hydroxy-1-methyl-pyrrolidine;

2-[2-{4-fluoro-2-[2-(4-fluorophenyl)ethyl]phenoxy}ethyl]-4-hydroxypyrrolidine;

2-[2-{4-fluoro-2-[2-(4- fluorophenyl)ethyl]phenoxy}ethyl]-1-methyl-4-palmitoyl-oxypyrrolidine;

2-[2-{4-fluoro-2-[2-(4-fluorophenyl)ethyl]phenoxy}ethyl]-1-methyl-4-succinyloxypyrrolidine;

2-[2-{4-fluoro-2-[2-(4-fluoro-3-methoxyphenyl)ethyl]phenoxy}ethyl]-4-hydroxy-1methylpyrrolidine;

2-[2-{4-fluoro-2-[2-(4-fluoro-3-methoxyphenyl)ethyl]phenoxy}ethyl]-4-hydroxpyrrolidine;

2-[2-{4-fluoro-2-[2-(4-fluoro-3-methoxyphenyl)ethyl]phenoxy}ethyl]-4-lauroyloxy-1-methylpyrrolidine;

2-[2-{4-fluoro-2-[2-(4-fluoro-3-methoxyphenyl)ethyl]phenoxy}ethyl]-1-methyl-4-succinyloxypyrrolidine;

2-[2-{2-[2-(3,4-difluorophenyl)ethyl]-4-fluorophenoxy}ethyl]-4-hydroxy-1-methylpyrrolidine;

2-[2-{2-[2-(3,4-difluorophenyl)ethyl]-4-fluorophenoxy}ethyl]-4-hydroxypyrrolidine;

2-[2-{2-[2-(3,4-difluorophenyl)ethyl]-4-fluorophenoxy}ethyl]-4-lauroyloxy-1-methylpyrrolidine; and 2-[2-{2-[2-(3,4-difluorophenyl)ethyl]-4-fluorophenoxy}ethyl]-1-methyl-4-succinyloxypyrrolidine;

and pharmaceutically acceptable salts thereof.

54. A method for the prevention or treatment of cardiovascular diseases in a mammal susceptible thereto, comprising administering to said mammal, an effective amount of an active compound having serotonin 2 receptor antagonist and squalene synthase inhibitory activities, said active compound being selected from the group consisting of compounds of formula (I) and pharmaceutically acceptable salts thereof, as claimed in claim 1.

55. The method of claim 54, wherein:

$R^1$ represents a pyrrolidinyl group, a piperidyl group, a morpholinyl group, a thiomorpholinyl group or a piperazinyl group, which is substituted on a carbon atom by at least one of substituents $\alpha^1$ and is unsubstituted or is substituted on a nitrogen atom by at least one of substituents $\beta^1$, defined below;

said substituents $\alpha^1$ are selected from the group consisting of hydroxy groups, alkoxycarbonyloxy groups having from 1 to 6 or from 8 to 18 carbon atoms in the alkoxy part, alkanoyloxy groups having from 1 to 20 carbon atoms, carboxy-substituted alkanoyloxy groups having from 3 to 6 carbon atoms in the alkanoyl part, carbamoyloxy groups, and mono- or di-alkylcarbamoyloxy groups having 1 or 2 carbon atoms in the or each alkyl part; and said substituents $\beta^1$ are selected from the group consisting of alkyl groups having from 1 to 4 carbon atoms, and phenyl groups which are unsubstituted or are substituted by at least one substituent selected from the group consisting of methyl groups, methoxy groups, fluorine atoms and chlorine atom;

$R^{3a}$, $R^{3b}$ and $R^{3c}$, which are the same as or different from each other, each represents a hydrogen atom, an alkyl group having from 1 to 4 carbon atoms, a halogen-substituted alkyl group having 1 or 2 carbon atoms, an alkenyl group having 3 or 4 carbon atoms, an alkynyl group having 3 or 4 carbon atoms, a hydroxy group, an alkoxy group having from 1 to 4 carbon atoms, a halogen-substituted alkoxy group having 1 or 2 carbon atoms, an alkoxycarbonyl group having from 1 to 4 carbon atoms in the alkoxy part, an alkanoyloxy group having from 2 to 5 carbon atoms, a carbamoyl group, a mono- or di-alkylcarbamoyl group having 1 or 2 carbon atoms in the or each alkyl part, a halogen atom, a cyano group, a nitro group, or a phenyl group which is unsubstituted or is substituted by at least one of substituents $\gamma^1$, defined below, and $R^{3d}$ represents a hydrogen atom;

said substituents $\gamma^1$ are selected from the group consisting of methyl, ethyl, methoxy and ethoxy groups and halogen atoms; and A represents a single bond or an alkylene group having from 1 to 4 carbon atoms.

56. The method of claim 54, wherein:

$R^1$ represents a pyrrolidinyl group, a piperidyl group, a morpholinyl group or a thiomorpholinyl group, which is substituted on a carbon atom by at least one of substituents $\alpha^2$ and is unsubstituted or is substituted on a nitrogen atom by at least one of substituents $\beta^2$, defined below;

said substituents $\alpha^2$ are selected from the group consisting of hydroxy groups, alkoxycarbonyloxy groups having from 1 to 4 or from 8 to 18 carbon atoms in the alkoxy part, alkanoyloxy groups having from 2 to 5 carbon atoms, alkanoyloxy groups having from 10 to 18 carbon atoms, carboxy-substituted alkanoyloxy groups having from 3 to 6 carbon atoms in the alkanoyl part, carbamoyloxy groups, and mono- or di-alkylcarbamoyloxy groups having 1 or 2 carbon atoms in the or each alkyl part; and said substituents p2 are selected from the group consisting of alkyl groups having from 1 to 4 carbon atoms;

$R^{3a}$, $R^{3b}$ and $R^{3c}$, which are the same as or different from each other, each represents a hydrogen atom, an alkyl group having from 1 to 4 carbon atoms, a halogen-substituted alkyl group having 1 or 2 carbon atoms, an alkenyl group having 3 or 4 carbon atoms, an alkynyl group having 3 or 4 carbon atoms, a hydroxy group, an alkoxy group having from 1 to 4 carbon atoms, a halogen-substituted alkoxy group having 1 or 2 carbon atoms, an alkoxycarbonyl group having from 1 to 4 carbon atoms in the alkoxy part, an alkanoyloxy group having from 2 to 5 carbon atoms, a carbamoyl group, a mono- or di-alkylcarbamoyl group having 1 or 2 carbon atoms in the or each alkyl part, a halogen atom, a cyano group, a nitro group, or a phenyl group which is unsubstituted or is substituted by at least one of substituents $\gamma^1$, defined below, and $R^{3d}$ represents a hydrogen atom;

said substituents $\gamma^1$ are selected from the group consisting of methyl, ethyl, methoxy and ethoxy groups and halogen atoms; and A represents a single bond or an alkylene group having from 1 to 4 carbon atoms.

57. The method of claim 54, wherein:

$R^1$ represents a pyrrolidinyl group, a piperidyl group, a morpholinyl group or a thiomorpholinyl group, which is substituted on a carbon atom by at least one of substituents $\alpha^3$ and is unsubstituted or is substituted on a nitrogen atom by at least one of substituents $\beta^3$, defined below;

said substituents $\alpha^3$ are selected from the group consisting of hydroxy, methoxycarbonyloxy, ethoxycarbonyloxy, isopropoxycarbonyloxy, t-butoxycarbonyloxy, octyloxycarbonyloxy, decyloxycarbonyloxy, hexadecyloxycarbonyloxy, octadecyloxycarbonyloxy, acetoxy, propionyloxy, butyryloxy, valeryloxy, pivaloyloxy, decanoyloxy, undecanoyloxy, lauroyloxy, myristoyloxy, palmitoyloxy, stearoyloxy, succinyloxy, glutaryloxy, carbamoyloxy, N-methylcarbamoyloxy, N-ethylcarbamoyloxy and N,N-dimethylcarbamoyloxy groups; and said substituents $\beta^3$ p are selected from the group consisting of methyl and ethyl groups;

$R^{3a}$, $R^{3b}$ and $R^{3c}$, which are the same as or different from each other, each represents a hydrogen atom, a methyl group, an ethyl group, a fluorine- or chlorine-substituted alkyl group having 1 or 2 carbon atoms, an allyl group, a propargyl group, a hydroxy group, a methoxy group, an ethoxy group, a fluoromethoxy group, a difluoromethoxy group, a chloromethoxy group, a 2-fluoroethoxy group, a 2-chloroethoxy group, a methoxycarbonyl group, an ethoxycarbonyl group, an alkanoyloxy group having 2 or 3 carbon atoms, a carbamoyl group, a methylcarbamoyl group, a dimethylcarbamoyl group, a fluorine atom, a chlorine atom, a bromine atom, a cyano group, a nitro group, or a phenyl group which is unsubstituted or is substituted by at least one of substituents $\gamma^2$, defined below, and $R^{3d}$ represents a hydrogen atom;

said substituents $\gamma^2$ are selected from the group consisting of methyl and methoxy groups and fluorine and chlorine atoms; and A represents a single bond, a methylene group, an ethylene group or a trimethylene group.

58. The method of claim 54, wherein:

$R^1$ represents a pyrrolidinyl group, a piperidyl group or a morpholinyl group, which is substituted on a carbon atom by at least one of substituents $\alpha^4$ and is unsubstituted or is substituted on a nitrogen atom by at least one of substituents $\beta^3$, defined below;

said substituents $\alpha^4$ are selected from the group consisting of hydroxy, ethoxycarbonyloxy, isopropoxycarbonyloxy, t-butoxycarbonyloxy, octyloxycarbonyloxy, hexadecyloxycarbonyloxy, octadecyloxycarbonyloxy, decanoyloxy, lauroyloxy, palmitoyloxy, stearyloxy, succinyloxy, carbamoyloxy and N,N-dimethylcarbamoyloxy groups; and said substituents $\beta^3$ are selected from the group consisting of methyl and ethyl groups;

$R^{3a}$, $R^{3b}$ and $R^{3c}$, which are the same as or different from each other, each represents a hydrogen atom, a methyl group, an ethyl group, a fluoromethyl group, a trifluoromethyl group, a chloromethyl group, a hydroxy group, a methoxy group, an ethoxy group, a fluoromethoxy group, a difluoromethoxy group, a 2-fluoroethoxy group, a fluorine atom, a chlorine atom, a bromine atom, a cyano group, a carbamoyl group or a phenyl group, and $R^{3d}$ represents a hydrogen atom; and A represents a single bond, a methylene group, an ethylene group or a trimethylene group.

59. The method of claim 54, wherein:

$R^1$ represents a 4-hydroxy-2-pyrrolidinyl group, a 4-ethoxycarbonyloxy-2-pyrrolidinyl group, a 4-isopropoxycarbonyloxy-2-pyrrolidinyl group, a 4-t-butoxycarbonyloxy-2-pyrrolidinyl group, a 4-octyloxycarbonyloxy-2-pyrrolidinyl group, a 4-hexadecyloxycarbonyloxy-2-pyrrolidinyl group, a 4-octadecyloxy-carbonyloxy-2-pyrrolidinyl group, a 4-acetoxy-2-pyrrolidinyl group, a 4-decanoyloxy-2-pyrrolidinyl group, a 4-lauroyloxy-2-pyrrolidinyl group, a 4-myristoyloxy-2-pyrrolidinyl group, a 4-palmitoyloxy-2-pyrrolidinyl group, a 4-stearoyloxy-2-pyrrolidinyl group, a 4-succinyloxy-2-pyrrolidinyl group, a 4-carbamoyloxy-2-pyrrolidinyl group, a 1-methyl-4-hydroxy-2-pyrrolidinyl group, a 1-methyl-4-ethoxycarbonyloxy-2-pyrrolidinyl group, a 1-methyl-4-isopropoxycarbonyloxy-2-pyrrolidinyl group, a 1-methyl-4-t-butoxycarbonyloxy-2-pyrrolidinyl group, 1-methyl-4-octyloxycarbonyloxy-2-pyrrolidinyl group, a 1-methyl-4-hexadecyloxycarbonyloxy-2-pyrrolidinyl group, a 1-methyl-4-octadecyloxycarbonyloxy-2-pyrrolidinyl group, a 1-methyl-4-acetoxy-2-pyrrolidinyl group, a 1-methyl-4-decanoyloxy-2-pyrrolidinyl group, a 1-methyl-4-lauroyloxy-2-pyrrolidinyl group, a 1-methyl-4-myristoyloxy-2-pyrrolidinyl group, a 1-methyl-4-palmitoyloxy-2-pyrrolidinyl group, a 1-methyl-4-stearoyloxy-2-pyrrolidinyl group, or a 1-methyl-4-succinyloxy-2-pyrrolidinyl group;

$R^{3a}$ and $R^{3b}$, which are the same as or different from each other, each represents a hydrogen atom, a methyl group, a hydroxy group, a methoxy group, an ethoxy group, a fluoromethoxy group, a difluoromethoxy group, a fluorine atom, a chlorine atom, a bromine atom or a cyano group, and $R^{3c}$ and $R^{3d}$ both represent hydrogen atoms; and A represents a single bond, a methylene group or an ethylene group.

60. The method of claim 54, wherein:

$R^1$ represents a 4-hydroxy-2-pyrrolidinyl group, a 4-ethoxycarbonyloxy-2-pyrrolidinyl group, a 4-t-butoxycarbonyloxy-2-pyrrolidinyl group, a 4-octyloxycarbonyloxy-2-pyrrolidinyl group, a 4-hexadecyloxycarbonyloxy-2-pyrrolidinyl group, a 4-octadecyloxycarbonyloxy-2-pyrrolidinyl group, a 4-decanoyloxy-2-pyrrolidinyl group, a 4-lauroyloxy-2-pyrrolidinyl group, a 4-myristoyloxy-2-pyrrolidinyl group, a 4-palmitoyloxy-2-pyrrolidinyl group, a 4-stearoyloxy-2-pyrrolidinyl group, a 1-methyl-4-hydroxy-2-pyrrolidinyl group, a 1-methyl-4-ethoxycarbonyloxy-2-pyrrolidinyl group, a 1-methyl-4-t-butoxycarbonyloxy-2-pyrrolidinyl group, 1-methyl-4-octyloxycarbonyloxy-2-pyrrolidinyl group, a 1-methyl-4-hexadecyloxycarbonyloxy-2-pyrrolidinyl group, a 1-methyl-4-octadecyloxycarbonyloxy-2-pyrrolidinyl group, a 1-methyl-4-decanoyloxy-2-pyrrolidinyl group, a 1-methyl-4-lauroyloxy-2-pyrrolidinyl group, a 1-methyl-4-myristoyloxy-2-pyrrolidinyl group, a 1-methyl-4-palmitoyloxy-2-pyrrolidinyl group or a 1-methyl-4-stearoyloxy-2-pyrrolidinyl group;

$R^{2a}$ represents a fluorine atom, and $R^{2b}$ and $R^{2c}$ both represent hydrogen atoms;

$R^{3a}$ and $R^{3b}$, which are the same as or different from each other, each represents a hydrogen atom, a methoxy group or a fluorine atom, and $R^{3c}$ and $R^{3d}$ both represent hydrogen atoms; and A represents an ethylene group.

61. The method of claim 54, wherein:

$R^1$ represents a 4-hydroxy-2-pyrrolidinyl group, a 4-decanoyloxy-2-pyrrolidinyl group, a 4-lauroyloxy-2-pyrrolidinyl group, a 4-myristoyloxy-2-pyrrolidinyl group, a 4-palmitoyloxy-2-pyrrolidinyl group, a 4-stearoyloxy-2-pyrrolidinyl group, a 1-methyl-4-hydroxy-2-pyrrolidinyl group, a 1-methyl-4-decanoyloxy-2-pyrrolidinyl group, a 1-methyl-4-lauroyloxy-2-pyrrolidinyl group, a 1-methyl-4-myristoyloxy-2-pyrrolidinyl group, a 1-methyl-4-palmitoyloxy-2-pyrrolidinyl group or a 1-methyl-4-stearoyloxy-2-pyrrolidinyl group;

$R^{2a}$ represents a fluorine atom, and $R^{2b}$ and $R^{2c}$ both represent hydrogen atoms;

$R^{3a}$ and $R^{3b}$, which are the same as or different from each other, each represents a hydrogen atom, a methoxy group or a fluorine atom, and $R^{3c}$ and $R^{3d}$ both represent hydrogen atoms; and A represents an ethylene group.

62. The method of claim 54, wherein said active compound is selected from the group consisting of:

2-{2-[4-fluoro-2-(2-phenylethyl)phenoxy]ethyl}-4-hydroxy-1-methylpyrrolidine;

2-{2-[4-fluoro-2-(2-phenylethyl)phenoxy]ethyl}-4-hydroxypyrrolidine;

2-{2-[4-fluoro-2-(2-phenylethyl)phenoxy]ethyl}-4-lauroyloxy-1-methylpyrrolidine;

2-{2-[4-fluoro-2-(2-phenylethyl)phenoxy]ethyl}-1-methyl-4-succinyloxypyrrolidine;

2-[2-{4-fluoro-2-[2-(3-methoxyphenyl)ethyl]phenoxy}ethyl]-4-hydroxy-1-methyl-pyrrolidine;

2-[2-{4-fluoro-2-[2-(3-methoxyphenyl)ethyl]phenoxy}ethyl]-4-lauroyloxy-1-methylpyrrolidine;

2-[2-{4-fluoro-2-[2-(3-methoxyphenyl)ethyl]phenoxy}ethyl]-1-methyl-4-succinyloxypyrrolidine;

2-[2-{4-fluoro-2-[2-(4-fluorophenyl)ethyl]phenoxy}ethyl]-4-hydroxy-1-methylpyrrolidine;

2-[2-{4-fluoro-2-[2-(4-fluorophenyl)ethyl]phenoxy}ethyl]-4-hydroxypyrrolidine;

2-[2-{4-fluoro-2-[2-(4-fluorophenyl)ethyl]
phenoxy}ethyl]-1-methyl-4-palmitoyloxypyrrolidine;
2-[2-{4-fluoro-2-[2-(4-fluorophenyl)ethyl]
phenoxy}ethyl]-1-methyl-4-succinyloxypyrrolidine;
2-[2-{4-fluoro-2-[2-(4-fluoro-3-methoxyphenyl)ethyl]
phenoxy}ethyl]-4-hydroxy-1-methylpyrrolidine;
2-[2-{4-fluoro-2-[2-(4-fluoro-3-methoxyphenyl)ethyl]
phenoxy}ethyl]-4-hydroxypyrrolidine;
2-[2-{4-fluoro-2-[2-(4-fluoro-3-methoxyphenyl)ethyl]
phenoxy}ethyl]-4-lauroyloxy-1-methylpyrrolidine;
2-[2-{4-fluoro-2-[2-(4-fluoro-3-methoxyphenyl)ethyl]
phenoxy}ethyl]-1-methyl-4-succinyloxypyrrolidine;
2-[2-{2-[2-(3,4-difluorophenyl)ethyl]-4-
fluorophenoxy}ethyl]-4-hydroxy-1-methylpyrrolidine;
2-[2-{2-[2-(3,4-difluorophenyl)ethyl]-4-
fluorophenoxy}ethyl]-4-hydroxypyrrolidine;
2-[2-{2-[2-(3,4-difluorophenyl)ethyl]-4-
fluorophenoxy}ethyl]-4-lauroyloxy-1-
methylpyrrolidine; and
2-[2-{2-[2-(3,4-difluorophenyl)ethyl]-4-
fluorophenoxy}ethyl]-1-methyl-4-
succinyloxypyrrolidine;
and pharmaceutically acceptable salts thereof.

63. The method of claim 54, wherein the mammal is a human.

64. The method of claim 63, wherein:

$R^1$ represents a pyrrolidinyl group, a piperidyl group, a morpholinyl group, a thiomorpholinyl group or a piperazinyl group, which is substituted on a carbon atom by at least one of substituents $\alpha^1$ and is unsubstituted or is substituted on a nitrogen atom by at least one of substituents $\beta^1$, defined below;

said substituents $\alpha^1$ are selected from the group consisting of hydroxy groups, alkoxycarbonyloxy groups having from 1 to 6 or from 8 to 18 carbon atoms in the alkoxy part, alkanoyloxy groups having from 1 to 20 carbon atoms, carboxy-substituted alkanoyloxy groups having from 3 to 6 carbon atoms in the alkanoyl part, carbamoyloxy groups, and mono- or di-alkylcarbamoyloxy groups having 1 or 2 carbon atoms in the or each alkyl part; and said substituents $\beta^2$ are selected from the group consisting of alkyl groups having from 1 to 4 carbon atoms, and phenyl groups which are unsubstituted or are substituted by at least one substituent selected from the group consisting of methyl groups, methoxy groups, fluorine atoms and chlorine atoms;

$R^{3a}$, $R^{3b}$ and $R^{3c}$, which are the same as or different from each other, each represents a hydrogen atom, an alkyl group having from 1 to 4 carbon atoms, a halogen-substituted alkyl group having 1 or 2 carbon atoms, an alkenyl group having 3 or 4 carbon atoms, an alkynyl group having 3 or 4 carbon atoms, a hydroxy group, an alkoxy group having from 1 to 4 carbon atoms, a halogen-substituted alkoxy group having 1 or 2 carbon atoms, an alkoxycarbonyl group having from 1 to 4 carbon atoms in the alkoxy part, an alkanoyloxy group having from 2 to 5 carbon atoms, a carbamoyl group, a mono- or di-alkylcarbamoyl group having 1 or 2 carbon atoms in the or each alkyl part, a halogen atom, a cyano group, a nitro group, or a phenyl group which is unsubstituted or is substituted by at least one of substituents $\gamma^1$, defined below, and $R^{3d}$ represents a hydrogen atom;

said substituents $\gamma^1$ are selected from the group consisting of methyl, ethyl, methoxy and ethoxy groups and halogen atoms; and A represents a single bond or an alkylene group having from 1 to 4 carbon atoms.

65. The method of claim 63, wherein:

$R^1$ represents a pyrrolidinyl group, a piperidyl group, a morpholinyl group or a thiomorpholinyl group, which is substituted on a carbon atom by at least one of substituents $\alpha^2$ and is unsubstituted or is substituted on a nitrogen atom by at least one of substituents $\beta^2$, defined below;

said substituents $\alpha^2$ are selected from the group consisting of hydroxy groups, alkoxycarbonyloxy groups having from 1 to 4 or from 8 to 18 carbon atoms in the alkoxy part, alkanoyloxy groups having from 2 to 5 carbon atoms, alkanoyloxy groups having from 10 to 18 carbon atoms, carboxy-substituted alkanoyloxy groups having from 3 to 6 carbon atoms in the alkanoyl part, carbamoyloxy groups, and mono- or di-alkylcarbamoyloxy groups having 1 or 2 carbon atoms in the or each alkyl part; and said substituents $\beta^1$ are selected from the group consisting of alkyl groups having from 1 to 4 carbon atoms;

$R^{3a}$, $R^{3b}$ and $R^3$, which are the same as or different from each other, each represents a hydrogen atom, an alkyl group having from 1 to 4 carbon atoms, a halogen-substituted alkyl group having 1 or 2 carbon atoms, an alkenyl group having 3 or 4 carbon atoms, an alkynyl group having 3 or 4 carbon atoms, a hydroxy group, an alkoxy group having from 1 to 4 carbon atoms, a halogen-substituted alkoxy group having 1 or 2 carbon atoms, an alkoxycarbonyl group having from 1 to 4 carbon atoms in the alkoxy part, an alkanoyloxy group having from 2 to 5 carbon atoms, a carbamoyl group, a mono- or di-alkylcarbamoyl group having 1 or 2 carbon atoms in the or each alkyl part, a halogen atom, a cyano group, a nitro group, or a phenyl group which is unsubstituted or is substituted by at least one of substituents $\gamma^1$, defined below, and $R^{3d}$ represents a hydrogen atom;

said substituents $\gamma^1$ are selected from the group consisting of methyl, ethyl, methoxy and ethoxy groups and halogen atoms; and A represents a single bond or an alkylene group having from 1 to 4 carbon atoms.

66. The method of claim 63, wherein:

$R^1$ represents a pyrrolidinyl group, a piperidyl group, a morpholinyl group or a thiomorpholinyl group, which is substituted on a carbon atom by at least one of substituents $\alpha^3$ and is unsubstituted or is substituted on a nitrogen atom by at least one of substituents $\beta^3$, defined below;

said substituents $\alpha^3$ are selected from the group consisting of hydroxy, methoxycarbonyloxy, ethoxycarbonyloxy, isopropoxycarbonyloxy, t-butoxycarbonyloxy, octyloxycarbonyloxy, decyloxycarbonyloxy, hexadecyloxycarbonyloxy, octadecyloxycarbonyloxy, acetoxy, propionyloxy, butyryloxy, valeryloxy, pivaloyloxy, decanoyloxy, undecanoyloxy, lauroyloxy, myristoyloxy, palmitoyloxy, stearoyloxy, succinyloxy, glutaryloxy, carbamoyloxy, N-methylcarbamoyloxy, N-ethylcarbamoyloxy and N,N-dimethylcarbamoyloxy groups; and said substituents $\beta^3$ are selected from the group consisting of methyl and ethyl groups;

$R^{3a}$, $R^{3b}$ and $R^{3c}$, which are the same as or different from each other, each represents a hydrogen atom, a methyl group, an ethyl group, a fluorine- or chlorine-substituted alkyl group having 1 or 2 carbon atoms, an allyl group, a propargyl group, a hydroxy group, a methoxy group, an ethoxy group, a fluoromethoxy group, a difluoromethoxy group, a chloromethoxy group, a 2-fluoroethoxy group, a 2-chloroethoxy group, a methoxycarbonyl group, an ethoxycarbonyl group, an alkanoyloxy group having 2 or 3 carbon atoms, a carbamoyl group, a methylcarbamoyl group, a dimethylcarbamoyl group, a fluorine atom, a chlorine atom, a bromine atom, a cyano group, a nitro group or a phenyl group which is unsubstituted or is substituted by at least one of substituents $\gamma^2$, defined below, and $R^{3d}$ represents a hydrogen atom;

said substituents $\gamma^2$ are selected from the group consisting of methyl and methoxy groups and fluorine and chlorine atoms; and A represents a single bond, a methylene group, an ethylene group or a trimethylene group.

67. The method of claim 63, wherein:

$R^1$ represents a pyrrolidinyl group, a piperidyl group or a morpholinyl group, which is substituted on a carbon atom by at least one of substituents $\alpha^4$ and is unsubstituted or is substituted on a nitrogen atom by at least one of substituents $\beta^3$, defined below;

said substituents $\alpha^4$ are selected from the group consisting of hydroxy, ethoxycarbonyloxy, isopropoxycarbonyloxy, t-butoxycarbonyloxy, octyloxycarbonyloxy, hexadecyloxycarbonyloxy, octadecyloxycarbonyloxy, decanoyloxy, lauroyloxy, palmitoyloxy, stearyloxy, succinyloxy, carbamoyloxy and N,N-dimethylcarbamoyloxy groups; and said substituents $\beta^3$ are selected from the group consisting of methyl and ethyl groups;

$R^{3a}$, $R^{3b}$ and $R^{3c}$, which are the same as or different from each other, each represents a hydrogen atom, a methyl group, an ethyl group, a fluoromethyl group, a trifluoromethyl group, a chloromethyl group, a hydroxy group, a methoxy group, an ethoxy group, a fluoromethoxy group, a difluoromethoxy group, a 2-fluoroethoxy group, a fluorine atom, a chlorine atom, a bromine atom, a cyano group, a carbamoyl group or a phenyl group, and $R^{3d}$ represents a hydrogen atom; and A represents a single bond, a methylene group, an ethylene group or a trimethylene group.

68. The method of claim 63, wherein: $R^1$ represents a 4-hydroxy-2-pyrrolidinyl group, a 4-ethoxycarbonyloxy-2-pyrrolidinyl group, a 4-isopropoxycarbonyloxy-2-pyrrolidinyl group, a 4-t-butoxycarbonyloxy-2-pyrrolidinyl group, a 4-octyloxycarbonyloxy-2-pyrrolidinyl group, a 4-hexadecyloxycarbonyloxy-2-pyrrolidinyl group, a 4-octadecyloxycarbonyloxy-2-pyrrolidinyl group, a 4-acetoxy-2-pyrrolidinyl group, a 4-decanoyloxy-2-pyrrolidinyl group, a 4-lauroyloxy-2-pyrrolidinyl group, a 4-myristoyloxy-2-pyrrolidinyl group, a 4-palmitoyloxy-2-pyrrolidinyl group, a 4-stearoyloxy-2-pyrrolidinyl group, a 4-succinyloxy-2-pyrrolidinyl group, a 4-carbamoyloxy-2-pyrrolidinyl group, a 1-methyl-4-hydroxy-2-pyrrolidinyl group, a 1-methyl-4-ethoxycarbonyloxy-2-pyrrolidinyl group, a 1-methyl-4-isopropoxycarbonyloxy-2-pyrrolidinyl group, a 1-methyl-4-t-butoxycarbonyloxy-2-pyrrolidinyl group, 1-methyl-4-octyloxycarbonyloxy-2-pyrrolidinyl group, a 1-methyl-4-hexadecyloxycarbonyloxy-2-pyrrolidinyl group, a 1-methyl-4-octadecyloxycarbonyloxy-2-pyrrolidinyl group, a 1-methyl-4-acetoxy-2-pyrrolidinyl group, a 1-methyl-4-decanoyloxy-2-pyrrolidinyl group, a 1-methyl-4-lauroyloxy-2-pyrrolidinyl group, a 1-methyl-4-myristoyloxy-2-pyrrolidinyl group, a 1-methyl-4-palmitoyloxy-2-pyrrolidinyl group, a 1-methyl-4-stearoyloxy-2-pyrrolidinyl group, or a 1-methyl-4-succinyloxy-2-pyrrolidinyl group;

$R^{3a}$ and $R^{3b}$, which are the same as or different from each other, each represents a hydrogen atom, a methyl group, a hydroxy group, a methoxy group, an ethoxy group, a fluoromethoxy group, a difluoromethoxy group, a fluorine atom, a chlorine atom, a bromine atom or a cyano group, and $R^{3c}$ and $R^{3d}$ both represent hydrogen atoms; and A represents a single bond, a methylene group or an ethylene group.

69. The method of claim 63, wherein:

$R^1$ represents a 4-hydroxy-2-pyrrolidinyl group, a 4-ethoxycarbonyloxy-2-pyrrolidinyl group, a 4-t-butoxycarbonyloxy-2-pyrrolidinyl group, a 4-octyloxycarbonyloxy-2-pyrrolidinyl group, a 4-hexadecyloxycarbonyloxy-2-pyrrolidinyl group, a 4-octadecyloxycarbonyloxy-2-pyrrolidinyl group, a 4-decanoyloxy-2-pyrrolidinyl group, a 4-lauroyloxy-2-pyrrolidinyl group, a 4-myristoyloxy-2-pyrrolidinyl group, a 4-palmitoyloxy-2-pyrrolidinyl group, a 4-stearoyloxy-2-pyrrolidinyl group, a 1-methyl-4-hydroxy-2-pyrrolidinyl group, a 1-methyl-4-ethoxycarbonyloxy-2-pyrrolidinyl group, a 1-methyl-4-t-butoxycarbonyloxy-2-pyrrolidinyl group, 1-methyl-4-octyloxycarbonyloxy-2-pyrrolidinyl group, a 1-methyl-4-hexadecyloxycarbonyloxy-2-pyrrolidinyl group, a 1-methyl-4-octadecyloxycarbonyloxy-2-pyrrolidinyl group, a 1-methyl-4-decanoyloxy-2-pyrrolidinyl group, a 1-methyl-4-lauroyloxy-2-pyrrolidinyl group, a 1-methyl-4-myristoyloxy-2-pyrrolidinyl group, a 1-methyl-4-palmitoyloxy-2-pyrrolidinyl group or a 1-methyl-4-stearoyloxy-2-pyrrolidinyl group;

$R^{2a}$ represents a fluorine atom, and $R^{2b}$ and $R^{2c}$ both represent hydrogen atoms;

$R^{3a}$ and $R^{3b}$, which are the same as or different from each other represents a hydrogen atom, a methoxy group or a fluorine atom, and $R^{3c}$ and $R^{3d}$ both represent hydrogen atoms; and A represents an ethylene group.

70. The method of claim 63, wherein:

$R^1$ represents a 4-hydroxy-2-pyrrolidinyl group, a 4-decanoyloxy-2-pyrrolidinyl group, a 4-lauroyloxy-2-pyrrolidinyl group, a 4-myristoyloxy-2-pyrrolidinyl group, a 4-palmitoyloxy-2-pyrrolidinyl group, a 4-stearoyloxy-2-pyrrolidinyl group, a 1-methyl-4-hydroxy-2-pyrrolidinyl group, a 1-methyl-4-decanoyloxy-2-pyrrolidinyl group, a 1-methyl-4-lauroyloxy-2-pyrrolidinyl group, a 1-methyl-4-myristoyloxy-2-pyrrolidinyl group, a 1-methyl-4-palmitoyloxy-2-pyrrolidinyl group or a 1-methyl-4-stearoyloxy-2-pyrrolidinyl group;

$R^{2a}$ represents a fluorine atom, and $R^{2b}$ and $R^{2c}$ both represent hydrogen atoms;

$R^{3a}$ and $R^{3b}$, which are the same as or different from each other, each represents a hydrogen atom, a methoxy group or a fluorine atom, and $R^{3c}$ and $R^{3d}$ both represent hydrogen atoms; and A represents an ethylene group.

71. The method of claim 63, wherein said active compound is selected from the group consisting of:

2-{2-[4-fluoro-2-(2-phenylethyl)phenoxy]ethyl}-4-hydroxy-1-methylpyrrolidine;

2-{2-[4-fluoro-2-(2-phenylethyl)phenoxy]ethyl}-4-hydroxypyrrolidine;

2-{2-[4-fluoro-2-(2-phenylethyl)phenoxy]ethyl}-4-lauroyloxy-1-methylpyrrolidine;

2-{2-[4-fluoro-2-(2-phenylethyl)phenoxy]ethyl}-1-methyl-4-succinyloxypyrrolidine;

2-[2-{4-fluoro-2-[2-(3-methoxyphenyl)ethyl]phenoxy}ethyl]-4-hydroxy-1-methylpyrrolidine;

2-[2-{4-fluoro-2-[2-(3-methoxyphenyl)ethyl]phenoxy}ethyl]-4-lauroyloxy-1-methyl-pyrrolidine;

2-[2-{4-fluoro-2-[2-(3-methoxyphenyl)ethyl]phenoxy}ethyl]-1-methyl-4-succinyloxypyrrolidine;

2-[2-{4-fluoro-2-[2-(4-fluorophenyl)ethyl]phenoxy}ethyl]-4-hydroxy-1-methylpyrrolidine;

2-[2-{4- fluoro-2-[2-(4-fluorophenyl)ethyl]phenoxy}ethyl]-4-hydroxypyrrolidine;

2-[2-{4-fluoro-2-[2-(4-fluorophenyl)ethyl]phenoxy}ethyl]-1-methyl-4-palmitoyl-oxypyrrolidine;

2-[2-{4-fluoro-2-[2-(4-fluorophenyl)ethyl]phenoxy}ethyl]-1-methyl-4-succinyloxypyrrolidine;

2-[2-{4-fluoro-2-[2-(4-fluoro-3-methoxyphenyl)ethyl]phenoxy}ethyl]-4-hydroxy-1-methylpyrrolidine;

2-[2-{4-fluoro-2-[2-(4-fluoro-3-methoxyphenyl)ethyl]phenoxy}ethyl]-4-hydroxypyrrolidine;

2-[2-{4-fluoro-2-[2-(4-fluoro-3-methoxyphenyl)ethyl]phenoxy}ethyl]-4-lauroyloxy-1-methylpyrrolidine;

2-[2-{4-fluoro-2-[2-(4-fluoro-3-methoxyphenyl)ethyl]phenoxy}ethyl]-1-methyl-4-succinyloxypyrrolidine;

2-[2-{2-[2-(3,4-difluorophenyl)ethyl]-4-fluorophenoxy}ethyl]-4-hydroxy-1-methylpyrrolidine;

2-[2-{2-[2-(3,4-difluorophenyl)ethyl]-4-fluorophenoxy}ethyl]-4-hydroxypyrrolidine;

2-[2-{2-[2-(3,4-difluorophenyl)ethyl]-4-fluorophenoxy}ethyl]-4-lauroyloxy-1-methylpyrrolidine; and 2-[2-{2-[2-(3,4-difluorophenyl)ethyl]-4-fluorophenoxy}ethyl]-1-methyl-4-succinyloxypyrrolidine;

and pharmaceutically acceptable salts thereof.

* * * * *